US012433949B2

(12) United States Patent
Adams et al.

(10) Patent No.: US 12,433,949 B2
(45) Date of Patent: Oct. 7, 2025

(54) SUSTAINED RELEASE DELIVERY SYSTEMS COMPRISING TRACELESS LINKERS

(71) Applicant: Novartis AG, Basel (CH)

(72) Inventors: Christopher M. Adams, Arlington, MA (US); Myriam April, Cambridge, MA (US); Tanzina Fazal, Burlington, MA (US); Cornelia Jutta Forster, Pelham, NH (US); Edward Charles Hall, Boston, MA (US); Cameron Chuck-munn Lee, Cambridge, MA (US)

(73) Assignee: Novartis AG, Basel (CH)

( * ) Notice: Subject to any disclaimer, the term of this patent is extended or adjusted under 35 U.S.C. 154(b) by 489 days.

(21) Appl. No.: 18/054,767

(22) Filed: Nov. 11, 2022

(65) Prior Publication Data

US 2023/0201353 A1 Jun. 29, 2023

Related U.S. Application Data

(62) Division of application No. 16/901,601, filed on Jun. 15, 2020, now abandoned, which is a division of application No. 15/957,474, filed on Apr. 19, 2018, now Pat. No. 10,751,417.

(60) Provisional application No. 62/487,888, filed on Apr. 20, 2017.

(51) Int. Cl.

| | |
|---|---|
| ***A61K 47/36*** | (2006.01) |
| ***A61K 9/00*** | (2006.01) |
| ***A61K 31/496*** | (2006.01) |
| ***A61K 47/10*** | (2017.01) |
| ***A61K 47/22*** | (2006.01) |
| ***A61K 47/61*** | (2017.01) |
| ***A61K 47/69*** | (2017.01) |
| ***A61P 27/02*** | (2006.01) |

(52) U.S. Cl.
CPC ............ *A61K 47/36* (2013.01); *A61K 9/0048* (2013.01); *A61K 31/496* (2013.01); *A61K 47/10* (2013.01); *A61K 47/22* (2013.01); *A61K 47/61* (2017.08); *A61K 47/6903* (2017.08); *A61P 27/02* (2018.01)

(58) Field of Classification Search
None
See application file for complete search history.

(56) References Cited

U.S. PATENT DOCUMENTS

| | | | |
|---|---|---|---|
| 5,051,407 | A | 9/1991 | Boeshagen et al. |
| 5,770,229 | A | 6/1998 | Tanihara et al. |
| 7,186,413 | B2 | 3/2007 | Bouhadir et al. |
| 8,512,752 | B2 | 8/2013 | Crescenzi et al. |
| 8,791,136 | B2 | 7/2014 | Goff et al. |
| 8,809,370 | B2 | 8/2014 | Goff et al. |
| 8,980,921 | B2 | 3/2015 | Goff et al. |
| 8,987,303 | B2 | 3/2015 | Goff et al. |
| 9,266,856 | B2 | 2/2016 | Goff et al. |
| 9,562,022 | B2 | 2/2017 | Garvey et al. |
| 10,751,417 | B2 | 8/2020 | Adams et al. |
| 2006/0002890 | A1 | 1/2006 | Hersel et al. |
| 2010/0291171 | A1 | 11/2010 | Crescenzi et al. |
| 2011/0027350 | A1 | 2/2011 | Jain et al. |
| 2011/0230497 | A1 | 9/2011 | Peterson et al. |
| 2014/0120069 | A1 | 5/2014 | Huerta-Angeles et al. |
| 2014/0256643 | A1 | 9/2014 | Johnson et al. |
| 2014/0256831 | A1 | 9/2014 | Ito et al. |
| 2015/0267196 | A1 | 9/2015 | Alsberg et al. |
| 2016/0229838 | A1 | 8/2016 | Goff et al. |
| 2016/0289219 | A1 | 10/2016 | Song et al. |
| 2017/0037018 | A1 | 2/2017 | Garvey et al. |
| 2018/0303945 | A1 | 10/2018 | Adams et al. |

FOREIGN PATENT DOCUMENTS

| | | | |
|---|---|---|---|
| CA | 2635889 | A1 | 7/2007 |
| CN | 104292454 | A | 1/2015 |
| EP | 2352730 | A2 | 8/2011 |
| EP | 2678326 | A1 | 1/2014 |
| EP | 2723758 | A2 | 4/2014 |
| EP | 2442644 | B1 | 8/2016 |
| EP | 3100723 | A1 | 12/2016 |
| EP | 2061816 | B1 | 2/2017 |
| GB | 2427360 | A | 12/2006 |
| JP | 2012533549 | A | 12/2012 |
| JP | 2013116858 | A | 6/2013 |
| JP | 2016172783 | A | 9/2016 |
| WO | 9809987 | A1 | 3/1998 |
| WO | 02059095 | A1 | 8/2002 |
| WO | 2005028502 | A1 | 3/2005 |
| WO | 2005068466 | A1 | 7/2005 |
| WO | 2005099768 | A2 | 10/2005 |

(Continued)

OTHER PUBLICATIONS

Sadekar, et al., Antibody Drug Conjugates: Application of Quantitative Pharmacology in Modality Design and Target Selection, The AAPS Journal, Jul. 2015, 828-836, 17(4).

(Continued)

*Primary Examiner* — Robert A Wax
*Assistant Examiner* — John Seungjai Kwon
(74) *Attorney, Agent, or Firm* — Seth E. Cockrum

(57) ABSTRACT

Described herein are drug delivery systems for delivering biologically active agents comprising primary or secondary amines, or a ring nitrogen atom of an azaheteroaryl ring, pharmaceutically acceptable salts thereof, drug delivery reagents related thereto, pharmaceutical compositions comprising the drug delivery systems, and the use of the drug delivery systems as sustained release therapeutics.

7 Claims, 13 Drawing Sheets

Specification includes a Sequence Listing.

(56) References Cited

FOREIGN PATENT DOCUMENTS

| | | | |
|---|---|---|---|
| WO | 2007003054 | A1 | 1/2007 |
| WO | 2007027493 | A2 | 3/2007 |
| WO | 2008097676 | A1 | 8/2008 |
| WO | 2008116107 | A2 | 9/2008 |
| WO | 2008119741 | A2 | 10/2008 |
| WO | 2008148839 | A2 | 12/2008 |
| WO | 2009095479 | A2 | 8/2009 |
| WO | 2010053861 | A2 | 5/2010 |
| WO | 2010069532 | A1 | 6/2010 |
| WO | 2010095049 | A1 | 8/2010 |
| WO | 2010099818 | A1 | 9/2010 |
| WO | 2010102663 | A1 | 9/2010 |
| WO | 2010147653 | A1 | 12/2010 |
| WO | 2011000945 | A2 | 1/2011 |
| WO | 2011012715 | A1 | 2/2011 |
| WO | 2011012718 | A1 | 2/2011 |
| WO | 2011012719 | A1 | 2/2011 |
| WO | 2011012721 | A1 | 2/2011 |
| WO | 2011012722 | A1 | 2/2011 |
| WO | 2011012723 | A1 | 2/2011 |
| WO | 2011042450 | A1 | 4/2011 |
| WO | 2011042453 | A1 | 4/2011 |
| WO | 2011051406 | A1 | 5/2011 |
| WO | 2011089214 | A1 | 7/2011 |
| WO | 2011089215 | A1 | 7/2011 |
| WO | 2011089216 | A1 | 7/2011 |
| WO | 2011130613 | A1 | 10/2011 |
| WO | 2011136645 | A1 | 11/2011 |
| WO | 2011140392 | A1 | 11/2011 |
| WO | 2012016217 | A1 | 2/2012 |
| WO | 2012041451 | A1 | 4/2012 |
| WO | 2012116250 | A1 | 8/2012 |
| WO | 2012146218 | A1 | 11/2012 |
| WO | 2012173952 | A1 | 12/2012 |
| WO | 2013024051 | A1 | 2/2013 |
| WO | 2013036748 | A1 | 3/2013 |
| WO | 2013036847 | A1 | 3/2013 |
| WO | 2013053856 | A1 | 4/2013 |
| WO | 2013078562 | A2 | 6/2013 |
| WO | 2013078564 | A2 | 6/2013 |
| WO | 2013111110 | A2 | 8/2013 |
| WO | 2013171485 | A1 | 11/2013 |
| WO | 2014056915 | A1 | 4/2014 |
| WO | 2014056923 | A1 | 4/2014 |
| WO | 2014056926 | A1 | 4/2014 |
| WO | 2014116717 | A1 | 7/2014 |
| WO | 2014124316 | A2 | 8/2014 |
| WO | 2014138687 | A1 | 9/2014 |
| WO | 2014150937 | A1 | 9/2014 |
| WO | 2014173759 | A1 | 10/2014 |
| WO | 2014173762 | A1 | 10/2014 |
| WO | 2014181287 | A1 | 11/2014 |
| WO | 2015020206 | A1 | 2/2015 |
| WO | 2015052154 | A1 | 4/2015 |
| WO | 2015061503 | A1 | 4/2015 |
| WO | 2015067791 | A1 | 5/2015 |
| WO | 2015130878 | A1 | 9/2015 |
| WO | 2016020373 | A1 | 2/2016 |
| WO | 2016025752 | A1 | 2/2016 |
| WO | 2016073915 | A1 | 5/2016 |
| WO | 2016110577 | A1 | 5/2016 |
| WO | 2016149501 | A2 | 9/2016 |
| WO | 2016161372 | A1 | 10/2016 |
| WO | 2016196124 | A2 | 12/2016 |
| WO | 2017086794 | A1 | 5/2017 |
| WO | 2017161174 | A1 | 9/2017 |
| WO | 2018011266 | A1 | 1/2018 |
| WO | 2018193408 | A1 | 10/2018 |

OTHER PUBLICATIONS

Verbeeck, et al., Generic substitution: The use of medicinal products containing different salts and implications for safety and efficacy, European Journal of Pharmaceutical Sciences, Jan. 18, 2006, 1-6, 28.

Agrebi, et al., Cyclization cascade of Hydrazono Ugi Adducts towards Pyrazoles, European Journal of Organic Chemistry, Aug. 1, 2013, 5805-5808.

An, et al., Retention of the Cis Proline Conformation in Tripeptide Fragments of Bovine Pancreatic Ribonuclease A Containing a Non-natural Proline Analogue, 5,5-Dimethylproline, Journal of the American Chemical Society, 1999, 11558-11566, 121(49).

CAS Registry 2039789-95-0, entered Nov. 28, 2016—517902-58-8, entered May 19, 2003.

Dommerholt, et al., Readily Accessible Bicyclononynes for Bioorthogonal Labeling and Three-Dimensional Imaging of Living Cells, Angewandte Chemie International Edition, 2010, 9422-9425, 49.

Dugel, et al., HAWK and HARRIER: Phase 3, Multicenter, Randomized, Double-Masked Trials of Brolucizumab for Neovascular Age-Related Macular Degeneration, Ophthalmology, Jan. 2020, 72-84, 127(1).

Gulevich, et al., The Ugi reaction with CF3-carbonyl compounds: . . . , Tetraheron, Oct. 10, 2008, 11706-11712, 64.

Halab, et al., Effect of Sequence on Peptide Geometry in 5-tert-Butylprolyl Type VI b-Turn Mimics, Journal of the American Chemical Society, 2002, 2474-2484, 124(11).

Machinaga, et al., A Controlled Release System for Long-Acting . . . , TVST, 2018, 1-8, 7(4).

Pubchem, Alexa Fluor 555, product information in PubChem, downloaded from https://pubchem.ncbi.nlm.nih.gov/compound/Alexa-Fluor-555 on May 19, 2020.

Puthenveetil, et al., Development of Solid-Phase Site-Specific Conjugation and its Application toward Generation of Dual Labeled Antibody and Fab Drug Conjugates, Bioconjugate Chemistry, Apr. 20, 2016, 1030-1039, 27(4).

Szymanski, et al., Studies on the application of the Passerini reaction and enzymatic procedures to the synthesis of tripeptide mimetics, Tetrahedron, May 17, 2007, 7647-7653, 63.

Tanihara, et al., A Novel Microbial Infection-Responsive Drug Release System, Journal of Pharmaceutical Sciences, May 1999, 510-514, 88(5).

Van Lierop, et al., 5,5-Dimethylproline dipeptides: an acid-stable class of pseudoproline, Tetrahedron, Jun. 9, 2010, 5357-5366, 66.

Weissleder, et al., Quantitation of Slow Drug Release . . . , Antimicrobial Agents and Chemotherapy, Apr. 1995, 839-845, 39(4).

Functionalized hyaluronic acid
Soluble polymer

SEQUENCE LISTING

```
Sequence total quantity: 7
SEQ ID NO: 1            moltype = AA  length = 112
FEATURE                 Location/Qualifiers
REGION                  1..112
                        note = brolucizumab VL sequence
source                  1..112
                        mol_type = protein
                        organism = synthetic construct
SEQUENCE: 1
MEIVMTQSPS TLSASVGDRV IITCQASEII HSWLAWYQQK PGKAPKLLIY LASTLASGVP  60
SRFSGSGSGA EFTLTISSLQ PDDFATYYCQ NVYLASTNGA NFGQGTKLTV LG          112

SEQ ID NO: 2            moltype = AA  length = 120
FEATURE                 Location/Qualifiers
REGION                  1..120
                        note = brolucizumab VH sequence
source                  1..120
                        mol_type = protein
                        organism = synthetic construct
SEQUENCE: 2
EVQLVESGGG LVQPGGSLRL SCTASGFSLT DYYYMTWVRQ APGKGLEWVG FIDPDDDPYY  60
ATWAKGRFTI SRDNSKNTLY LQMNSLRAED TAVYYCAGGD HNSGWGLDIW GQGTLVTVSS  120

SEQ ID NO: 3            moltype = AA  length = 20
FEATURE                 Location/Qualifiers
REGION                  1..20
                        note = brolucizumab synthetic linker sequence
source                  1..20
                        mol_type = protein
```

```
                         organism = synthetic construct
SEQUENCE: 3
GGGGSGGGGS GGGGSGGGGS                                              20

SEQ ID NO: 4             moltype = AA  length = 252
FEATURE                  Location/Qualifiers
REGION                   1..252
                         note = brolucizumab scFv
DISULFID                 24..89
                         note = disulfide
DISULFID                 149..228
                         note = disulfide
source                   1..252
                         mol_type = protein
                         organism = synthetic construct
SEQUENCE: 4
MEIVMTQSPS TLSASVGDRV IITCQASEII HSWLAWYQQK PGKAPKLLIY LASTLASGVP  60
SRFSGSGSGA EFTLTISSLQ PDDFATYYCQ NVYLASTNGA NFGQGTKLTV LGGGGGSGGG  120
GSGGGGSGGG GSEVQLVESG GGLVQPGGSL RLSCTASGFS LTDYYYMTWV RQAPGKGLEW  180
VGFIDPDDDP YYATWAKGRF TISRDNSKNT LYLQMNSLRA EDTAVYYCAG GDHNSGWGLD  240
IWGQGTLVTV SS                                                      252

SEQ ID NO: 5             moltype = AA  length = 102
FEATURE                  Location/Qualifiers
REGION                   1..102
                         note = D2 Peptide
source                   1..102
                         mol_type = protein
                         organism = synthetic construct
SEQUENCE: 5
GPTLCGAELV DALQFVCGDR GFYFNKPTGY GSSSRAAPQT GIVDECCFRS CDLRRLEMYC  60
APLKPAKSAV RAQRHTDMPK TQKEVHLKNA SRGSAGNKNY RM                     102

SEQ ID NO: 6             moltype = AA  length = 102
FEATURE                  Location/Qualifiers
REGION                   1..102
                         note = D3 Peptide, N-term. Pegylated
MOD_RES                  1
                         note = pegylation
MOD_RES                  1
                         note = N-terminal pegylation
source                   1..102
                         mol_type = protein
                         organism = synthetic construct
SEQUENCE: 6
GPTLCGAELV DALQFVCGDR GFYFNKPTGY GSSSRAAPQT GIVDECCFRS CDLRRLEMYC  60
APLKPAKSAV RAQRHTDMPK TQKEVHLKNA SRGSAGNKNY RM                     102

SEQ ID NO: 7             moltype = AA  length = 13
FEATURE                  Location/Qualifiers
REGION                   1..13
                         note = D4 synthetic peptide
MOD_RES                  1
                         note = PyroGlu
DISULFID                 6..12
                         note = disulfide
MOD_RES                  11
                         note = Nle
source                   1..13
                         mol_type = protein
                         organism = synthetic construct
SEQUENCE: 7
ERPRLCHKGP LCF                                                     13
```

SUSTAINED RELEASE DELIVERY SYSTEMS COMPRISING TRACELESS LINKERS

PRIORITY CLAIM

This application is a divisional of U.S. application Ser. No. 16/901,601 filed 15 Jun. 2020, which is a divisional of U.S. Pat. No. 10,751,417 issued 25 Aug. 2020, which claims priority to U.S. Application No. 62/487,888 filed 20 Apr. 2017, the contents of which are incorporated herein by reference in their entirety.

SEQUENCE LISTING

This application contains a sequence listing that has been submitted electronically in XML format and is hereby incorporated by reference in its entirety. The XML copy, created on Nov. 10, 2022, is named PAT057447-US-DIV_SL.xml.

TECHNICAL FIELD

Described herein are drug delivery systems for delivering biologically active agents comprising primary or secondary amines, or a ring nitrogen atom of an azaheteroaryl ring, pharmaceutically acceptable salts thereof, drug delivery reagents related thereto, pharmaceutical compositions comprising the drug delivery systems, and the use of the drug delivery systems as sustained release therapeutics.

BACKGROUND

Modulation of the physicochemical or pharmacokinetic properties of a drug in vivo may be affected by conjugation of the drug with a carrier. In particular, conjugation of a drug with a carrier is frequently used as a means to increase the therapeutic duration of action, reduce the maximum concentration of the drug after administration or localize delivery of the drug to a desired tissue or compartment or a combination of these purposes. Typically, carriers in drug delivery systems are either (a) used in a non-covalent fashion with the drug physicochemically formulated into a solvent-carrier mixture or (b) linked by covalent attachment of a carrier reagent to a functional group present in the drug.

Non-covalent approaches require a highly efficient drug encapsulation to prevent uncontrolled burst release of the drug that may occur either at initial administration of the carrier-drug system or during degradation of the carrier after administration to a subject. Restraining the diffusion of an unbound, water-soluble drug molecule requires strong van der Waals contacts, frequently mediated through hydrophobic moieties, hydrogen-bonding, or electrostatic binding mediated through charged moieties. Many conformationally sensitive drugs, such as proteins, peptides, or antibodies are rendered dysfunctional during the encapsulation process and/or during subsequent storage of the encapsulated drug.

Alternatively, a drug may be covalently conjugated to a carrier via a stable linker or via a reversible linker moiety from which the drug is released. If the drug is stably connected to the carrier, such a conjugate needs to exhibit sufficient residual activity to have a pharmaceutical effect and the conjugate is constantly in an active form.

If the drug is conjugated to the carrier through a cleavable linker, such conjugates are typically referred to as carrier-linked drugs. This approach can be applied to various classes and sizes of biologically active molecules, from low molecular weight organic molecules, natural products, antibodies and analogs thereof, proteins, peptides, and the like. An important consideration for carrier-linked drugs is the mechanism for releasing the drug from the carrier. The release mechanism may be enzymatic, pH-dependent, or via autonomous hydrolysis. Typically, the drug release is not easily controllable and difficult to sustain over long time periods.

There continues to be a need for new drug delivery systems suitable for the sustained release of biologically active moieties in therapeutic applications. Described herein are drug delivery systems that provide sustained release of biologically active moieties for therapeutically relevant applications.

SUMMARY

Described herein are drug delivery systems comprising biologically active molecules, carriers, and traceless linkers that provide a means for connecting the biologically active molecule to a carrier, pharmaceutical compositions comprising the drug delivery systems, and the use of the drug delivery systems as sustained release therapeutics.

One embodiment described herein is a drug delivery system or pharmaceutically acceptable salt thereof comprising D-R, that is represented by Formula (I), where D is a biologically active moiety comprising at least one primary or secondary amine or a ring nitrogen atom of an azaheteroaryl ring; and R is a linker suitable for release of biologically active moiety D:

(I)

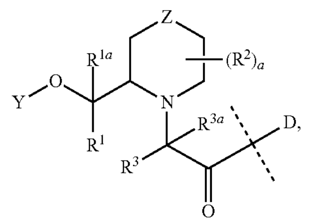

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)N\ R^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —$(OCHR^3CH_2)_b$O—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is CH-L-A, CH-A, N-L-A, or N-A;

L is an optionally substituted bivalent linker;

A is hydrogen, $C_1$-$C_8$alkyl, C(O)$C_1$-$C_8$alkyl, C(O)N(H) $C_1$-$C_8$alkyl, C(O)O$C_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula (I) to a carrier; and $R^{11}$ is a carrier.

In one aspect, D comprises a protein, peptide, polypeptide, nucleic acid, oligo- or poly-nucleotide, carbohydrate, oligo- or poly-saccharide, or small molecule each of which comprises at least one primary amine, secondary amine, or a ring nitrogen atom of an azaheteroaryl ring and the small molecule has a molecular weight of between 100 g/mol and about 2000 g/mol.

In another aspect, D comprises a protein, peptide, nucleic acid, Fab, scFv, monoclonal antibody, or small molecule. In another aspect, D comprises brolucizumab (D1) (SEQ ID NO:4), D2 (SEQ ID NO:5), D3 (SEQ ID NO:6), D4 (SEQ ID NO:7), abciximab, adalimumab, aflibercept, alemtuzumab, basiliximab, belimumab, bevacizumab, brentuximab, canakinumab, certolizumab, cetuximab, daclizumab, daratumumab, denosumab, eculizumab, efalizumab, golimumab, ibritumomab, infliximab, ipilimumab, lampalizumab, muromonab-CD3, natalizumab, nivolumab, ofatumumab, omalizumab, palivizumab, panitumumab, pegpleranib pembrolizumab, ranibizumab, rituximab, tocilizumab, tositumomab, trastuzumab, ustekinumab, or vedolizumab, or combinations thereof. In another aspect, D comprises one or more biologically active peptides including, but not limited to C-type natriuretic peptide (CNP), atrial natriuretic peptide (ANP), exendin-4, insulin, adrenocorticotropic hormone, adrenomedullin, adropin, ω-agatoxin, agouti-related protein, angiotensin(s), apelin 12, apelin 13, apelin 36, or derivatives thereof, bradykinin, calcitonin, cocaine- and amphetamine-regulated transcript (CART), corticotropin releasing factor (CRF), α-defensins, β-defensins, delta sleep-inducing peptide (DSIP), elastase-specific inhibitor (Elafin), endokinins, endomorphins, endorphins, endothelins, exendin, fibronectin active fragment, galanin, galanin-like peptide, big gastrin, gastrin I, gastrin related peptide, gastric inhibitory polypeptide, gastrin releasing peptide, ghrelin, des-acyl ghrelin, glucagon, glucagon-like peptide, growth hormone releasing factor, *Grammostola spatulata* GsMTx-4, guangxitoxin-1E, guanylin, hepcidin 1, hepcidin/LEAP-1, histatin 5, human growth hormone, humanin, huwentoxin, iberiotoxin, imperatoxin A, insulin like growth factors, intermedin, TRL 1620, joining peptide, kaliotoxin, kisspeptins, kurtoxin, lipotropin, lipotropin, liver-cell growth factor, liver-expressed antimicrobial peptide 2, luteinizing hormone releasing hormone, lysenin, LL-37, margatoxin, mastoparan, mast cell degranulating peptide, melanin-concentrating hormone, melanocyte stimulating hormone, MSH-release inhibiting factor, midkine, molluscan cardioexcitatory neuropeptide, morphine tolerance peptide, motilin, muscarinic toxins, neuroendocrine regulatory peptide-2, neurokinin A, neurokinin B, neuromedins, neuronostatin-13, neuropeptides, neurotensin, neurotoxin NSTX-3, nocistatin, nociceptin, obestatin, opioid peptides (enkephalins, endorphins, BAM-12P, casomorphin, dynorphins, endomorphins, neo-endorphins, nociceptin), orexin-A/-B, orphanin, osteocalci, oxytocin, pancreastatin, parathyroid hormone, parathyroid hormone related protein, peptide 234, peptide histidine-methionine, peptide T, peptide YY, Physalaemin, pituitary adenylate cyclase activating polypeptides, platelet factor-4, plectasin, pleiotrophin, proadrenomedullin, prolactin-releasing peptide, psalmotoxin 1, purotoxin-1, pyroglutamylated RFamide peptide, renin, RFamide-related peptide-1, RFamide-related peptide-3, salusin-α/β, sarafotoxins, schizophrenia related peptide, scyllatoxin, secretin, serelaxin, serum thymic factor, sodium potassium ATPase inhibitor-1, somatostatin, stichodactyla toxin, substance K, stresscopin, stresscopin-related peptide, substance P, tachykinins, tarantula SNX-482, tarantula ProTx-I, tarantula ProTx-II, tertiapin, tityustoxin Ka, thyrotropin releasing hormone, tuftsin, uroguanylin, uroguanylin isomer A or B, urocortin, urocortin II, urotensin II, urotensin II-related peptide, vasoactive intestinal peptide, vasopressin, vasotocin, virus replication inhibiting peptide, xenin, or combinations thereof.

In another aspect, D is a small molecule having a molecular weight of between about 100 g/mol to about 2000 g/mol or less, that is connected to R through a primary amine, secondary amine, or a ring nitrogen atom of an azaheteroaryl ring.

In another aspect, the small molecule comprises 5-(5,6,7,8-tetrahydro-pyrido[3,4-d]pyrimidin-4-yloxy)-indole-1-carboxylic acid [5-(1-methyl-cyclopropyl)-2H-pyrazol-3-yl]-amide; 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide; N-(1-methyl-5-(trifluoromethyl)-1H-pyrazol-3-yl)-5-((6-((methylamino)methyl)pyrimidin-4-yl)oxy)-1H-indole-1-carboxamide; (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, or combinations thereof.

In another aspect, $R^1$ is hydrogen or methyl, $R^{1a}$ is hydrogen or methyl, or $CR^1R^{1a}$, taken in combination form a cyclopropan-1,1-diyl group. In another aspect, $R^3$ and $R^{3a}$ are each hydrogen. In another aspect, X is O. In another aspect, Y is C(O)$R^4$ and $R^4$ is $C_1$-$C_6$alkyl, $C_3$-$C_6$cycloalkyl or $C_1$-$C_2$alkoxy$C_1$-$C_2$alkyl. In another aspect, $R^4$ is methyl, ethyl, propyl, isopropyl, 1-methyl-cyclopropyl, or methoxymethyl. In another aspect, Y is $SiR^5R^6R^7$; $R^5$ and $R^6$ are each methyl, ethyl, propyl or isopropyl; and $R^7$ is $C_1$-$C_4$ alkyl, ethoxy, propoxy, isopropoxy, butoxy, iso-butoxy, sec-butoxy, 2-ethoxyethoxy, 2-isopropoxy-ethoxy, tetrahydropyranyloxy, or —$(OCHR^3CH_2)_b$O—$C_1$-$C_4$alkyl, where b is 2, 3, or 4.

In another aspect, Z is CH-L-A, CH-A, N-L-A, or N-A;

L is an optionally substituted bivalent linker Q-[Sp-Q]$_h$-Q;

Q is independently selected at each occurrence from a bond, O, C(O), N(H), N($C_1$-$C_4$alkyl), C(O)NH, C(O)N($C_1$-$C_4$alkyl), N(H)C(O), N($C_1$-$C_4$alkyl)C(O), N(H)C(O)O, N($C_1$-$C_4$alkyl)C(O)O, OC(O)N(H), OC(O)N($C_1$-$C_4$alkyl), N(H)C(O)N(H), N($C_1$-$C_4$alkyl)C(O)N(H), N(H)C(O)N($C_1$-$C_4$alkyl), N($C_1$-$C_4$alkyl)C(O)N($C_1$-$C_4$alkyl), C(O)O, OC(O), OC(O)O, S, $S(O)_2$, N(H)$S(O)_2$, N($C_1$-$C_4$alkyl)$S(O)_2$, $S(O)_2$N(H), $S(O)_2$N($C_1$-$C_4$alkyl), $C_1$-$C_2$alkyl-C(O)N(H), N(H)C(O)$C_1$-

$C_2$alkyl, $C_1$-$C_2$alkyl-C(O)O, OC(O)$C_1$-$C_2$alkyl, 1,2,3-triazole, $OP(O)_2$, $P(O)_2O$, $C_1$-$C_4$alkyl-$P(O)_2$—O, or O—$P(O)_2$—$C_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, $[W—O]_g$, $C_1$-$C_8$alkyl-$[O—W]_g$, $[O—W]_g$—O—$C_1$-$C_8$alkyl, $C_1$-$C_8$Calkyl-$[O—W]_g$—O—$C_1$-$C_8$alkyl, oligopeptide;

h is an integer of between 1 and 20;

g is a weighted average number of between about 2 and about 50;

W is $C_2$-$C_4$alkyl-1,2-diyl in which the hydrogen, methyl, or ethyl side chain may be present on either backbone carbon atom;

A is hydrogen, $C_1$-$C_8$alkyl, C(O)$C_1$-$C_8$alkyl, C(O)O$C_1$-$C_8$alkyl, C(O)N(H)$C_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula (I) to a carrier; and $R^{11}$ is a carrier.

In another aspect, Z is $NR^9$; $R^9$ is C(O)—$(CH_2)$n-Q-A or —C(O)$(CH_2)_q[O—W]_g(NHC(O))_m(CH_2)_q[O—W]_p$-Q-A; n is an integer of 1 to 8; and A is $R^{10}$ or $R^{11}$. In another aspect, $R^{10}$ is azidyl, alkynyl, substituted or unsubstituted $C_7$-$C_{12}$ cycloalkynyl, substituted or unsubstituted $C_7$-$C_{12}$ heterocycloalkynyl, substituted or unsubstituted $C_7$-$C_{12}$ cycloalkenyl, norbornyl, substituted or unsubstituted vinyl carboxyl, substituted or unsubstituted vinyl sulfonyl, substituted or unsubstituted $C_2$-$C_7$ alkenyl, amino, thiol, substituted or unsubstituted $C_1$-$C_8$ carboxyl, substituted or unsubstituted $C_1$-$C_8$ carbonyl, —O—$NH_2$, hydrazidyl, maleimide, alpha-halo carbonyl, furan, substituted or unsubstituted tetrazinyl, lysine, glutamine, cyclodextrin, or adamantanyl. In another aspect, $R^{10}$ comprises a reactive functional group suitable for coupling Formula (I) to a carrier. In another aspect, $R^{11}$ is biodegradable. In another aspect, $R^{11}$ comprises a polymer or cross-linked polymer. In another aspect, $R^{11}$ comprises a hydrogel comprising one or more cross-linked polymers. In another aspect, $R^{11}$ comprises a polymer, cross-linked polymer, or hydrogel comprising one or more of hyaluronic acid, polyethylene glycol, polypropylene glycol, polyethylene oxide, polypropylene oxide, polyglutamate, polylysine, polysialic acid, polyvinyl alcohol, polyacrylate, polymethacrylate, polyacrylamide, polymethacrylamide, polyvinyl pyrrolidone, polyoxazoline, polyiminocarbonate, polyamino acid, hydrophilic polyester, polyamide, polyurethane, polyurea, dextran, agarose, xylan, mannan, carrageenan, alginate, gelatin, collagen, albumin, cellulose, methylcellulose, ethylcellulose, hydroxypropylmethylcellulose, hydroxyethyl starch, chitosan, nucleic acids, derivatives thereof, co-polymers thereof, or combinations thereof. In another aspect, $R^{11}$ comprises hyaluronic acid, polyethylene glycol, a cross-linked hydrogel of hyaluronic acid, a cross-linked hydrogel of polyethylene glycol, or combinations thereof. In another aspect, $R^{11}$ comprises hyaluronic acid or polyethylene glycol. In another aspect, $R^{11}$ comprises a hydrogel comprising cross-linked hyaluronic acid or cross-linked polyethylene glycol. In another aspect, the hyaluronic acid or polyethylene glycol are functionalized with at least one functional group comprising azidyl, alkynyl, substituted or unsubstituted $C_7$-$C_{12}$ cycloalkynyl, substituted or unsubstituted $C_7$-$C_{12}$ heterocycloalkynyl, $C_7$-$C_{12}$ cycloalkenyl, norbornyl, vinyl carboxyl, vinyl sulfonyl, $C_2$-$C_8$ alkenyl, amino, thiol, $C_1$-$C_8$ carboxyl, $C_1$-$C_8$ carbonyl, —O—$NH_2$, carbohydrazide, maleimide, alpha-halo carbonyl, furan, substituted or unsubstituted tetrazinyl, lysine, glutamine, cyclodextrin, adamantanyl, or combinations thereof. In another aspect, $R^{11}$ comprises a hydrogel comprising cross-linked hyaluronic acid, wherein the hyaluronic acid comprises at least one side chain selected from —NH(W1)$(O(W1))_d$-V, wherein W1 is $C_2$-$C_4$alkyl-1,2-diyl in which the hydrogen, methyl, or ethyl side chain may be present on either backbone carbon atom; d is a number average of 0 to 500; and V is a suitable functional group comprising azidyl, alkynyl, substituted or unsubstituted $C_7$-$C_{12}$ cycloalkynyl, substituted or unsubstituted $C_7$-$C_{12}$ heterocycloalkynyl, $C_7$-$C_{12}$ cycloalkenyl, norbornyl, vinyl carboxyl, vinyl sulfonyl, $C_2$-$C_8$ alkenyl, amino, thiol, $C_1$-$C_8$ carboxyl, $C_1$-$C_8$ carbonyl, —O—$NH_2$, carbohydrazide, maleimide, alpha-halo carbonyl, furan, substituted or unsubstituted tetrazinyl, lysine, glutamine, cyclodextrin, or adamantanyl. In one aspect, V is azide.

Another embodiment described herein is a process for making a cross-linked carrier formulation, the process comprising: (a) functionalizing a carrier molecule, $R^{11}$; (b) preparing a reactive cross-linker; and (c) reacting the functionalized carrier molecule with the reactive cross-linker to form a cross-linked carrier by incubation for about 0.5 hours to about 48 hours at a temperature of about 4° C. to about 60° C. In one aspect, the carrier molecule $R^{11}$ comprises a polymer or cross-linked polymer. In another aspect, $R^{11}$ comprises a hydrogel comprising one or more cross-linked polymers. In one aspect, the carrier molecule comprises hyaluronic acid or polyethylene glycol. In another aspect, the carrier molecule is functionalized with azide, sulfhydryl, amine, aminoxy (O—$NH_2$) or aldehyde moieties to provide reactive functional groups for cross-linking. In another aspect, the preparation of the reactive crosslinker comprises reacting a polyethylene glycol with 1-((tert-butoxycarbonyl)amino)cyclopropane-1-carboxylic acid, 3-((tert-butoxycarbonyl)amino)propanoic acid, 1-(tert-butoxycarbonyl)piperidine-4-carboxylic acid, 2-(1-(((tert-butoxycarbonyl)amino)methyl)cyclopropyl)acetic acid, 2-methyl-3-((tert-butoxycarbonyl)amino)propanoic acid, or 7-((tert-butoxycarbonyl)amino)heptanoic acid and deprotecting the functionalized polyethylene glycol ester. In another aspect, the preparation of the reactive crosslinker further comprises introduction at least two bicyclo[6.1.0]non-4-yn-9-yl)methyl groups after deprotection of the functionalized polyethylene glycol ester. In another aspect, the preparation of the reactive crosslinker further comprises reaction of the deprotected functionalized polyethylene glycol ester with a suitable reagent or reagents to introduce terminal reactive groups, such as alkynyl, cycloalkynyl, heterocyloalkynyl, carboxylic acid or activated carboxylic acid, aldehyde or ketone, amino or aminoxy moieties to provide reactive functional groups for cross-linking to the carrier molecules.

Another embodiment described herein is a cross-linked hydrogel obtainable using the methods described herein. In one aspect, the carrier molecule is functionalized with azide.

Another embodiment described herein is a process for preparing a drug adduct, comprising a traceless linker, R, coupled to a biologically-active agent, D, the process comprising: (a) providing a biologically active agent, D, comprising a primary amine, secondary amine, or a ring nitrogen atom of an azaheteroaryl ring; (b) reacting the biologically active agent with a traceless linker, R, that has an activated carbonyl functional group; and (c) purifying the drug adduct from the reagents. In one aspect, R is as defined above in formula (I).

Another embodiment described herein is a drug adduct obtainable using the processes described herein.

Another embodiment described herein is a process for making a drug delivery system, the process comprising: (a)

preparing a carrier molecule, $R^{11}$, where $R^{11}$ is a cross-linked hydrogel, then this step comprises the process used to prepare that hydrogel; the carrier molecule may optionally be purified at this stage; (b) separately conjugating the traceless linker, R, to a biologically active agent, D, comprising a primary amine, secondary amine, or a ring nitrogen atom of an azaheteroaryl ring, thereby forming the traceless linker-D adduct; the traceless linker-D adduct may optionally be purified at this stage, (c) conjugating the carrier molecule, $R^{11}$, with the traceless linker-D adduct; and (d) purifying the drug delivery system from the reagents.

Another embodiment described herein is a drug delivery system obtainable using the using the methods described herein.

Another embodiment described herein is a method for treating an ocular disorder, such as macular degeneration (i.e., wet age-related macular degeneration), comprising administering to a subject in need thereof a drug delivery system or pharmaceutically acceptable salt thereof comprising a conjugate D-R, that is represented by Formula (I), where D is a biologically active moiety comprising at least one primary or secondary amine or a ring nitrogen atom of an azaheteroaryl ring, comprising brolucizumab (SEQ ID NO:4), aflibercept, pegpleranib, ranibizumab, 5-(5,6,7,8-tetrahydro-pyrido[3,4-d]pyrimidin-4-yloxy)-indole-1-carboxylic acid [5-(1-methyl-cyclopropyl)-2H-pyrazol-3-yl]-amide; 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide; N-(1-methyl-5-(trifluoromethyl)-1H-pyrazol-3-yl)-5-((6-((methylamino)methyl)pyrimidin-4-yl)oxy)-1H-indole-1-carboxamide; (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, or combinations thereof; R is a linker suitable for release of biologically active moiety D:

(I)

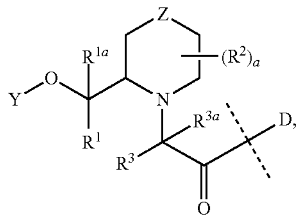

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or $—(OCHR^3CH_2)_bO—C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is $CHR^8$ or $NR^9$;

$R^8$ and $R^9$ are each independently selected from hydrogen, $C_1$-$C_8$ alkyl, $C(O)C_1$-$C_8$ alkyl, or $—C(O)(CH_2)_q[O—W]_g(NHC(O))_m(CH_2)_q[O—W]_p$-Q-A, wherein the alkyl group is optionally substituted with 0 or 1 Q-A;

q is 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or N($C_1$-$C_4$alkyl);

A is hydrogen, $C_1$-$C_8$alkyl, $C(O)C_1$-$C_8$alkyl, C(O)N(H) $C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula (I) to a carrier; and $R^{11}$ is a carrier.

Another embodiment described herein is a method for treating musculoskeletal disorders comprising administering to a subject in need thereof a drug delivery system or pharmaceutically acceptable salt thereof comprising a conjugate D-R, that is represented by Formula (I), where D is a biologically active moiety comprising at least one primary or secondary amine or a ring 5 nitrogen atom of an azaheteroaryl ring comprising D2 (SEQ ID NO:4), D3 (SEQ ID NO:5), other insulin like growth factors, or a combination thereof; R is a linker suitable for release of biologically active moiety D:

(I)

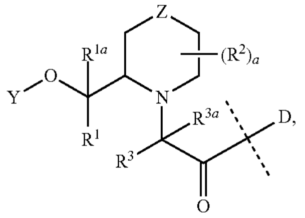

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or $-(OCHR^3CH_2)_bO-C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is $CHR^8$ or $NR^9$;

$R^8$ and $R^9$ are each independently selected from hydrogen, $C_1$-$C_8$ alkyl, $C(O)C_1$-$C_8$ alkyl, or $-C(O)(CH_2)_q[O-W]_g(NHC(O))_m(CH_2)_q[O-W]_p$-Q-A, wherein the alkyl group is optionally substituted with 0 or 1 Q-A;

q is 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or N($C_1$-$C_4$alkyl);

A is hydrogen, $C_1$-$C_8$alkyl, $C(O)C_1$-$C_8$alkyl, C(O)N(H) $C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula (I) to a carrier; and $R^{11}$ is a carrier.

Another embodiment described herein is a method for treating cardiac disorders comprising administering to a subject in need thereof a drug delivery system or pharmaceutically acceptable salt thereof comprising a conjugate D-R, that is represented by Formula (I), where D is a biologically active moiety comprising at least one primary or secondary amine or a ring nitrogen atom of an azaheteroaryl ring comprising serelaxin or SEQ ID NO:7; R is a linker suitable for release of biologically active moiety D:

(I)

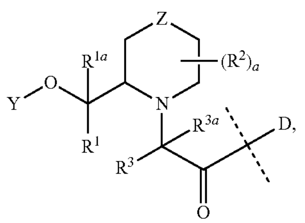

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl; Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or $-(OCHR^3CH_2)_bO-C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is $CHR^8$ or $NR^9$;

$R^8$ and $R^9$ are each independently selected from hydrogen, $C_1$-$C_8$ alkyl, $C(O)C_1$-$C_8$ alkyl, or $-C(O)(CH_2)_q[O-W]_g(NHC(O))_m(CH_2)_q[O-W]_p$-Q-A, wherein the alkyl group is optionally substituted with 0 or 1 Q-A;

q is 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or N($C_1$-$C_4$alkyl);

A is hydrogen, $C_1$-$C_8$alkyl, $C(O)C_1$-$C_8$alkyl, C(O)N(H) $C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

Another embodiment described herein is a method for treating a disease or disorder comprising administering to a subject in need thereof a drug delivery system or pharmaceutically acceptable salt thereof comprising a conjugate D-R, that is represented by Formula (I), where D is a biologically active moiety comprising at least one primary or secondary amine or a ring nitrogen atom of an azaheteroaryl ring; R is a linker suitable for release of biologically active moiety D:

(I)

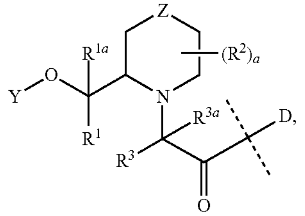

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or $—(OCHR^3CH_2)_bO—C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is $CHR^8$ or $NR^9$;

$R^8$ and $R^9$ are each independently selected from hydrogen, $C_1$-$C_8$ alkyl, $C(O)C_1$-$C_8$ alkyl, or $—C(O)(CH_2)_q[O—W]_g(NHC(O))_m(CH_2)_q[O—W]_p$-Q-A, wherein the alkyl group is optionally substituted with 0 or 1 Q-A;

q is 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or N($C_1$-$C_4$alkyl);

A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

Another embodiment described herein is a means for extending half-life of a biologically active moiety, D, comprising at least one primary amine, secondary amine, or ring nitrogen atom of an azaheteroaryl ring, the means comprising attaching D to R, that is represented by Formula (I), where R is a linker suitable for release of biologically active moiety D:

(I)

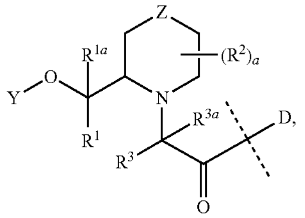

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —$(OCHR^3CH_2)_b$O—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is $CHR^8$ or $NR^9$;

$R^8$ and $R^9$ are each independently selected from hydrogen, $C_1$-$C_8$ alkyl, C(O)$C_1$-$C_8$ alkyl, or —C(O)$(CH_2)_q$[O—W$]_g$(NHC(O)$)_m$$(CH_2)_q$[O—W$]_p$-Q-A, wherein the alkyl group is optionally substituted with 0 or 1 Q-A;

q is 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or N($C_1$-$C_4$alkyl);

A is hydrogen, $C_1$-$C_8$alkyl, C(O)$C_1$-$C_8$alkyl, C(O)N(H) $C_1$-$C_8$alkyl, C(O)O$C_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

Another embodiment described herein is a drug delivery system comprising Formula (III):

(III)

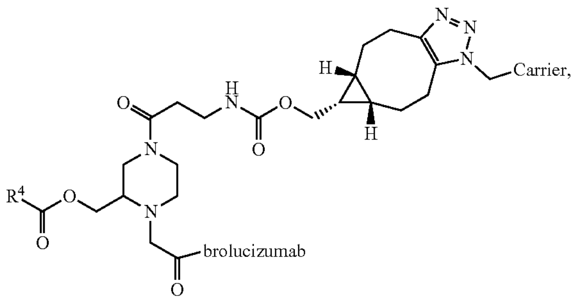

wherein brolucizumab comprises D1, SEQ ID NO:4; $R^4$ is $CH_3$—, $CH_3$—O—$CH_2$—, $CH_3CH_2$—, or $(CH_3)_2CH$—; and carrier comprises hyaluronic acid, polyethylene glycol, a hydrogel thereof, a cross-linked hydrogel thereof, or combinations thereof.

Another embodiment described herein is a drug delivery system comprising Formula (IV):

(IV)

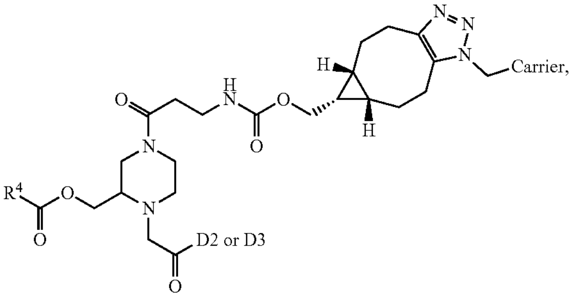

wherein D2 comprises SEQ ID NO:5, D3 comprises SEQ ID NO:6; $R^4$ is $CH_3$—, $CH_3$—O—$CH_2$—, $CH_3CH_2$—, or $(CH_3)_2CH$—; and carrier comprises hyaluronic acid, polyethylene glycol, a hydrogel thereof, a cross-linked hydrogel thereof, or combinations thereof.

Another embodiment described herein is a drug delivery system comprising D-R—$R^{11}$, wherein R comprises a traceless linker, coupled to a biologically-active agent, D; D comprises a biologically active moiety comprising at least one primary amine, secondary amine, or ring nitrogen atom of an azaheteroaryl ring; and $R^{11}$ comprises a plurality of hyaluronic acid monomers each of which comprises a random series of unfunctionalized hyaluronic acid monomers, hyaluronic acid monomers functionalized with one or more cross-linked hyaluronic acid monomers and one or more drug adducts, D-R. In one aspect, D comprises brolucizumab (SEQ ID NO:4), D2 (SEQ ID NO:5), D3 (SEQ ID NO:6), D4 (SEQ ID NO:7), serelaxin, aflibercept, pegpleranib, ranibizumab, 5-(5,6,7,8-tetrahydro-pyrido[3,4-d]pyrimidin-4-yloxy)-indole-1-carboxylic acid [5-(1-methyl-cyclopropyl)-2H-pyrazol-3-yl]-amide; 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide; N-(1-methyl-5-(trifluoromethyl)-1H-pyrazol-3-yl)-5-((6-((methylamino)methyl)pyrimidin-4-yl)oxy)-1H-indole-1-carboxamide; (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, or combinations thereof. In one aspect, the traceless linker R is as described herein.

Another embodiment described herein is a drug delivery system or pharmaceutically acceptable salt thereof comprising D-R, that is represented by Formula (XXIV), where D is a biologically active moiety comprising at least one primary or secondary amine or a ring nitrogen atom of an azaheteroaryl ring; and R is a linker suitable for release of biologically active moiety (XXIV)

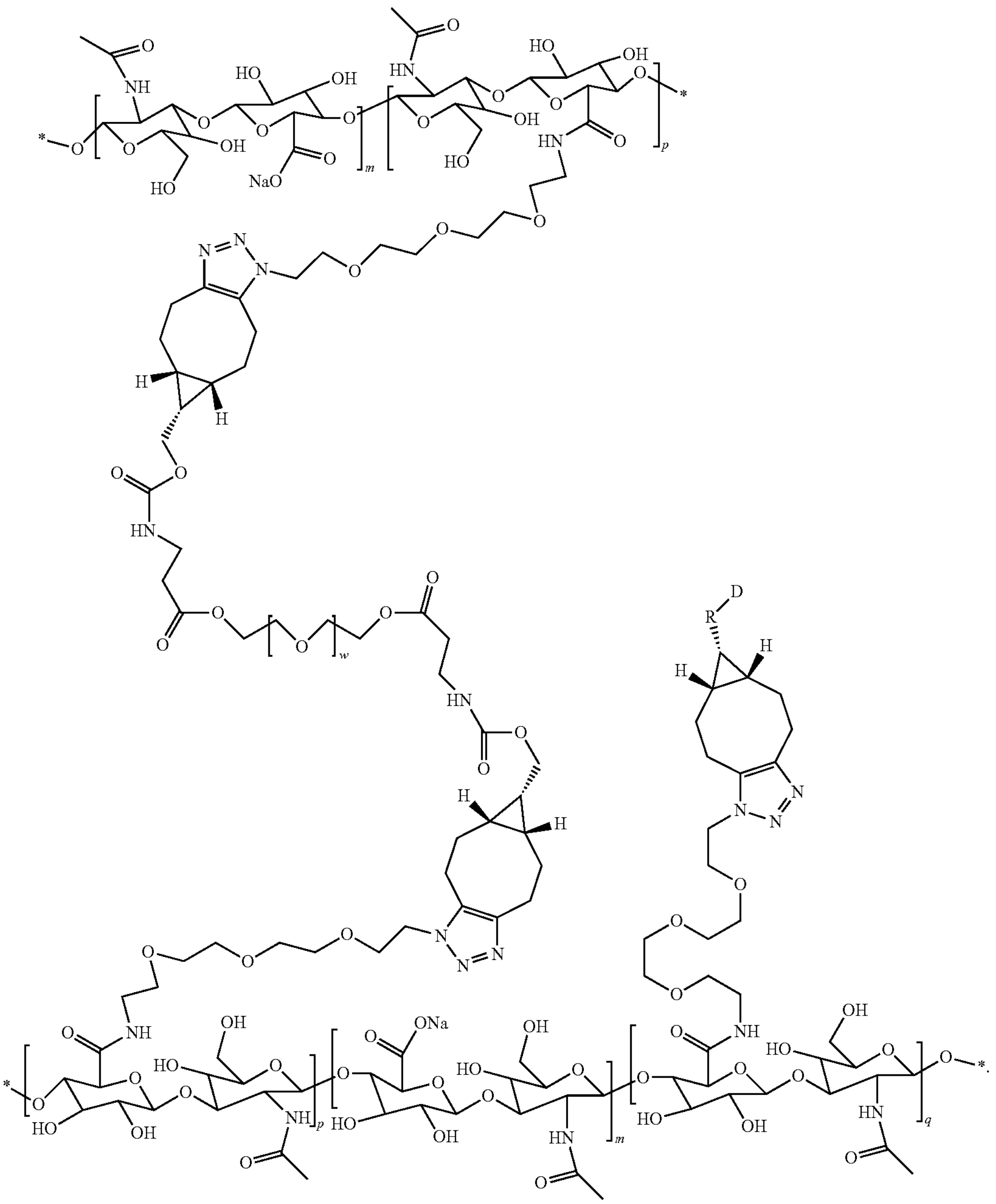

Another embodiment described herein is a drug delivery system or pharmaceutically acceptable salt thereof comprising D-R, that is represented by Formula (XXV), where D is a biologically active moiety comprising at least one primary or secondary amine or a ring nitrogen atom of an azaheteroaryl ring; and R is a linker suitable for release of biologically active moiety D:

(XXV)

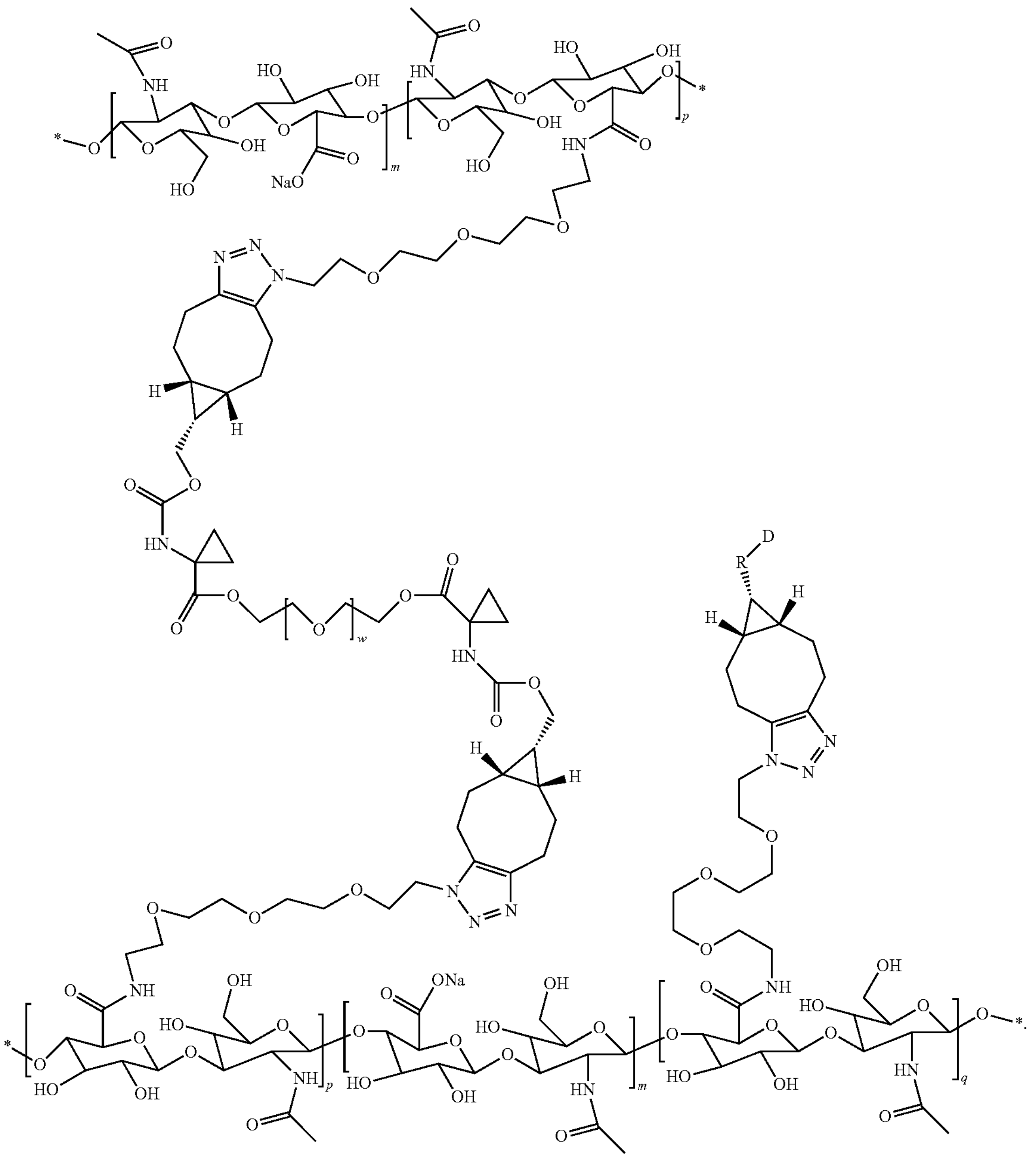

Another embodiment described herein is a drug delivery system or pharmaceutically acceptable salt thereof comprising D-R, that is represented by Formula (XXVI), where D is a biologically active moiety comprising at least one primary or secondary amine or a ring nitrogen atom of an azaheteroaryl ring; and R is a linker suitable for release of biologically active moiety D:

(XXVI)

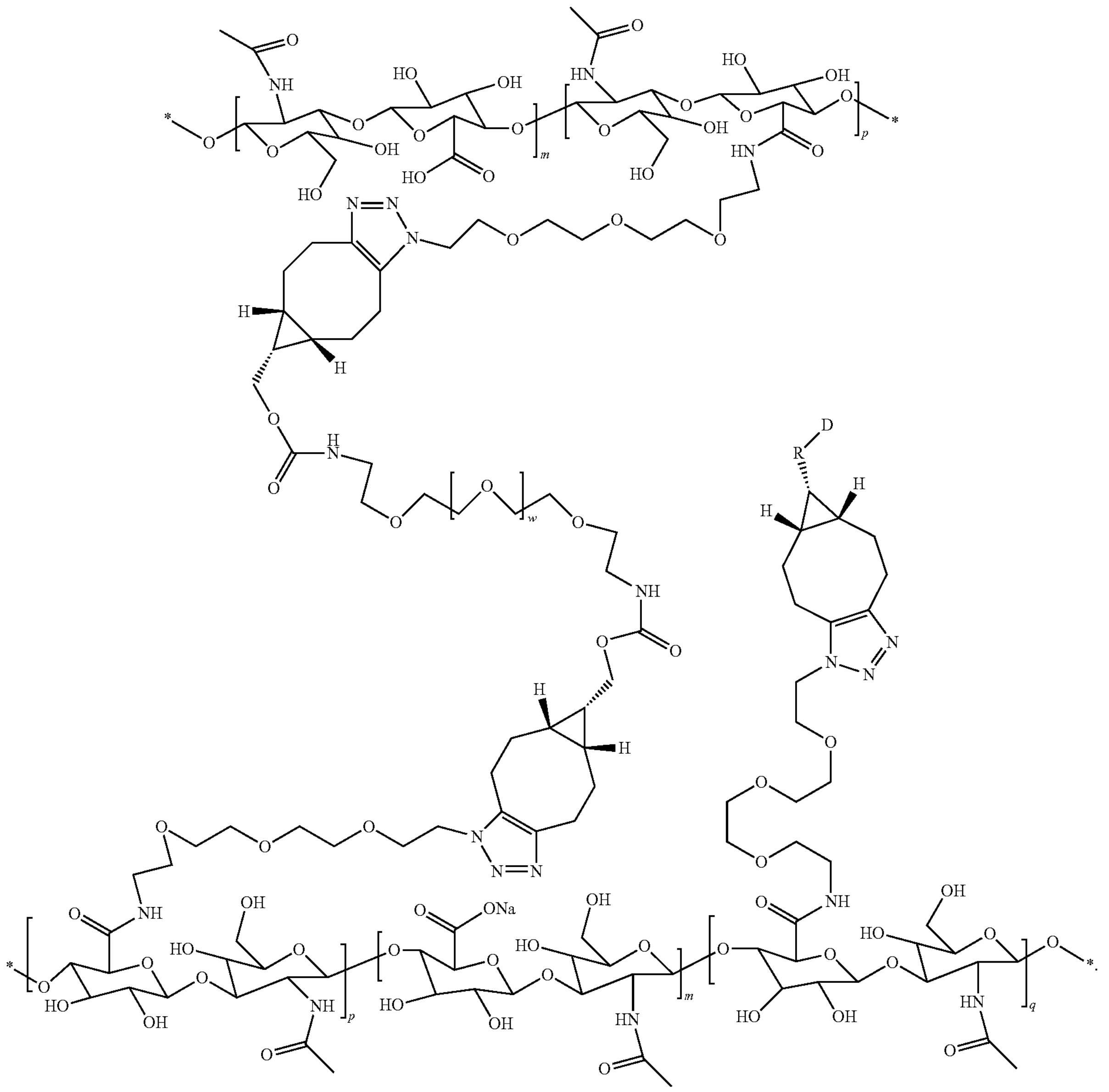

Another embodiment described herein is a drug delivery system or pharmaceutically acceptable salt thereof comprising D-R, that is represented by Formula (XXVII), where D is a biologically active moiety comprising at least one primary or secondary amine or a ring nitrogen atom of an azaheteroaryl ring; and R is a linker suitable for release of biologically active moiety D:

(XXVII)

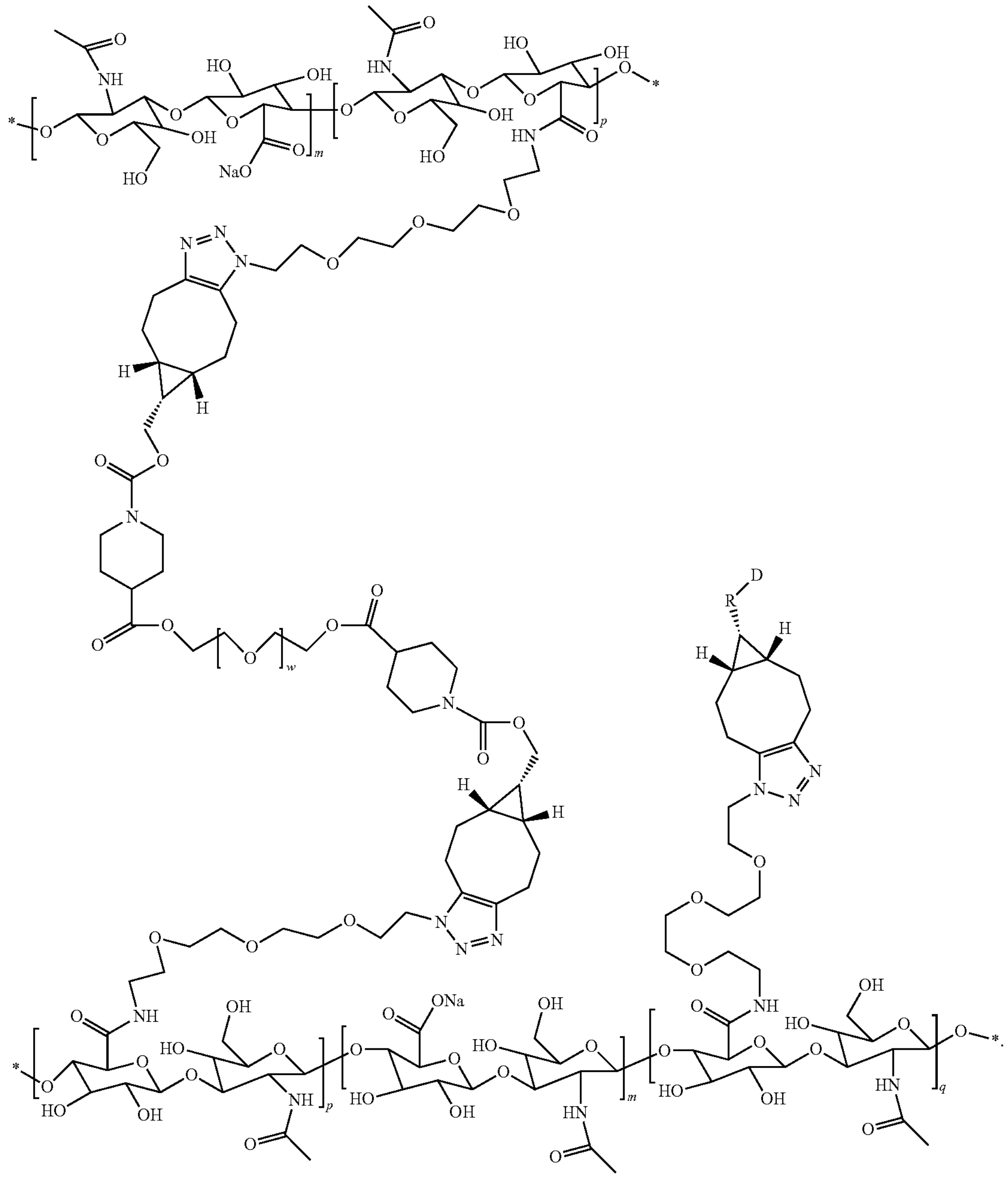

Another embodiment described herein is a drug delivery system or pharmaceutically acceptable salt thereof comprising D-R, that is represented by Formula (XXVIII), where D is a biologically active moiety comprising at least one primary or secondary amine or a ring nitrogen atom of an azaheteroaryl ring; and R is a linker suitable for release of biologically active moiety D:

(XXVIII)

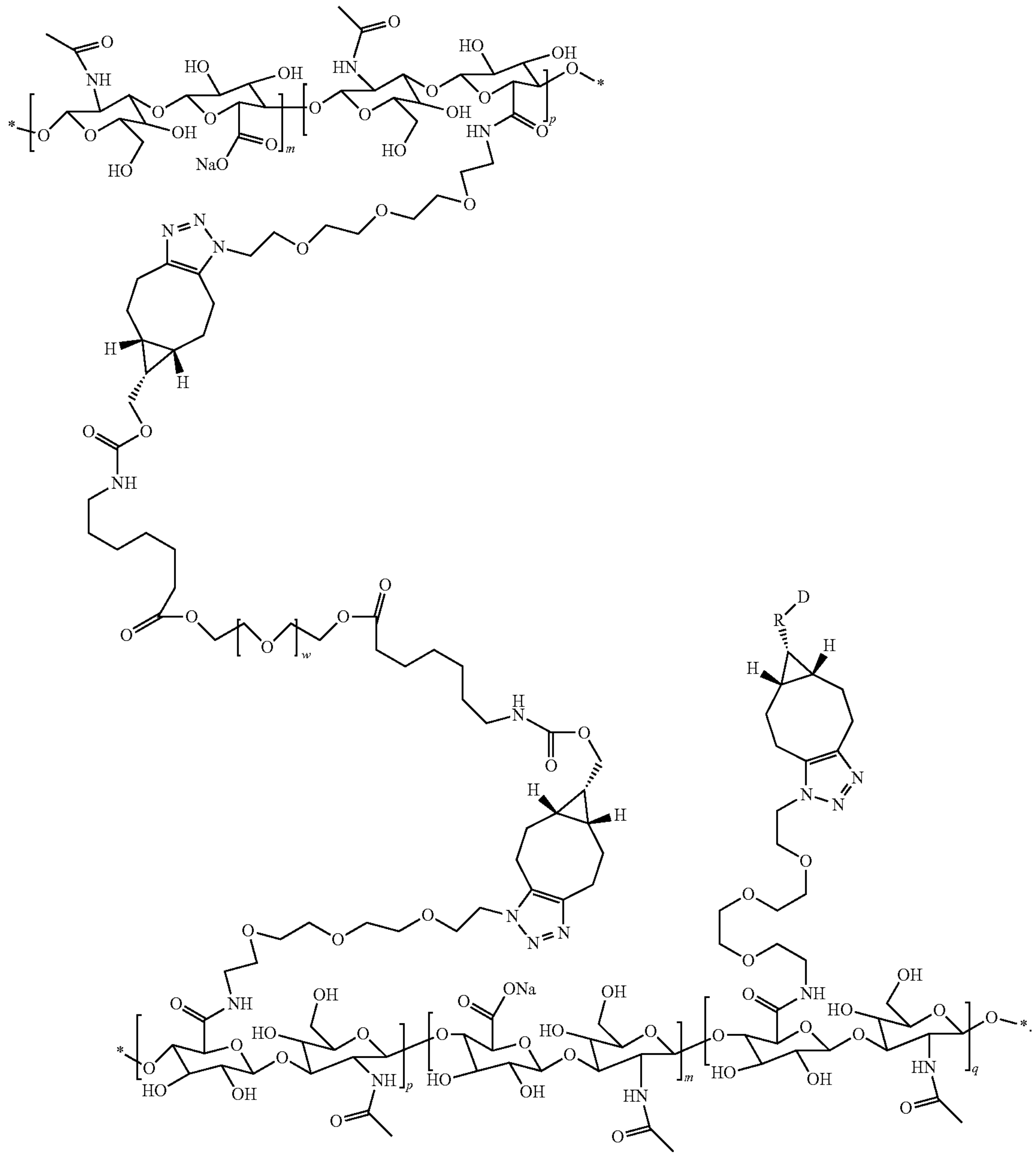

Another embodiment described herein is a drug delivery system or pharmaceutically acceptable salt thereof comprising D-R, that is represented by Formula (XXIX), where D is a biologically active moiety comprising at least one primary or secondary amine or a ring nitrogen atom of an azaheteroaryl ring; and R is a linker suitable for release of biologically active moiety D:

(XXIX)

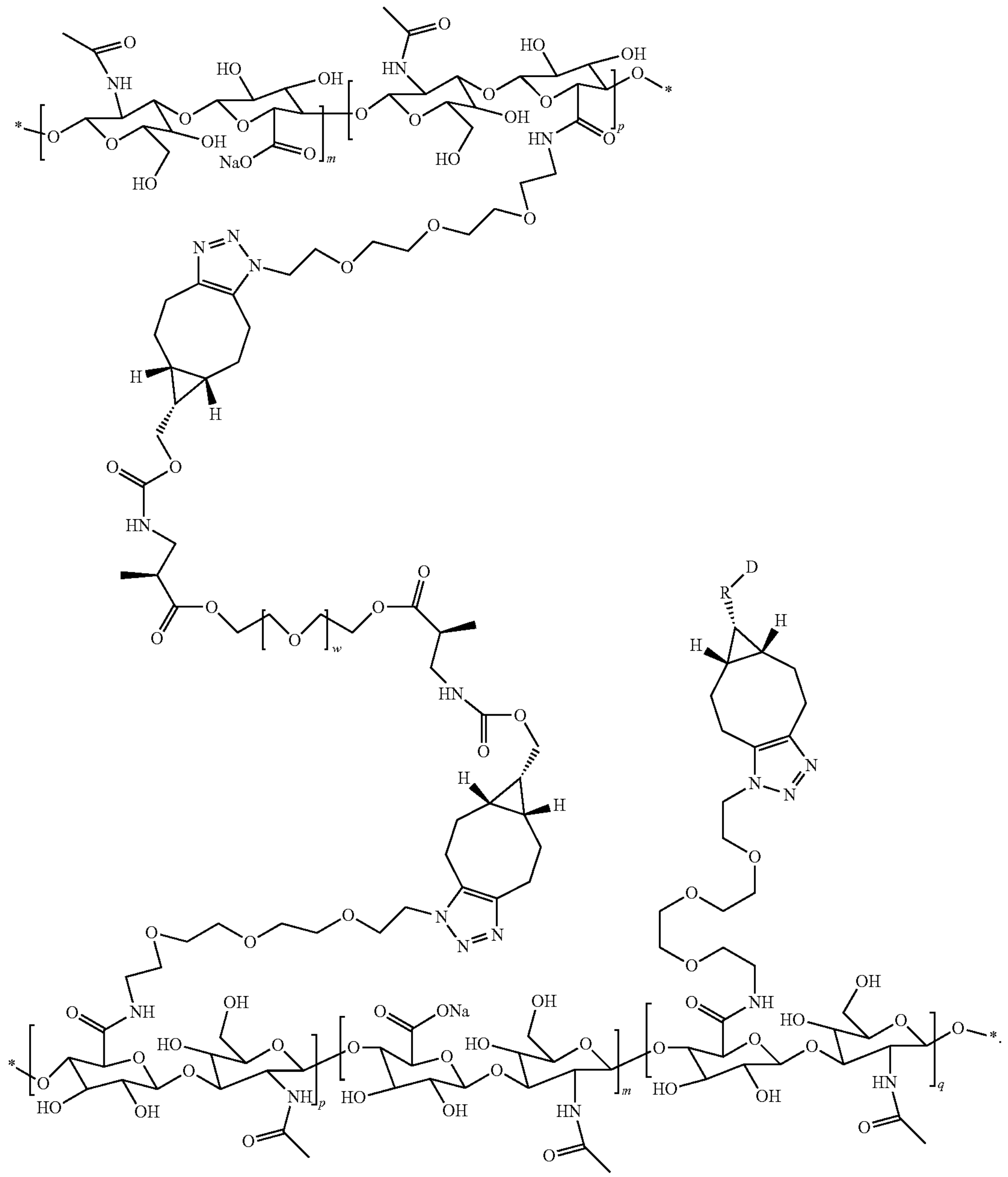

Another embodiment described herein is a drug delivery system or pharmaceutically acceptable salt thereof that is represented by Formula (XXX), where D is a biologically active moiety comprising at least one primary or secondary amine or a ring nitrogen atom of an azaheteroaryl ring; and $R^4$ is methyl, ethyl, propyl, isopropyl, 1-methyl-cyclopropyl, or methoxymethyl:

(XXX)

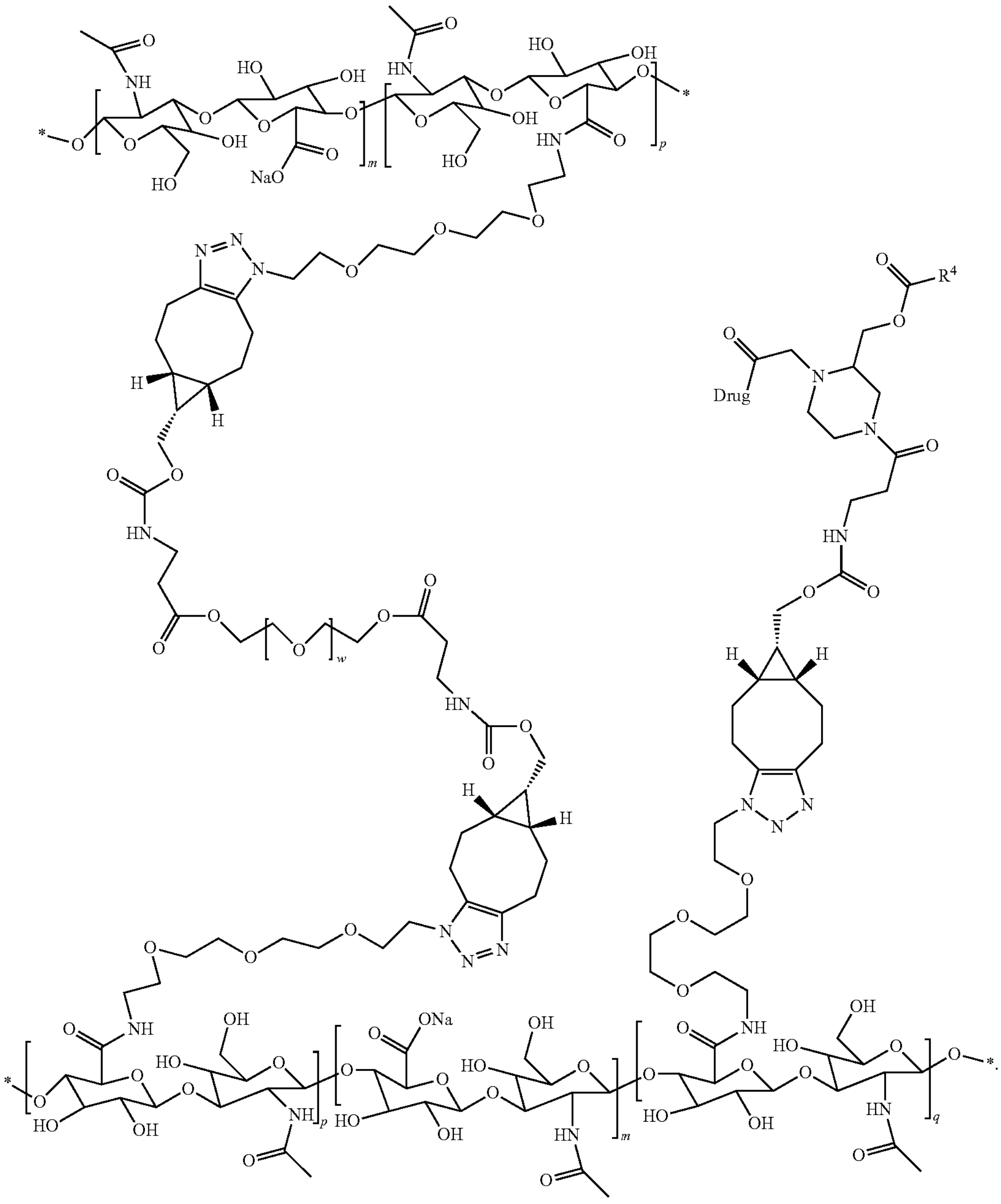

Another embodiment described herein is a drug delivery system or pharmaceutically acceptable salt thereof comprising D-R, that is represented by Formula (XXXI), where D is a biologically active moiety comprising at least one primary or secondary amine or a ring nitrogen atom of an azaheteroaryl ring; and R is a linker suitable for release of biologically active moiety D:

(XXXI)

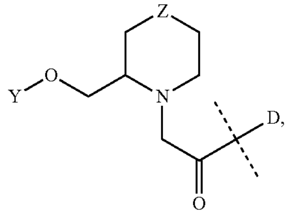

where the dashed line indicates attachment to the primary amine, secondary amine, or ring nitrogen atom of an azaheteroaryl ring;

Y is $C(O)R^4$;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

Z is N-L-A;

L is $C(O)CH_2CH_2NH$;

A is $R^{11}$;

$R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[3-(((((1R,8S,9s)-bicyclo[6.1.0]non-4-yn-9-yl)methoxy)carbonyl)amino)propanoate]. In one aspect, D is brolucizumab and $R^4$ is $CH_2CH_3$. In another aspect, D is brolucizumab and $R^4$ is $CH(CH_3)CH_3$.

Another embodiment described herein is a drug delivery system or pharmaceutically acceptable salt thereof that is represented by Formula (XXXII), where D is a biologically active moiety comprising at least one primary or secondary amine or a ring nitrogen atom of an azaheteroaryl ring; and $R^4$ is methyl, ethyl, propyl, isopropyl, 1-methyl-cyclopropyl, or methoxymethyl:

(XXXII)

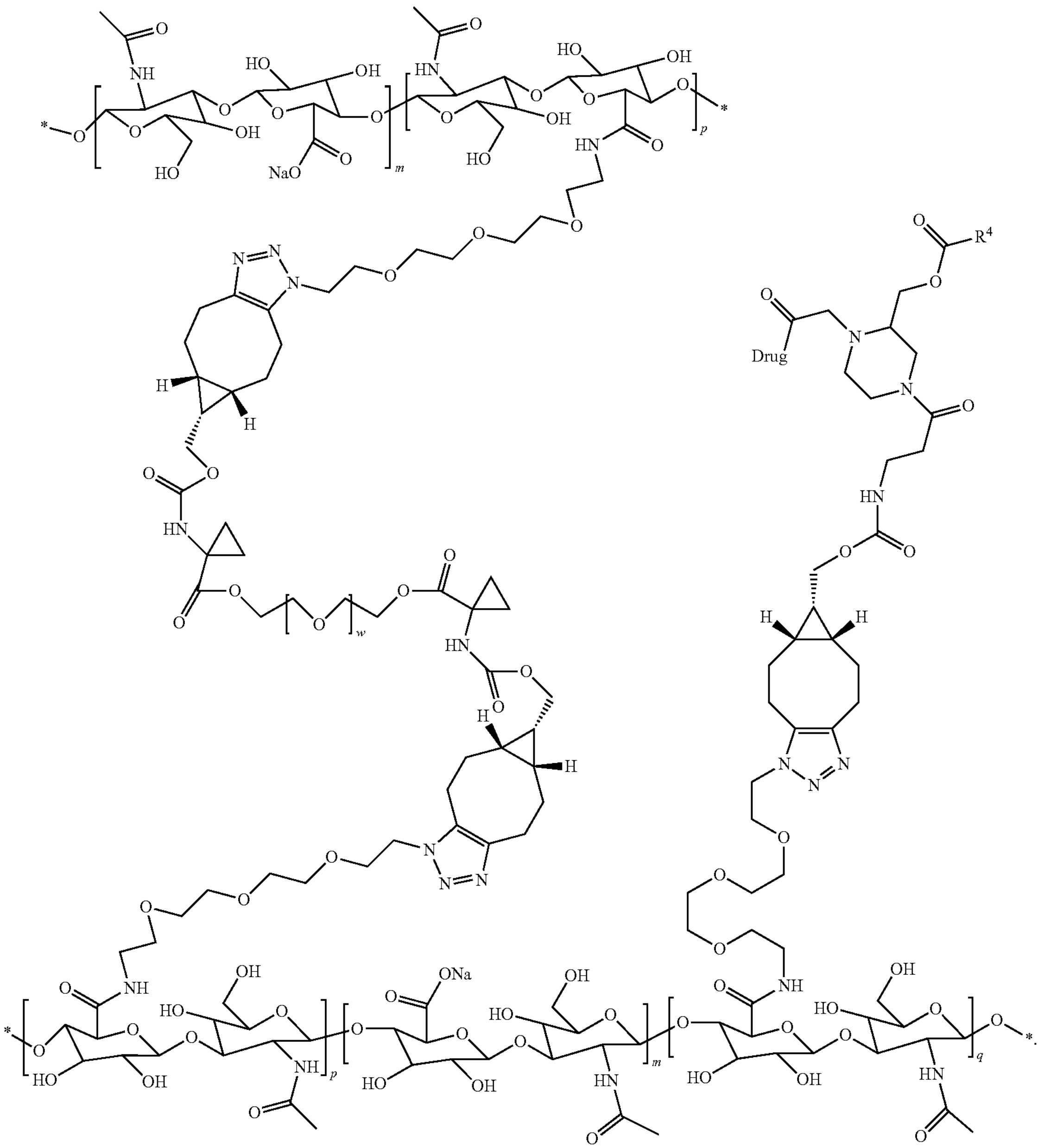

In one aspect, D is brolucizumab and $R^4$ is $CH_2CH_3$. In another aspect, D is brolucizumab and $R^4$ is $CH(CH_3)CH_3$.

Another embodiment described herein is a drug delivery system or pharmaceutically acceptable salt thereof comprising D-R, that is represented by Formula XXXIII, where D is a biologically active moiety comprising at least one primary or secondary amine or a ring nitrogen atom of an azaheteroaryl ring; and R is a linker suitable for release of biologically active moiety D:

(XXXIII)

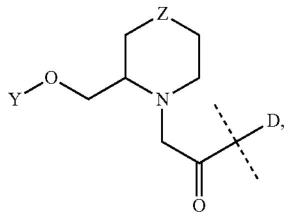

where the dashed line indicates attachment to the primary amine, secondary amine, or ring nitrogen atom of an azaheteroaryl ring;

Y is $C(O)R^4$;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

Z is N-L-A;

L is $C(O)CH_2CH_2NH$;

A is $R^{11}$;

$R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[1-((((1'R,8'S,9's)-bicyclo[6.1.0]non-4'-yn-9'-yl)methoxy)carbonyl)amino-cyclopropane-1-carboxylic acid ester]. In one aspect, D is brolucizumab and $R^4$ is $CH_2CH_3$. In another aspect, D is brolucizumab and $R^4$ is $CH(CH_3)CH_3$.

Another embodiment described herein is a drug delivery system or pharmaceutically acceptable salt thereof that is represented by Formula (XXXIV), where D is a biologically active moiety comprising at least one primary or secondary amine or a ring nitrogen atom of an azaheteroaryl ring; and $R^4$ is methyl, ethyl, propyl, isopropyl, 1-methyl-cyclopropyl, or methoxymethyl:

(XXXIV)

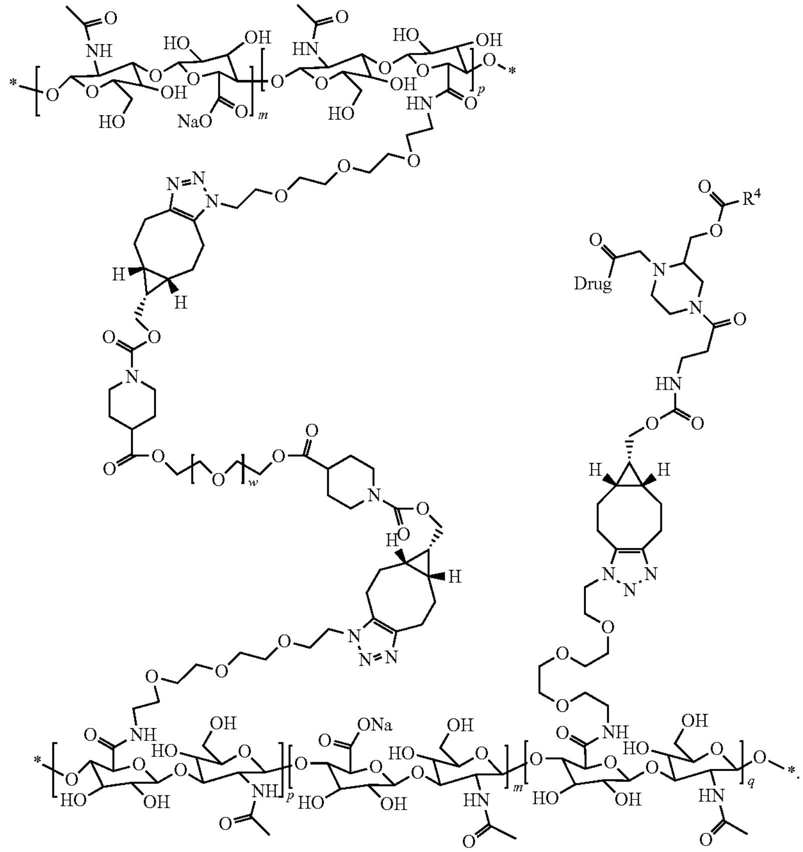

In one aspect, D is brolucizumab and $R^4$ is $CH_2CH_3$. In another aspect, D is brolucizumab and $R^4$ is $CH(CH_3)CH_3$.

Another embodiment described herein is a drug delivery system or pharmaceutically acceptable salt thereof comprising D-R, that is represented by Formula XXXV, where D is a biologically active moiety comprising at least one primary or secondary amine or a ring nitrogen atom of an azaheteroaryl ring; and R is a linker suitable for release of biologically active moiety D:

(XXXV)

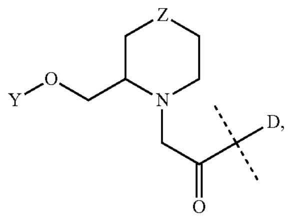

where the dashed line indicates attachment to the primary amine, secondary amine, or ring nitrogen atom of an azaheteroaryl ring;

L is $C(O)CH_2CH_2NH$;

A is $R^{11}$;

$R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[1-((((1'R,8'S,9's)-bicyclo[6.1.0]non-4'-yn-9'-yl)methoxy)carbonyl)piperidine-4-carboxylic acid ester].

In one aspect, D is brolucizumab and $R^4$ is $CH_2CH_3$. In another aspect, D is brolucizumab and $R^4$ is $CH(CH_3)CH_3$.

Another embodiment described herein is a drug delivery system or pharmaceutically acceptable salt thereof that is represented by Formula (XXXVI), where D is a biologically active moiety comprising at least one primary or secondary amine or a ring nitrogen atom of an azaheteroaryl ring; and $R^4$ is methyl, ethyl, propyl, isopropyl, 1-methyl-cyclopropyl, or methoxymethyl:

(XXXVI)

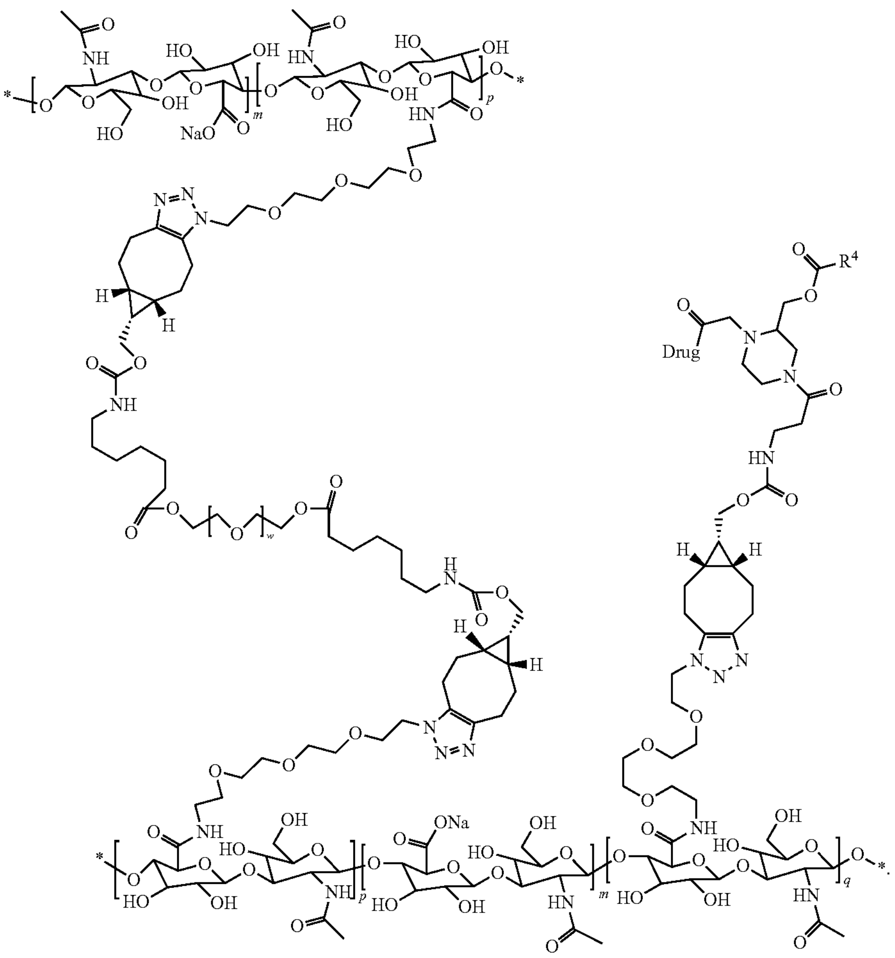

Y is $C(O)R^4$;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

Z is N-L-A;

In one aspect, D is brolucizumab and $R^4$ is $CH_2CH_3$. In another aspect, D is brolucizumab and $R^4$ is $CH(CH_3)CH_3$.

Another embodiment described herein is a drug delivery system or pharmaceutically acceptable salt thereof comprising D-R, that is represented by Formula XXXVII, where D is a biologically active moiety comprising at least one primary or secondary amine or a ring nitrogen atom of an azaheteroaryl ring; and R is a linker suitable for release of biologically active moiety D:

(XXXVII)

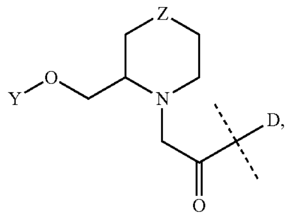

where the dashed line indicates attachment to the primary amine, secondary amine, or ring nitrogen atom of an azaheteroaryl ring;

Y is $C(O)R^4$;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

Z is N-L-A;

L is $C(O)CH_2CH_2NH$;

A is $R^{11}$;

$R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[7-(((((1'R,8'S,9's)-bicyclo[6.1.0]non-4'-yn-9'-yl)methoxy)carbonyl)amino)heptanoate].

In one aspect, D is brolucizumab and $R^4$ is $CH_2CH_3$. In another aspect, D is brolucizumab and $R^4$ is $CH(CH_3)CH_3$.

Another embodiment described herein is a drug delivery system or pharmaceutically acceptable salt thereof that is represented by Formula (XXXVIII), where D is a biologically active moiety comprising at least one primary or secondary amine or a ring nitrogen atom of an azaheteroaryl ring; and $R^4$ is methyl, ethyl, propyl, isopropyl, 1-methylcyclopropyl, or methoxymethyl:

(XXXVIII)

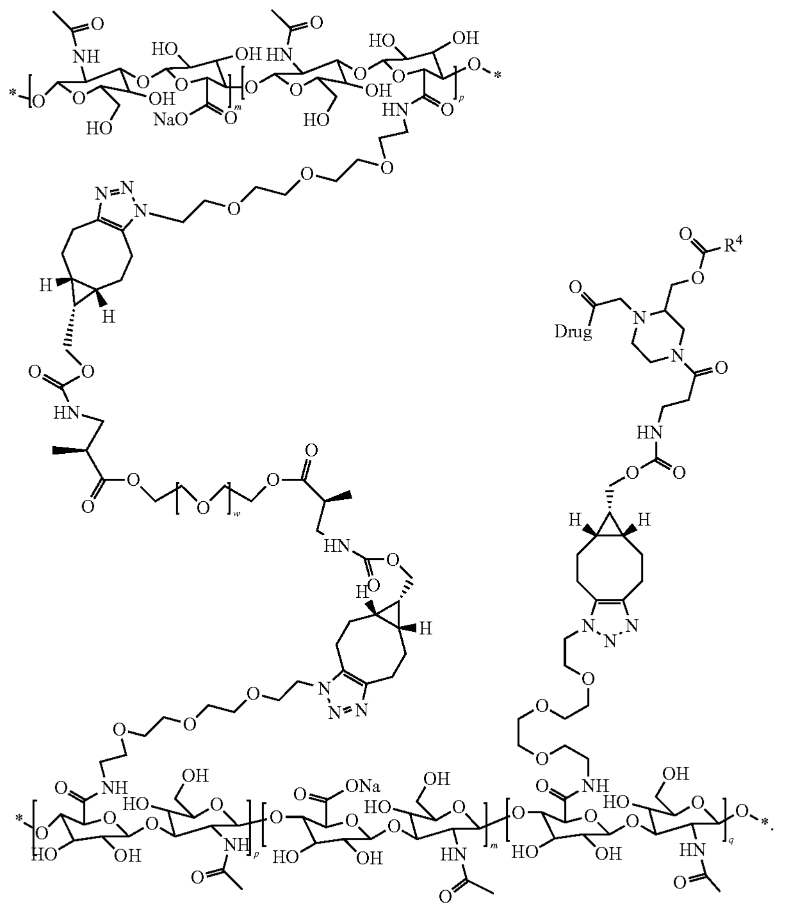

In one aspect, D is brolucizumab and $R^4$ is $CH_2CH_3$. In another aspect, D is brolucizumab and $R^4$ is $CH(CH_3)CH_3$.

Another embodiment described herein is a drug delivery system or pharmaceutically acceptable salt thereof comprising D-R, that is represented by Formula (XXXIX), where D is a biologically active moiety comprising at least one primary or secondary amine or a ring nitrogen atom of an azaheteroaryl ring; and R is a linker suitable for release of biologically active moiety D:

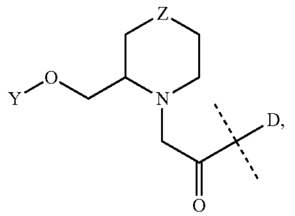

(XXXIX)

where the dashed line indicates attachment to the primary amine, secondary amine, or ring nitrogen atom of an azaheteroaryl ring;

Y is $C(O)R^4$;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

Z is N-L-A;

L is $C(O)CH_2CH_2NH$;

A is $R^{11}$;

$R^{11}$ is a hydrogel derived from a cross-linked hyaluronic acid, wherein the hyaluronic acid comprises at least one amide-linked side chain of $N(H)(CH_2CH_2O)_3CH_2CH_2N_3$, and wherein the cross-linker used to form the hydrogel comprises PEG(2000)-bis-[2-methyl-3-(((((1'R,8'S,9's)-bicyclo[6.1.0]non-4'-yn-9'-yl)methoxy)carbonyl)amino)propanoate]. In one aspect, D is brolucizumab and $R^4$ is $CH_2CH_3$. In another aspect, D is brolucizumab and $R^4$ is $CH(CH_3)CH_3$.

Another embodiment described herein is a carrier system or a pharmaceutically acceptable salt thereof, represented by formula:

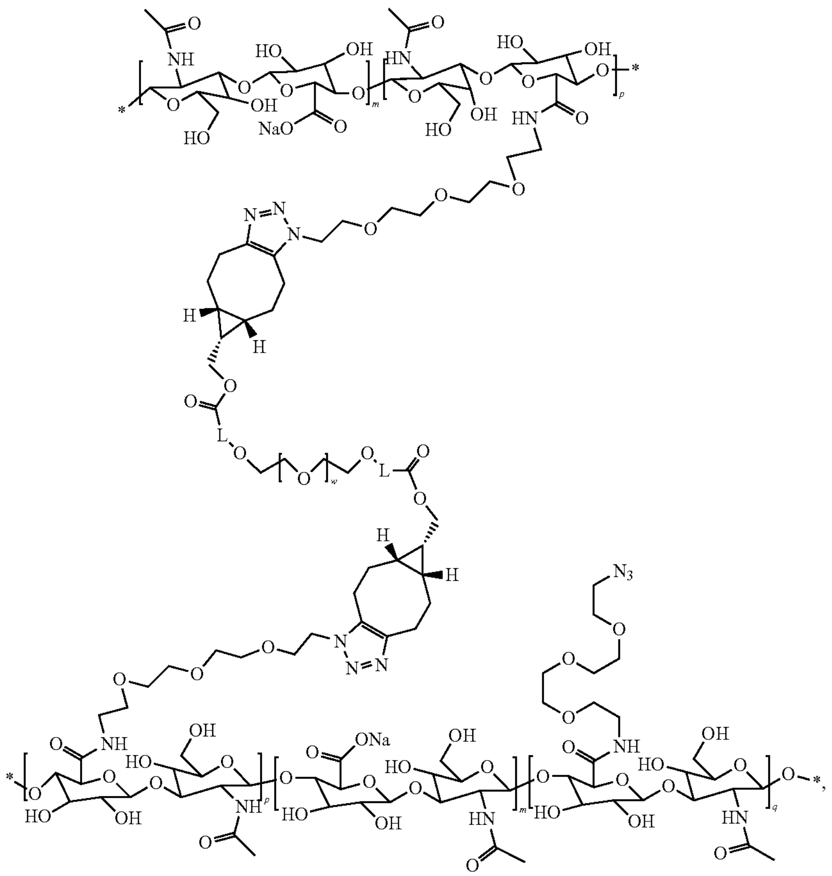

wherein

L is an optionally substituted bivalent linker Q-$[Sp-Q]_h$-Q;

Q is independently selected at each occurrence from a bond, O, C(O), N(H), N($C_1$-$C_4$alkyl), C(O)NH, C(O)N($C_1$-$C_4$alkyl), N(H)C(O), N($C_1$-$C_4$alkyl)C(O), N(H)C(O)O, N($C_1$-$C_4$alkyl)C(O)O, OC(O)N(H), OC(O)N($C_1$-$C_4$alkyl), N(H)C(O)N(H), N($C_1$-$C_4$alkyl)C(O)N(H), N(H)C(O)N($C_1$-$C_4$alkyl), N($C_1$-$C_4$alkyl)C(O)N($C_1$-$C_4$alkyl), C(O)O, OC(O), OC(O)O, S, $S(O)_2$, N(H)$S(O)_2$, N($C_1$-$C_4$alkyl)$S(O)_2$, $S(O)_2$N(H), $S(O)_2$N($C_1$-$C_4$alkyl), $C_1$-$C_2$alkyl-C(O)N(H), N(H)C(O)$C_1$-$C_2$alkyl, $C_1$-$C_2$alkyl-C(O)O, OC(O)$C_1$-$C_2$alkyl, 1,2,3-triazole, $OP(O)_2$, $P(O)_2O$, $C_1$-$C_4$alkyl-$P(O)_2$—O, or O—$P(O)_2$—$C_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, $[W—O]_g$, $C_1$-$C_8$alkyl-$[O—W]_g$, $[O—W]_g$—O—$C_1$-$C_8$alkyl, $C_1$-$C_8$Calkyl-$[O—W]_g$—O—$C_1$-$C_8$alkyl, or oligopeptide;

h is an integer of between 1 and 20;

g is a weighted average number of between about 2 and about 50;

W is $C_2$-$C_4$alkyl-1,2-diyl in which a hydrogen, methyl, or ethyl side chain may be present on either backbone carbon atom; and $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy.

BRIEF DESCRIPTION OF THE DRAWINGS

In FIG. 2 and throughout the specification, polymeric molecules, such as hyaluronic acid, are represented as $[P]_n$, where P represents the monomeric repeating unit and n represents an average number of repeating unit of the monomer. The number of repeating units is a random distribution for any given polymer population. In addition, the relative connectivity of the independent molecules for hydrogels or drug delivery systems described herein is random within a population. Structural depictions of hydrogels or drug delivery systems represent a single potential structural unit in two dimensions, whereas these complexes are three-dimensional with many structural subunits.

FIG. 4B shows comparative release in vitro of brolucizumab from hydrogel conjugates C1a, C2a, C3a, and C4a.

FIG. 7A shows fluorescein leakage data from the rabbit VEGF challenge model. FIG. 7B shows the levels of brolucizumab, D1, measured in liquid vitreous humor from the same rabbits in FIG. 7A.

DETAILED DESCRIPTION

Figure 1:
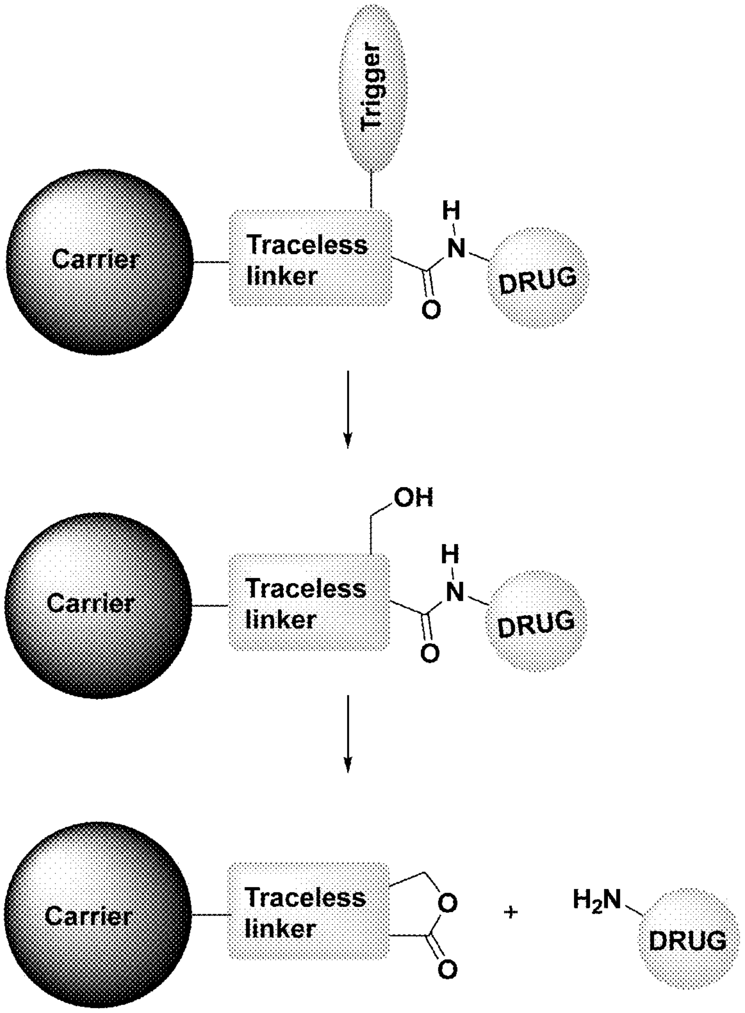
FIG. 1 shows a cartoon of a drug delivery system comprising a drug conjugated to a carrier by a traceless linker, and the drug after release. Reaction of the trigger generates a nucleophilic functional group that cleaves the amide bond linking the drug to the drug delivery system. In this non-limiting example, the drug is linked via a primary amine group.
Figure 2:
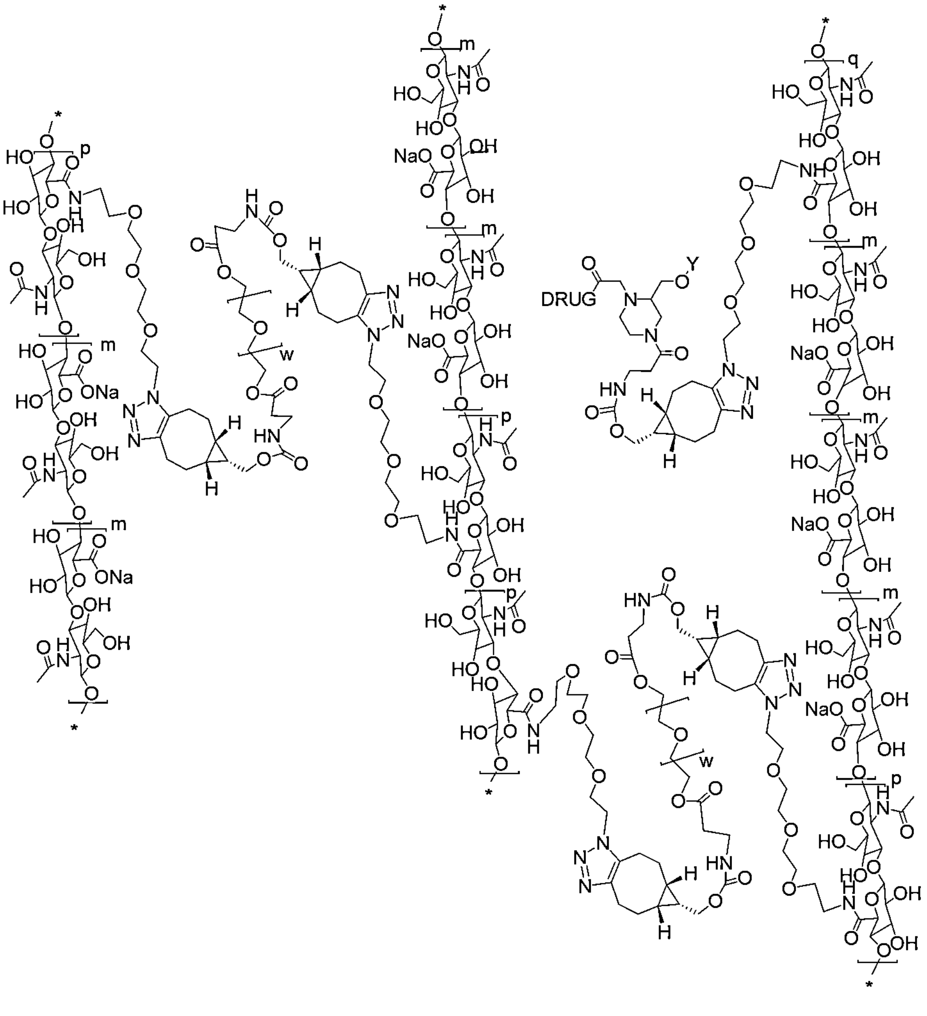
FIG. 2 shows a partial chemical representation of a hydrogel-drug conjugate, where the hydrogel is comprised of hyaluronic acid cross-linked with a PEG and drug is conjugated to the hydrogel by a traceless linker with trigger Y.
Figure 3A:
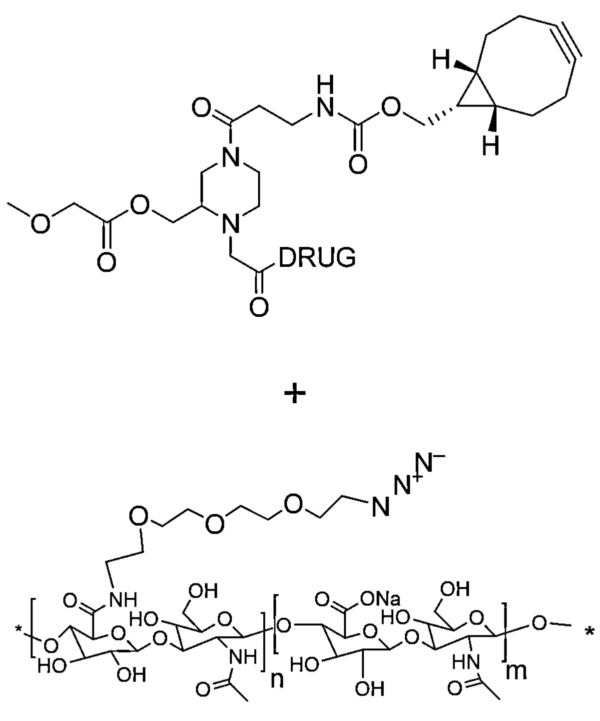
FIG. 3A shows an exemplary reaction of a traceless linker with an azide-functionalized hyaluronic acid polymer.
Figure 3A:
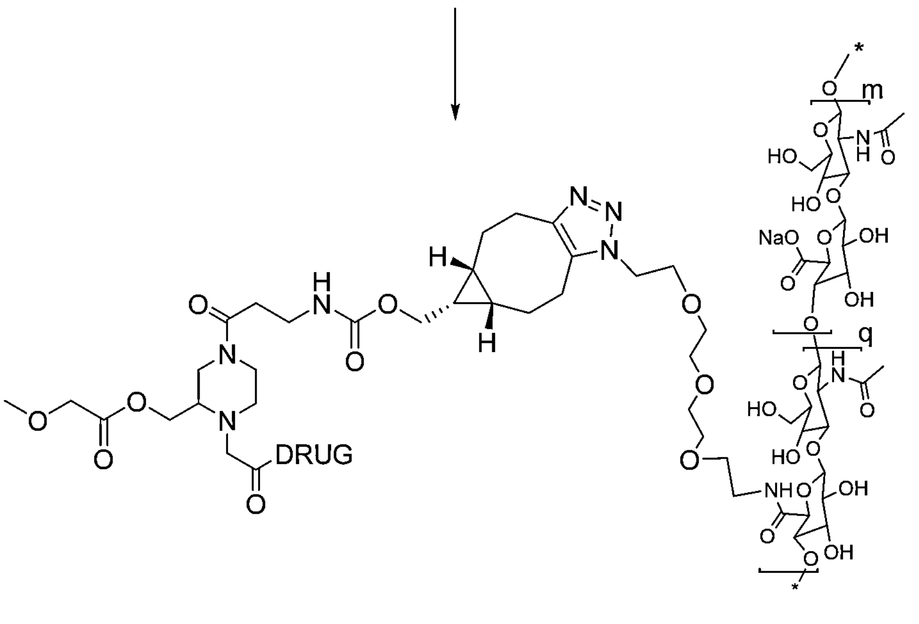
Figure 3B:
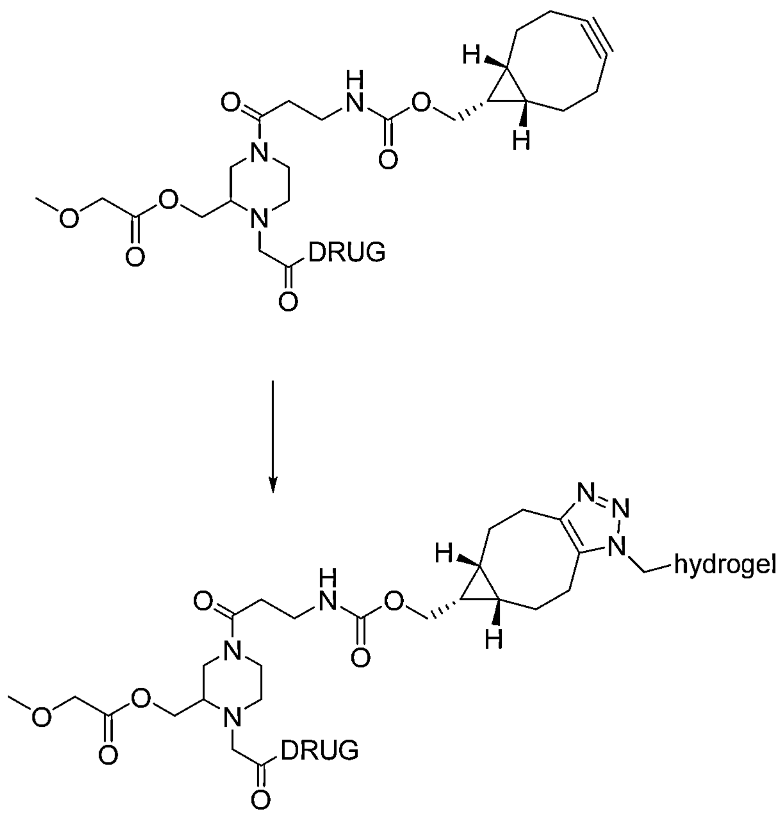
FIG. 3B shows an exemplary reaction of a traceless linker with an azide-functionalized hydrogel.

Described herein are drug delivery systems for delivering biologically active agents comprising primary or secondary amines, or a ring nitrogen atom of an azaheteroaryl ring, pharmaceutically acceptable salts thereof, drug delivery reagents related thereto, pharmaceutical compositions comprising the drug delivery systems, and the use of the drug delivery systems as sustained release therapeutics.

As used herein, the term "alkyl" refers to a straight chain, branched or cyclic carbon chain. Unless otherwise specified, one or more hydrogen atoms of an alkyl carbon may be replaced by a substituent. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. When two moieties of a molecule are linked by the alkyl group, it is referred to also as alkylene. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "lower alkyl" is intended to include both substituted and unsubstituted alkyl or lower alkyl unless otherwise indicated and these groups may be substituted with additional organic and/or inorganic groups, including but not limited to groups selected from halo (e.g., to form haloalkyl), alkyl, haloalkyl, alkenyl, alkynyl, cycloalkyl, cycloalkylalkyl, aryl, arylalkyl, heterocyclic, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, cyanoalkyl-$S(O)_m$, haloalkyl-$S(O)_m$, alkenyl-S(O)n, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, or heterocycloalkyl-$S(O)_m$, where m=0, 1, 2, or 3.

As used herein, the term "alkenyl" alone or as part of another group, refers to a straight or branched chain hydrocarbon containing from 1 to 10, 20, or 30 or more carbon atoms (or in lower alkenyl 1 to 4 carbon atoms), which include 1 to 4, 5, or 6 or more double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "lower alkenyl" is intended to include both substituted and unsubstituted alkenyl or lower alkenyl unless otherwise indicated and these groups may be substituted with groups as described in connection with alkyl and lower alkyl above.

As used herein, the term "alkynyl" As used herein, alone or as part of another group, refers to a straight or branched chain hydrocarbon containing from 1 to 10, 20, 30, or 40 or more carbon atoms (or in lower alkynyl 1 to 4 carbon atoms)

which include 1, 2, or 3 or more triple bonds in the normal chain. Representative examples of alkynyl include, but are not limited to, 2-propynyl, 3-butynyl, 2-butynyl, 4-pentynyl, 3-pentynyl, and the like. The term "alkynyl" or "lower alkynyl" is intended to include both substituted and unsubstituted alkynyl or lower alknynyl unless otherwise indicated and these groups may be substituted with the same groups as set forth in connection with alkyl and lower alkyl above.

As used herein, the term "cycloalkynyl" refers to a cyclic hydrocarbon ring system having between 6 and 16 carbon atoms and 1, 2, or 3 rings that are fused or bridged including at least 1 or more triple bonds in the ring structure.

As used herein, the term "heterocycloalkynyl" refers to a cyclic hydrocarbon ring system having between 6 and 16 carbon atoms, 1, 2, 3, or 4 heteroatoms independently selected from oxygen, nitrogen and sulfur, and 1, 2 or 3 rings which are fused or bridged including at least 1 or more triple bonds in the ring structure.

As used herein, the term "cycloalkyl" alone or as part of another group, refers to a saturated or partially unsaturated cyclic hydrocarbon group containing from 3, 4, 5, 6, 7, or 8 carbons (which carbons may be replaced in a heterocyclic group as discussed below). Representative examples of cycloalkyl include cyclopropyl, cyclobutyl, cyclopentyl, cyclohexyl, cycloheptyl, and cyclooctyl. These rings may be optionally substituted with additional substituents as described herein such as halo or lower alkyl. The term "cycloalkyl" is generic and intended to include heterocyclic groups as discussed below unless specified otherwise.

As used herein, the term "heterocyclic" or "heterocyclyl" alone or as part of another group, refers to an aliphatic (e.g., fully or partially saturated heterocyclic) or aromatic (e.g., heteroaryl) monocyclic- or bicyclic-ring system. Monocyclic ring systems are exemplified by any 3- to 8-membered ring containing 1, 2, 3, or 4 heteroatoms independently selected from oxygen, nitrogen and sulfur. The 5-membered ring has from 0-2 double bonds and the 6-membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with additional organic and/or inorganic groups, including but not limited to groups selected from halo, alkyl, haloalkyl, alkenyl, alkynyl, cycloalkyl, cycloalkylalkyl, aryl, arylalkyl, heterocyclic, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, cyano, alkyl-$S(O)_m$ haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, where m=0, 1, 2, or 3.

As used herein, the term "heteroaryl" is as described in connection with heterocyclic above.

As used herein, the term "cycloalkylalkyl," "cycloalkylalkenyl," and "cycloalkylalkynyl" As used herein, alone or as part of another group, refers to a cycloalkyl group, as defined herein, appended to the parent molecular moiety through an alkyl, alkenyl, or alkynyl group, respectively, as defined herein.

As used herein, the term "alkoxy" alone or as part of another group, refers to an alkyl or lower alkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like. In some aspects, alkoxy groups, when part of a more complex molecule, comprise an alkoxy substituent attached to an alkyl or lower alkyl via an ether linkage.

As used herein, the term "halo" or "halogen" refers to any suitable halogen, including —F, —Cl, —Br, or —I.

As used herein, the term "acyl" alone or as part of another group refers to a —C(O)R' radical, wherein R' is any suitable substituent such as aryl, alkyl, alkenyl, alkynyl, cycloalkyl or other suitable substituent as described herein.

As used herein, the term "alkylthio" alone or as part of another group, refers to an alkyl group, as defined herein, appended to the parent molecular moiety through a thiol moiety, as defined herein. Representative examples of alkylthio include, but are not limited, methylthio, ethylthio, tert-butylthio, hexylthio, and the like.

As used herein, the term "amide", "amido", or "amidyl" As used herein, alone or as part of another group refers to a —$C(O)NR_aR_b$ radical, where $R_a$ and $R_b$ are independently any suitable substituent such as alkyl, hydrogen, cycloalkyl, alkenyl, alkynyl or aryl.

As used herein, the term "ester" alone or as part of another group refers to a —C(O)OR' radical, where R' is any suitable substituent such as alkyl, cycloalkyl, alkenyl, alkynyl or aryl.

As used herein, the term "ether" alone or as part of another group refers to a —COR' radical where R' is any suitable substituent such as alkyl, cycloalkyl, alkenyl, alkynyl, or aryl.

As used herein, the term "sulfone" alone or as part of another group refers to a —S(O)(O)R' radical, where R' is any suitable substituent such as alkyl, cycloalkyl, alkenyl, alkynyl or aryl.

As used herein, the term "sulfonamide" alone or as part of another group refers to a —$S(O)_2NR_aR_b$ radical, where $R_a$ and $R_b$ are independently any suitable substituent such as H, alkyl, cycloalkyl, alkenyl, alkynyl or aryl.

As used herein, the term "carboxyl" refers to refers to the radical —C(O)OH.

As used herein, the term "hydroxyl" refers to the radical —OH.

As used herein, the term "amino" refers to the radical —$NH_2$.

As used herein, vinyl refers to the radical —$CH_2CH_2$.

As used herein, the term "sulfonate" refers to the radical —S(O)(O)OR', where R' is any suitable substituent such as alkyl, cycloalkyl, alkenyl, alkynyl or aryl.

As used herein, the term "sulfonyl" refers to the radical —S(O)(O)R', where R' is any suitable substituent such as alkyl, cycloalkyl, alkenyl, alkynyl or aryl.

As used herein, thiol refers to the radical —SH.

As used herein, oxyamine or aminoxy refers to the radical —$ONH_2$.

As used herein, "hydrazide" or "hydrazidyl" refers to the radical —C(O)—NH—$NH_2$.

As used herein, "maleimide or maleimidyl" refers to a cyclic compound with the molecular formula $C_2H_2(C(O))_2NH$ or the radical —$N(C(O))_2C_2H_2$ having at least one C═C double bond.

As used herein, furan refers to a five-membered aromatic ring with four carbon atoms and one oxygen.

As used herein, "tetrazine" or "tetrazinyl" refers to a six-membered aromatic ring containing four nitrogen atoms with the molecular formula $C_2H_2N_4$ or the radical —$C_2HN_4$.

As used herein, the term "azide," "azidyl," or "azido" refers to an —$N_3$ group.

As used herein, the term "BCN" refers to a bicyclo[6.1.0]non-4-yn-9-yl)methyl radical, in which the exocyclic methylene can have an exo or endo orientation relative to the bicycle as shown:

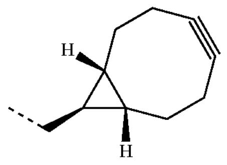

exo BCN

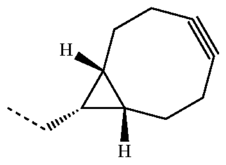

endo BCN

As used herein, throughout the specification, as a matter of convenience most structures do not depict stereochemistry and thus represent all possible stereoisomers.

Specifically with regard to the structure of the triazole products of the reaction between a BCN and azido compound, As used herein, throughout the specification, the N-linked substitutent on the triazole ring is shown in a single regiochemistry position as a matter of convenience. One of ordinary skill in the art will recognize that the reaction of a BCN alkyne with an azido compound will result in a stereoisomeric mixture of products with the N-linked substituent on the 1- and 3-position of the triazole as shown:

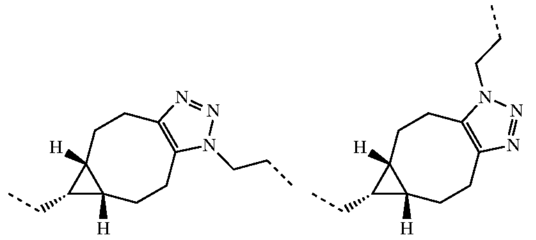

Stereoisomer reaction products of endo BCN with alkyl azide

-continued

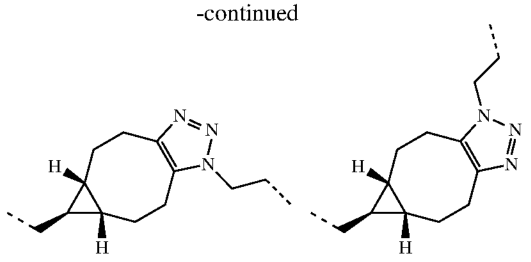

Stereoisomer reaction products of exo BCN with alkyl azide

As used herein, "reactive functional group" refers to a functional group, which is suitable for orthogonal coupling reactions. Suitable reactive functional groups are those that readily undergo orthogonal reactions. Exemplary and non-limiting orthogonal chemical reactions include functional groups shown in Table 1.

As used herein, "trigger" refers to a functional group present in the drug traceless linker adduct D-R, which is capable of undergoing a chemical reaction resulting in a new functional group. The presence of the new functional group substantially decreases the stability of the bond between the drug and the traceless linker relative and results in an increased probability of drug release.

The term "number average molecular weight" or "$M_n$" refers to the statistical average molecular weight of all molecules in the sample expressed in units of g/mol. The number average molecular weight may be determined by techniques known in the art, such as gel permeation chromatography (wherein $M_n$ can be calculated based on known standards based on an online detection system such as a refractive index, ultraviolet, or other detector), viscometry, mass spectrometry, or colligative methods (e.g., vapor pressure osmometry, end-group determination, or proton NMR). The number average molecular weight is defined by the equation below, $$M_n = \frac{\sum N_i M_i}{\sum N_i}$$

wherein $M_i$ is the molecular weight of a molecule and $N_i$ is the number of molecules of that molecular weight.

The term "weight average molecular weight" or "MW" refers to the statistical average molecular weight of all molecules, taking into account the weight of each molecule in determining its contribution to the molecular weight average, expressed in units of g/mol. The higher the molecular weight of a given molecule, the more that molecule will contribute to the Mw value. The weight average molecular weight may be calculated by techniques known in the art that are sensitive to molecular size, such as static light scattering, small angle neutron scattering, X-ray scattering, and sedimentation velocity. The weight average molecular weight is defined by the equation below, $$M_w = \frac{\sum N_i M_i^2}{\sum N_i M_i}$$

wherein '$M_i$' is the molecular weight of a molecule and '$N_i$' is the number of molecules of that molecular weight.

The term "viscosity average molecular weight" or "$M_v$" refers to the statistical average molecular weight of all molecules, taking into account the weight of each molecule in determining its contribution to the molecular weight average, expressed in units of g/mol. Large molecules or polymers have higher viscosities than smaller molecules. The viscosity average molecular weight is defined by the equation below, $$M_v = \left( \frac{\sum N_i M_i^{(1+a)}}{\sum N_i M_i} \right)^{1/a}$$

wherein '$M_i$' is the molecular weight of a molecule and '$N_i$' is the number of molecules of that molecular weight, and a is constant determined by the molecule, solvent, and temperature.

Flexible polymeric molecules have a values of $0.5 \leq a \leq 0.8$. Semi-flexible polymeric molecules have $a \geq 0.8$. The viscosity average molecular weight can be determined from intrinsic viscosity experiments or size exclusion chromatography.

As used herein, a "drug" comprises one or more biologically active moieties comprising at least one primary or secondary amine or a ring nitrogen atom of an azaheteroaryl ring. The biologically active moieties may be small molecules, macromolecules such as proteins, peptides, or nucleic acids, or combinations thereof. With specific regard to a traceless linker, R, the drug or biologically active moiety comprises "D" in the D-R representation. The terms or phrases "drug", "biologically active molecule," "biologically active moiety," "biologically active agent," "active agent," refer to any substance that can affect any physical or biochemical properties of a biological organism, including but not limited to viruses, bacteria, fungi, plants, animals, and humans. In particular, drugs or biologically active molecules include any substance intended for diagnosis, cure, mitigation, treatment, or prevention of disease in humans or other animals, or to otherwise enhance physical or mental well-being of humans or animals. As used herein, several drugs are referred to throughout as D1-D4. D1 comprises brolucizumab (SEQ ID NO: 4). D2 comprises (SEQ ID NO: 5). D3 comprises (SEQ ID NO: 6). D4 comprises (SEQ ID NO: 7).

As used herein, a "biologically active moiety comprising at least one primary amine, secondary amine, or ring nitrogen atom of an azaheteroaryl ring" refers to both the free biologically active moiety prior to attachment to a traceless linker or to the free biologically active moiety "D-H," which results after cleavage from the traceless linker adduct "D-R." In some aspects, the drug adduct, D-R, may have biological activity.

As used herein, "free form" of a drug or biologically active moiety refers to the drug in its unmodified, pharmacologically active form, such as prior to being attached to a traceless linker or after being released from a traceless linker in a drug delivery system.

As used herein, a "traceless linker," R, is a linker that is represented by Formula (I) suitable for release of biologically active moiety D comprising at least one primary or secondary amine or a ring nitrogen atom of an azaheteroaryl ring:

(I)

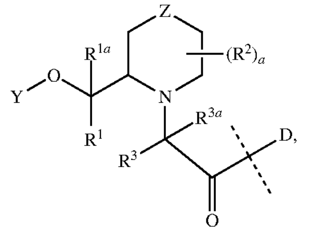

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or $-(OCHR^3CH_2)_bO-C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups; b is an integer of from 1 to 10;

Z is CH-L-A, CH-A, N-L-A, or N-A;

L is an optionally substituted bivalent linker;

A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In another embodiment, R, is a linker that is represented by Formula (I) suitable for release of biologically active moiety D comprising at least one primary or secondary amine or a ring nitrogen atom of an azaheteroaryl ring:

(I)

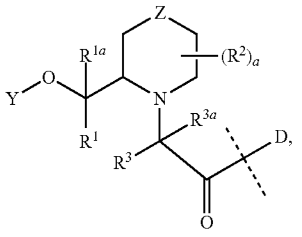

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —$(OCHR^3CH_2)_bO$—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is CH-L-A, CH-A, N-L-A, or N-A;

L is an optionally substituted bivalent linker $Q$-$[Sp$-$Q]_h$-$Q$;

Q is independently selected at each occurrence from a bond, O, C(O), N(H), $N(C_1$-$C_4alkyl)$, C(O)NH, $C(O)N(C_1$-$C_4alkyl)$, N(H)C(O), $N(C_1$-$C_4alkyl)C(O)$, N(H)C(O)O, $N(C_1$-$C_4alkyl)C(O)O$, OC(O)N(H), $OC(O)N(C_1$-$C_4alkyl)$, N(H)C(O)N(H), $N(C_1$-$C_4alkyl)C(O)N(H)$, $N(H)C(O)N(C_1$-$C_4alkyl)$, $N(C_1$-$C_4alkyl)C(O)N(C_1$-$C_4alkyl)$, C(O)O, OC(O), OC(O)O, S, $S(O)_2$, $N(H)S(O)_2$, $N(C_1$-$C_4alkyl)S(O)_2$, $S(O)_2N(H)$, $S(O)_2N(C_1$-$C_4alkyl)$, $C_1$-$C_2$alkyl-C(O)N(H), $N(H)C(O)C_1$-$C_2$alkyl, $C_1$-$C_2$alkyl-C(O)O, $OC(O)C_1$-$C_2$alkyl, 1,2,3-triazole, $OP(O)_2$, $P(O)_2O$, $C_1$-$C_4$alkyl-$P(O)_2$—O, or O—$P(O)_2$—$C_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, $[W—O]_g$, $C_1$-$C_8$alkyl-$[O—W]_g$, $[O—W]_g$—O—$C_1$-$C_8$alkyl, $C_1$-$C_8$Calkyl-$[O—W]_g$—O—$C_1$-$C_8$alkyl, oligopeptide;

h is an integer of between 1 and 20;

g is a weighted average number of between about 2 and about 50;

W is $C_2$-$C_4$alkyl-1,2-diyl in which the hydrogen, methyl, or ethyl side chain may be present on either backbone carbon atom;

A is hydrogen, $C_1$-$C_8$alkyl, $C(O)C_1$-$C_8$alkyl, $C(O)OC_1$-$C_8$alkyl, $C(O)N(H)C_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In another embodiment, R, is a linker that is represented by Formula (I) suitable for release of biologically active moiety D comprising at least one primary or secondary amine or a ring nitrogen atom of an azaheteroaryl ring:

(I)

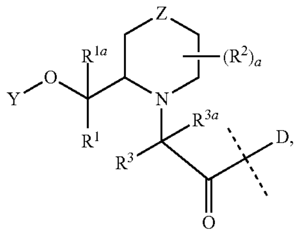

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or —$(OCHR^3CH_2)_bO$—$C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is $CHR^8$ or $NR^9$;

$R^8$ and $R^9$ are each independently selected from hydrogen, $C_1$-$C_8$ alkyl, $C(O)C_1$-$C_8$ alkyl, or $—C(O)(CH_2)_q[O—W]_g(NHC(O))_m(CH_2)_q[O—W]_p$-Q-A, wherein the alkyl group is optionally substituted with 0 or 1 Q-A;

q is independently at each occurrence 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or $N(C_1$-$C_4$alkyl);

A is hydrogen, $C_1$-$C_8$alkyl, $C(O)C_1$-$C_8$alkyl, C(O)N(H) $C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In one aspect, the traceless linker is a linker suitable for sustained release of a biologically active moiety. In one aspect, "R" is a traceless linker in the representation D-R, wherein "D" refers to a drug comprising a biologically active moiety comprising at least one primary amine, secondary amine, or ring nitrogen atom of an azaheteroaryl ring.

As used herein, a "drug adduct" is a drug, D linked to a traceless linker, R. With specific regard to a traceless linker, R, the drug adduct comprises "D-R."

As used herein, a "carrier" is a soluble polymer, biopolymer, or a cross-linked polymer or biopolymer. Carriers comprise proteins, nucleic acids, carbohydrates, or polyethylene glycols. In one aspects, the carrier or multiple carriers are cross-linked intermolecularly, intramolecularly, or a combination thereof. In one aspect, the cross-linked carrier comprises a hydrogel. With specific regard to a traceless linker, R, the carrier comprises $R^{11}$. In one aspect, Z is linked to a carrier, typically a polymer or a hydrogel. The carrier is attached to the traceless linker, R, either directly or via a non-cleavable spacer. As non-limiting examples, carriers can comprise polyethylene glycols, hyaluronic acid polymers, or cross-linked hyaluronic acid or polyethylene glycol that are capable of forming hydrogels.

As used herein, a "polymer" refers to a molecule comprised of repeating structural units (monomers) connected by chemical bonds in a linear, circular, branched, or dendrimeric way or a combination thereof, that can be of synthetic or biological origin or a combination of both. Typically, a polymer has an average molecular weight of at least 1 kDa. A copolymer is a polymer comprised of at least two chemically distinct monomers. Typically, a polymer is comprised of molecules having a distribution of molecular weights. One way to describe the molecular weight distribution of a polymer is the average molecular weight. Typically, a polymer is comprised of molecules having a distribution of degree of polymerization. One way to describe the degree of polymerization distribution of a polymer is the average degree of polymerization.

As described herein and depicted in the structures herein, polymeric molecules, such as polyethylene glycol or hyaluronic acid, are represented as $[P]_n$, where P represents the monomeric repeating unit and n represents the average degree of polymerization of the monomer in the polymer. One of ordinary skill in the art will understand that two polymeric molecules depicted with identical repeating unit P but different n are considered equivalent if the difference is about 10% or less of n. For the hyaluronic acid copolymers described and depicted in the structures herein, the distribution of monomers in the polymer is undefined and assumed to be random. In addition, the relative connectivity of the independent molecules for hydrogels or drug delivery systems described herein is random within a population. Structural depictions of hydrogels or drug delivery systems represent a single potential structural unit in two dimensions, whereas these complexes are three-dimensional with many structural subunits.

As described herein, the exact position of amide bond formation is not precisely known for a traceless linker-drug adduct, R-D. This can occur when D contains more than one primary or secondary amine, or ring nitrogen atom of an azaheteroaryl ring capable of forming an amide bond with a linker R (e.g., a protein). As a matter of convenience, adducts where the position of amide bond formation is not precisely known are depicted herein as follows:

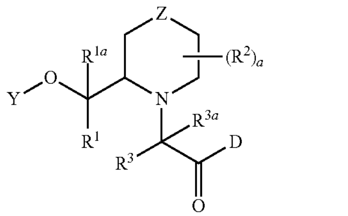

R =

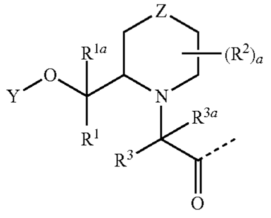

As used herein, a "hydrogel" refers to a three-dimensional, hydrophilic or amphiphilic polymeric network capable of taking up large quantities of water. The networks are composed of homopolymers or copolymers, and are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and water soluble solutes with dimensions smaller than the pores are able to diffuse in and out of the network.

As used herein, a "linker" or "non-biologically active linker" refers to a linker that does not produce any pharmacological effects. In some embodiments, the linker comprises a bi- or multi-valent organic linker that is compatible with biological systems. "Bivalent" refers to having a reactive group suitable for attachment to a traceless linker or drug, D, at each terminus of the polymer. "Multivalent" refers having a reactive group suitable for attachment to a traceless linker or drug, D, at each terminus of the polymer with additional reactive moieties interspersed along the linker molecule.

As used herein, a "drug delivery system" comprises a carrier linked to a drug adduct, D-R—$R^{11}$, wherein the carrier comprises $R^{11}$. The drug delivery system as described herein is the molecular conjugate comprising one or more drugs, D; one or more traceless linkers, R; and one or more carriers, $R^{11}$. In some embodiments, there can be multiple, distinct drug species conjugated to a drug delivery system. For example, two different drugs, such as D1 and D2 may be conjugated in a single drug delivery system.

As used herein, the phrase "water-insoluble" refers to a swellable three-dimensionally crosslinked molecular network forming the hydrogel. The hydrogel if suspended in a large surplus of water or aqueous buffer of physiological osmolality may take up a substantial amount of water, e.g., up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

As used herein, "sustained release" or "sustained release rate" refers to the situation where the intervals between subsequent doses of the respective drug delivery system required to achieve a desired therapeutic effect are expanded. Drugs with a daily dosage may for example be turned into a sustained release form with a week-long or even longer interval between two administrations.

As used herein, a "functional group" refers to a group of atoms within molecules that exhibit a specific chemical activity. Examples are amides, amines, alcohols, carbonyls, carboxylic acids, thiols.

As used herein, a "protective group" refers to a moiety that temporarily protects a functional group of a molecule during synthesis to obtain chemoselectivity in subsequent chemical reactions. Protective groups for alcohols are, for example, benzyl and trityl, protective groups for amines are, for example, tert-butyloxycarbonyl, 9-fluorenylmethyloxycarbonyl and benzyl and for thiols examples of protective groups are 2,4,6-trimethoxybenzyl, phenylthiomethyl, acetamidomethyl, p-methoxybenzyloxycarbonyl, tert-butylthio, triphenylmethyl, 3-nitro-2-pyridylthio, 4-methyltrityl.

As used herein, a "protected functional group" means a functional group protected by one or more protective groups.

As used herein, "PBS" refers to phosphate buffered saline.

As used herein, the term "pharmaceutically acceptable salts" refers to salts that retain the biological effectiveness and properties of the biologically active agent and, that typically are not biologically or otherwise undesirable. In many cases, the biologically active agent is capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine, or tromethamine.

The pharmaceutically acceptable salts can be synthesized from a parent compound, a basic or acidic moiety, by conventional chemical methods.

Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 18th ed., Mack Publishing Company, Easton, Pa., (1990); and in "Handbook of Pharmaceutical Salts: Properties, Selection, and Use" by Stahl and Wermuth (Wiley-VCH, Weinheim, Germany, 2002).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, e.g., Remington's Pharmaceutical Sciences, 18th ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a biologically active agent refers to an amount of the biologically active agent that will elicit the biological or medical response of a subject, for example, amelioration of a symptom, alleviation of a condition, slow or delay disease progression, or prevention of a disease, etc.

In another non-limiting embodiment, the term "a therapeutically effective amount" refers to the amount of the biologically active agent that, when administered to a cell, or a tissue, or a non-cellular biological material, or a medium, is effective to at least partially treat the disease or disorder. As will be appreciated by those of ordinary skill in the art, the absolute amount of a particular agent that is effective may vary depending on such factors as the desired biological endpoint, the agent to be delivered, the target tissue, etc.

Those of ordinary skill in the art understand that "a therapeutically effective amount" may be administered in a single dose or may be achieved by administration of multiple doses. For example, in the case of an agent to treat heart failure, an effective amount may be an amount sufficient to result in clinical improvement of the patient, e.g., increased exercise tolerance/capacity, increased blood pressure, decrease fluid retention, and/or improved results on a quantitative test of cardiac functioning, e.g., ejection fraction, exercise capacity (time to exhaustion), etc.

As used herein, the term "subject" refers to an animal. Typically, the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit," "inhibition," or "inhibiting" refers to the reduction or suppression of a given condition, symptom, or disorder, or disease, or a significant decrease in the baseline activity of a biological activity or process.

As used herein, the term "treat," "treating," or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those that may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of the disease or disorder. As used herein, the terms "prevent," "preventing," and "prevention" refer to the prevention of the recurrence, onset, or development of one or more symptoms of a disorder in a subject resulting from the administration of a therapy (e.g., a therapeutic agent), or the administration of a combination of therapies (e.g., a combination of therapeutic agents).

As used herein, a subject is "in need of" or "in need thereof" a treatment if such subject would benefit biologically, medically, or in quality of life from such treatment.

As used herein, the term "a," "an," "the" and similar terms used herein (especially in the context of the claims) are to be construed to cover both the singular and plural unless otherwise indicated herein or clearly contradicted by the context.

As used herein, the term "about" refers to any values, including both integers and fractional components that are within a variation of up to ±10% of the value modified by the term "about." The term "or" can be conjunctive or disjunctive such that "or" encompasses "and/or." One embodiment described herein is a drug adduct comprising a drug and a traceless linker, D-R, wherein R, is a linker that is represented by Formula (I) suitable for release of biologically active moiety D comprising at least one primary or secondary amine or a ring nitrogen atom of an azaheteroaryl ring:

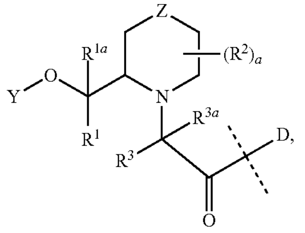

(I)

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or $-(OCHR^3CH_2)_bO-C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is CH-L-A, CH-A, N-L-A, or N-A;

L is an optionally substituted bivalent linker;

A is hydrogen, $C_1$-$C_8$alkyl, $C(O)C_1$-$C_8$alkyl, $C(O)N(H)C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

Another embodiment described herein is a drug adduct comprising a drug and a traceless linker, D-R, wherein R, is a linker that is represented by Formula (I) suitable for release of biologically active moiety D comprising at least one primary or secondary amine or a ring nitrogen atom of an azaheteroaryl ring:

(I)

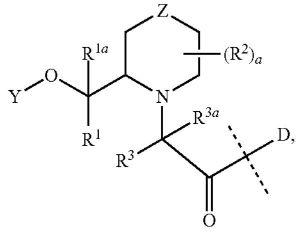

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or $—(OCHR^3CH_2)_bO—C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is CH-L-A, CH-A, N-L-A, or N-A;

L is an optionally substituted bivalent linker Q-[Sp-Q]$_h$-Q;

Q is independently selected at each occurrence from a bond, O, C(O), N(H), N($C_1$-$C_4$alkyl), C(O)NH, C(O)N($C_1$-$C_4$alkyl), N(H)C(O), N($C_1$-$C_4$alkyl)C(O), N(H)C(O)O, N($C_1$-$C_4$alkyl)C(O)O, OC(O)N(H), OC(O)N($C_1$-$C_4$alkyl), N(H)C(O)N(H), N($C_1$-$C_4$alkyl)C(O)N(H), N(H)C(O)N($C_1$-$C_4$alkyl), N($C_1$-$C_4$alkyl)C(O)N($C_1$-$C_4$alkyl), C(O)O, OC(O), OC(O)O, S, $S(O)_2$, N(H)$S(O)_2$, N($C_1$-$C_4$alkyl)$S(O)_2$, $S(O)_2$N(H), $S(O)_2$N($C_1$-$C_4$alkyl), $C_1$-$C_2$alkyl-C(O)N(H), N(H)C(O)$C_1$-$C_2$alkyl, $C_1$-$C_2$alkyl-C(O)O, OC(O)$C_1$-$C_2$alkyl, 1,2,3-triazole, $OP(O)_2$, $P(O)_2O$, $C_1$-$C_4$alkyl-$P(O)_2$—O, or O—$P(O)_2$—$C_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, $[W—O]_g$, $C_1$-$C_8$alkyl-$[O—W]_g$, $[O—W]_g$—O—$C_1$-$C_8$alkyl, $C_1$-$C_8$Calkyl-$[O—W]_g$—O—$C_1$-$C_8$alkyl, oligopeptide;

h is an integer of between 1 and 20;

g is a weighted average number of between about 2 and about 50;

W is $C_2$-$C_4$alkyl-1,2-diyl in which the hydrogen, methyl, or ethyl side chain may be present on either backbone carbon atom;

A is hydrogen, $C_1$-$C_8$alkyl, C(O)$C_1$-$C_8$alkyl, C(O)O$C_1$-$C_8$alkyl, C(O)N(H)$C_1$-$C_8$alkyl, $R^{10}$, or $R^{11}$, wherein the alkyl group is optionally substituted with 0 or 1 $R^{10}$ $R^{10}$ is a reactive functional group suitable for coupling Formula I to a carrier; and $R^{11}$ is a carrier.

Another embodiment described herein is a drug adduct comprising a drug and a traceless linker, D-R, wherein R, is a linker that is represented by Formula (I) suitable for release of biologically active moiety D comprising at least one primary or secondary amine or a ring nitrogen atom of an azaheteroaryl ring:

(I)

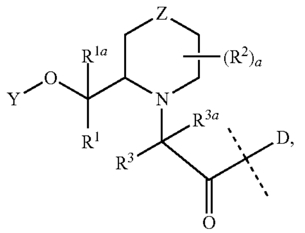

where the dashed line indicates attachment to the primary amine, secondary amine, or ring nitrogen atom of an azaheteroaryl ring;

$R^1$ is hydrogen or $C_1$-$C_4$alkyl;

$R^{1a}$ is hydrogen or $C_1$-$C_4$alkyl, or $CR^1R^{1a}$, taken in combination form a $C_3$-$C_6$cycloalk-1,1-diyl;

$R^2$ is independently selected at each occurrence from $C_1$-$C_4$alkyl or oxo, or two $R^2$ groups taken in combination form a fused $C_3$-$C_6$ cycloalkyl or spiro $C_3$-$C_6$cycloalk-1,1-diyl group;

a is 0, 1, 2, 3 or 4;

$R^3$ is hydrogen or $C_1$-$C_4$alkyl;

$R^{3a}$ is hydrogen, $C_1$-$C_4$alkyl, or $CR^3R^{3a}$, taken in combination form a $C_3$-$C_6$cycloalk-1,1-diyl;

Y is $C(O)R^4$, $C(O)OR^4$, $C(O)NHR^4$, $C(O)NR^5R^6$, $SiR^5R^6R^7$, or $CR^{12}R^{12a}OR^{13}$;

$R^{12}$ is hydrogen or $C_1$-$C_4$alkyl;

$R^{12a}$ is hydrogen or $C_1$-$C_4$alkyl, or $CR^{12}R^{12a}$, taken in combination form a $C_3$-$C_6$cycloalk-1,1-diyl;

$R^{13}$ is $C_1$-$C_4$alkyl; or $CHR^{12}OR^{13}$, taken in combination form a 5, 6, or 7-member cyclic ether;

$R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy;

$R^5$ and $R^6$ are each independently selected from $C_1$-$C_4$alkyl and $C_3$-$C_6$cycloalkyl;

$R^7$ is $C_1$-$C_8$alkyl, $C_3$-$C_7$cycloalkyl, $C_1$-$C_8$alkoxy, $C_3$-$C_7$cycloalkyloxy, heterocycloalkyloxy, or $—(OCHR^3CH_2)_bO—C_1$-$C_4$alkyl, wherein the heterocycloalkyloxy is a 4 to 7 member saturated heterocyclic ring having one ring heteroatom selected from N, O, and S and optionally substituted with 0, 1, or 2 independently selected $C_1$-$C_4$alkyl groups;

b is an integer of from 1 to 10;

Z is $CHR^8$ or $NR^9$;

$R^8$ and $R^9$ are each independently selected from hydrogen, $C_1$-$C_8$ alkyl, $C(O)C_1$-$C_8$ alkyl, or $—C(O)(CH_2)_q[O—W]_g(NHC(O))_m(CH_2)_q[O—W]_p$-Q-A, wherein the alkyl group is optionally substituted with 0 or 1 Q-A;

q is independently at each occurrence 1, 2, or 3;

g and p each independently have a weighted average length of between about 2 and about 50;

m is 1 or 0;

W is $C_2$-$C_4$alkyl-1,2-diyl in which the hydrogen, methyl, or ethyl side chain may be present on either backbone carbon atom;

Q is a bond, O, N(H) or $N(C_1$-$C_4$alkyl);

A is hydrogen, $C_1$-$C_8$alkyl, $C(O)C_1$-$C_8$alkyl, C(O)N(H) $C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In some aspects, $R^1$-$R^8$ of Formula (I) have the following meanings. In one aspect, $R^1$ is hydrogen or methyl. In another aspect, $R^{1a}$ is hydrogen, or methyl. In another aspect, $R^1$ and $R^{1a}$, taken in combination form a $C_3$-$C_6$cycloalk-1,1-diyl. In another aspect, $R^2$ is methyl. In another aspect, two $R^2$ groups taken in combination form a fused or spiro $C_3$-$C_6$ cycloalkyl group. In another aspect, $R^3$ is hydrogen or methyl. In another aspect, $R^{3a}$ is hydrogen or methyl. In another aspect, $R^3$ and $R^{3a}$ taken in combination form a $C_3$-$C_6$cycloalk-1,1-diyl. In another aspect, Y is $C(O)R^4$ and $R^4$ is $C_1$-$C_6$alkyl, $C_1$-$C_2$alkoxy, $C_1$-$C_2$alkyl or $C_1$-$C_6$alkoxy. In another aspect, $R^4$ is methyl, ethyl, propyl, isopropyl, 1-methyl-cyclopropyl, or methoxymethyl. In another aspect, Y is $SiR^5R^6OR^7$; and $R^5$ and $R^6$ are each methyl, ethyl, propyl or isopropyl; and $R^7$ is ethyl, propyl, isopropyl, butyl, isobutyl, secbutyl, ethoxyethyl, ethoxyisopropyl, tetrahydropyranyl, or $—(OCHR^3CH_2)_bO—C_1$-$C_4$alkyl where b is 2, 3, or 4.

In some aspects, $R^8$ and $R^9$ of Formula (I) have the following meanings. In one aspect, $R^9$ is, $C(O)C_2$ carbamoyl. In another aspect, $R^9$ is $C(O)C_2$ amidyl. In another aspect, $R^9$ is $C(O)C_5$ alkyl. In another aspect, $R^9$ is $C(O)C_2$ alkyl. In another aspect, $R^9$ is $C(O)C_1$ alkyl. In another aspect, $R^9$ is $C(O)CH_2CH_2NHC(O)CH_2CH_2CH_2CH_2$. In another aspect, $R^9$ is $C(O)(CH_2CH_2O)_bCH_2CH_2$ where b is 1, 2, 3, or 4. In another aspect, $R^9$ is amidyl. In another aspect, $R^9$ is carbamoyl. In another aspect, $R^9$ is $C_1$ alkyl amidyl. In another aspect, $R^9$ is $C_2$ alkyl amidyl.

In some aspects, Z is CH-L-A, CH-A, N-L-A, or N-A;

L is an optionally substituted bivalent linker;

A is hydrogen, $C_1$-$C_8$alkyl, $C(O)C_1$-$C_8$alkyl, C(O)N(H) $C_1$-$C_8$alkyl, $C(O)OC_1$-$C_8$alkyl, $R^{10}$, or $R^{11}$, wherein the alkyl group is optionally substituted with 0 or 1 $R^{10}$;

$R^{10}$ is a reactive functional group suitable for coupling Formula I to a carrier; and $R^{11}$ is a carrier.

In some aspects, Z is CH-L-A, CH-A, N-L-A, or N-A;

L is an optionally substituted bivalent linker $Q$-$[Sp$-$Q]_h$-Q;

Q is independently selected at each occurrence from a bond, O, C(O), N(H), $N(C_1$-$C_4$alkyl), C(O)NH, C(O) $N(C_1$-$C_4$alkyl), N(H)C(O), $N(C_1$-$C_4$alkyl)C(O), N(H) C(O)O, $N(C_1$-$C_4$alkyl)C(O)O, OC(O)N(H), OC(O)N $(C_1$-$C_4$alkyl), N(H)C(O)N(H), $N(C_1$-$C_4$alkyl)C(O)N (H), N(H)C(O)$N(C_1$-$C_4$alkyl), $N(C_1$-$C_4$alkyl)C(O)N $(C_1$-$C_4$alkyl), C(O)O, OC(O), OC(O)O, S, $S(O)_2$, N(H) $S(O)_2$, $N(C_1$-$C_4$alkyl)$S(O)_2$, $S(O)_2N(H)$, $S(O)_2N(C_1$-$C_4$alkyl), $C_1$-$C_2$alkyl-C(O)N(H), $N(H)C(O)C_1$-$C_2$alkyl, $C_1$-$C_2$alkyl-C(O)O, $OC(O)C_1$-$C_2$alkyl, 1,2,3-triazole, $OP(O)_2$, $P(O)_2O$, $C_1$-$C_4$alkyl-$P(O)_2$—O, or O—$P(O)_2$—$C_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, $[W—O]_g$, $C_1$-$C_8$alkyl-$[0$-$W]_g$, $[O—W]_g—O—C_1$-$C_8$alkyl, $C_1$-$C_8$Calkyl-$[0$-$W]_g—O—C_1$-$C_8$alkyl, oligopeptide;

h is an integer of between 1 and 20;

g is a weighted average number of between about 2 and about 50;

W is $C_2$-$C_4$alkyl-1,2-diyl in which the hydrogen, methyl, or ethyl side chain may be present on either backbone carbon atom;

A is hydrogen, $C_1$-$C_8$alkyl, $C(O)C_1$-$C_8$alkyl, $C(O)OC_1$-$C_8$alkyl, $C(O)N(H)C_1$-$C_8$alkyl, $R^{10}$, or $R^{11}$, wherein the alkyl group is optionally substituted with 0 or 1 $R^{10}$ $R^{10}$ is a reactive functional group suitable for coupling Formula I to a carrier; and $R^{11}$ is a carrier.

In certain aspects, g and h are 1 to about 25 or from 1 to about 10.

In some aspects, Z of Formula (I) is $NR^9$. In one aspect, $R^9$ is further substituted with $R^{10}$. In another aspect, $R^9$ is further substituted with $R^{11}$.

According to Formula (I), $R^{10}$ is a reactive functional group that is suitable for orthogonal coupling reactions. Suitable reactive functional groups are those that readily undergo orthogonal reactions. Exemplary and non-limiting orthogonal chemical reactions include functional groups shown in Table 1. For a given row in Table 1, a functional group X (left column) is suitable for a coupling reaction with a functional group Y (right column). Coupling reactions may be covalent bonds or intermolecular complexes. In most embodiments, the coupling reaction results in a covalent bond. In other reactions, such as adamantane with cyclodextran, the coupling is a non-covalent molecular association. In one aspect, the functional group is selected from azidyl, alkynyl, substituted or unsubstituted $C_6$-$C_{12}$ cycloalkynyl, $C_6$-$C_{12}$ heterocycloalkynyl, $C_6$-$C_{12}$ cycloalkenyl, norbornyl, vinyl carboxyl, vinyl sulfonyl, $C_2$-$C_8$ alkenyl, substituted or unsubstituted $C_1$-$C_8$ alkoxy, thiol, $C_1$-$C_8$ carboxyl, $C_1$-$C_8$ carbonyl, oxyamine, carbohydrazide, maleimide, alpha-halo carbonyl, furan, substituted or unsubstituted tetrazinyl, lysine, glutamine, cyclodextrin, and adamantanyl. In another aspect, the functional group is a substituted $C_6$-$C_{12}$ cycloalkynyl, wherein the substitution includes a fused cyclopropyl group. In another aspect, the functional group is bicyclo[6.1.0]non-4-yn-9-yl. In another aspect, the functional group is azidyl.

TABLE 1

Exemplary Orthogonal Chemistry

| Compound (or polymer) 1-X X: | Compound (or polymer) 2-Y Y: |
|---|---|
| 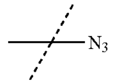 | —C≡CH |
| | 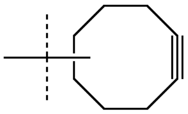 |

TABLE 1-continued
| Exemplary Orthogonal Chemistry | |
|---|---|
| Compound (or polymer) 1-X<br>X: | Compound (or polymer) 2-Y<br>Y: |
| | 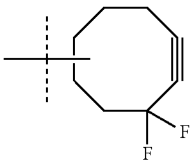 |
| | 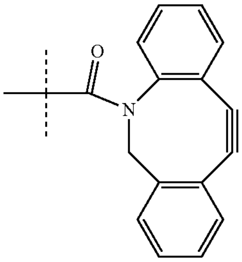 |
| | 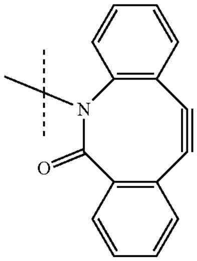 |
| | 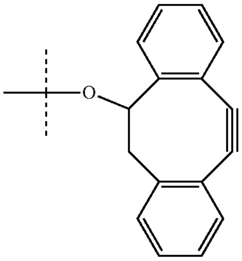 |
| —C≡CH | 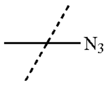 |
| 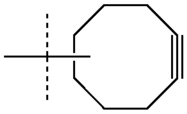 | |
| 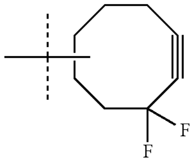 | |
TABLE 1-continued
| Exemplary Orthogonal Chemistry | |
|---|---|
| Compound (or polymer) 1-X<br>X: | Compound (or polymer) 2-Y<br>Y: |
| 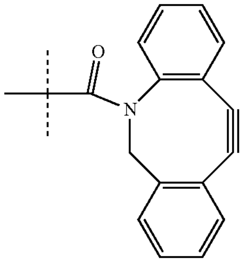 | |
| 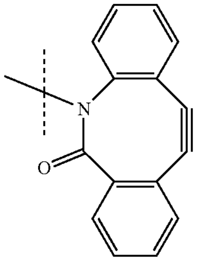 | |
| 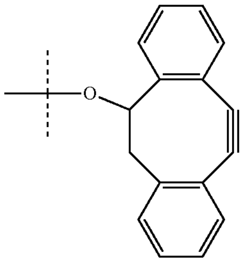 | |
| 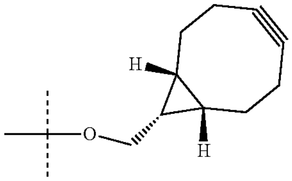 | 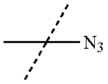 |
| 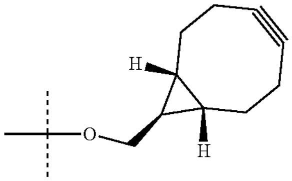 | |
| 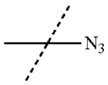 | 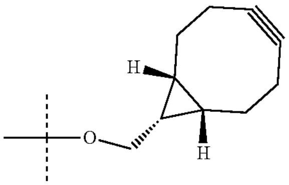 |

TABLE 1-continued
| Exemplary Orthogonal Chemistry | |
|---|---|
| Compound (or polymer) 1-X<br>X: | Compound (or polymer) 2-Y<br>Y: |
| 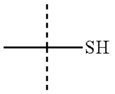 | 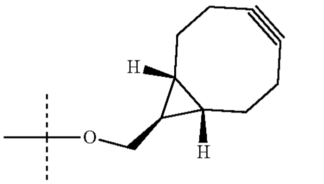<br>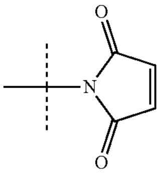<br>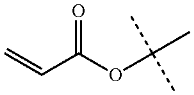<br>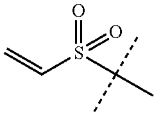<br>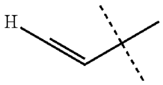<br>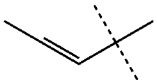<br>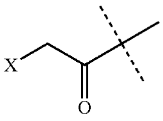<br>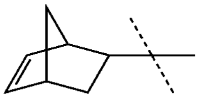<br>X = halogen |
| 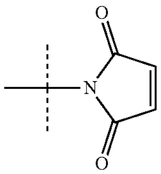<br>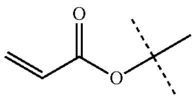<br>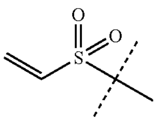 | 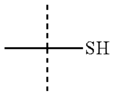 |
TABLE 1-continued
| Exemplary Orthogonal Chemistry | |
|---|---|
| Compound (or polymer) 1-X<br>X: | Compound (or polymer) 2-Y<br>Y: |
| 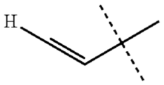<br>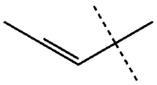<br>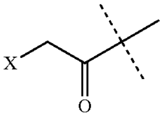<br>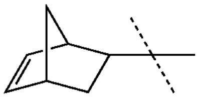<br>X = halogen | |
| 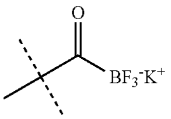 | 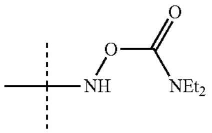 |
| 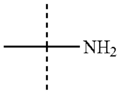 | 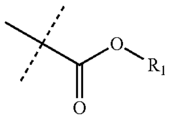<br>$R_1$ = H or activated ester |
| 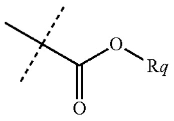<br>$R_q$ = H or activated ester | 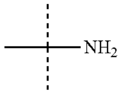 |
| 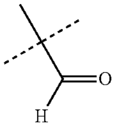 | 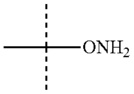 |
| 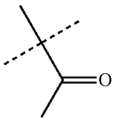 | 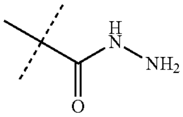 |
| 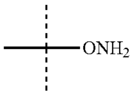 | 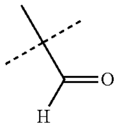 |

TABLE 1-continued

| Exemplary Orthogonal Chemistry | |
|---|---|
| Compound (or polymer) 1-X<br>X: | Compound (or polymer) 2-Y<br>Y: |
| 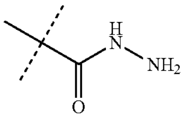 | 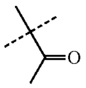 |
| 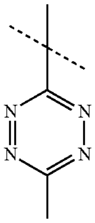 | 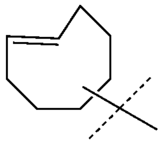 |
| 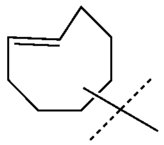 | 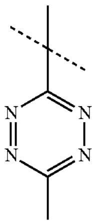 |
| 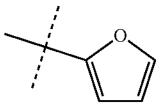 | 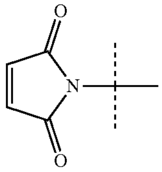 |
| 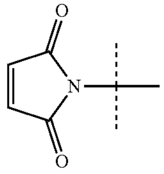 | 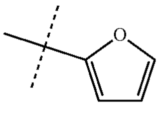 |
| 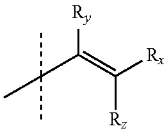 | 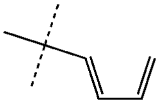 |
| 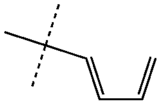 | 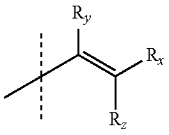 |
| 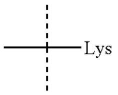 | 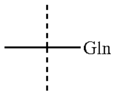 |
| 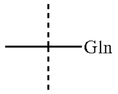 | 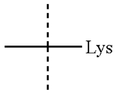 |

TABLE 1-continued

| Exemplary Orthogonal Chemistry | |
|---|---|
| Compound (or polymer) 1-X<br>X: | Compound (or polymer) 2-Y<br>Y: |
|  cyclodextrin or other host molecule | |
|  adamantane or other host molecule |  cyclodextrin or other host molecule |

In some embodiments, the traceless linker, R, comprises Formula (II):

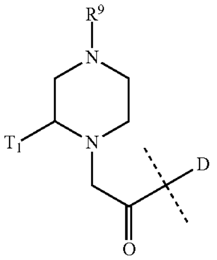

(II)

wherein, $R^9$ and D are both as defined for Formula (I) above and $T_1$ comprises a substituted or unsubstituted $C_2$-$C_{10}$ ester, a substituted or unsubstituted $C_3$-$C_{10}$ silyl ether containing one or more heteroatoms selected from nitrogen or oxygen.

In some aspects, $T_1$ is —$CR^1R^{1a}OY$, which contains a trigger moiety and comprises one of the following structures in Table 2.

TABLE 2

| Trigger Moieties |
|---|
| Y = 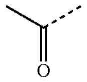<br>$R^1 = R^{1A} = H$ |
| Y = 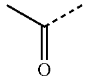<br>$R^1 = H$; $R^{1A} = CH_3$ |
| Y = 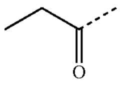<br>$R^1 = R^{1A} = H$ |
| Y = 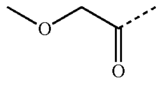<br>$R^1 = R^{1A} = H$ |

TABLE 2-continued
| Trigger Moieties |
| --- |
| Y = 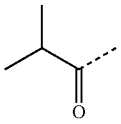<br>$R^1 = R^{1A} = H$ |
| Y = 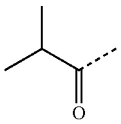<br>$R^1 = H; R^{1A} = CH_3$ |
| Y = 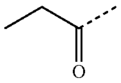<br>$R^1 = R^{1A} = H$ |
| Y = 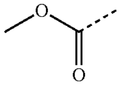<br>$R^1 = R^{1A} = H$ |
| Y = 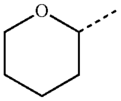<br>$R^1 = R^{1A} = H$ |
| Y = 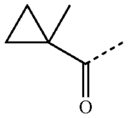<br>$R^1 = R^{1A} = H$ |
| Y = 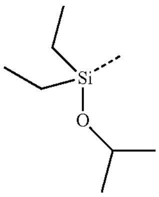<br>$R^1 = R^{1A} = H$ |
| Y = 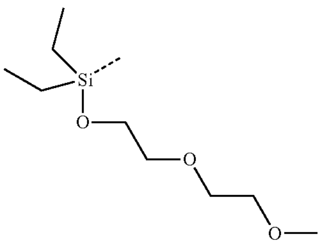<br>$R^1 = R^{1A} = H$ |
TABLE 2-continued
| Trigger Moieties |
| --- |
| Y = 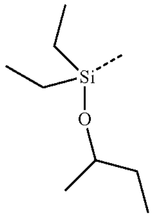<br>$R^1 = R^{1A} = H$ |
| Y = 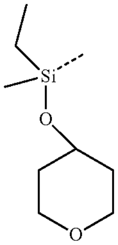<br>$R^1 = R^{1A} = H$ |
| Y = 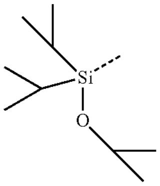<br>$R^1 = R^{1A} = H$ |
| Y = 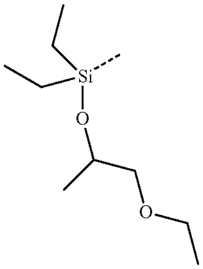<br>$R^1 = R^{1A} = H$ |
| Y = 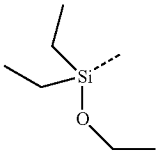<br>$R^1 = R^{1A} = H$ |
| Y = 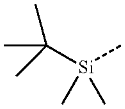<br>$R^1 = R^{1A} = H$ |

TABLE 2-continued
| Trigger Moieties |
|---|
| 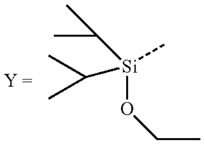 |
| $R^1 = R^{1A} = H$ |
| — |
In some embodiments, the traceless linker, R, according to either Formula I or II comprises any one of the following structures in Table 3.
TABLE 3
| Exemplary Tracelss Linkers |
|---|
| 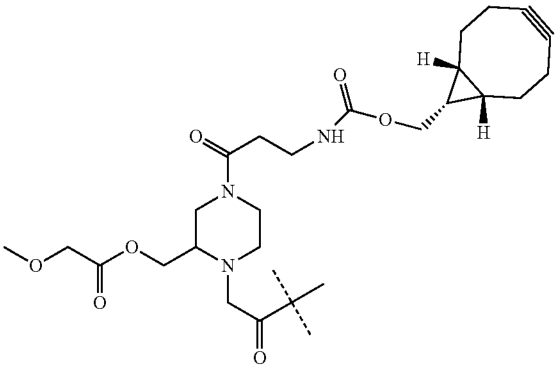 |
| 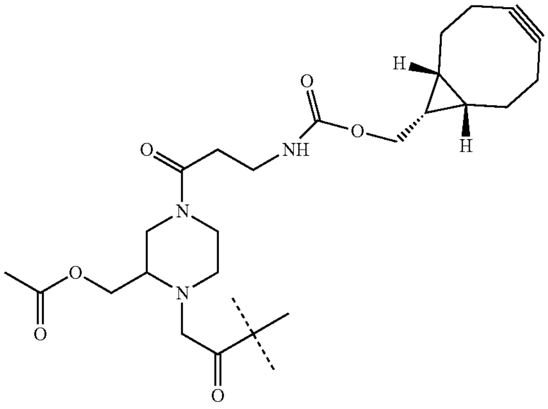 |
| 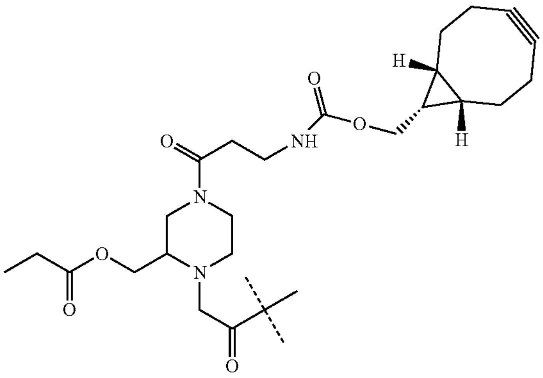 |
TABLE 3-continued
| Exemplary Tracelss Linkers |
|---|
| 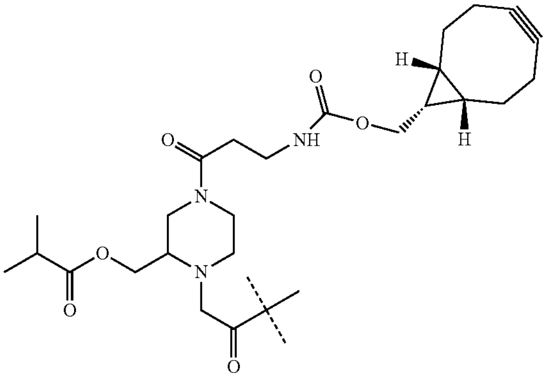 |
| 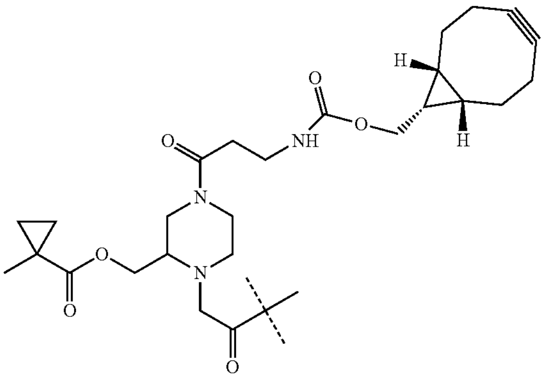 |
| 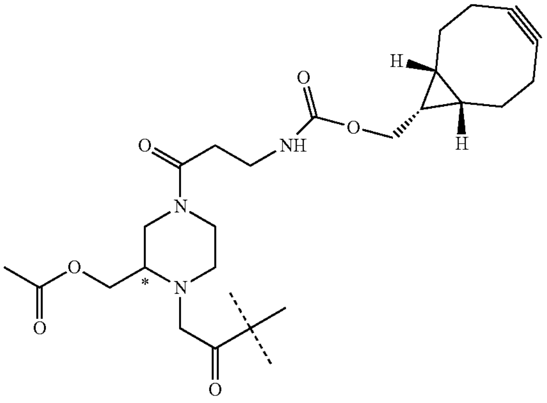 |
| 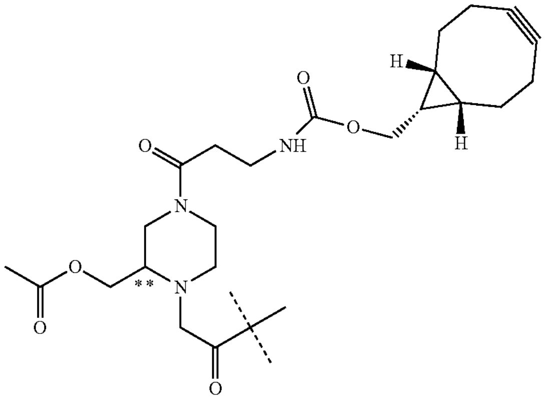 |

TABLE 3-continued
| Exemplary Tracelss Linkers |
| --- |
| 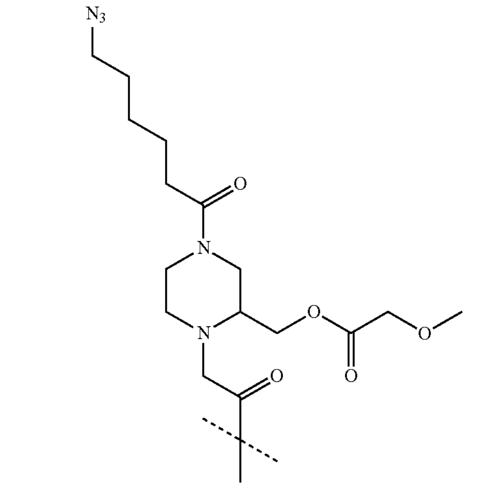 |
| 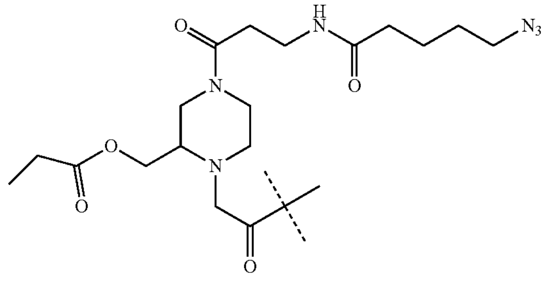 |
| 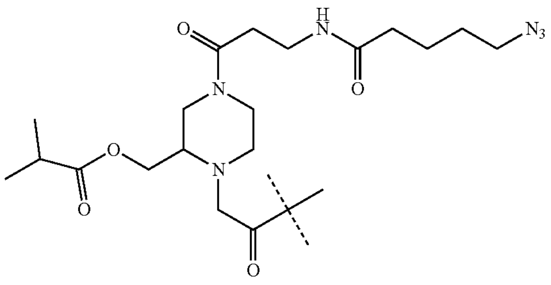 |
| 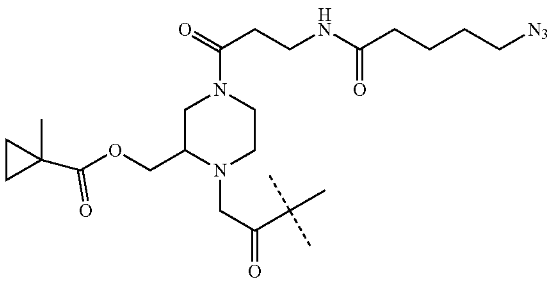 |
TABLE 3-continued
| Exemplary Tracelss Linkers |
| --- |
| 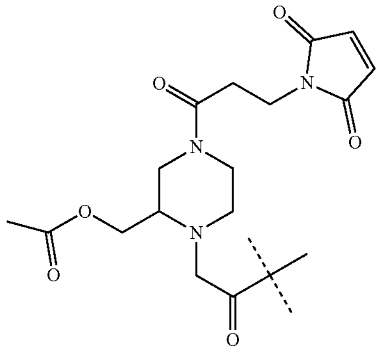 |
| 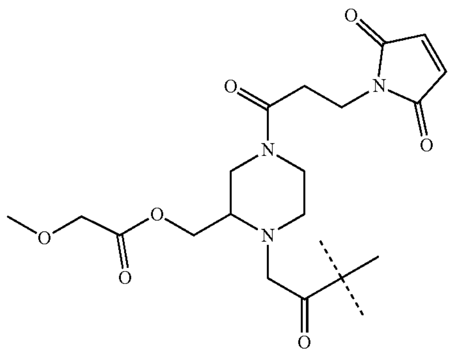 |
| 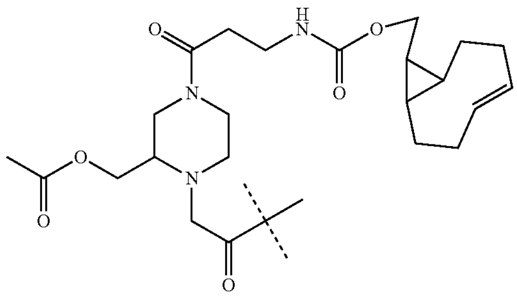 |
| 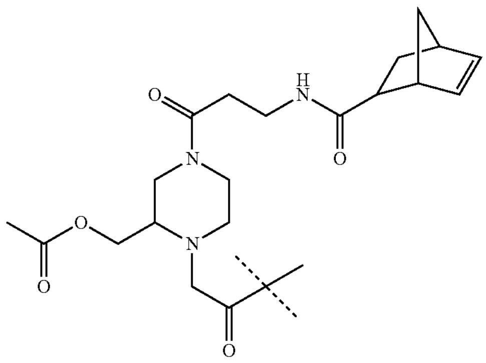 |

TABLE 3-continued
| Exemplary Tracelss Linkers |
| --- |
| 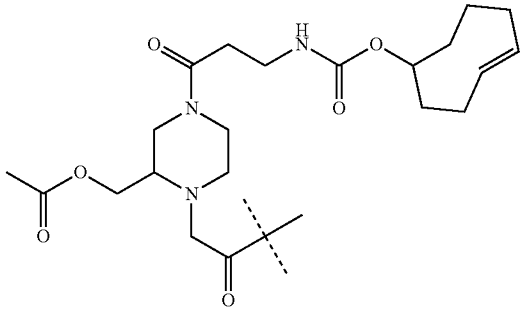 |
| 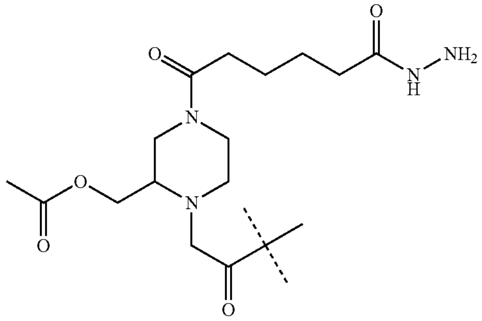 |
| 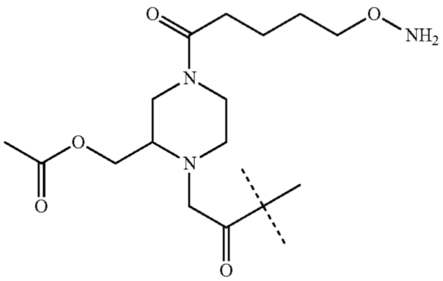 |
| 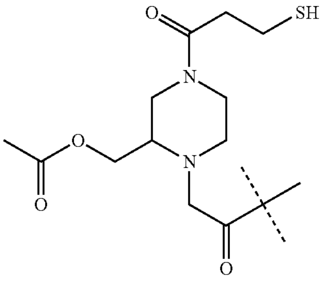 |
| 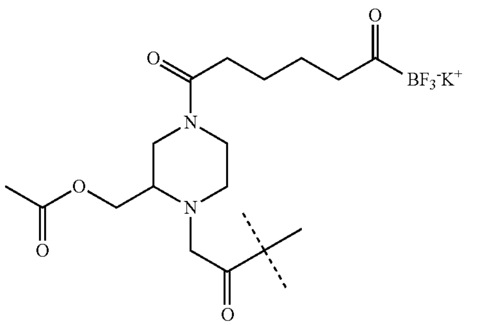 |
In another embodiment, the traceless linker, R, of Formula (I) or Formula (II) is conjugated to a drug or bioactive moeity. In one aspect, the conjugated drug traceless linker comprises any one of the following structures in Table 4.
TABLE 4
| Exemplary Traceless Linkers |
| --- |
| 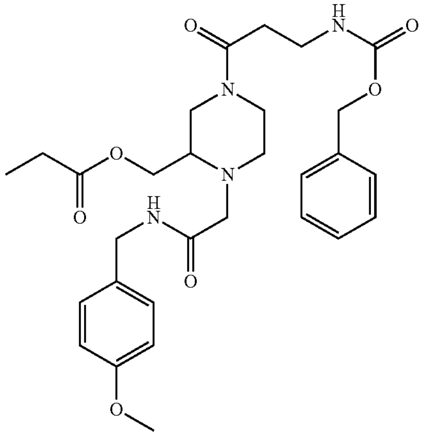 [SMILES: CCC(=O)OCC1CN(C(=O)CCNC(=O)OCc2ccccc2)CCN1CC(=O)NCc1ccc(OC)cc1] |
| 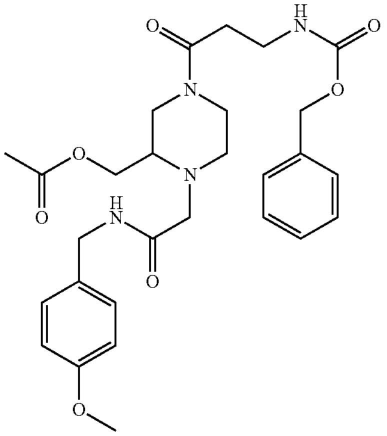 [SMILES: COc1ccc(CNC(=O)CN2CCN(C(=O)CCNC(=O)OCc3ccccc3)CC2COC(C)=O)cc1] |
| 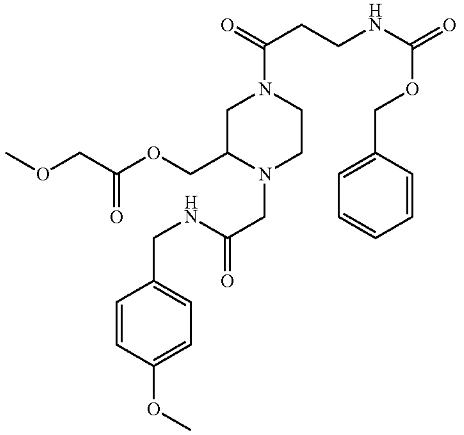 [SMILES: COCC(=O)OCC1CN(C(=O)CCNC(=O)OCc2ccccc2)CCN1CC(=O)NCc1ccc(OC)cc1] |

TABLE 4-continued
| Exemplary Traceless Linkers |
| --- |
| 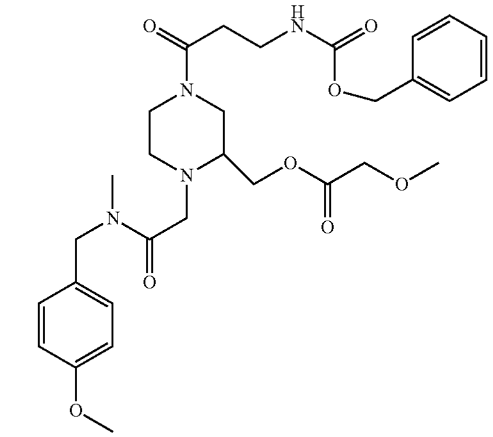 [SMILES: COCC(=O)OCC1CN(C(=O)CCNC(=O)OCc2ccccc2)CCN1CC(=O)N(C)Cc1ccc(OC)cc1] |
| 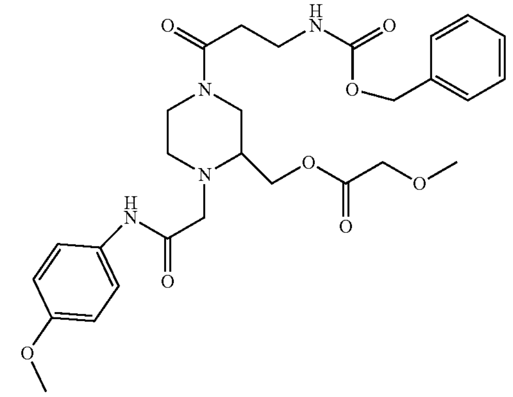 [SMILES: COCC(=O)OCC1CN(C(=O)CCNC(=O)OCc2ccccc2)CCN1CC(=O)Nc1ccc(OC)cc1] |
| 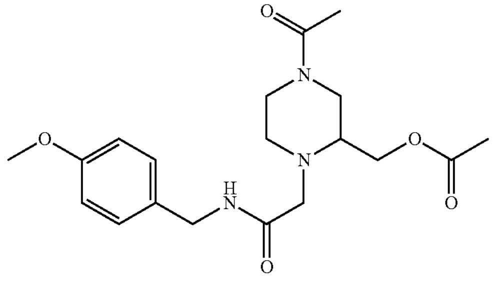 [SMILES: COc1ccc(CNC(=O)CN2CCN(C(C)=O)CC2COC(C)=O)cc1] |
| 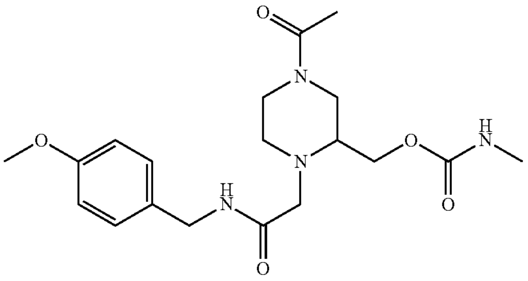 |
TABLE 4-continued
| Exemplary Traceless Linkers |
| --- |
| 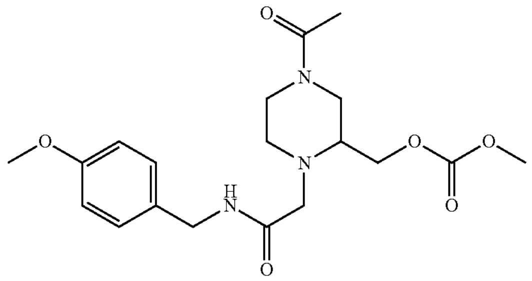 |
| 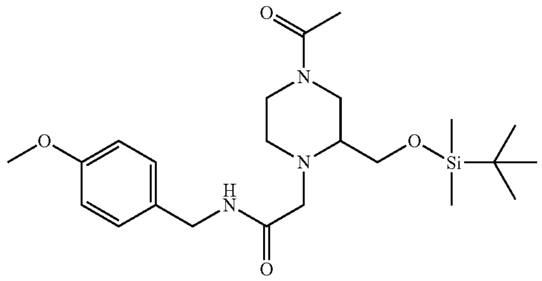 [SMILES: COc1ccc(CNC(=O)CN2CCN(C(C)=O)CC2CO[Si](C)(C)C(C)(C)C)cc1] |
| 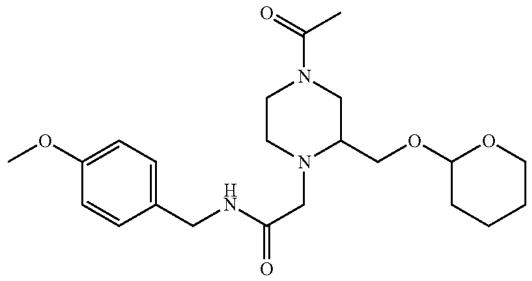 [SMILES: COc1ccc(CNC(=O)CN2CCN(C(C)=O)CC2COC2CCCCO2)cc1] |
| 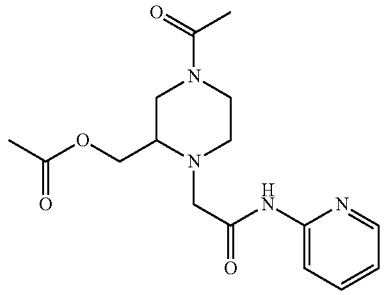 [SMILES: CC(=O)OCC1CN(C(C)=O)CCN1CC(=O)Nc1ccccn1] |
| 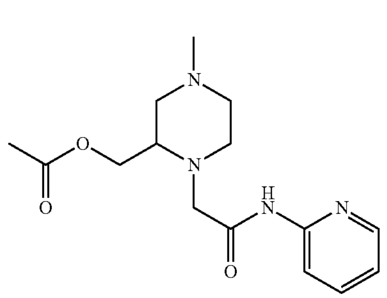 [SMILES: CC(=O)OCC1CN(C)CCN1CC(=O)Nc1ccccn1] |

TABLE 4-continued
| Exemplary Traceless Linkers |
| --- |
| 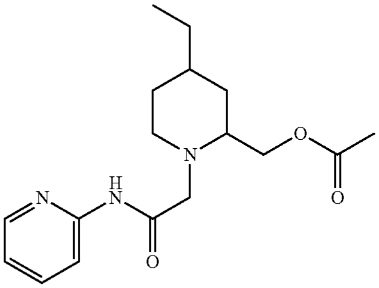 [SMILES: CCC1CCN(CC(=O)Nc2ccccn2)C(COC(C)=O)C1] |
| 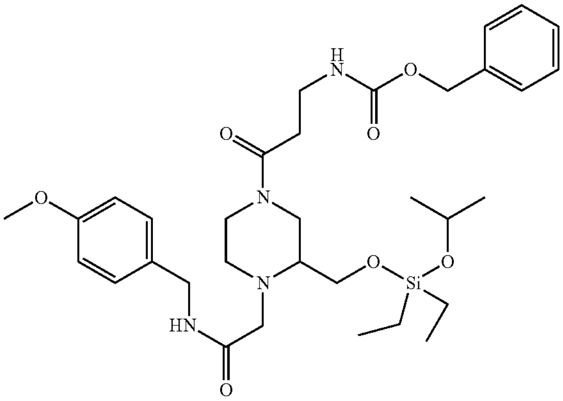 [SMILES: CC[Si](CC)(OCC1CN(C(=O)CCNC(=O)OCc2ccccc2)CCN1CC(=O)NCc1ccc(OC)cc1)OC(C)C] |
| 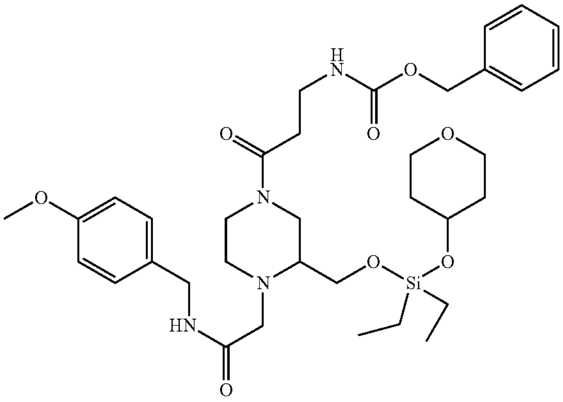 [SMILES: CC[Si](CC)(OCC1CN(C(=O)CCNC(=O)OCc2ccccc2)CCN1CC(=O)NCc1ccc(OC)cc1)OC1CCOCC1] |
| 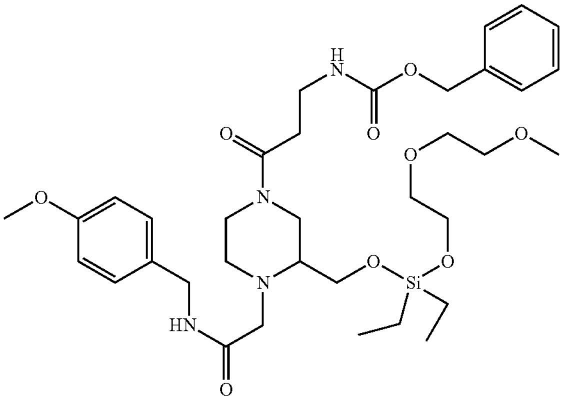 |
TABLE 4-continued
| Exemplary Traceless Linkers |
| --- |
| 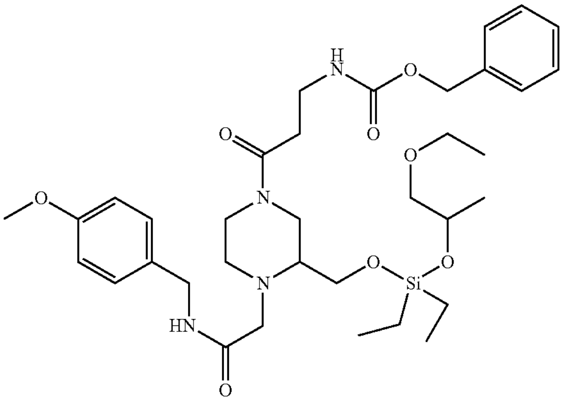 [SMILES: CCOCC(C)O[Si](CC)(CC)OCC1CN(C(=O)CCNC(=O)OCc2ccccc2)CCN1CC(=O)NCc1ccc(OC)cc1] |
| 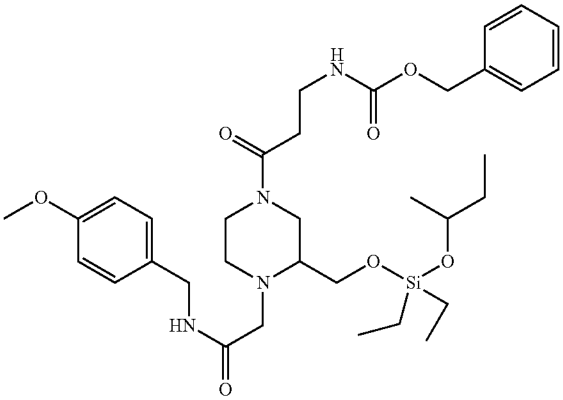 [SMILES: CCC(C)O[Si](CC)(CC)OCC1CN(C(=O)CCNC(=O)OCc2ccccc2)CCN1CC(=O)NCc1ccc(OC)cc1] |
| 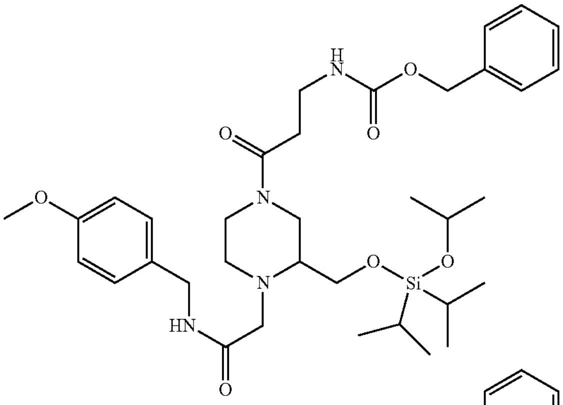 |
| 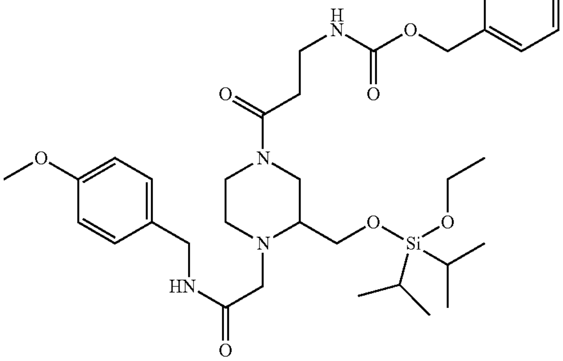 |

Synthesis of a Traceless Linker, R

Another embodiment is a method for manufacturing a traceless linker, R, of Formula (I) comprising any one of the steps: (A) reacting the N4 nitrogen of a piperazine compound containing a nucleophilic group at the C2 position with a functionalized acyl linker compound to form an N4-acylpiperazine; (B) carboxymethylating the N1 nitrogen of the piperazine ring of the N4-acylpiperazine, wherein the carboxyl group is covalently attached to a suitable protecting group; (C) reacting the nucleophilic group of the N4-acylpiperazine with a trigger compound described herein; (D) if necessary, elaborating the functionalized acyl linker on N4 to contain a functional group suitable for attaching the traceless linker to a carrier compound. In one aspect, the nucleophilic group at the C2 position of the piperazine compound comprises a hydroxyl. In another aspect, the nucleophilic group at the C2 position of the piperazine compound is a primary alcohol. In another aspect, the primary alcohol present in the piperazine compound of step (A) or (D) is conjugated to a suitable protecting group or trigger group. In another aspect, the protecting group or trigger group comprises an ester, silyl ether, acetal, carbamate, carbonate, or a disiloxane containing compound. In one aspect, the N4 carboxymethyl ester protecting group is deprotected to form a carboxylic acid, which is suitable for forming an amide bond to a biologically active agent comprising at least one primary or secondary amine or a ring nitrogen atom of an azaheteroaryl ring. In another aspect, in the carboxymethylation step, the carboxyl group of the carboxymethylating reagent is covalently attached via an amide bond to a biologically active agent comprising at least one primary or secondary amine or a ring nitrogen atom of an azaheteroaryl ring. In one aspect, the functional group of step A is suitable for attaching the traceless linker to a carrier compound.

Another embodiment is a method for manufacturing a traceless linker, R, of Formula (I) comprising any one of the steps: (A) carboxymethylating the N1 nitrogen of a piperazine compound containing a nucleophilic group at the C2 position, wherein the carboxyl group is covalently attached to a suitable protecting group; (B) reacting the N4 nitrogen of the piperazine compound with a functionalized alkyl linker to form an N4-alkylpiperazine; (C) reacting the nucleophilic group of the N4-alkylpiperazine with a trigger compound described herein; (D) if necessary, elaborating the functionalized alkyl linker on N4 to contain functional group suitable for attaching the traceless linker to a carrier compound. In one aspect, the reactive group on the piperazine compound comprises a hydroxyl. In another aspect, the nucleophilic group at the C2 position of the piperazine compound is a primary alcohol. In another aspect, the primary alcohol present on the piperazine compound of step (A) or (D) is conjugated to a suitable protecting group or trigger group. In another aspect, the trigger compound comprises an ester, silyl ether, acetal, carbamate, carbonate, or a disiloxane containing compound. In one aspect, the N4 carboxymethyl ester protecting group is deprotected to form a carboxylic acid, which is suitable for forming an amide bond to a biologically active agent comprising at least one primary or secondary amine or a ring nitrogen atom of an azaheteroaryl ring. In another aspect, in the carboxymethylation step, the carboxyl group of the carboxymethylating reagent is covalently attached via an amide bond to a biologically active agent comprising at least one primary or secondary amine or a ring nitrogen atom of an azaheteroaryl ring. In one aspect, the functional group of step A is suitable for attaching the traceless linker to a carrier compound.

Another embodiment is a method for manufacturing a traceless linker, R, of Formula (I) comprising any one of the steps: (A) introducing a functionalized linker at the C4-position of a pyridine compound containing a nucleophilic group at the C2 position via a cross coupling or substitution reaction; (B) hydrogenating the 4-substituted pyridine compound to form a 4-substituted piperidine compound; (C) carboxymethylating the N1 nitrogen of the 4-substituted piperidine compound, wherein the carboxyl group is covalently attached to a suitable protecting group; (D) reacting the nucleophilic group of the 4-substituted piperidine compound with a trigger compound described herein; (E) if necessary, elaborating the functionalized alkyl linker on C4 to contain a functional group suitable for attaching the traceless linker to a carrier compound. In one aspect, the nucleophilic group on the pyridine or piperidine compounds comprises a hydroxyl. In another aspect, the nucleophilic group at the C2 position of the pyridine or piperidine compounds is a primary alcohol. In another aspect, the trigger compound comprises an ester, silyl ether, acetal, carbamate, carbonate, or a disiloxane containing compound. In one aspect, the N4 carboxymethyl ester protecting group is deprotected to form a carboxylic acid, which is suitable for forming an amide bond to a biologically active agent comprising at least one primary or secondary amine or a ring nitrogen atom of an azaheteroaryl ring. In another aspect, in the carboxymethylation step, the carboxyl group of the carboxymethylating reagent is covalently attached via an amide bond to a biologically active agent comprising at least one primary or secondary amine or a ring nitrogen atom of an azaheteroaryl ring. In one aspect, the functional group of step A is suitable for attaching the traceless linker to a carrier compound.

Suitable protecting groups are moieties that are reversibly connected to reactive functional groups or chemical functional groups to render them incapable of reacting with for example other chemical functional groups. Exemplary and non-limiting amino protecting groups include a fluorenylmethylenoxy group (FMOC), tert-butyloxycarbonyl (BOC), carboxybenzyl (Cbz), and the like. Exemplary and non-limiting alcohol protecting groups include t-butyl ether, allyl ether, benzyl ether, tert-butyldimethylsilyl ethers (TBDMS), and the like. Deprotecting groups may be added or removed as needed throughout the synthesis to block and expose particular moieties.

In one embodiment, the method for manufacturing a traceless linker is according to reaction Schemes 1-3. The following schemes are general and non-limiting schemes for manufacturing traceless linkers. As shown in the Examples herein some synthesis routes do not specifically conform to these general schemes. In another aspect, the method for manufacturing a traceless linker according to the reaction schemes provided in Example 1.

Scheme 1

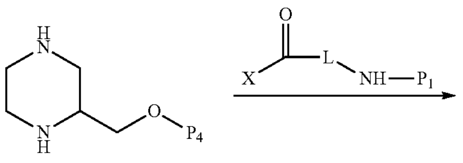

-continued

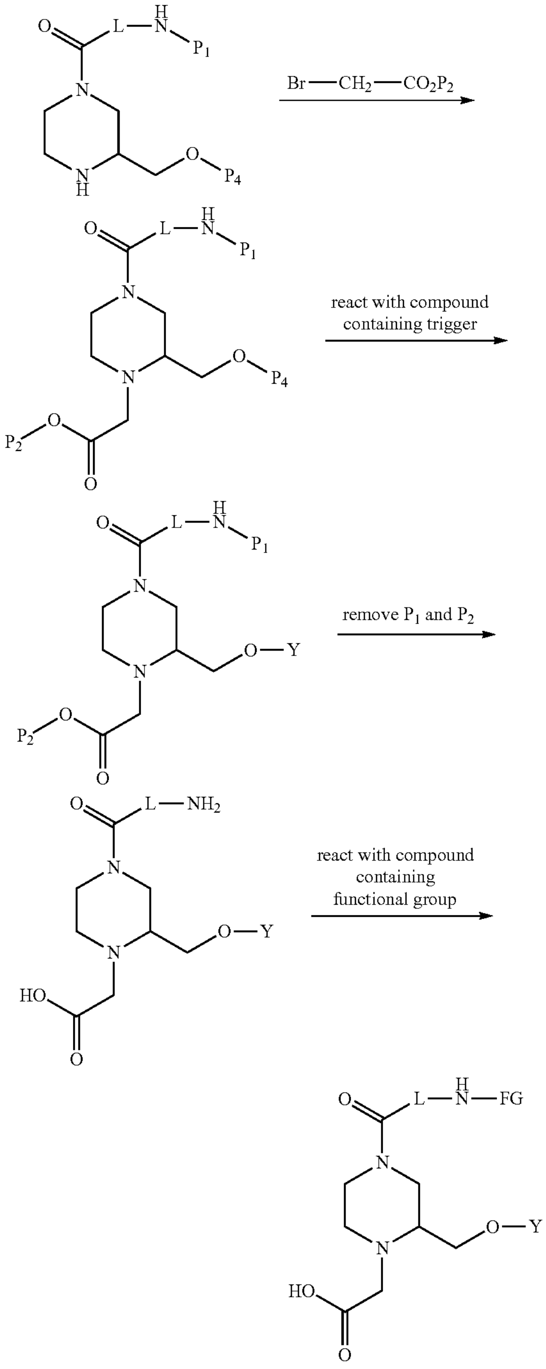

wherein one or more of the steps shown above may be performed in a different sequential order or omitted depending on the reagents utilized;

X is an activating group comprising Cl, O—NHS, O(C═O)—$R^{2a}$, or X—OH and the reaction includes standard peptide coupling reagents such as 1-[Bis(dimethylamino)methylene]-1H-1,2,3-triazolo[4,5-b] pyridinium 3-oxide hexafluorophosphate (HATU);

$R^{2a}$ is $C_1$-$C_8$ alkyl or aryl;

$P_4$ is a suitable protecting group or H;

L is an optionally substituted bivalent linker;

$P_1$ and $P_2$ are protecting groups that may be identical;

Y is a suitable trigger provided in Table 2; and

FG comprises a suitable functional group(s) capable of conjugating to a carrier described herein.

Scheme 2

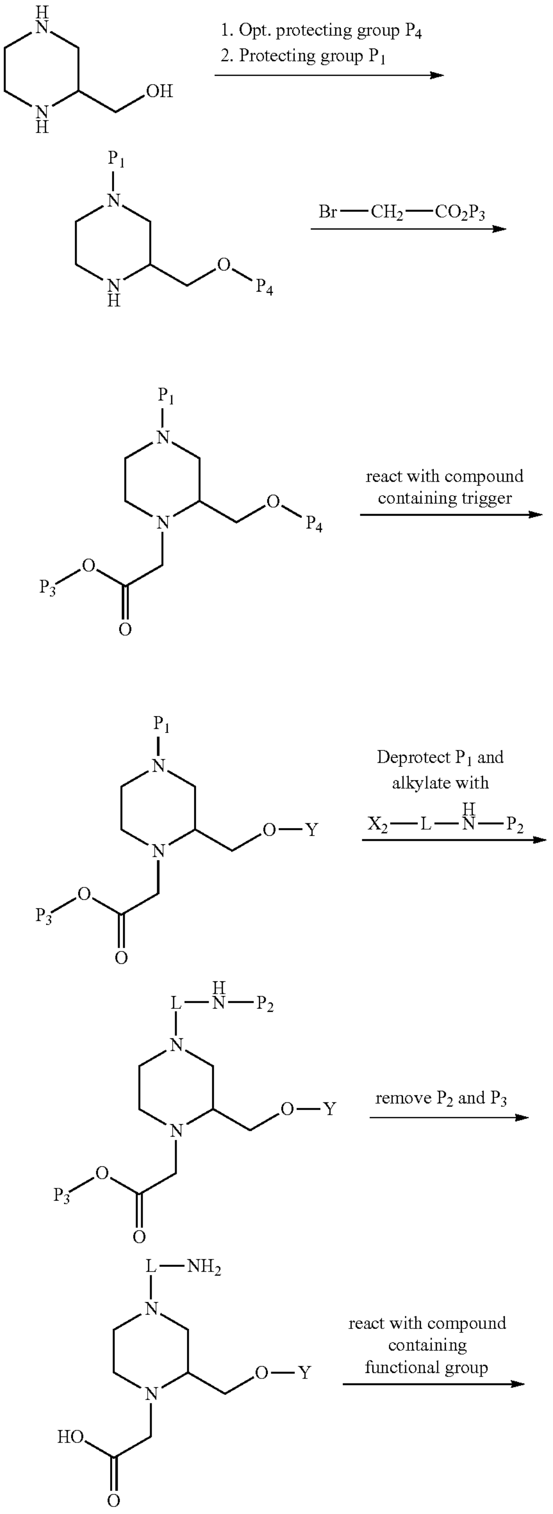

-continued

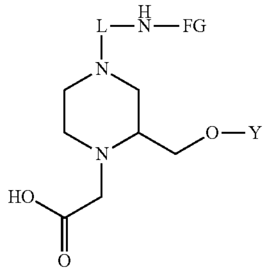

wherein one or more of the steps shown above may be performed in a different sequential order or omitted depending on the reagents utilized;

where, $X_2$ is an activating group such as Cl, Br, I, or triflate;

Y, L, $P_1$, $P_2$, $P_4$, and FG are as described in Scheme 1;

$P_3$ is a protecting group that may be identical to $P_1$ and $P_2$.

Scheme 3

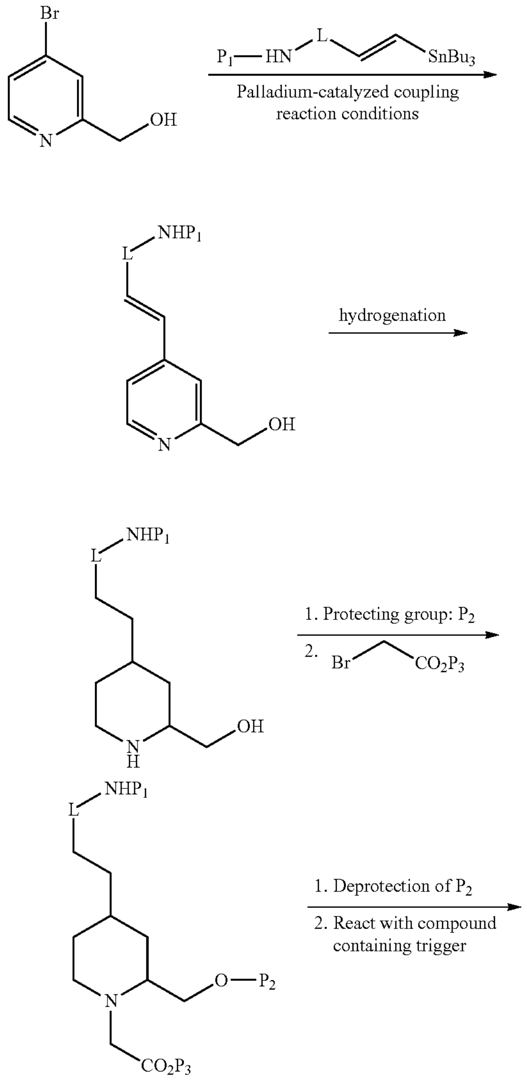

-continued

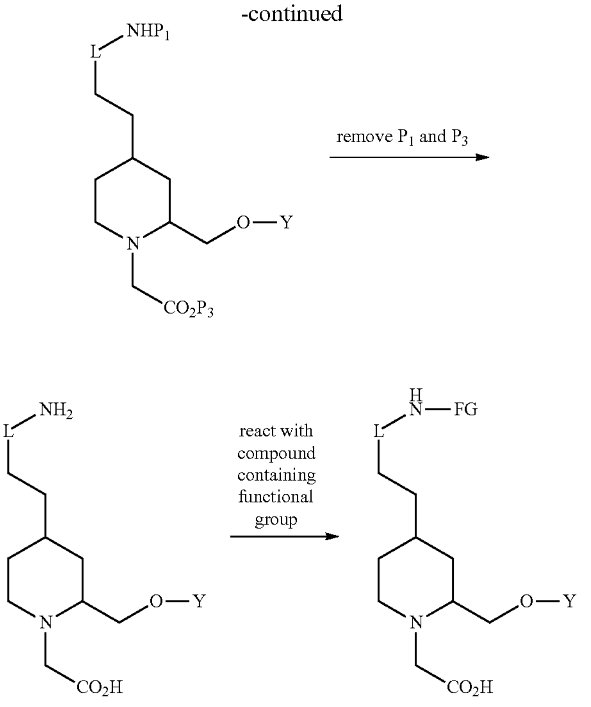

wherein one or more of the steps shown above may be performed in a different sequential order or omitted depending on the reagents utilized; and L, $P_1$, $P_2$, $P_3$, Y, and FG are as described in Scheme 2.

As described herein, the adduct D-R of Formula (I) or Formula (II) is prepared by reacting the carboxylic acid form of traceless linker R with an amino group of a biologically active agent comprising at least one primary or secondary amine or a ring nitrogen atom of an azaheteroaryl ring to form an amide bond. This process is described in Scheme 4. A suitable carboxylic acid activating agent is used to promote the amide bond forming reaction. As an example, the carboxylic acid may be converted to an amino-reactive form by the action of disuccinimidyl carbonate to form an NHS ester; the NHS ester of traceless linker R is then reacted with amino-containing drug D to form adduct D-R.

In Scheme 4, L, Y, and FG are as described in Schemes 1-3; D is a biologically active agent comprising at least one primary or secondary amine or a ring nitrogen atom of an azaheteroaryl ring.

Scheme 4

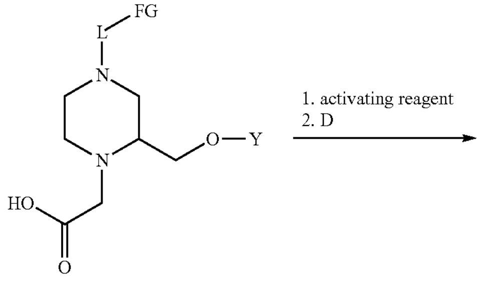

-continued

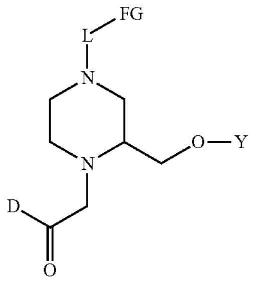

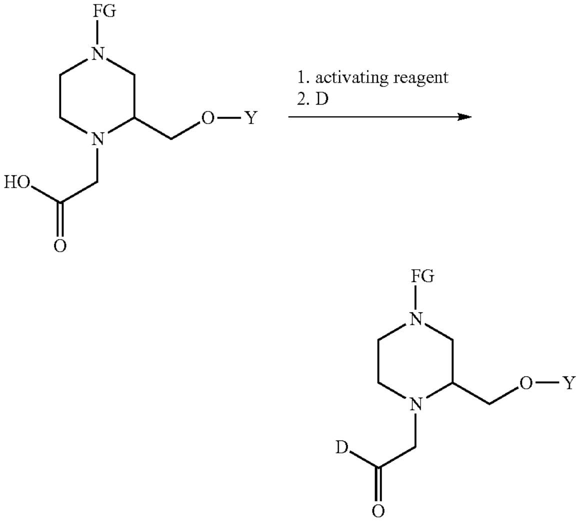

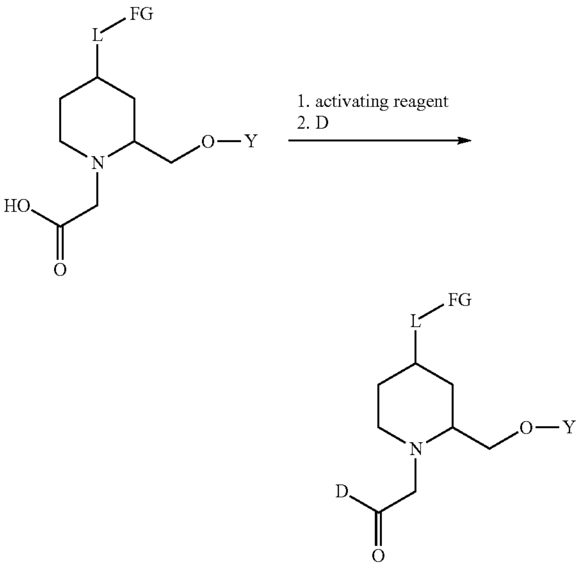

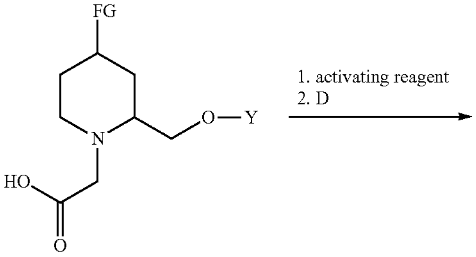

-continued

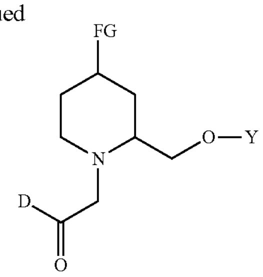

One embodiment described herein is a traceless linker, R, of Formula (I) or Formula (II) attached to a carrier composition through a linker having one or more functional groups. In one aspect, the carrier composition comprises $R^{11}$ of a traceless linker as described herein. In one aspect, $R^{11}$ comprises a polymer, biopolymer, or polyethylene glycol connected to $R^8$ or $R^9$ through a linker. In one aspect, the carrier composition is a hydrogel. In one aspect, the hydrogel composition comprises hyaluronic acid, polyethylene glycol, polypropylene glycol, polyethylene oxide, polyglutamate, polylysine, polysialic acid, polyvinyl alcohol, polyacrylate, polymethacrylate, polyacrylate/polymethacrylate copolymers, polyacrylamide, polymethacrylamide, polyvinylpyrrolidone, polyoxazoline, polyiminocarbonate, polyamino acid, hydrophilic polyester, polyamide, polyurethane, polyurea, dextran, agarose, xylan, mannan, carrageenan, alginate, gelatin, collagen, albumin, cellulose, methylcellulose, ethylcellulose, hydroxypropylmethylcellulose, hydroxyethyl starch, chitosan, nucleic acids, derivatives thereof, co-polymers thereof, or combinations thereof. In another aspect, $R^{11}$ comprises a nanoparticle or a molecular surface. In one aspect, the hydrogel comprises hyaluronic acid or polyethylene glycol. In another aspect, $R^{11}$ comprises a cross-linked hydrogel of hyaluronic acid or polyethylene glycol. In one aspect, where the drug delivery system is utilized in the eye or in the synovial joints, $R^{11}$ comprises hyaluronic acid or cross-linked hyaluronic acid.

As described herein, $R^{11}$ carrier compositions can be cross-linked to join multiple molecules together and facilitate hydrogel formation. Cross-linking can be accomplished using any means known in the art (see, for example, Liu et al., *Chem. Commun.* 51, (2015). In one embodiment described herein, hyaluronic acid or polyethylene glycol are functionalized with one or more functional groups shown in Table 1 to provide reactive functional groups for cross-linking. In another aspect, the hyaluronic acid or polyethylene glycol are functionalized with a functional group selected from azidyl, alkynyl, substituted or unsubstituted C7-C12 cycloalkynyl, C7-C12 cycloalkenyl, substituted or unsubstituted C7-C12 heterocycloalkynyl, vinyl carboxyl, vinyl sulfonyl, C2-C8 alkenyl, amino, thiol, C1-C8 carboxyl, C1-C8 carbonyl, oxyamine, carbohydrazide, maleimide, alpha-halo carbonyl, furan, substituted or unsubstituted tetrazinyl, lysine, glutamine, cyclodextrin, and adamantanyl. In another aspect, the hyaluronic acid is functionalized with an azidyl group.

The degree of functionalization can determine the porosity of the hydrogel. In one aspect, about 5% to about 50% of the carrier polymer is functionalized, including all integers within the specified range. In one aspect, the carrier polymer is functionalized about 5%, about 10%, about 15%, about 20%, about 25%, about 30%, about 35%, about 40%, about 45%, about 50%, or even greater.

In one aspect, the carrier is hyaluronic acid. In another aspect, hyaluronic acid is reacted with 4-(4,6-dimethoxy-1, 3,5-triazin-2-yl)-4-methylmorpholin-4-ium chloride (CAS number 3945-69-5) and 2-(2-(2-(2-azidoethoxy)ethoxy) ethoxy)ethanamine (CAS Number 134179-38-7) to form an azide functionalized hyaluronic acid ($[HA-N_3]$). In one aspect, the reaction is:

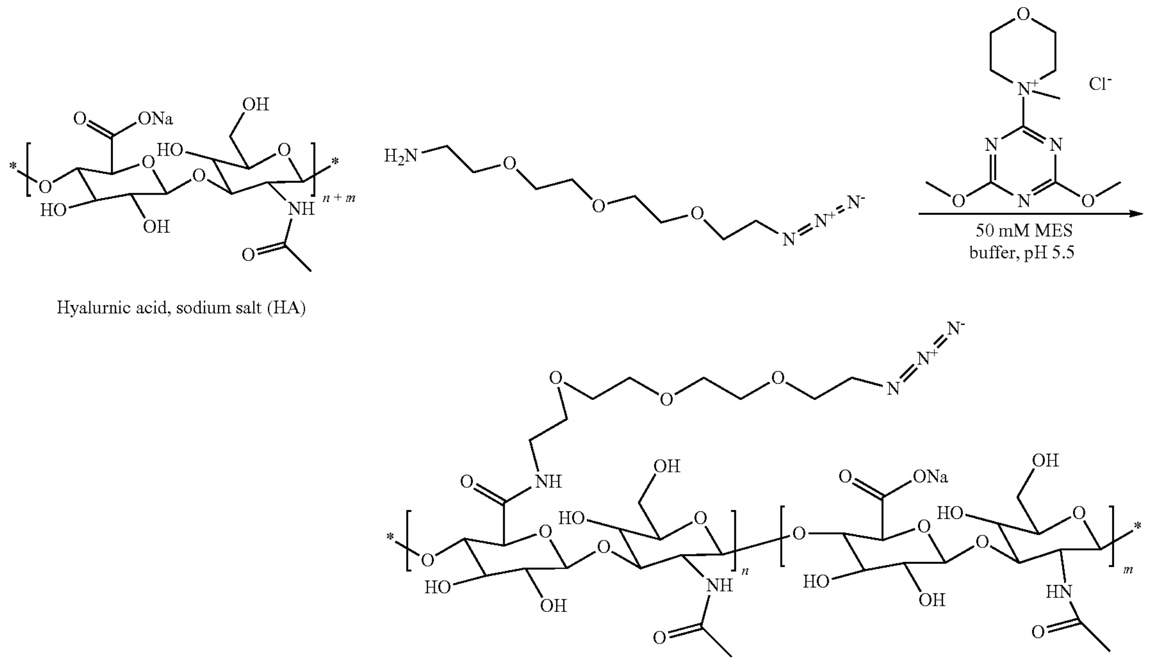

Hyalurnic acid, sodium salt (HA)

$[HA-N_3]$

Experimental conditions are described in Example 3. In one aspect, about 5% to about 50% of the hyaluronic acid is functionalized, including all integers within the specified range. In one aspect, the hyaluronic acid is functionalized about 5%, about 10%, about 15%, about 20%, about 25%, about 30%, about 35%, about 40%, about 45%, about 50%, or even greater.

In another embodiment, polyethylene glycol is functionalized with various reagents to form cross-linkers for linking the functionalized hyaluronic acid monomers as discussed above.

Synthesis of 2 kDa 2-Arm PEG-BCN Crosslinker

In one aspect, $M_n$~2 kDa polyethylene glycol diamine hydrochloride is reacted as shown. Reaction conditions are described in Example 4.

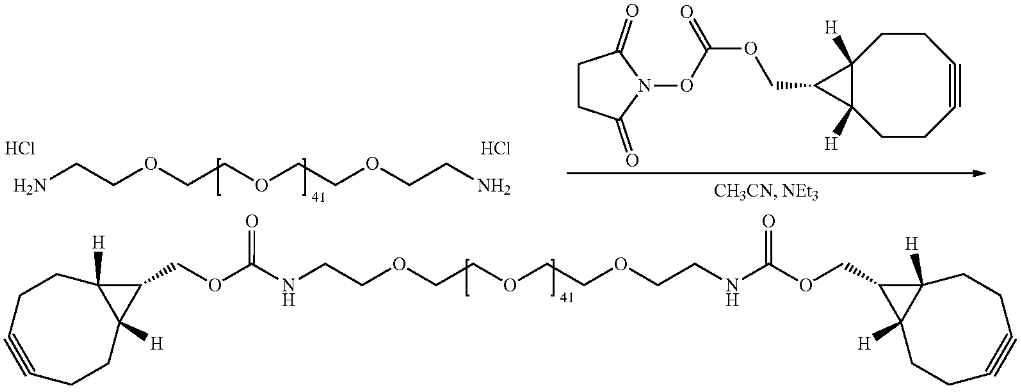

Synthesis of 10 kDa 4-Arm PEG-BCN Crosslinker

In another aspect, $M_n$~10 kDa 4-arm polyethylene glycol amine hydrochloride (pentaerythritol core, JenKem Technology) is reacted as shown. Reaction conditions are described in Example 4.

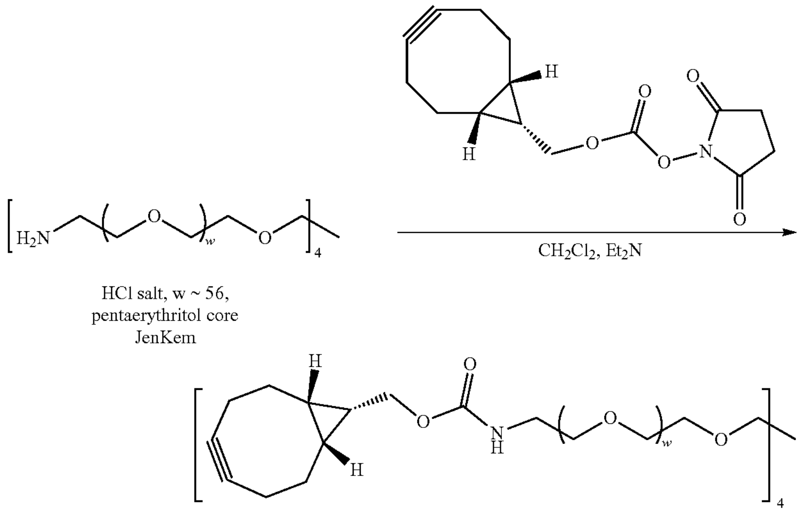

Synthesis of 2 kDa 2-Arm Beta-Alanine PEG-BCN Crosslinker

In another aspect, $M_n$~2 kDa polyethylene glycol and 3-((tert-butoxycarbonyl)amino)propanoic acid are reacted as shown. Reaction conditions are described in Example 4.

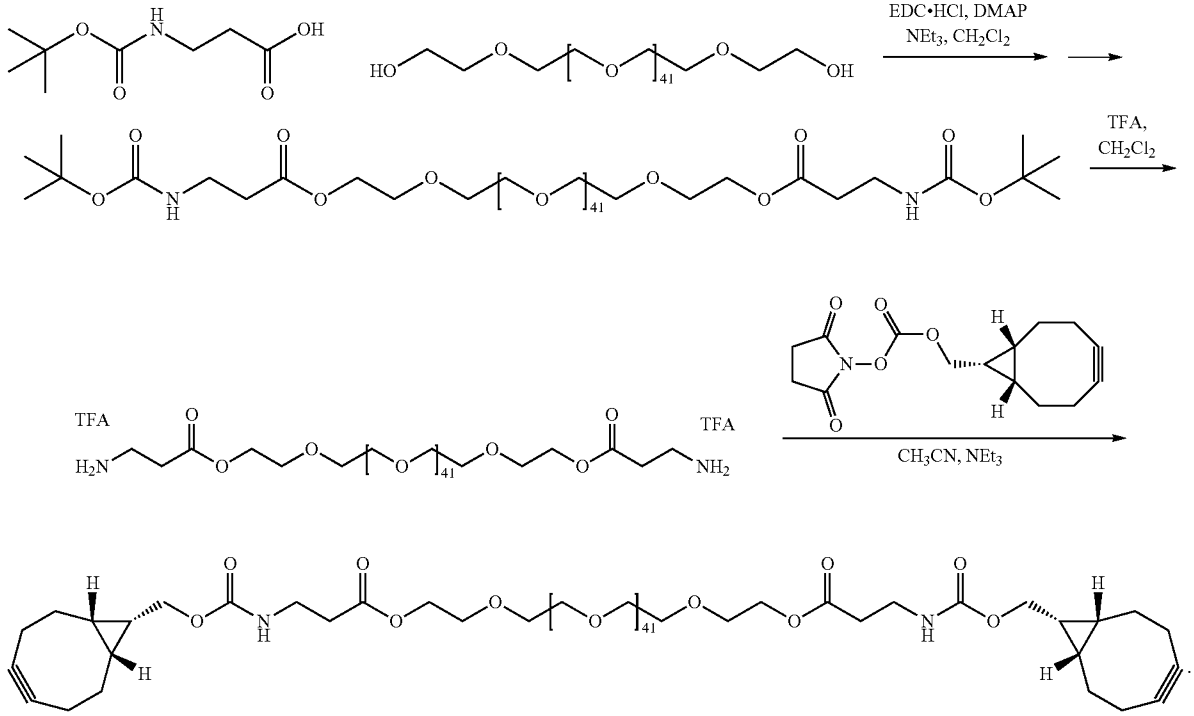

Synthesis of 2 kDa 2-Arm Aminocyclopropanecarboxylic Acid PEG-BCN Crosslinker In another aspect, $M_n$~2 kDa polyethylene glycol and 1-((tert-butoxycarbonyl)amino)cyclopropane-1-carboxylic acid are reacted as shown. Reaction conditions are described in Example 4.

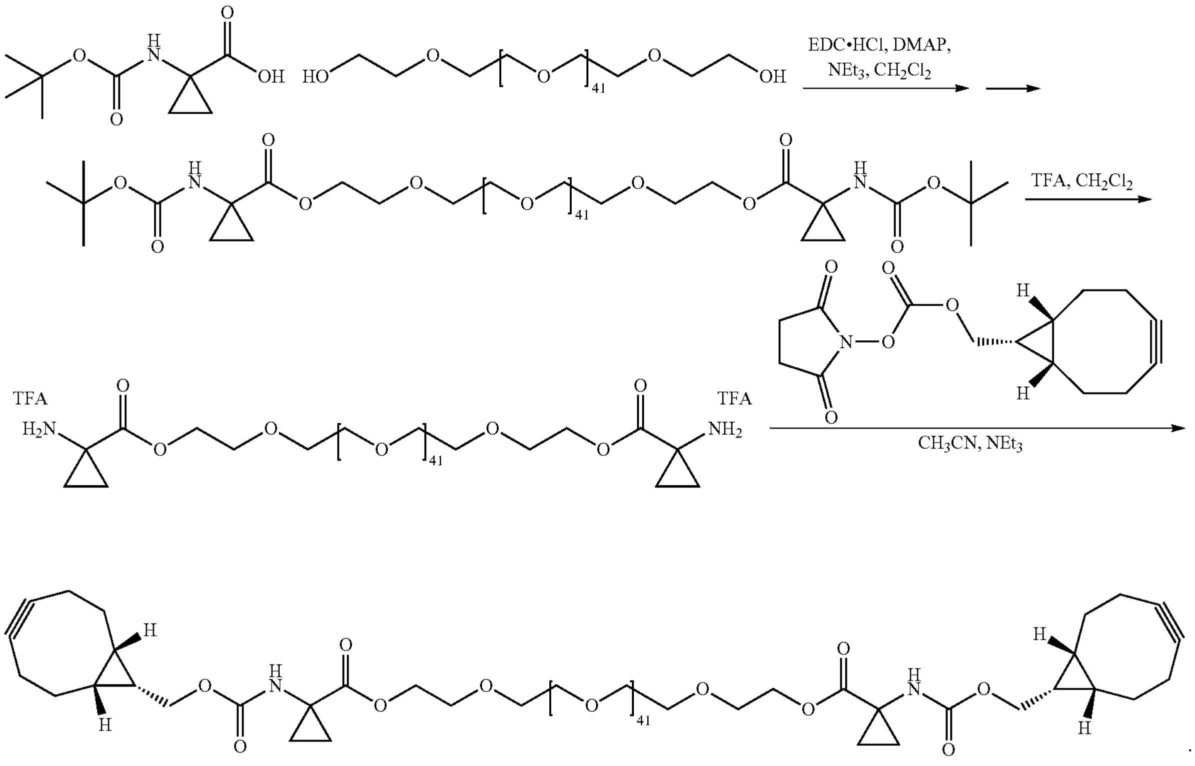

Another embodiment described herein is one or more cross-linking agents. In one aspect, the cross-linking agent comprises Formula V:

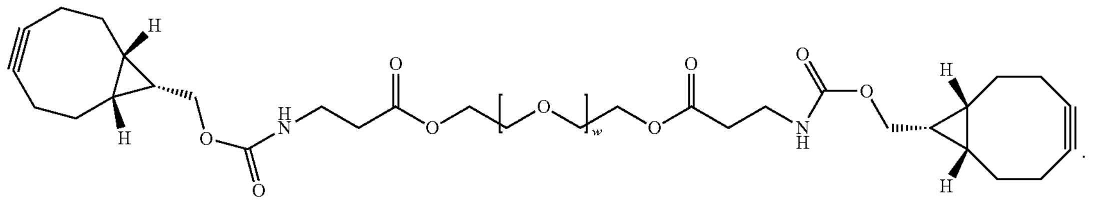

In another aspect, the cross-linking agent comprises Formula VI:

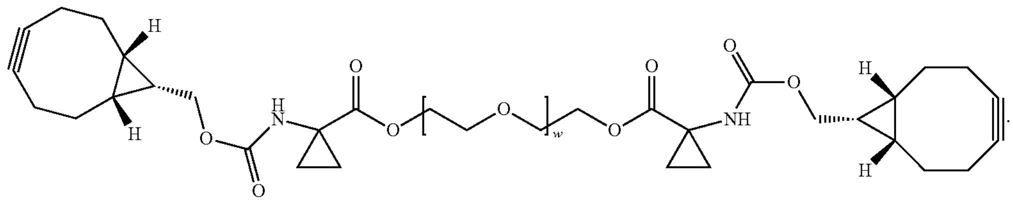

In another aspect, the cross-linking agent comprises Formula VIa:
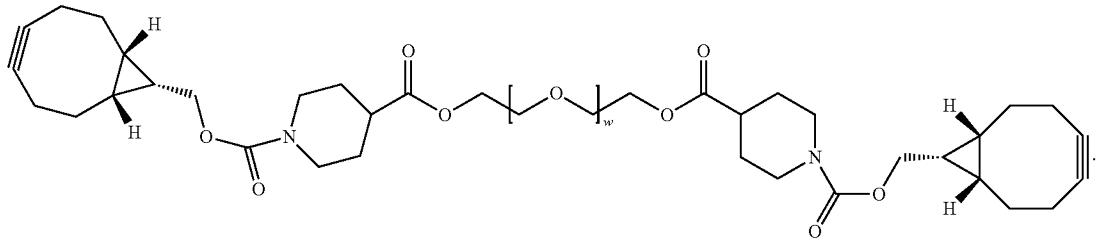
In another aspect, the cross-linking agent comprises Formula VIb:
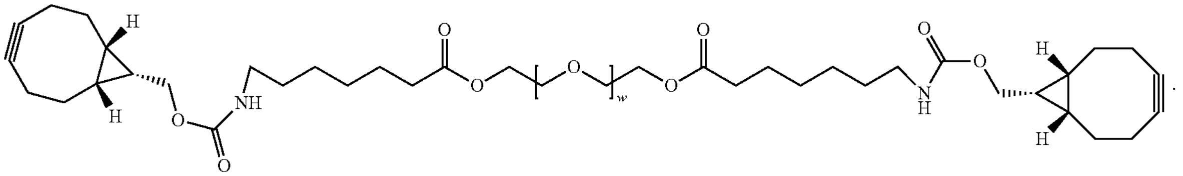
In another aspect, the cross-linking agent comprises Formula VIc:
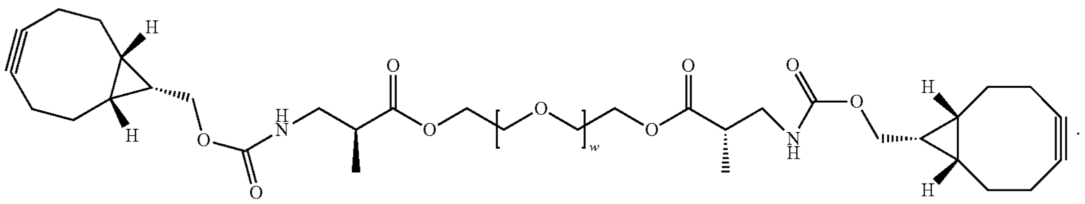
In another aspect, the cross-linking agent comprises Formula VII:
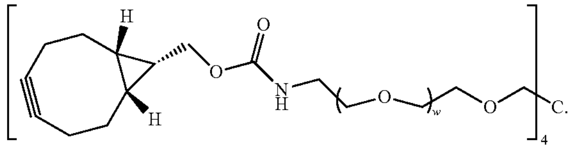
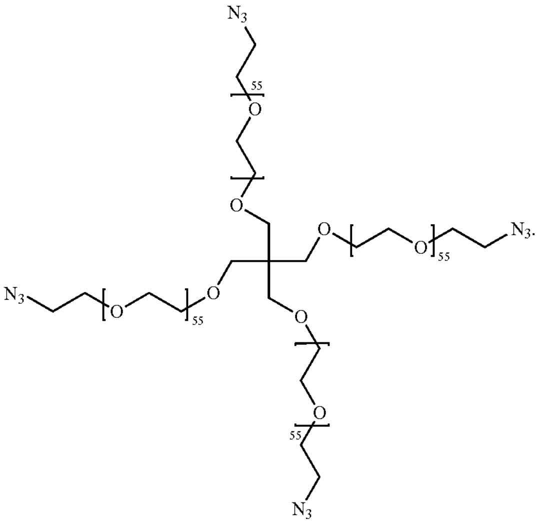
In another aspect the cross-linking agent comprises Formula VIII:

In another aspect, the cross-linking agent comprises Formula IX:

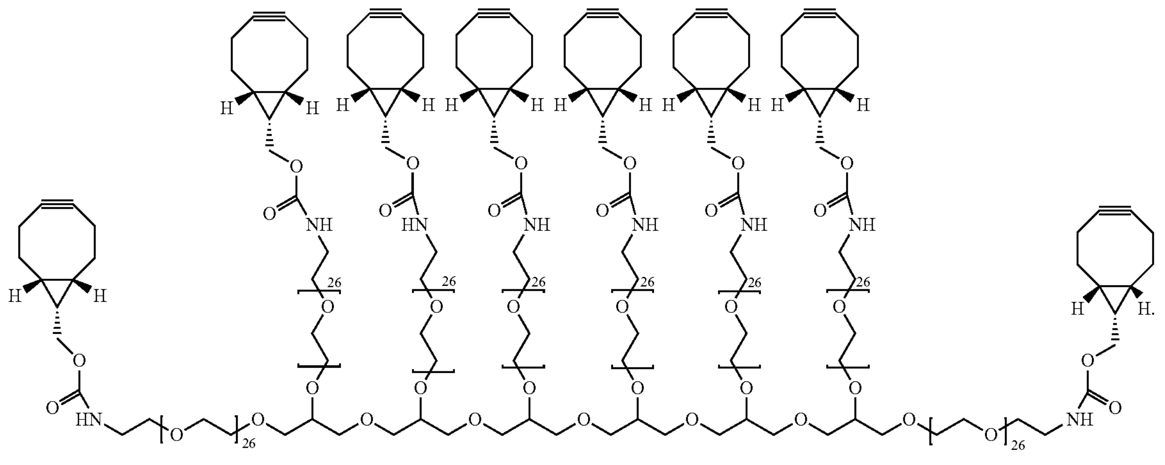

In another embodiment described herein, $R^{11}$ comprises a functionalized carrier that has been reacted with one or more cross-linking agents to form a cross-linked carrier. In one embodiment, the cross-linked carrier forms a hydrogel. In one aspect, the cross-linked carrier is hyaluronic acid that has been functionalized and cross-linked with one or more polyethylene glycol cross linkers as described herein to form a hydrogel.

In one embodiment, a cross-linked carrier comprising hyaluronic acid can be prepared by reacting appropriately functionalized polymers as shown:

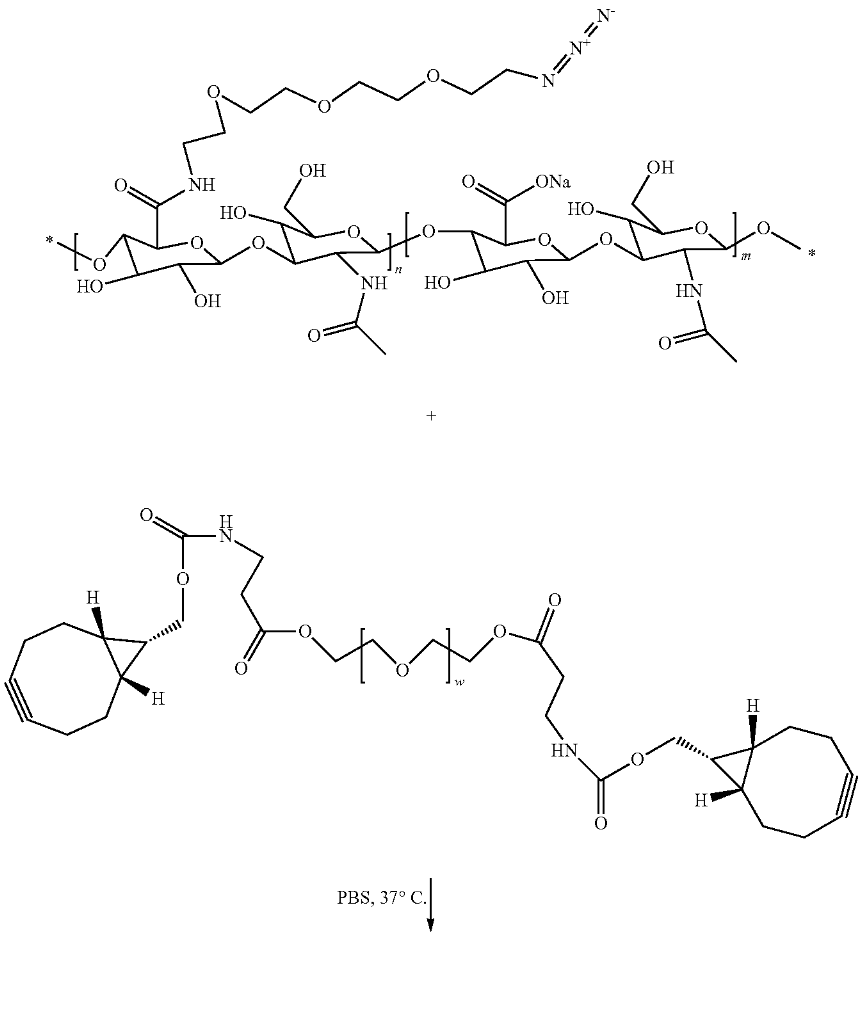

-continued

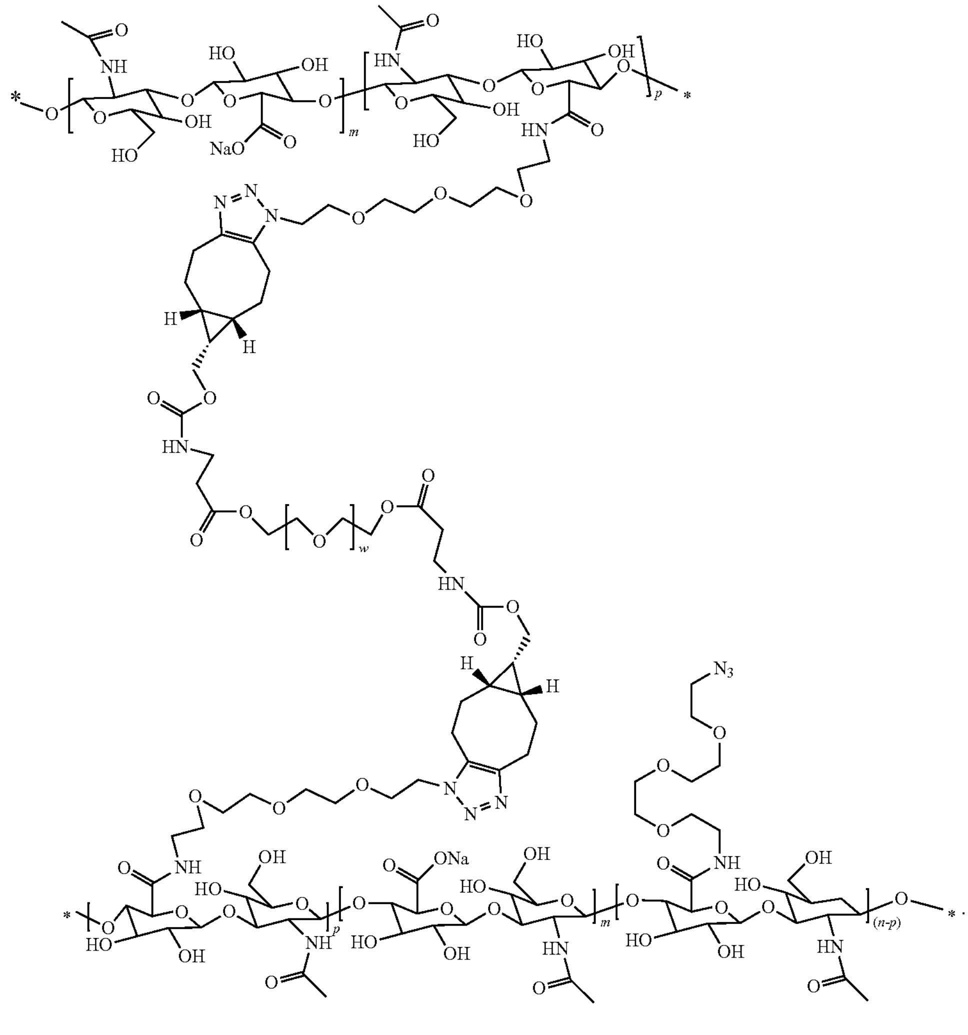

While not being bound by any particular example and by way of illustration, in one embodiment, hyaluronic acid sodium salt labeled by the supplier, Lifecore Biomedical (HA200K, Chaska, MN) as having a nominal average molecular weight varying from batch to batch in the range of 151-300 kDa, as determined by viscometry. For the purposes of this illustration, a molecule of hyaluronic acid sodium salt with an assumed nominal average molecular weight of 200 kDa would consist of an average of approximately 500 monomer units. In this and following structures the unmodified monomer unit is defined as "m," the monomer unit modified with an azido group as "n," the azido-monomer unit conjugated to the crosslinking molecule as "p" and the azido monomer unit conjugated to the traceless linker-drug adduct as "q." For a polymer chain comprising ≈500 monomer units, (n+m+p+q≈500). If the percent modification of the hyaluronic acid sodium salt molecule is 25%, then m=75% and (n+p+q)=25%.

Similarly, the PEG unit present in one embodiment of the cross linker is derived from a starting PEG described as having a nominal average molecular weight of 2 kDa, and would consist of approximately 44 repeating PEG monomer units, described in these depicted structures as "w."

In the following Formulae, in one embodiment, the sum of the unmodified disaccharide repeating unit of hyaluronic acid (m) plus the modified disaccharide repeating unit of hyaluronic acid (n+p+q) in a random distribution (=m+n+p+q) may comprise about 500 units for a nominal average molecular weight as determined by viscometry of approximately 200 kDa. This applies to Formulae X to XXII.

In one aspect, the cross-linked carrier comprises Formula X:
(X)
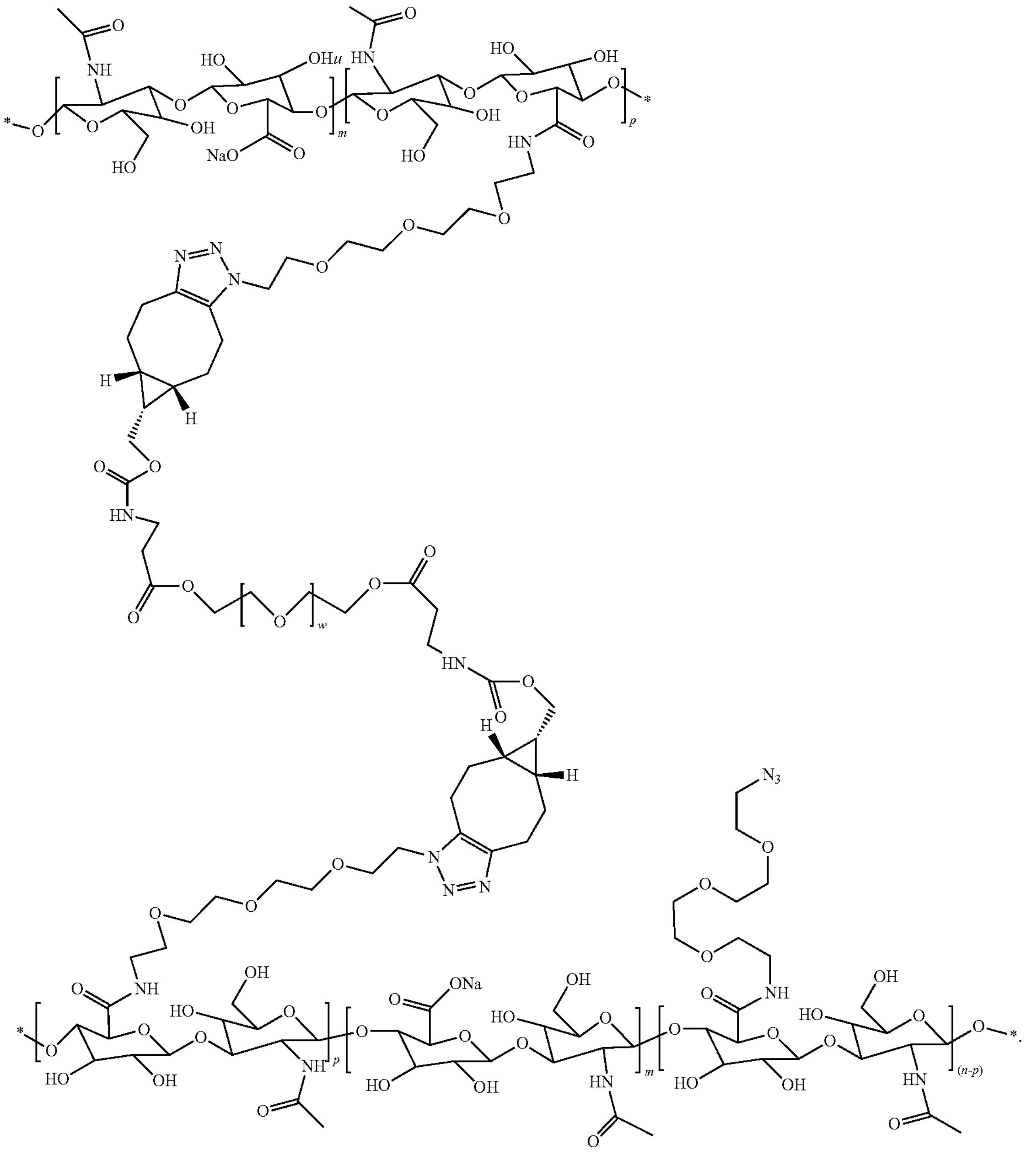

In another aspect, the cross-linked carrier comprises Formula XI:
(XI)
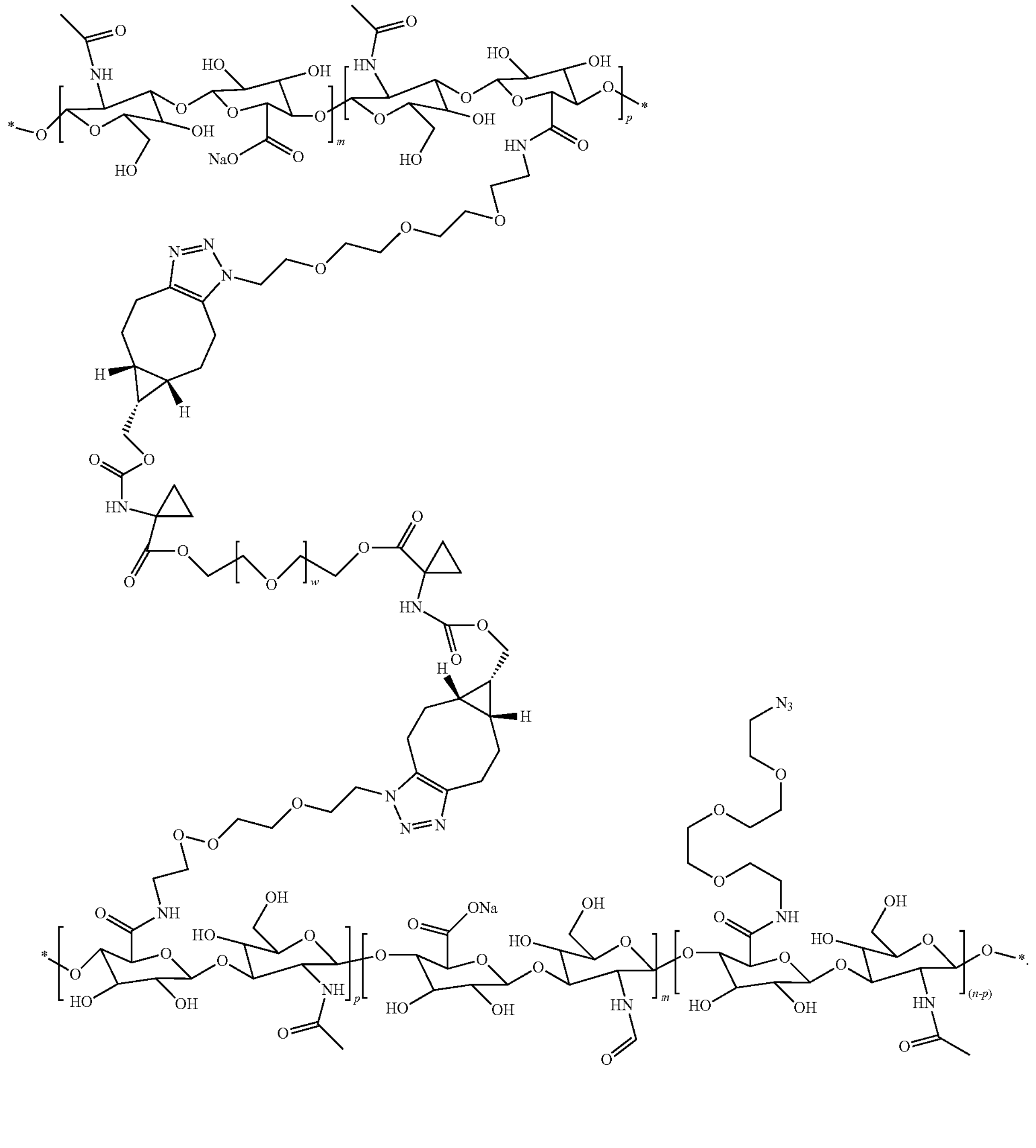

In another aspect, the cross-linked carrier comprises Formula XII:
(XII)
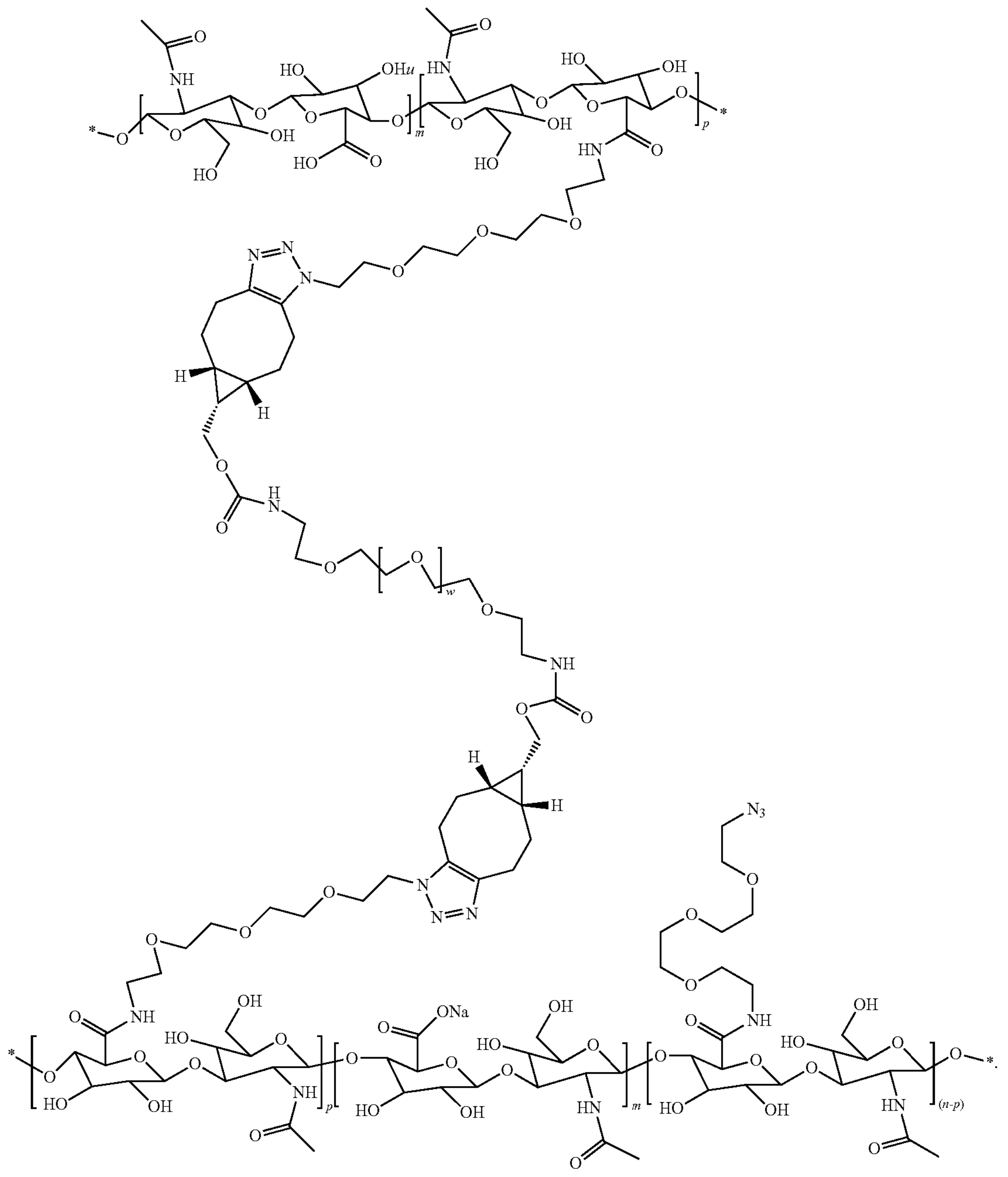

In another aspect, the cross-linked carrier comprises Formula XIIa:
(XIIa)
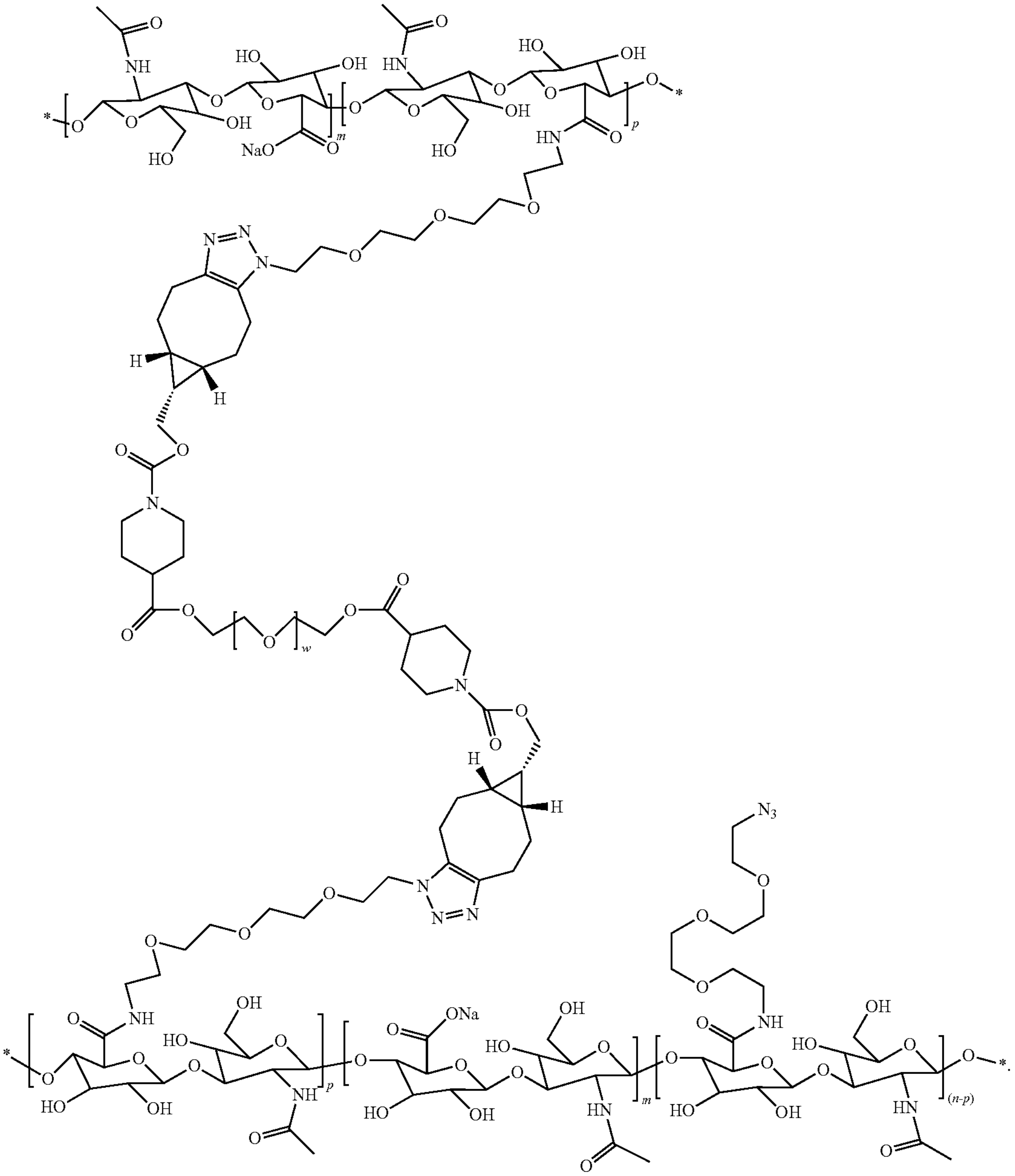

In another aspect, the cross-linked carrier comprises Formula XIIb:
(XIIb)
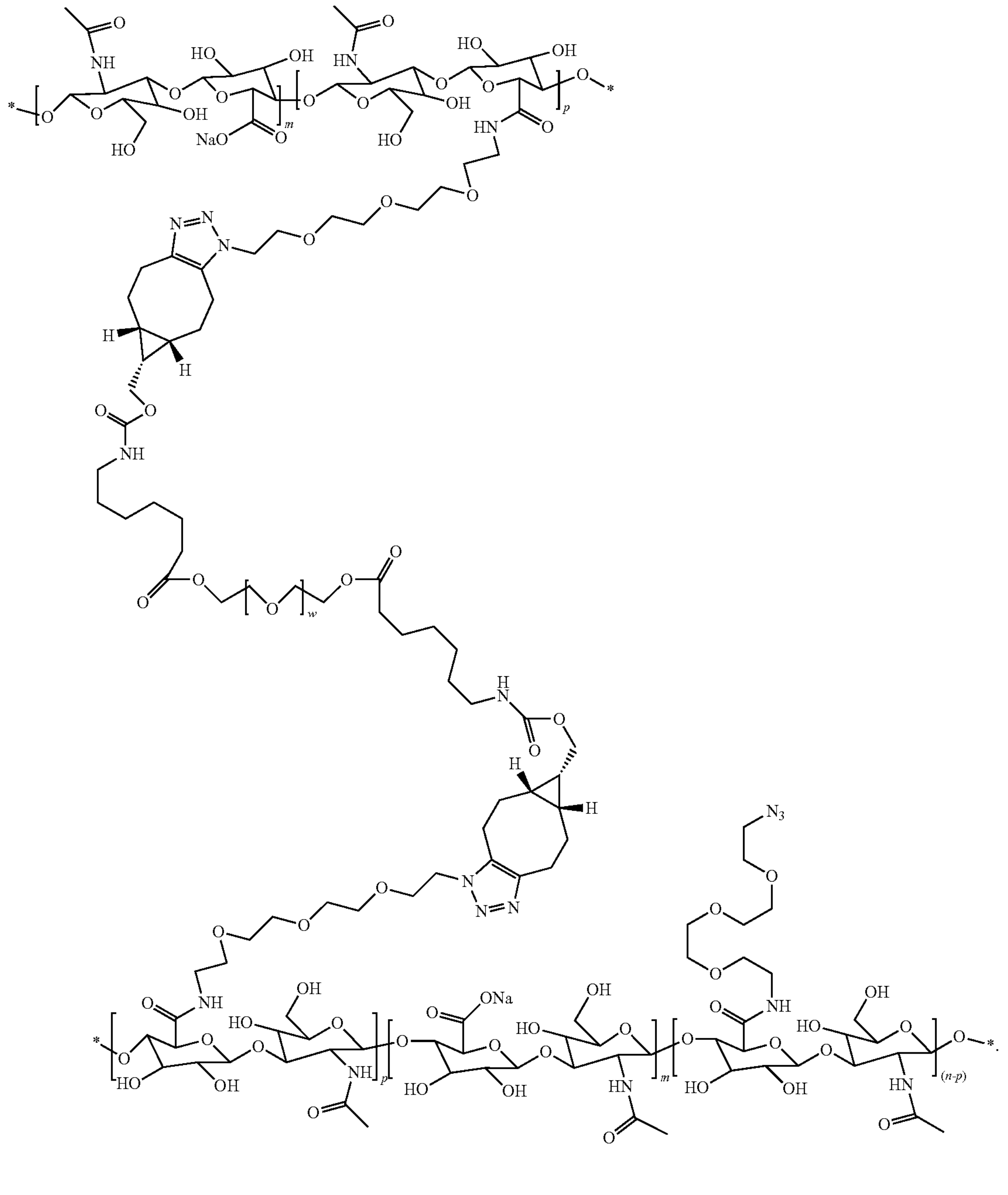

In another aspect, the cross-linked carrier comprises Formula XIIc:
(XIIc)
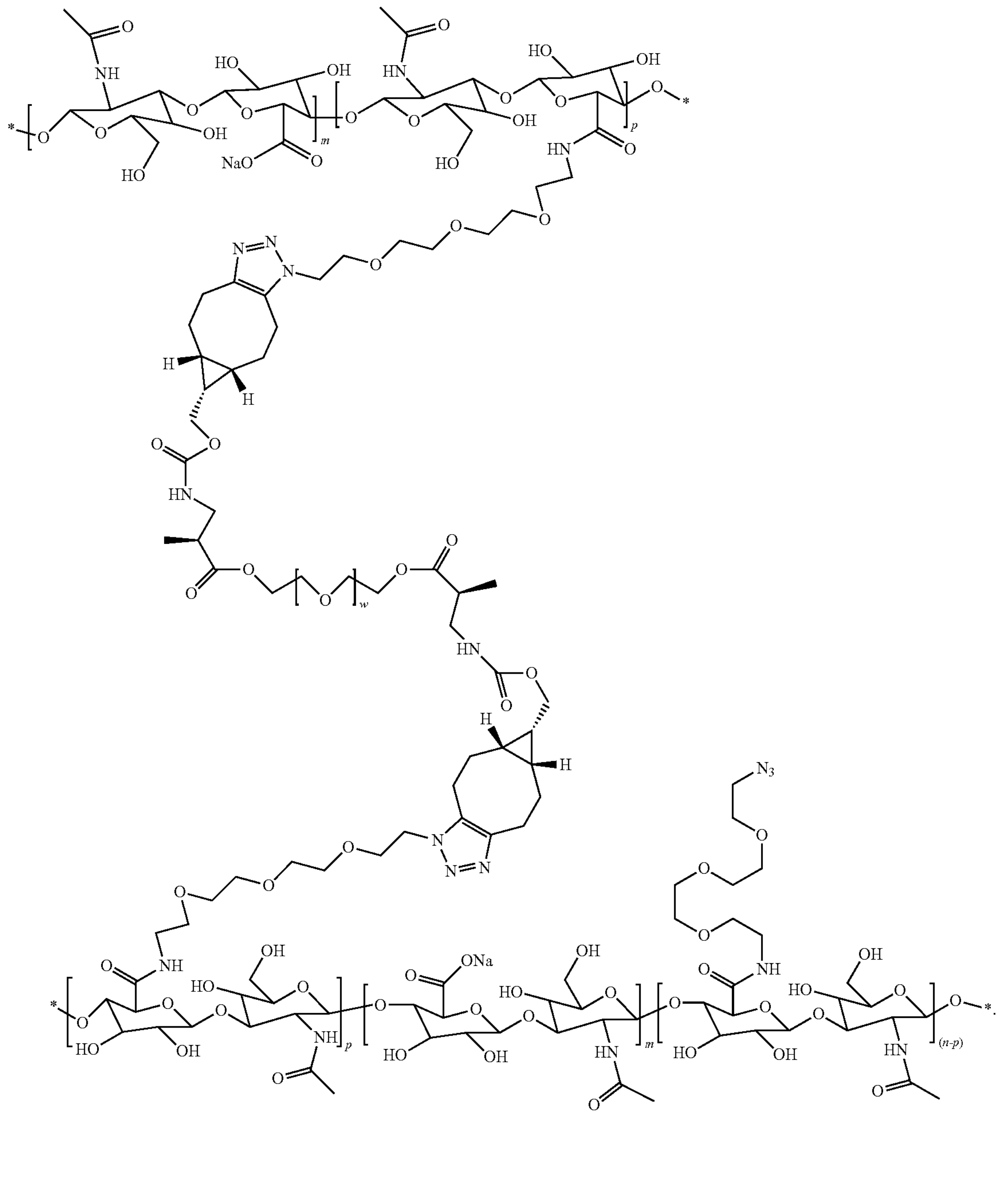
In another aspect, the cross-linked carrier comprises Formula XIII.

(XIII)
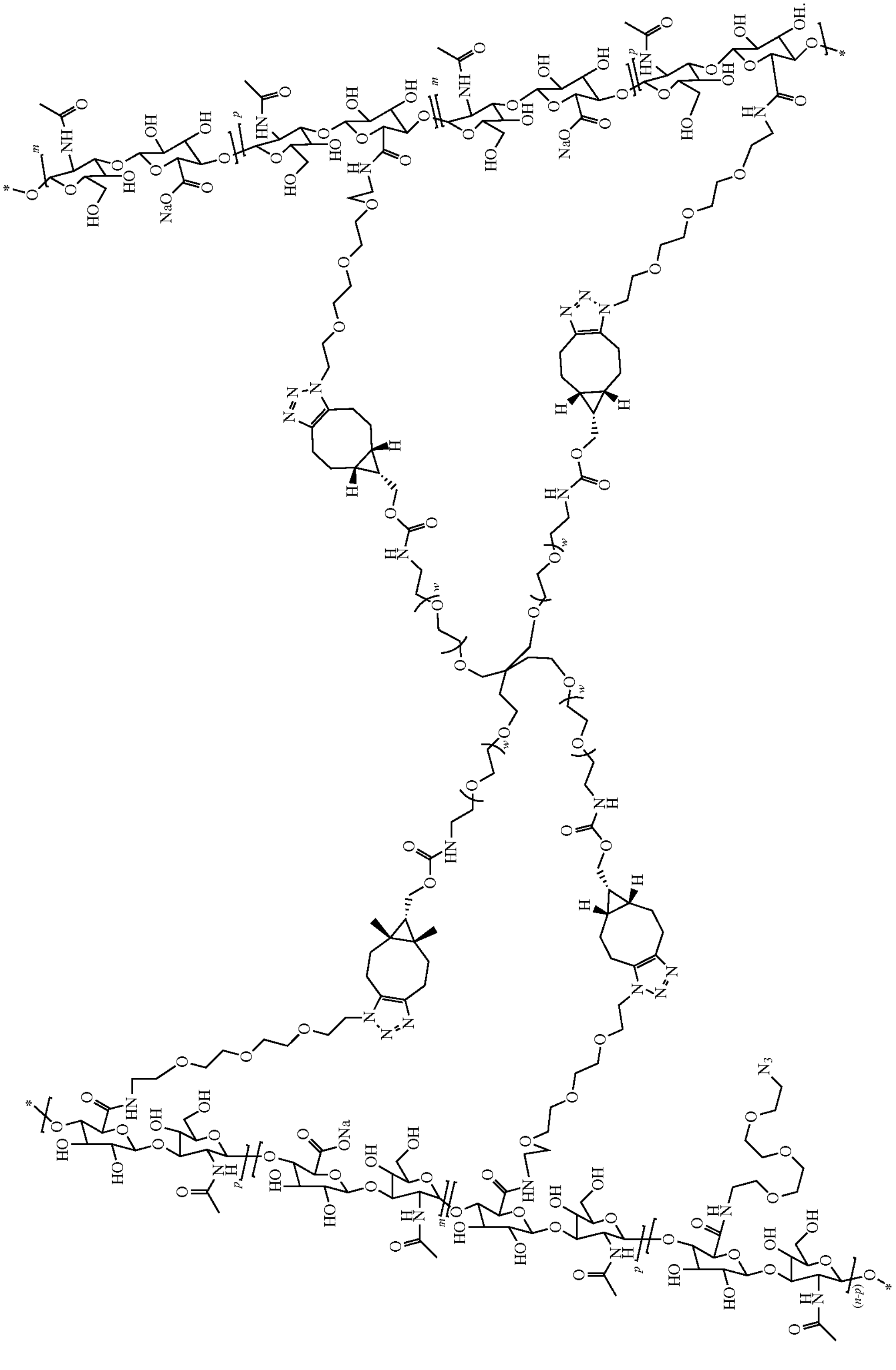

Another embodiment described herein is a drug adduct, D-R, wherein D is a biologically active moiety comprising at least one primary amine, secondary amine, or ring nitrogen atom of an azaheteroaryl ring; and R is a linker suitable for release of a biologically active moiety. In one aspect, D comprises a protein, nucleic acid, carbohydrate, peptide, nucleotide, oligosaccharide, or small molecule each of which has at least one primary or secondary amine and the small molecule has a molecular weight of between about 100 g/mol and about 2000 g/mol.

In one embodiment described herein, D comprises a low molecular weight biologically active molecule. In one aspect, D comprises a biologically active molecule comprising at least one primary amine, secondary amine, or ring nitrogen atom of an azaheteroaryl ring and a molecular weight of about 100 g/mol to about 2000 g/mol, including all integers within the specified range. In one aspect, D comprises a biologically active molecule comprising at least one primary amine, secondary amine, or ring nitrogen atom of an azaheteroaryl ring and a molecular weight of about 100 g/mol, about 150 g/mol, about 200 g/mol, about 250 g/mol, about 300 g/mol, about 350 g/mol, about 400 g/mol, about 450 g/mol, about 500 g/mol, about 550 g/mol, about 600 g/mol, about 650 g/mol, about 700 g/mol, about 750 g/mol, about 800 g/mol, about 850 g/mol, about 900 g/mol, about 950 g/mol, about 1000 g/mol, about 1050 g/mol, about 1100 g/mol, about 1150 g/mol, about 1200 g/mol, about 1250 g/mol, about 1300 g/mol, about 1350 g/mol, about 1400 g/mol, about 1450 g/mol, about 1500 g/mol, about 1550 g/mol, about 1600 g/mol, about 1650 g/mol, about 1700 g/mol, about 1750 g/mol, about 1800 g/mol, about 1850 g/mol, about 1900 g/mol, about 1950 g/mol, or about 2000 g/mol.

In another embodiment, D comprises a biologically active molecule comprising at least one primary amine, secondary amine, or ring nitrogen atom of an azaheteroaryl ring and a molecular weight of about 100 g/mol to about 2000 g/mol that modulates at least one biologically relevant target in a therapeutically beneficial manner. In one aspect, D comprises central nervous system-active agents, anti-infectives, anti-allergics, immunomodulating agents, anti-obesity agents, anticoagulants, antidiabetic agents, anti-neoplastics, antibacterials, anti-fungals, analgesics, contraceptives, anti-inflammatories, anti-angiogenic, anti-glaucoma, regenerative agents, steroids, vasodilating agents, vasoconstricting agents, or cardiovascular agents. In one aspect, D comprises acarbose, alaproclate, alendronate, amantadine, amikacin, amineptine, aminoglutethimide, amisulpride, amlodipine, amotosalen, amoxapine, amoxicillin, amphetamine, amphotericin B, ampicillin, amprenavir, aminone, anileridine, apraclonidine, apramycin, articaine, atenolol, atomoxetine, avizafone, baclofen, benazepril, benserazide, benzocaine, betaxolol, bleomycin, bromfenac, brofaromine, carvedilol, cathine, cathinone, carbutamid, cefalexine, clinafloxacin, ciprofloxacin, deferoxamine, delavirdine, desipramine, daunorubicin, dexmethylphenidate, dexmethylphenidate, diaphenylsulfon, dizocilpine, dopamin, dobutamin, dorzolamide, doxorubicin, duloxetine, eflornithine, enalapril, epinephrine, epirubicin, ergoline, ertapenem, esmolol, enoxacin, ethambutol, fenfluramine, fenoldopam, fenoterol, fingolimod, flecamide, fluvoxamine, fosamprenavir, frovatriptan, furosemide, fluoexetine, gabapentin, gatifloxacin, gemiflocacin, gentamicin, grepafloxacin, hexylcaine, hydralazine, hydrochlorothiazide, icofungipen, idarubicin, imiquimod, inversine, isoproterenol, isradipine, kanamycin A, ketamine, labetalol, lamivudine, levobunolol, levodopa, levothyroxine, lisinopril, lomefloxacin, loracarbef, maprotiline, mefloquine, melphalan, memantine, meropenem, mesalazine, mescaline, methyldopa, methylenedioxymethamphetamine, metoprolol, milnacipran, mitoxantron, moxifloxacin, norepinephrine, norfloxacin, nortriptyline, neomycin B, nystatin, oseltamivir, pamidronic acid, paroxetine, pazufloxacin, pemetrexed, perindopril, phenmetrazine, phenelzine, pregabalin, procaine, pseudoephedrine, protriptyline, reboxetine, ritodrine, sabarubicin, salbutamol, serotonin, sertraline, sitagliptin, sotalol, spectinomycin, sulfadiazin, sulfamerazin, sertraline, spectinomycin, sulfalen, sulfamethoxazol, tacrine, tamsulosin, terbutaline, timolol, tirofiban, tobramycin, tocamide, tosufloxacin, trandolapril, tranexamic acid, tranylcypromine, trimetrexate, trovafloxacin, valaciclovir, valganciclovir, vancomycin, viomycin, viloxazine, and zalcitabine.

In another embodiment, D comprises one or more biologically active peptides including, but not limited to C-type natriuretic peptide (CNP), atrial natriuretic peptide (ANP), exendin-4, insulin, adrenocorticotropic hormone, adrenomedullin, adropin, ω-agatoxin, agouti-related protein, angiotensin(s), apelin 12, apelin 13, apelin 36, or derivatives thereof, bradykinin, calcitonin, cocaine- and amphetamine-regulated transcript (CART), corticotropin releasing factor (CRF), α-defensins, β-defensins, delta sleep-inducing peptide (DSIP), elastase-specific inhibitor (Elafin), endokinins, endomorphins, endorphins, endothelins, exendin, fibronectin active fragment, galanin, galanin-like peptide, big gastrin, gastrin I, gastrin related peptide, gastric inhibitory polypeptide, gastrin releasing peptide, ghrelin, des-acyl ghrelin, glucagon, glucagon-like peptide, growth hormone releasing factor, *Grammostola spatulata* GsMTx-4, guangxitoxin-1E, guanylin, hepcidin 1, hepcidin/LEAP-1, histatin 5, human growth hormone, humanin, huwentoxin, iberiotoxin, imperatoxin A, insulin like growth factors, intermedin, TRL 1620, joining peptide, kaliotoxin, kisspeptins, kurtoxin, lipotropin, lipotropin, liver-cell growth factor, liver-expressed antimicrobial peptide 2, luteinizing hormone releasing hormone, lysenin, LL-37, margatoxin, mastoparan, mast cell degranulating peptide, melanin-concentrating hormone, melanocyte stimulating hormone, MSH-release inhibiting factor, midkine, molluscan cardioexcitatory neuropeptide, morphine tolerance peptide, motilin, muscarinic toxins, neuroendocrine regulatory peptide-2, neurokinin A, neurokinin B, neuromedins, neuronostatin-13, neuropeptides, neurotensin, neurotoxin NSTX-3, nocistatin, nociceptin, obestatin, opioid peptides (enkephalins, endorphins, BAM-12P, casomorphin, dynorphins, endomorphins, neoendorphins, nociceptin), orexin-A/-B, orphanin, osteocalci, oxytocin, pancreastatin, parathyroid hormone, parathyroid hormone related protein, peptide 234, peptide histidine-methionine, peptide T, peptide YY, Physalaemin, pituitary adenylate cyclase activating polypeptides, platelet factor-4, plectasin, pleiotrophin, proadrenomedullin, prolactin-releasing peptide, psalmotoxin 1, purotoxin-1, pyroglutamylated RFamide peptide, renin, RFamide-related peptide-1, RFamide-related peptide-3, salusin-α/β, sarafotoxins, schizophrenia related peptide, scyllatoxin, secretin, serelaxin, serum thymic factor, sodium potassium ATPase inhibitor-1, somatostatin, stichodactyla toxin, substance K, stresscopin, stresscopin-related peptide, substance P, tachykinins, tarantula SNX-482, tarantula ProTx-I, tarantula ProTx-II, tertiapin, tityustoxin Ka, thyrotropin releasing hormone, tuftsin, uroguanylin, uroguanylin isomer A or B, urocortin, urocortin II, urotensin II, urotensin II-related peptide, vasoactive intestinal peptide, vasopressin, vasotocin, virus replication inhibiting peptide, xenin, or combinations thereof.

In another aspect, D comprises one or more of ACTH, adenosine deaminase, agalsidase, alfa-1 antitrypsin (AAT), alfa-1 proteinase inhibitor (API), alteplase, amylins (amylin, symlin), anistreplase, ancrod serine protease, antibodies (monoclonal or polyclonal, and fragments or fusions), antithrombin III, antitrypsins, aprotinin, asparaginases, atosiban, biphalin, bivalirudin, bone-morphogenic proteins, bovine pancreatic trypsin inhibitor (BPTI), cadherin fragments, calcitonin (salmon), collagenase, complement C1 esterase inhibitor, conotoxins, cytokine receptor fragments, DNase, dynorphin A, endorphins, enfuvirtide, enkephalins, erythropoietins, exendins, factor VII, factor VIIa, factor VIII, factor VIIIa, factor IX, fibrinolysin, fibroblast growth factor (FGF), growth hormone releasing peptide 2 (GHRP2), fusion proteins, follicle-stimulating hormones, gramicidin, ghrelin, desacyl-ghrelin, granulocyte colony stimulating factor (G-CSF), galactosidase, glucagon, glucagon-like peptides, glucocerebrosidase, granulocyte macrophage colony stimulating factor (GM-CSF), human heat shock proteins (HSP), phospho lipase-activating protein (PLAP), gonadotropin chorionic (hCG), hemoglobins, hepatitis B vaccines, hirudin, human serine protease inhibitor, hyaluronidases, iduronidase, immune globulins, influenza vaccines, interleukins (1 alfa, 1 beta, 2, 3, 4, 6, 10, 11, 12, 13, 21), IL-1 receptor antagonist (rhIL-Ira), insulins, insulin like growth factors, insulin-like growth factor binding protein (rhIGFBP), interferons (alfa 2a, alfa 2b, alfa 2c, beta 1a, beta 1b, gamma 1a, gamma 1b), intracellular adhesion molecule, keratinocyte growth factor (KGF), P-selectin glycoprotein ligand (PSGL), transforming growth factors, lactase, leptin, leuprolide, levothyroxine, luteinizing hormone, lyme vaccine, natriuretic peptides (ANP, BNP, CNP and fragments), neuropeptide Y, pancrelipase, pancreatic polypeptide, papain, parathyroid hormone, PDGF, pepsin, peptide YY, platelet activating factor acetylhydrolase (PAF-AH), prolactin, protein C, thymalfasin, octreotide, secretin, sermorelin, soluble tumor necrosis factor receptor (TNFR), superoxide dismutase (SOD), somatropin (growth hormone), somatostatin, streptokinase, sucrase, terlipressin, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urodilatin, urate oxidase, urokinase, vaccines, vascular endothelial growth factor (VEGF), vasoactive intestinal peptide, vasopressin, ziconotide, lectin, ricin, or combinations thereof.

In another embodiment, D comprises abciximab, adalimumab, aflibercept, alemtuzumab, basiliximab, belimumab, bevacizumab, brentuximab, canakinumab, certolizumab, cetuximab, daclizumab, daratumumab, denosumab, eculizumab, efalizumab, golimumab, ibritumomab, infliximab, ipilimumab, lampalizumab, muromonab-CD3, natalizumab, nivolumab, ofatumumab, omalizumab, palivizumab, panitumumab, pegpleranib, pembrolizumab, ranibizumab, rituximab, tocilizumab, tositumomab, trastuzumab, ustekinumab, vedolizumab, or derivatives or combinations thereof.

In another embodiment, D comprises abatacept, albumin, alefacept, alpha-I protease inhibitor, alpha-galactosidase A, alpha-L-iduronidase, botulinum toxin A, botulinum toxin B, darbepoetin, denileukin, dornase alfa, collagenase, complement proteins, erythropoietin, etanercept, Factor VIII, fibrin, fibrinogen, filgrastim, follicle-stimulating hormone, glucocerebrosidase, granulocyte colony-stimulating factor (G-CSF), sargramostim, human growth hormone, human chorionic gonadotropin, hyaluronidase, insulin, insulin like growth factors, insulin-like growth factor 1 (IGF-1), interferons (IF), lutropin, oprelvekin, pramlintide, mecasermin, N-acetylgalactosamine-4-sulfatase (galsulfase), tissue plasminogen activator (TPA), protein-based vaccines, or combinations thereof.

In another embodiment, D comprises one or more of proteins, peptides, antibodies, humanized antibodies, antibody fragments, Fabs, scFvs, nucleic acids, carbohydrates, small molecules, or combinations thereof.

In another embodiment, D comprises one or more of nucleotides, oligonucleotides, polynucleotides, nucleic acids, including but not limited to DNAs, RNAs, PNAs, siRNAs, miRNAs, mRNAs, tRNAs, rRNAs, or combinations thereof.

In one embodiment, D comprises brolucizumab (SEQ ID NO:4), D2 (SEQ ID NO:5), D3 (SEQ ID NO:6), or D4 (SEQ ID NO:7), ranibizumab, bevacizumab, 5-(5,6,7,8-Tetrahydro-pyrido[3,4-d]pyrimidin-4-yloxy)-indole-1-carboxylic acid [5-(1-methyl-cyclopropyl)-2H-pyrazol-3-yl]-amide; 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide; N-(1-methyl-5-(trifluoromethyl)-1H-pyrazol-3-yl)-5-((6-((methylamino)methyl)pyrimidin-4-yl)oxy)-1H-indole-1-carboxamide; (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, or combinations thereof.

Another embodiment described herein is a drug delivery system comprising a carrier-traceless linker biologically-active agent conjugate, D-R—$R^{11}$, wherein D comprises a biologically active moiety comprising at least one primary amine, secondary amine, or ring nitrogen atom of an azaheteroaryl ring as described herein, R comprises a traceless linker as described herein attached to $R^{11}$, comprising a carrier polymer or hydrogel as described herein. In one aspect, $R^{11}$ comprises hyaluronic acid, cross-linked hyaluronic acid, polyethylene glycol, cross-linked polyethylene glycol or other suitable polymer as described herein. In another aspect, R comprises a traceless linker as described herein. In another aspect, D comprises one or more of proteins, peptides, antibodies, Fabs, Fcs, scFvs, nucleic acids, siRNAs, miRNAs, mRNAs, carbohydrates, peptide nucleic acids (PNAs), small organic molecules comprising at least one primary amine, secondary amine, or ring nitrogen atom of an azaheteroaryl ring, or combinations thereof. In one aspect, D comprises brolucizumab (SEQ ID NO:4), D2 (SEQ ID NO:5), D3 (SEQ ID NO:6), or D4 (SEQ ID NO:7), ranibizumab, bevacizumab, 5-(5,6,7,8-Tetrahydro-pyrido[3,4-d]pyrimidin-4-yloxy)-indole-1-carboxylic acid [5-(1-methyl-cyclopropyl)-2H-pyrazol-3-yl]-amide; 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide; N-(1-methyl-5-(trifluoromethyl)-1H-pyrazol-3-yl)-5-((6-((methylamino)methyl)pyrimidin-4-yl)oxy)-1H-indole-1-carboxamide; (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, or combinations thereof.

In another embodiment, D-R—$R^{11}$ comprises Formula XIV, wherein "Drug" can be one or more of brolucizumab (SEQ ID NO:4), D2 (SEQ ID NO:5), D3 (SEQ ID NO:6), or D4 (SEQ ID NO:7), ranibizumab, bevacizumab, 5-(5,6,7,8-tetrahydro-pyrido[3,4-d]pyrimidin-4-yloxy)-indole-1-carboxylic acid [5-(1-methyl-cyclopropyl)-2H-pyrazol-3-yl]-amide; 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide; N-(1-methyl-5-(trifluoromethyl)-1H-pyrazol-3-yl)-5-((6-((methylamino)methyl)pyrimidin-4-yl)oxy)-1H-indole-1-carboxamide; (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, or combinations thereof.

In some embodiments, D-R-$R^{11}$ comprises any of the species shown in Formulas XIV-XXIII.

In one embodiment, the drug or biologically active agent D, comprises polypeptides D2 (SEQ ID NO:5), or a pegylated version thereof, such as for example, D3 (SEQ ID NO:6). The D2 and D3 polypeptides, as well as derivatives thereof, can be prepared as described in International Patent Application Publication No. WO 2007/146689, which is incorporated by reference herein for such teachings.

In another embodiment, the drug or biologically active agent D, comprises brolucizumab (SEQ ID NO:4). Brolucizumab is a single chain variable fragment (scFv) comprising a VH region (SEQ ID NO:1), a VL region (SEQ ID NO:2), and a linker region (SEQ ID NO:3). Brolucizumab, as well as derivatives thereof, can be prepared as described in International Patent Application Publication No. WO 2009/155724, which is incorporated by reference herein for such teachings.

A methionine derived from the start codon is present in the VL of brolucizumab. In some cases, the methionine can be cleaved posttranslationally before being assembled into a drug delivery system as described herein.

In another embodiment, the drug or biologically active agent D, comprises D4 (SEQ ID NO:7). D4 is a 13 amino acid peptide comprising the sequence pE-R-P-R-L-C-H-K-G-P-Nle-C-F-OH (SEQ ID NO:7), comprising a disulfide bond between $C_6$ and $C_{12}$ and where pE indicates pyroglutamate and Nle indicates norleucine. D4 as well as derivatives thereof, can be prepared as described in International Patent Application Publication No. WO 2013/111110, which is incorporated by reference herein for such teachings.

In another embodiment, the drug or biologically active agent D, comprises apelin 12, apelin 13, apelin 36, or a derivative thereof. Apelin and derivatives are disclosed in WO2013/111110, WO 2014/081702, WO 2015/013168, WO 2015/013165, or WO 2015/013167, which are each incorporated by reference herein for such teachings.

In another embodiment, the drug or biologically active agent D, comprises one or more anti-vascular endothelial growth factor drugs, such as bevacizumab or ranibizumab. Bevacizumab is a recombinant humanized monoclonal IgG1 antibody that binds to and inhibits the biologic activity of human vascular endothelial growth factor (VEGF) in in vitro and in vivo assay systems. Bevacizumab contains human framework regions and the complementarity-determining regions of a murine antibody that binds to VEGF. The antibody has an approximate molecular weight of 149 kDa. Bevacizumab is produced in Chinese Hamster Ovary expression system in a nutrient medium. Ranibizumab is a recombinant humanized IgG1 kappa isotype monoclonal antibody fragment designed for intraocular use. Ranibizumab binds to and inhibits the biologic activity of human vascular endothelial growth factor A (VEGF-A). Ranibizumab, which lacks an Fc region, has a molecular weight of approximately 48 kDa and is produced by an *E. coli* expression system in a nutrient medium. Bevacizumab and ranibizumab are described in International Patent Application Publication Nos. WO 1994/004679 and WO 1998/45331, respectively, which are both incorporated by reference herein for such teachings.

In another embodiment, the drug or biologically active agent D, comprises 5-(5,6,7,8-tetrahydro-pyrido[3,4-d]pyrimidin-4-yloxy)-indole-1-carboxylic acid [5-(1-methyl-cyclopropyl)-2H-pyrazol-3-yl]-amide; 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide; N-(1-methyl-5-(trifluoromethyl)-1H-pyrazol-3-yl)-5-((6-((methylamino)methyl)pyrimidin-4-yl)oxy)-1H-indole-1-carboxamide; or (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide. The synthesis of these molecules are described in International Patent Application Publication Nos. WO 2010/066684, which is incorporated by reference herein for such teachings.

Another embodiment described herein is a process for assembling a drug delivery system; the process may comprise one of the following sequence of steps:

(a) preparing a carrier molecule, $R^{11}$, where $R^{11}$ is a cross-linked hydrogel, then this step comprises the process used to prepare that hydrogel; the carrier molecule may optionally be purified at this stage;
(b) separately conjugating the traceless linker, R, to a biologically active agent, D, comprising a primary amine, secondary amine, or a ring nitrogen atom of an azaheteroaryl ring, thereby forming the traceless linker-D adduct; the traceless linker-D adduct may optionally be purified at this stage,
(c) conjugating the carrier molecule, $R^{11}$, with the traceless linker-D adduct; and
(d) purifying the drug delivery system from the reagents.

This process is shown in Scheme 5A below.

Another embodiment described herein is a process for assembling a drug delivery system comprising the following steps:

(a) preparing a carrier molecule, $R^{11}$, where $R^{11}$ is a cross-linked hydrogel, then this step comprises the process used to prepare that hydrogel; the carrier molecule may optionally be purified at this stage;
(b) conjugating the traceless linker, R, to the carrier molecule, $R^{11}$, thereby forming the carrier molecule-traceless linker adduct, which may optionally be purified at this stage;
(c) conjugating the biologically active agent, D, comprising a primary amine, secondary amine, or a ring nitrogen atom of an azaheteroaryl ring, to the carrier molecule-traceless linker adduct; and
(d) purifying the drug delivery system from the reagents.

This process is shown in Scheme 5B below.

Another embodiment described herein is a process for assembling a drug delivery system comprising the following steps:

(a) preparing a non-cross-linked carrier molecule, $R^{11}$, the carrier molecule may optionally be purified at this stage;
(b) separately conjugating the traceless linker, R, to a biologically active agent, D, comprising a primary amine, secondary amine, or a ring nitrogen atom of an azaheteroaryl ring, thereby forming the traceless linker-D adduct; the traceless linker-D adduct may optionally be purified at this stage;
(c) conjugating the carrier molecule, $R^{11}$, with the traceless linker-D adduct, which may optionally be purified at this stage;
(d) preparing the cross-linked hydrogel by incubating the non-cross-linked carrier molecule-traceless linker-biologically active agent, $R^{11}$—R-D, with the appropriate cross-linking reagent to form the hydrogel; and
(e) purifying the drug delivery system from the reagents.

This process is shown in Scheme 5C below.

Another embodiment described herein is a process for assembling a drug delivery system comprising the following steps:

(a) preparing a non-cross-linked carrier molecule, $R^{11}$, the carrier molecule may optionally be purified at this stage;

(b) conjugating the traceless linker, R, to the carrier molecule, $R^{11}$, thereby forming the carrier molecule-traceless linker adduct, which may optionally be purified at this stage; and (c) conjugating the biologically active agent, D, comprising a primary amine, secondary amine, or a ring nitrogen atom of an azaheteroaryl ring, to the carrier molecule-traceless linker adduct;

(d) preparing the cross-linked hydrogel by incubating the non-cross-linked carrier molecule-traceless linker-biologically active agent, $R^{11}$—R-D, with the appropriate cross-linking reagent to form the hydrogel; and (e) purifying the drug delivery system from the reagents. This process is shown in Scheme 5D below.

Another embodiment described herein is a process for assembling a drug delivery system comprising the following steps:

(a) preparing a non-cross-linked carrier molecule, $R^{11}$, the carrier molecule may optionally be purified at this stage;

(b) conjugating the traceless linker, R, to the carrier molecule, $R^{11}$, thereby forming the carrier molecule-traceless linker adduct, which may optionally be purified at this stage;

(c) preparing the cross-linked hydrogel by incubating the non-cross-linked carrier molecule-traceless linker-adduct, $R^{11}$—R, with the appropriate cross-linking reagent to form the hydrogel, which may optionally be purified at this stage;

(d) conjugating the biologically active agent, D, comprising a primary amine, secondary amine, or a ring nitrogen atom of an azaheteroaryl ring, to the cross-linked carrier molecule-traceless linker adduct, which may optionally be purified at this stage; and (e) purifying the drug delivery system from the reagents. This process is shown in Scheme 5E below.

Schemes 5A-E. Scheme 5 shows five processes, A-E, for assembling drug delivery systems as described herein.

Legend:

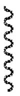 Carrier molecule, $R^{11}$, non-crosslinked crosslinker

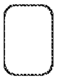 Carrier molecule, $R^{11}$, crosslinked hydrogel traceless linker, R

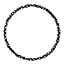 biologically active agent, D

Scheme 5A

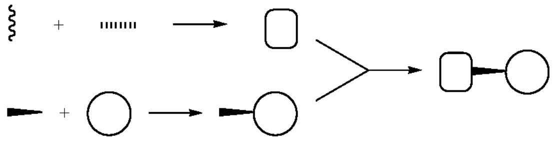

Scheme 5B

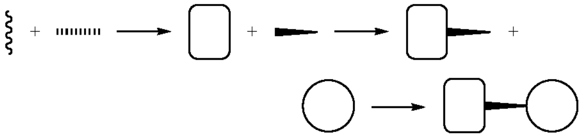

Scheme 5C

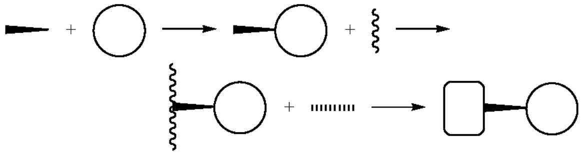

Scheme 5D

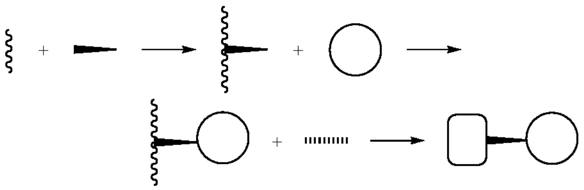

Scheme 5E

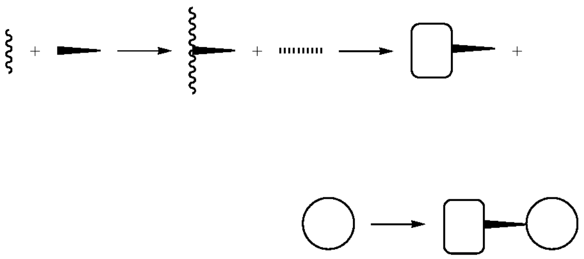

In one embodiment, the drug delivery system can comprise Formula (XIV):

(XIV)
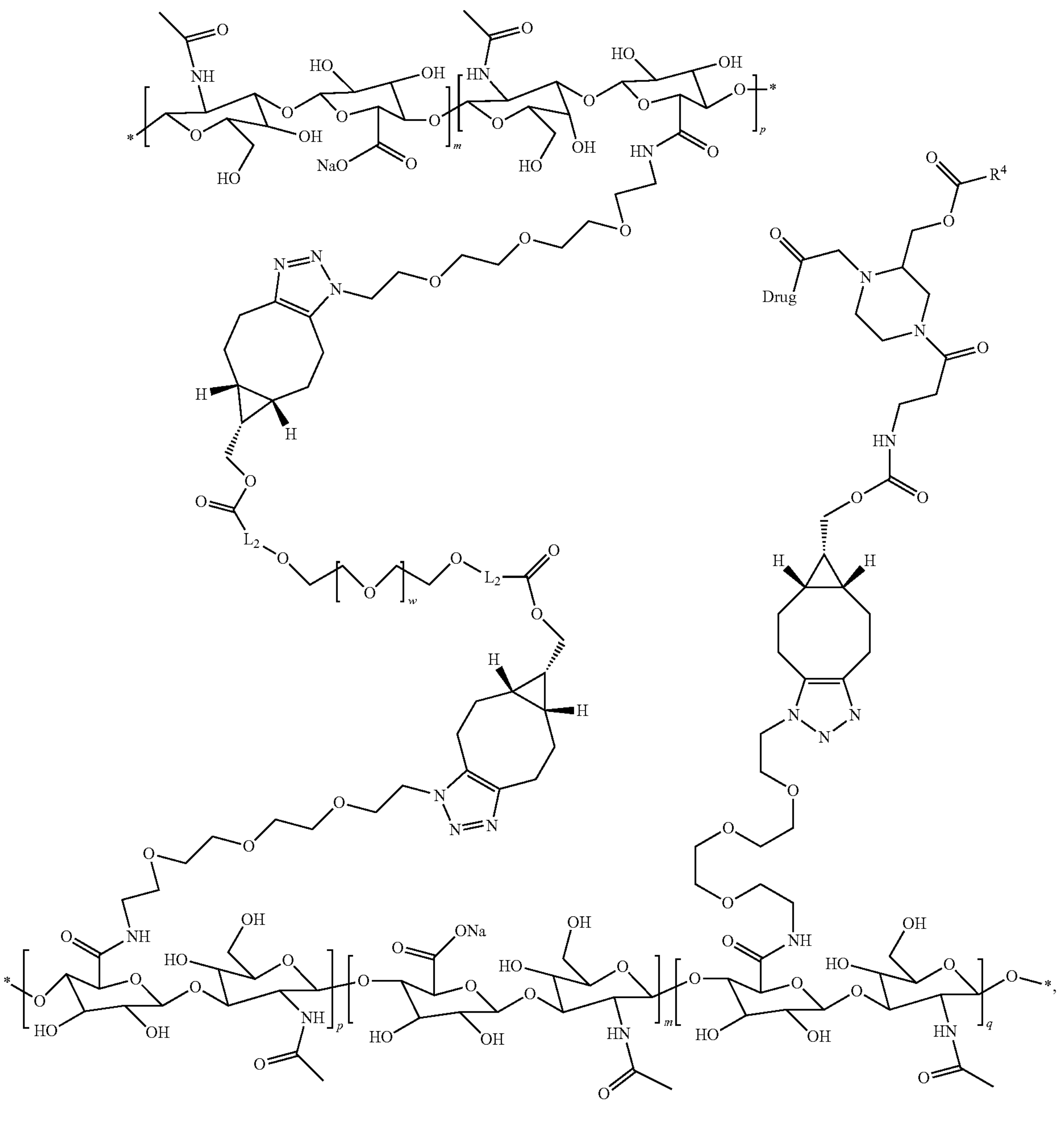
wherein $L_2$ represents a spacer group, which can be specific to a particular cross-linker, and "Drug" represents a biologically active molecule comprising at least one primary amine, secondary amine, or ring nitrogen atom of an azaheteroaryl ring that modulates at least one biologically relevant target in a therapeutically beneficial manner.

In one embodiment, spacers, $L_2$, comprise any species shown in Table 5.
TABLE 5
| Exemplary $L_2$ Spacers<br>In the table below, $L_2$ represents the spacerbetween O and C(O)O.<br>For Example: |
|---|
| 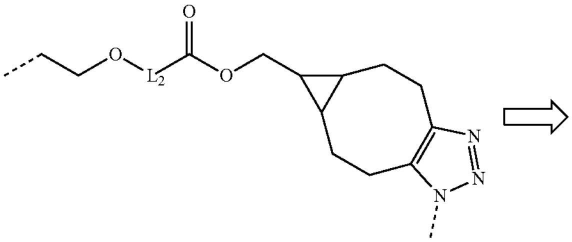 |
| 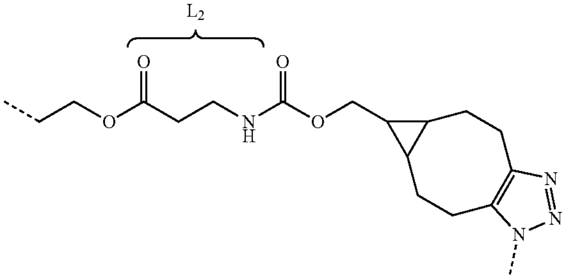 |
| $L_2$ = 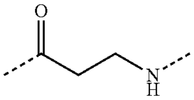 |
| 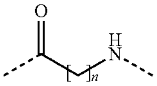<br>n = 1-10 |
| 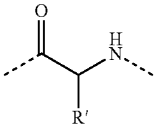<br>R' = Me, Et, Pr, iPr,<br>C1-C6 alkyl, C1-C6<br>cycloalkyll |
TABLE 5-continued
| |
|---|
| 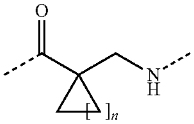<br>n = 1-6 |
| 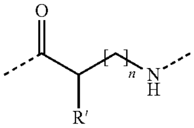<br>R' = Me, Et, Pr, iPr,<br>C1-C6 alkyl, C1-C6<br>cycloalkyl<br>n = 1-5 |
| 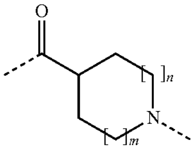<br>n = 0-2<br>m = 0-2 |
| 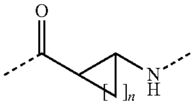<br>n = 1-5 |
| 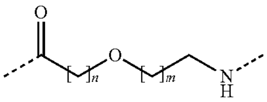<br>n = 1-6<br>m = 1-6 |
| 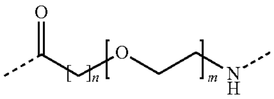<br>n = 1-6<br>m = 1-6 |

In another embodiment, the drug delivery system can comprise Formula (XV) with the drug being brolucizumab:
(XV)
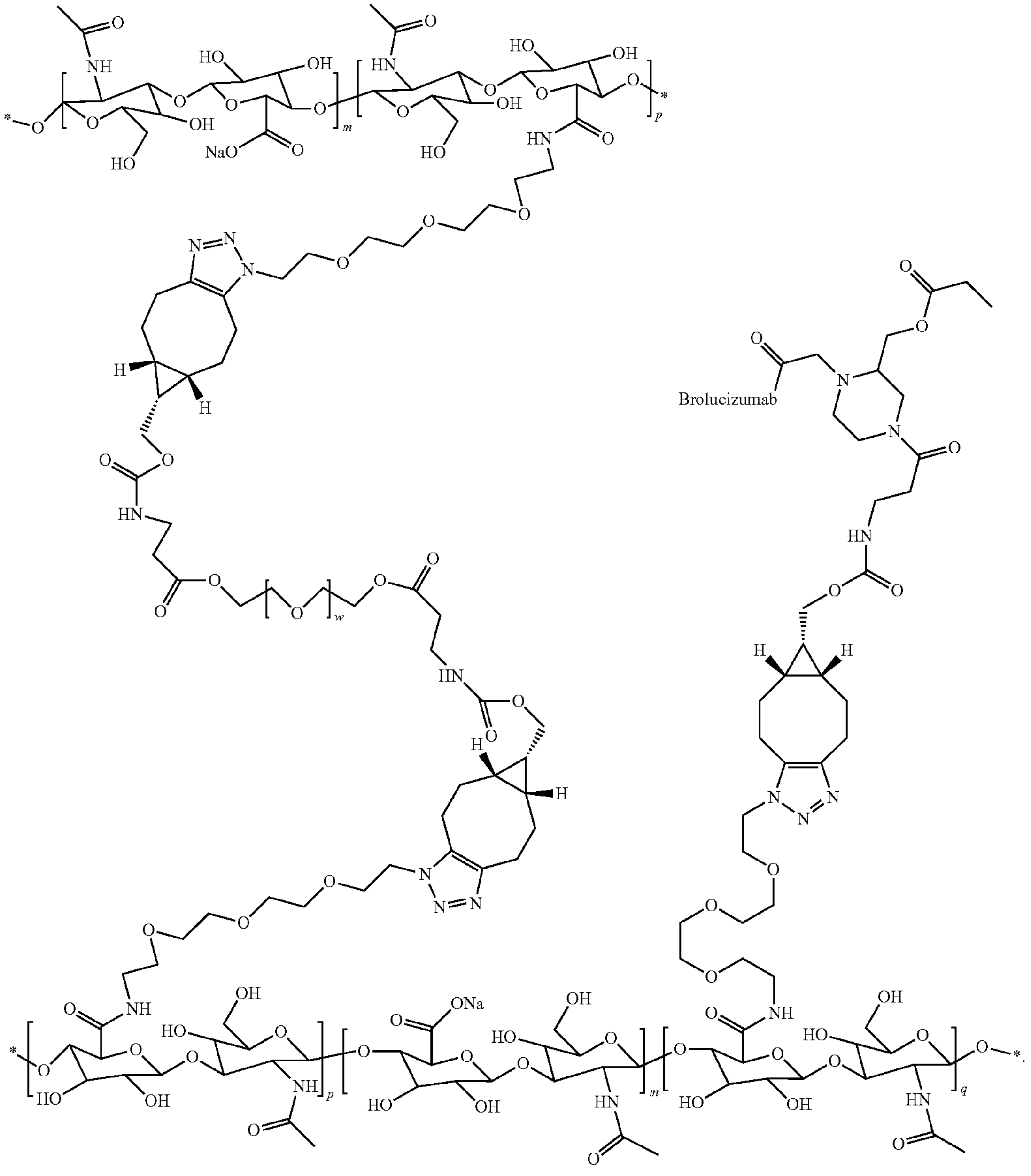

In another embodiment, the drug delivery system can comprise Formula (XVI) with the drug being brolucizumab:
(XVI)
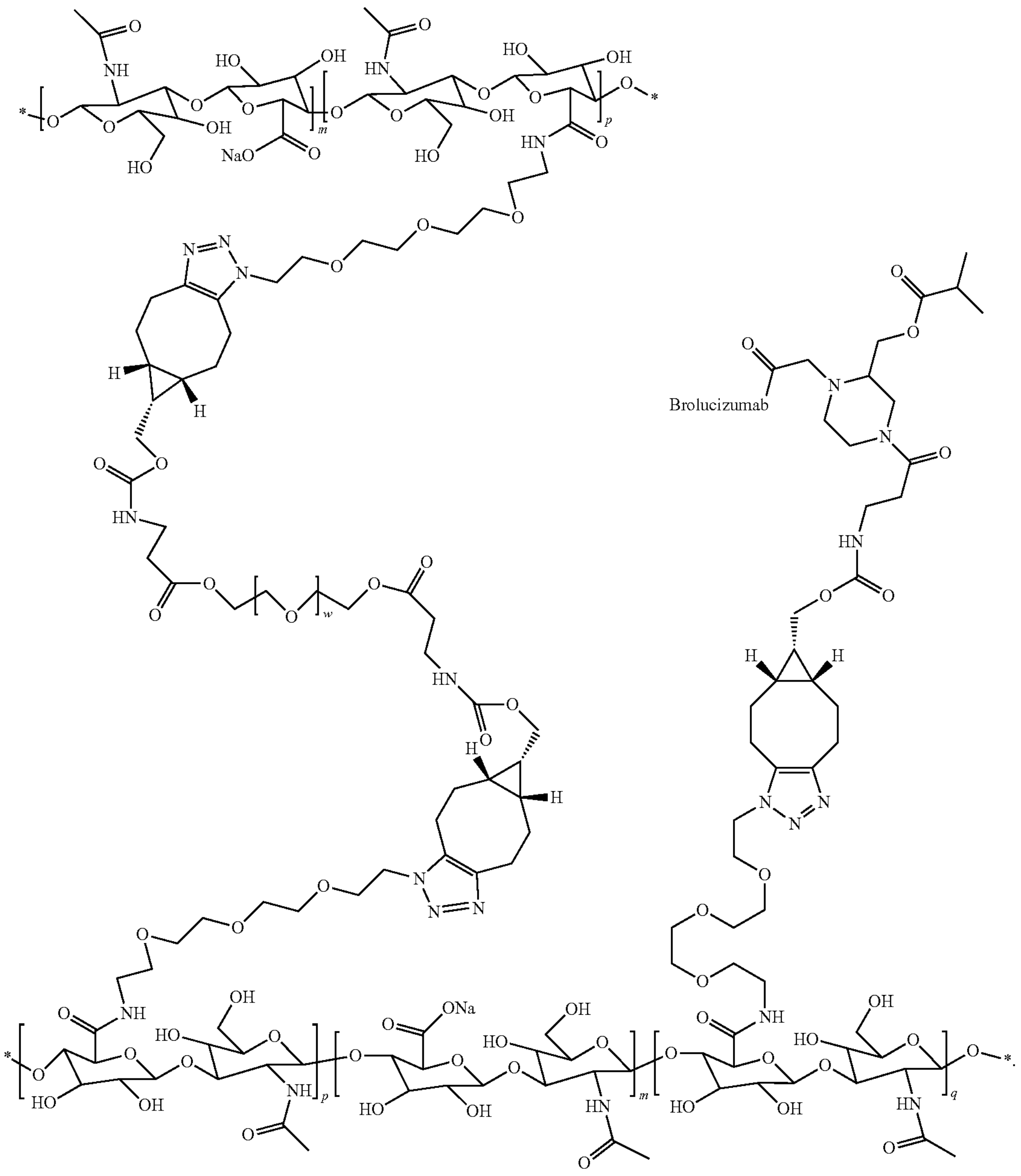

In another embodiment, the drug delivery system can comprise Formula (XVII) with the drug being brolucizumab:
(XVII)
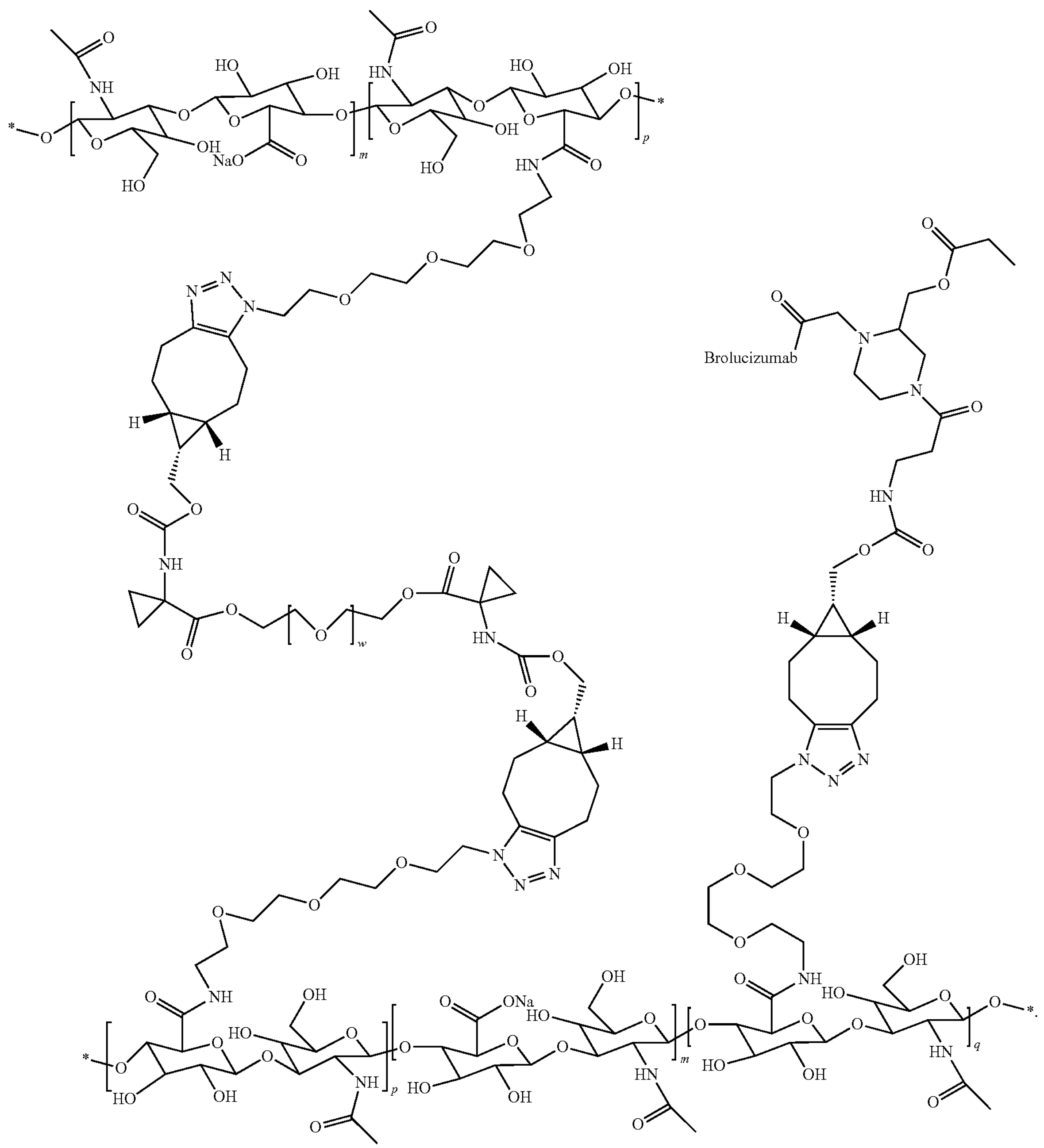

In another embodiment, the drug delivery system can comprise Formula (XVIII) with the drug being brolucizumab:
(XVIII)
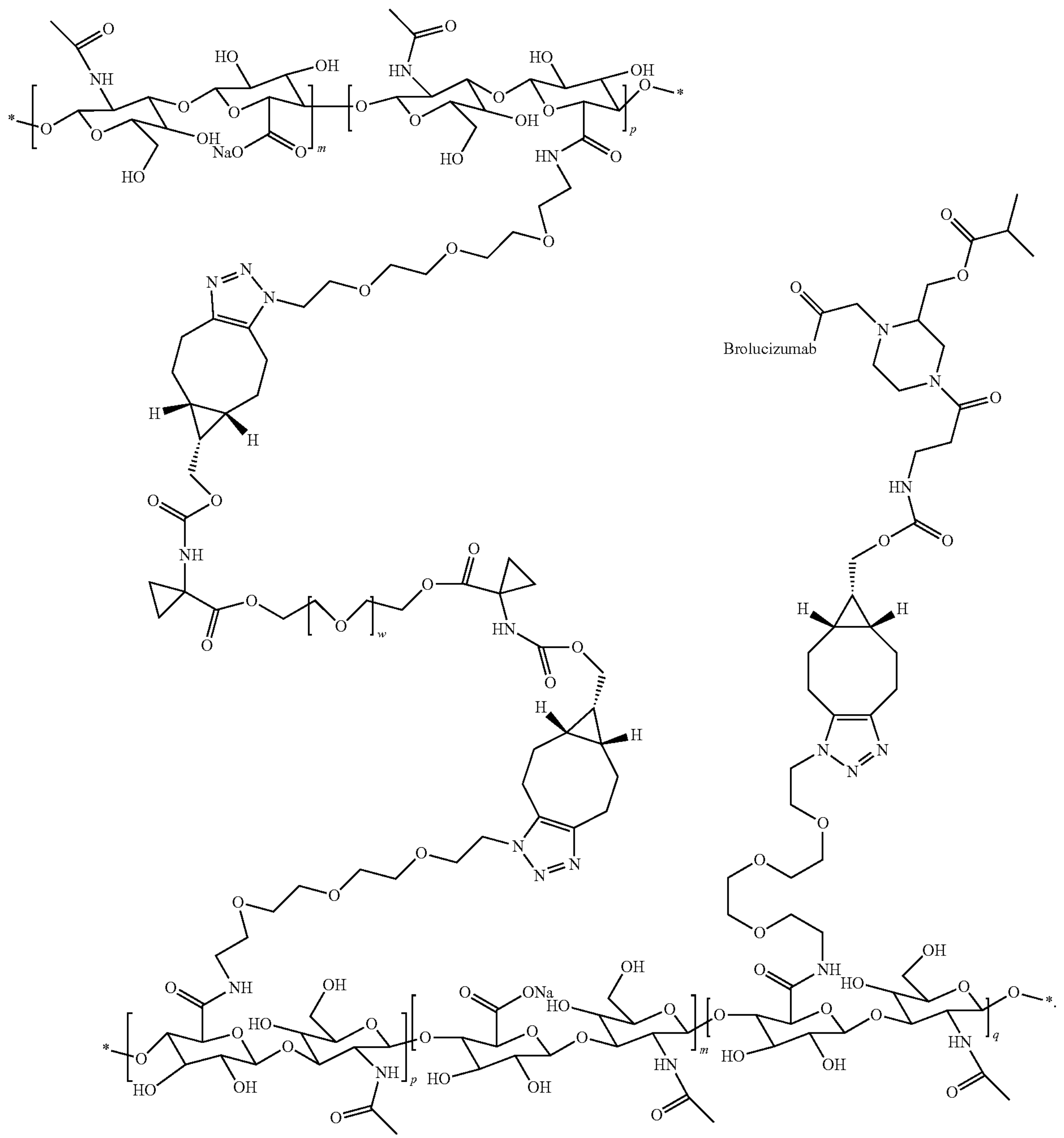

In another embodiment, the drug delivery system can comprise Formula (XVIIIa) with the drug being brolucizumab:
(XVIIIa)
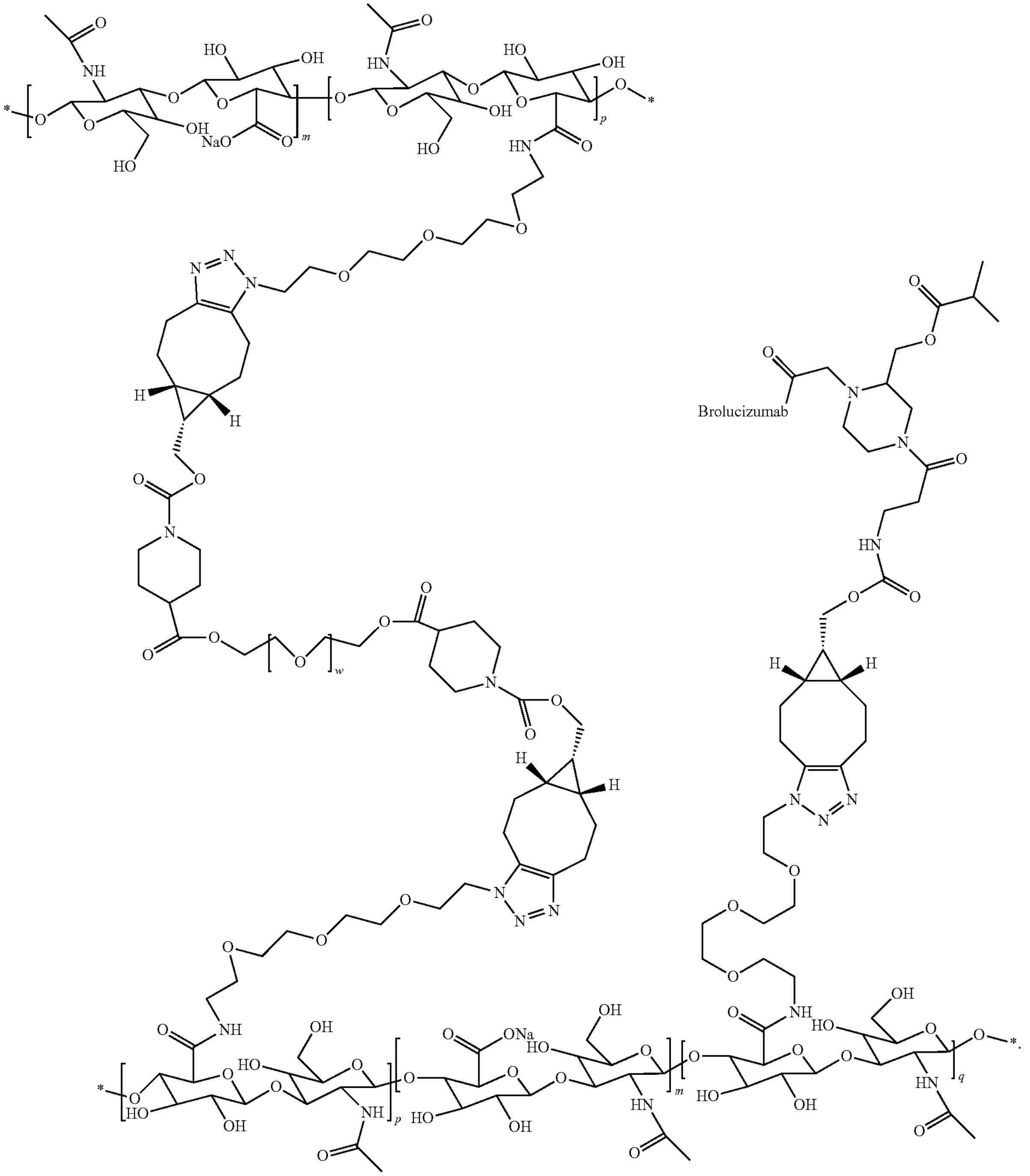

In another embodiment, the drug delivery system can comprise Formula (XVIIIb) with the drug being brolucizumab:
(XVIIIb)
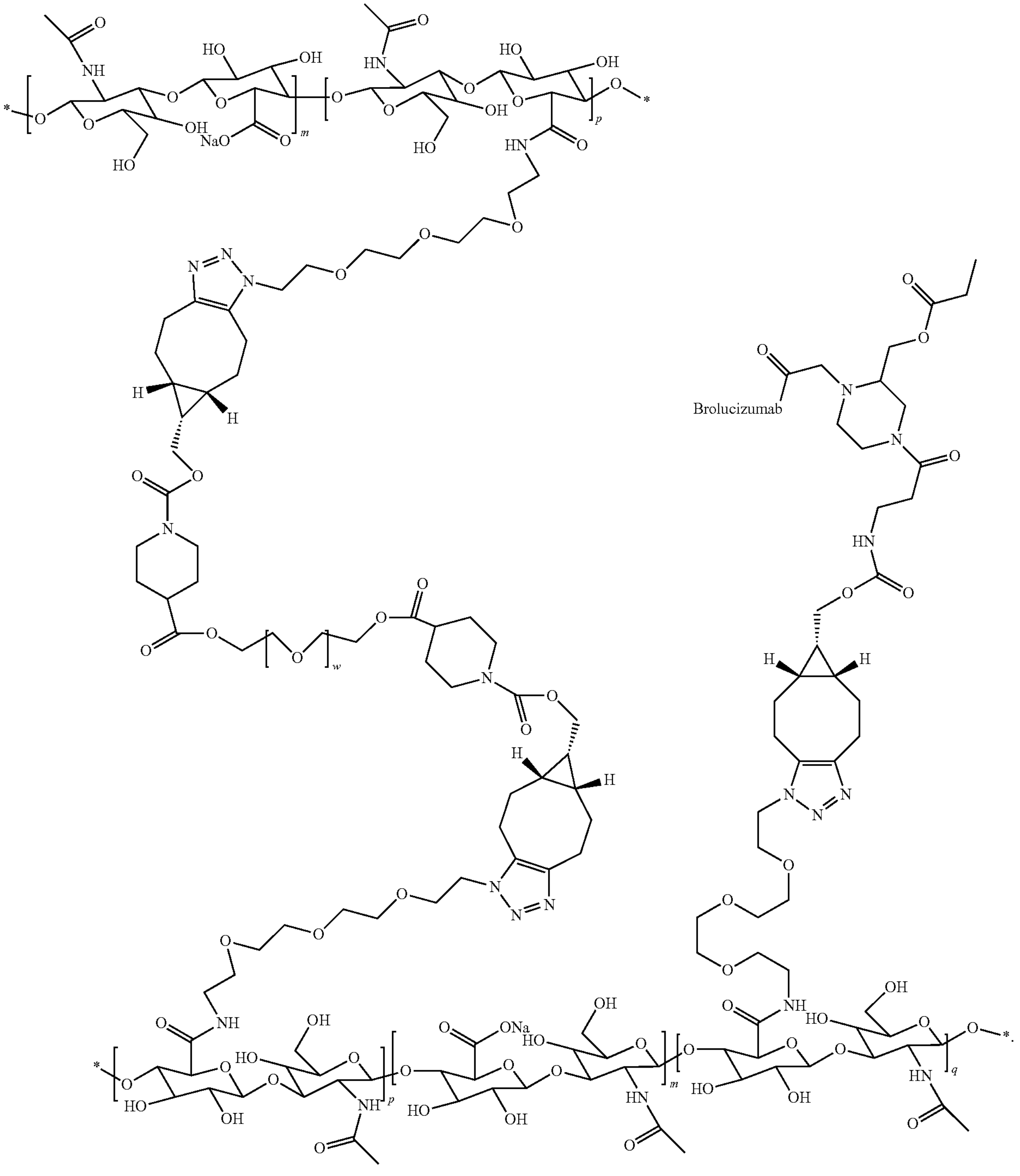

In another embodiment, the drug delivery system can comprise Formula (XVIIIc) with the drug being brolucizumab:
In another embodiment, the drug delivery system can comprise Formula (XVIIIc) with the drug being brolucizumab:
(XVIIIc)
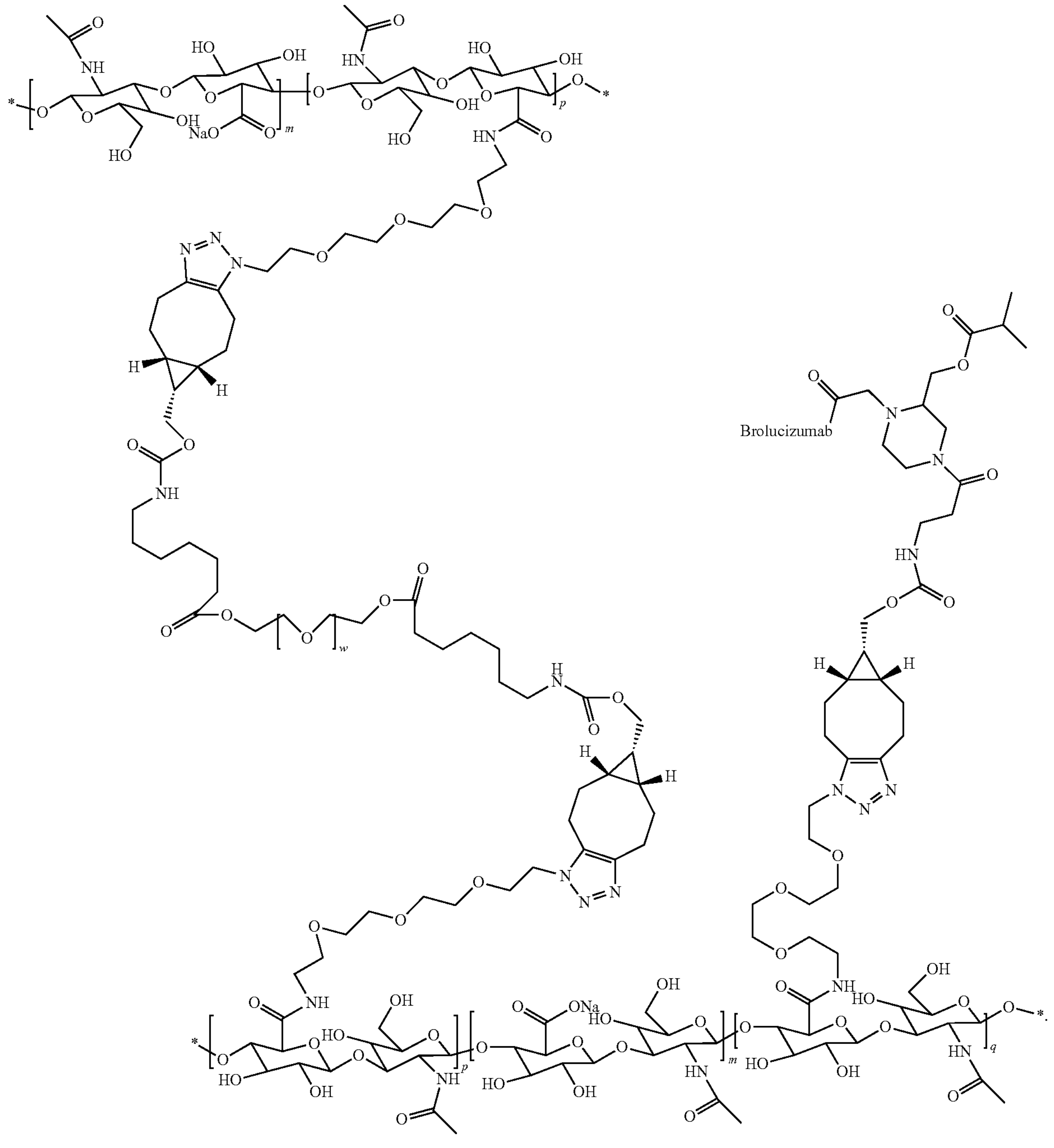

(XVIIId)
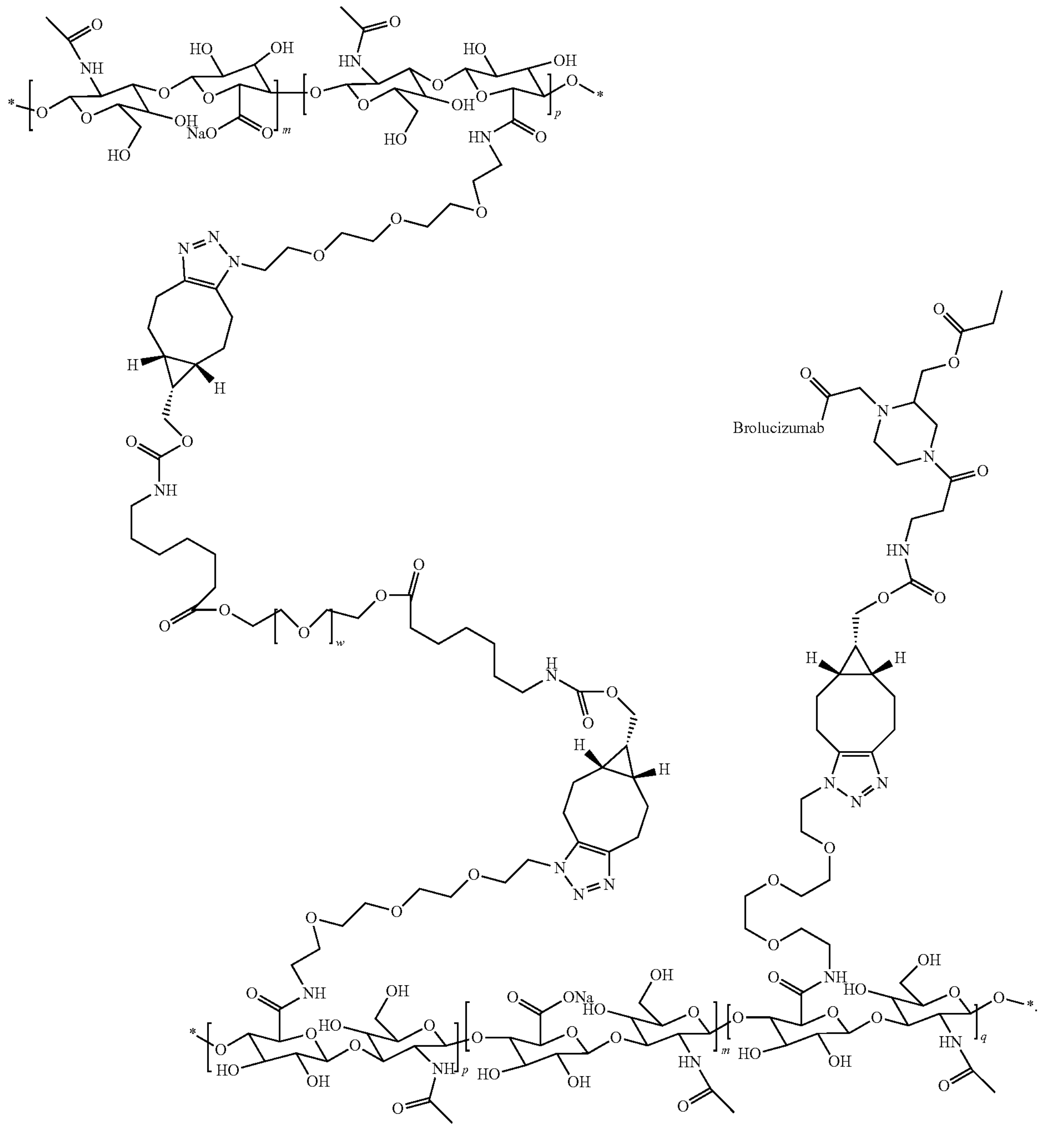
In another embodiment, the drug delivery system can comprise Formula (XVIIIe) with the drug being brolucizumab:

In another embodiment, the drug delivery system can comprise Formula (XVIIId) with the drug being brolucizumab:
(XVIIIe)
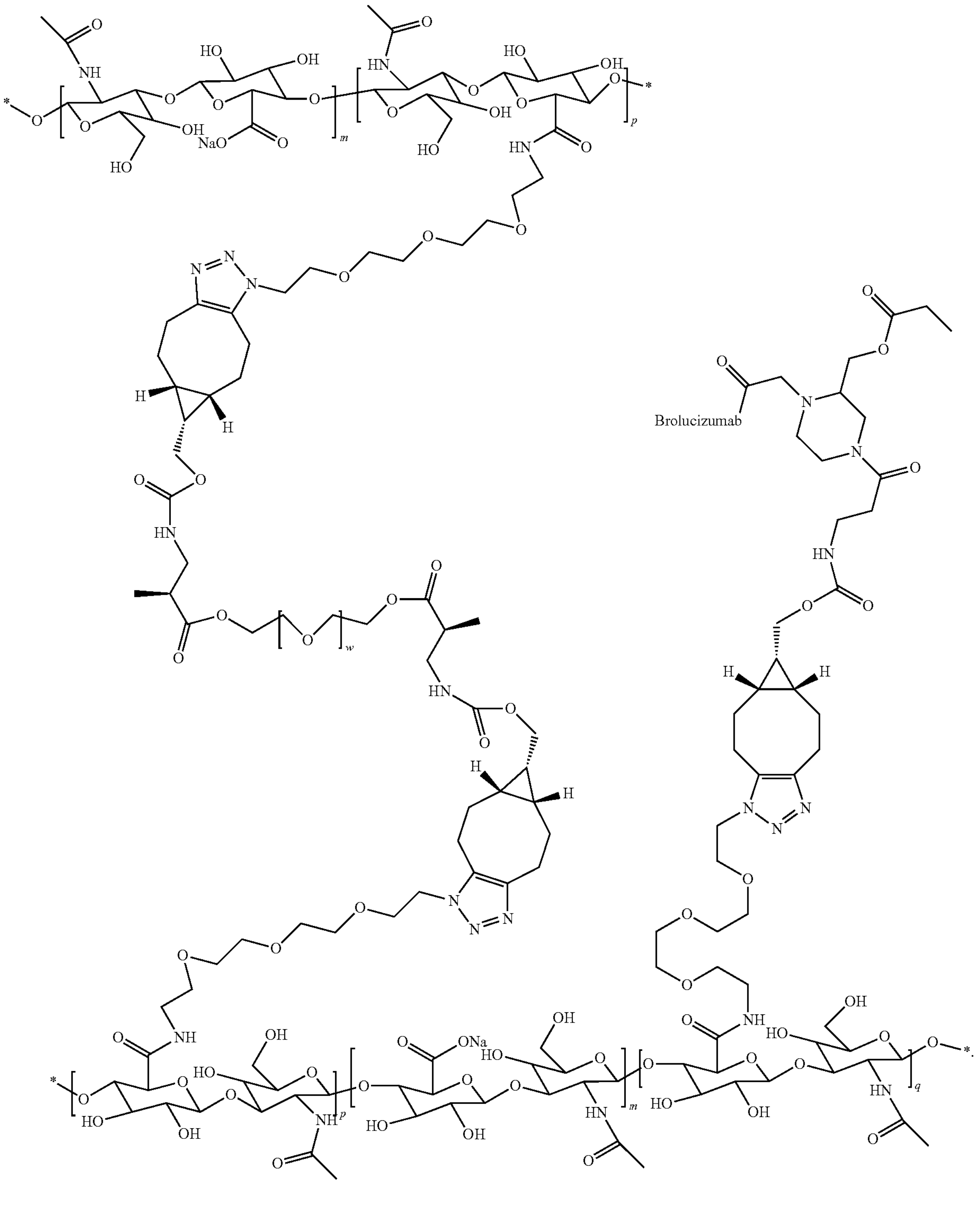

In another embodiment, the drug delivery system can comprise Formula (XVIIIf) with the drug being brolucizumab:
(XVIIIf)
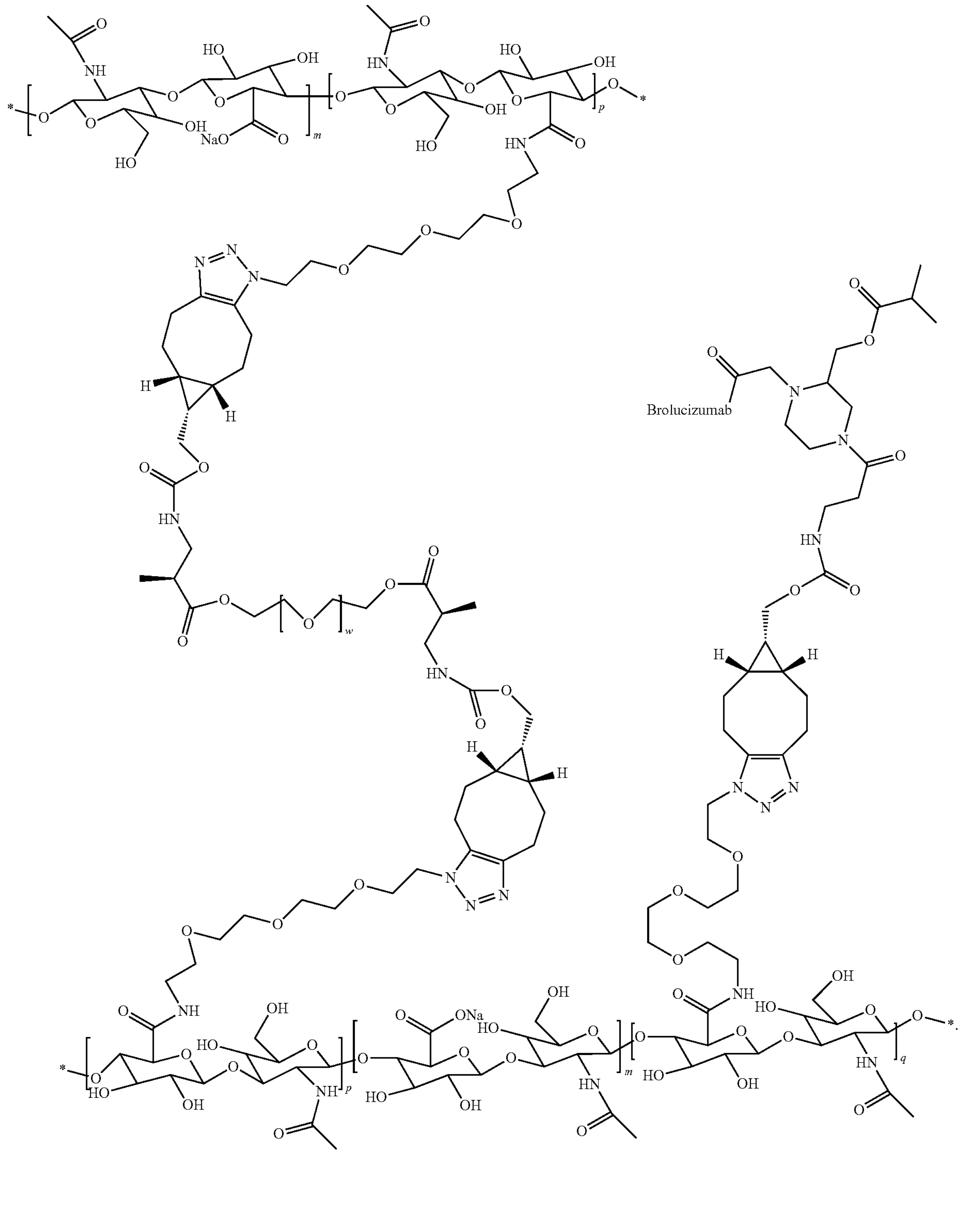

In another embodiment, the drug delivery system can comprise Formula (XIX) with the drug being D2:
(XIX)
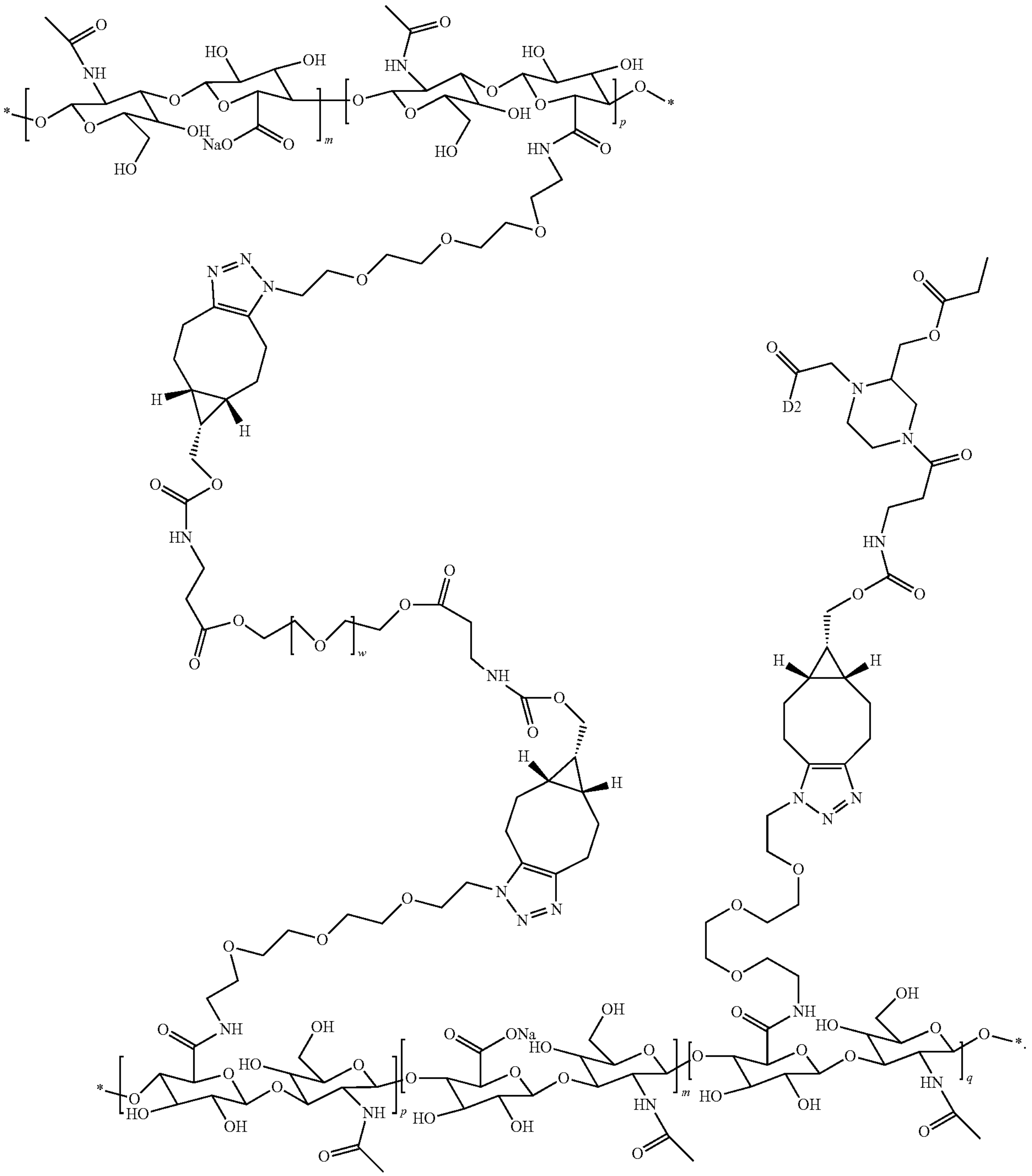

In another embodiment, the drug delivery system can comprise Formula (XX) with the drug being D2:
(XX)
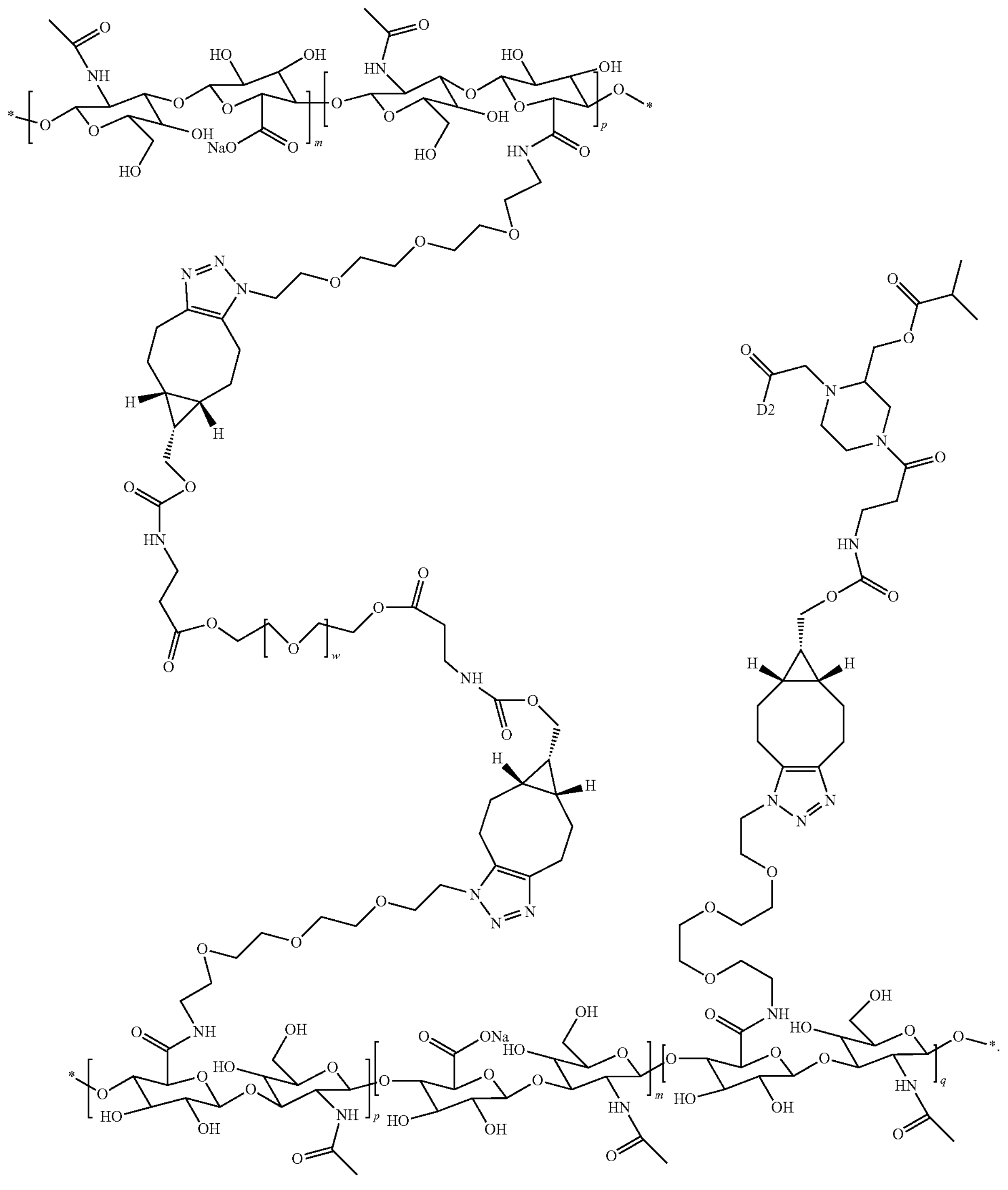

In another embodiment, the drug delivery system can comprise Formula (XXI) with the drug being D2:
In another embodiment, the drug delivery system can comprise Formula (XXI) with the drug being D2:
(XXI)
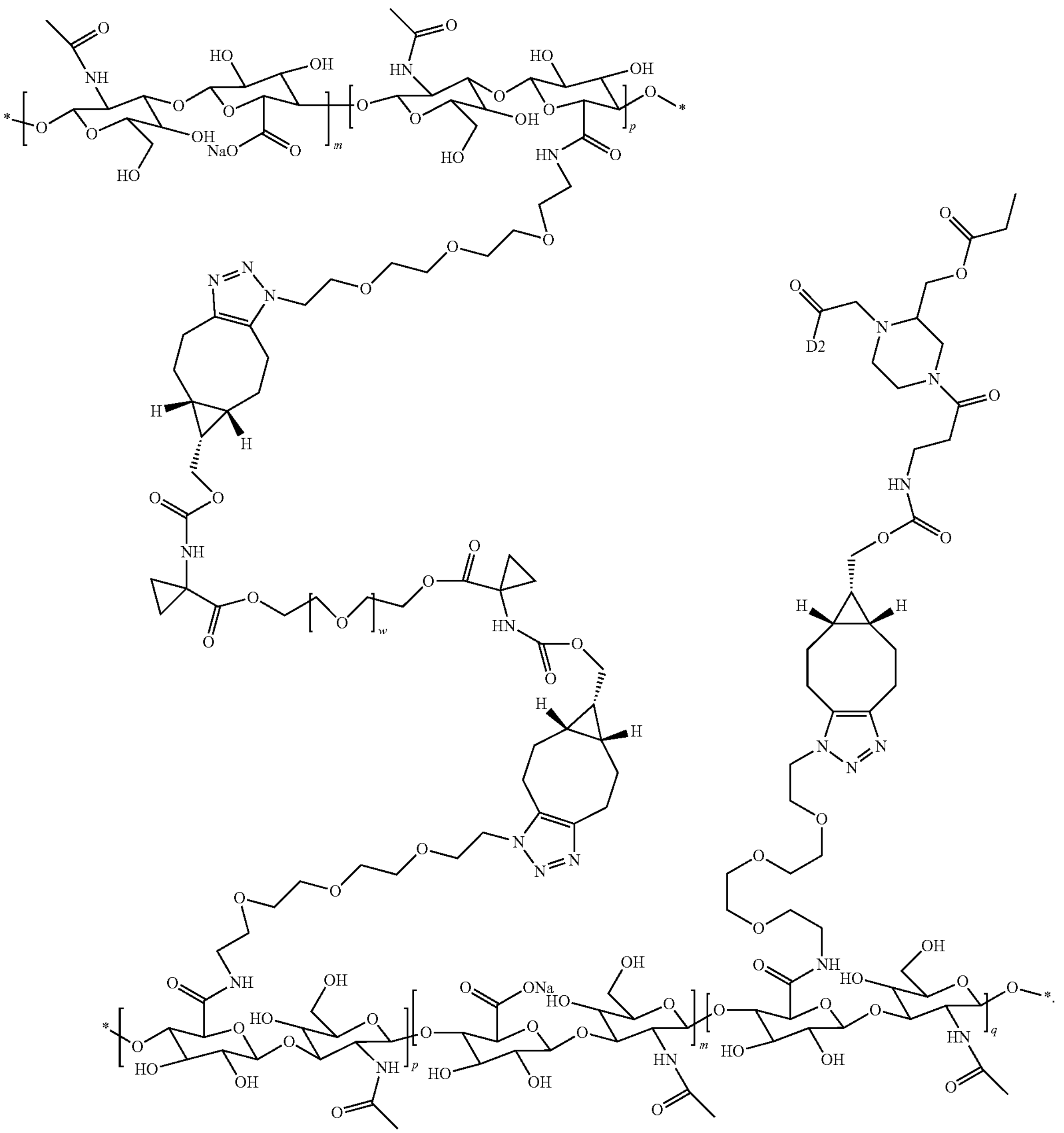

In another embodiment, the drug delivery system can comprise Formula (XXII) with the drug being D2:
(XXII)
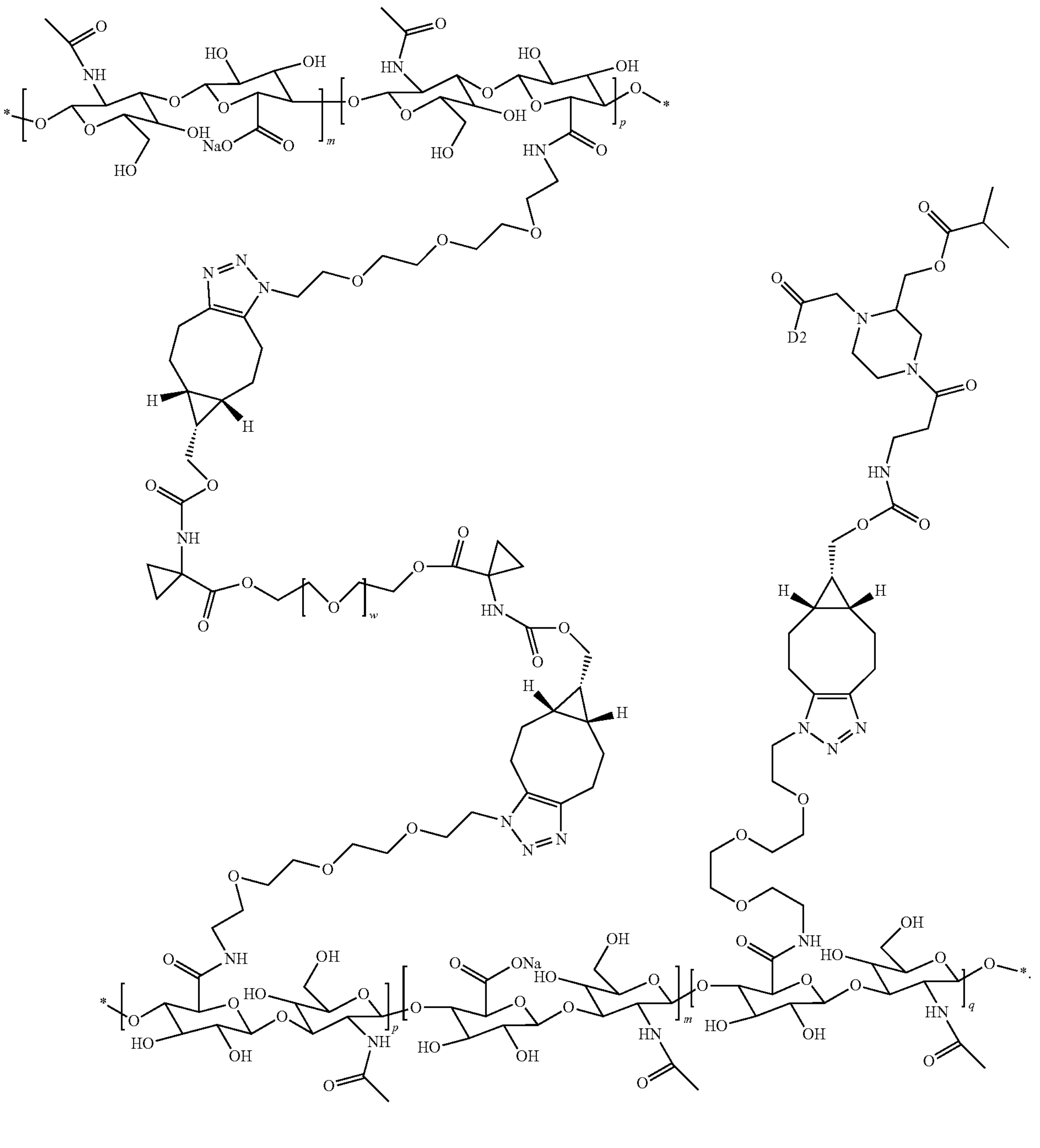

In another embodiment, the drug delivery system can comprise Formula (XXIII) with the drug being D4:

(XXIII)

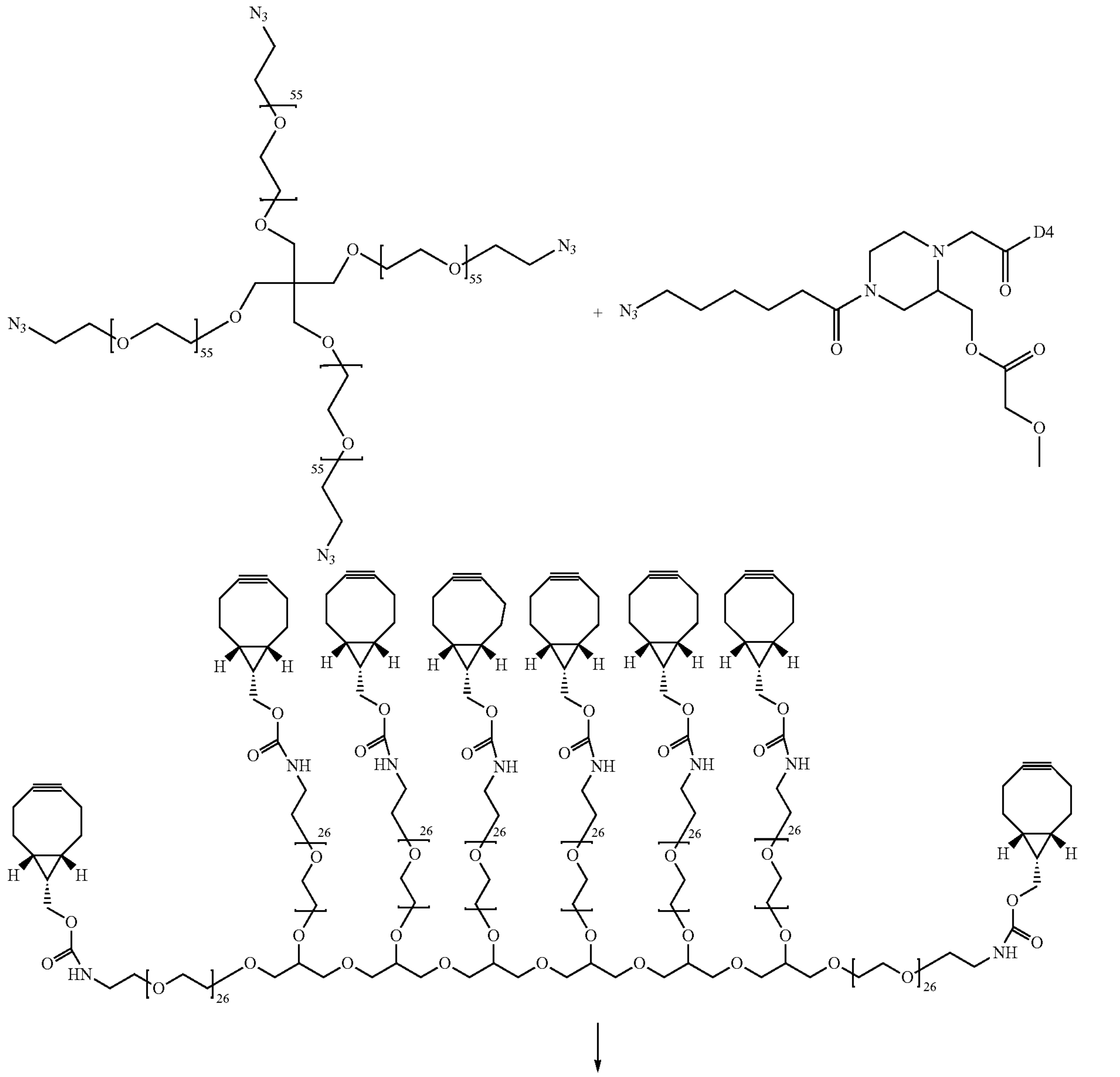

[hydrogel-drug conjugate].

Another embodiment described herein is a method for treating diseases or disorders using the drug delivery systems described herein. Another embodiment described herein relates to the drug delivery system or a pharmaceutically acceptable salt thereof comprising D-R represented by Formula (I) for use as a medicament. Another embodiment is the use of the drug delivery system or a pharmaceutically acceptable salt thereof comprising D-R represented by Formula (I) for the manufacture of a medicament for the treatment of a cardiac disorder, musculoskeletal disorder, an ocular disorder including but not limited to wet age-related macular degeneration, macular edema, branch retinal vein occlusion, central retinal vein occlusion, glaucoma, Hereditary Hemorrhagic Telangiectasia (HHT), proliferative diabetic retinopathy, uveitis, Paroxysmal Nocturnal Hemoglobinuria (PNH), geographic atrophy, dry age-related macular degeneration, neovascularization, diabetic macular edema or intermediate age-related macular degeneration. In one aspect, pharmaceutical compositions of the drug delivery systems described herein can be administered to a subject in need thereof by injection. In one aspect, administration may be made by injection or surgical implantation.

One embodiment described herein is a method for treating disorders of the eye, including but not limited to wet age-related macular degeneration, macular edema, branch retinal vein occlusion, central retinal vein occlusion, glaucoma, Hereditary Hemorrhagic Telangiectasia (HHT), proliferative diabetic retinopathy, uveitis, Paroxysmal Nocturnal Hemoglobinuria (PNH), geographic atrophy, dry age-related macular degeneration, neovascularization, diabetic macular edema or intermediate age-related macular degeneration, the method comprising administering a drug delivery system as described herein, D-R, wherein D comprises ranibizumab, bevacizumab, brolucizumab (SEQ ID NO:4), 5-(5,6,7,8-Tetrahydro-pyrido[3,4-d]pyrimidin-4-yloxy)-indole-1-carboxylic acid [5-(1-methyl-cyclopropyl)-2H-pyrazol-3-yl]-amide; 5-(6,7-dihydro-5H-pyrrolo[3,4 d]pyrimidin-4-yloxy)-indole-1-carboxylic acid [5-(1-methyl-cyclopropyl)-2H-pyrazol-3-yl]-amide; N-(1-methyl-5-(trifluoromethyl)-1H-pyrazol-3-yl)-5-((6-((methylamino) methyl)pyrimidin-4-yl)oxy)-1H-indole-1-carboxamide; (S)-5-(6-methyl-5,6,7,8-tetrahydropyrido[3,4-d]pyrimidin-4-yloxy)-N-(5-(1-methylcyclopropyl)-1H-pyrazol-3-yl)-1H-indole-1-carboxamide, or combinations thereof. In one aspect, the composition is a solution or suspension that is injected into the eye. In one aspect, the injection is an intraocular injection (e.g. an intravitreal injection). In another aspect, the composition is a gel or semi-solid composition that is implanted in the eye using surgical means or by injection.

Another embodiment described herein is a method for treating musculoskeletal disorders, including but not limited to cartilage regeneration, tendon healing, wound healing, or bulbospinal muscular atrophy, comprising administering a drug delivery system as described herein, D-R, wherein D comprises D2 (SEQ ID NO:5), a pegylated version of D2, e.g., D3 (SEQ ID NO:6), or a combination thereof.

Another embodiment described herein relates to the drug delivery system or a pharmaceutically acceptable salt thereof comprising D-R represented by Formula (I), wherein D comprises D2 (SEQ ID NO:5), a pegylated version of D2, e.g., D3 (SEQ ID NO:6), or a combination thereof for use in the treatment of a cardiac disorder, musculoskeletal disorder or an ocular disorder including but not limited to wet age-related macular degeneration, macular edema, branch retinal vein occlusion, central retinal vein occlusion, glaucoma, Hereditary Hemorrhagic Telangiectasia (HHT), proliferative diabetic retinopathy, uveitis, Paroxysmal Nocturnal Hemoglobinuria (PNH), geographic atrophy, dry age-related macular degeneration, neovascularization, diabetic macular edema or intermediate age-related macular degeneration. In one aspect, the composition is a solution or suspension that is injected into the joint. In another aspect, the composition is a gel or semi-solid composition that is implanted in the joint using surgical means or by large-bore injection. In another aspect, the composition is in the form of particles that are injected into a joint or in the proximity of a joint. In another aspect, the composition is implanted in or around the joint as a biodegradable mesh or gauze that is eventually absorbed or processed in situ. In another aspect, the composition is impregnated into sutures, staples, plates, meshes, or similar articles that are utilized during surgery to reattach or repair tendons, ligaments, cartilage, bone, or other joint components following trauma or disease.

Another embodiment described herein is a method for treating a cardiac disorder, such as heart failure, acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) or preeclampsia, comprising administering a drug delivery system as described herein, D-R, wherein D comprises D4 (SEQ ID NO:7). In one aspect, the composition is a solution or suspension that is delivered intravenously, intraarterially, subcutaneously, intramuscularly, or intraperitoneally. In another aspect, the composition is a gel or semi-solid composition that is implanted using surgical means or large-bore injection. In another aspect, the composition is a gel or semi-solid composition that is applied topically or directly to cutaneous wounds.

In one embodiment, the drug delivery system as described herein releases the biologically active agent at a particular release rate. In one aspect, the release rate can be tuned or modulated by the "trigger" component of the traceless linker, R. Without being bound by any theory, it is believed that reaction of the trigger under physiological conditions generates a nucleophilic functional group, for example a hydroxyl functional group that in an intramolecular fashion cleaves the amide bond linking the drug to the drug delivery system. In one embodiment, the reaction of the trigger is a hydrolysis reaction resulting in the formation of a hydroxyl functional group. Without being bound by any theory, it is believed that steric hindrance of the trigger moiety is correlated with slower reaction of the trigger and the presence and proximity of electron withdrawing groups is correlated with faster reaction of the trigger.

In one embodiment the half-life for the release of the biologically active moiety is about 0.5 hours, about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1 day, about 2 days, about 3 days, about 4 days, about 5 days, about 6 days, about 7 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 1 year, about 1.5 years, about 2 years, about 2.5 years, about 3 years, about 3.5 years, about 4, or greater than 4 years. In one aspect, the biologically active moiety release half-life is about 2.5 days, about 4.5 days, about 7 days, about 10 days, about 11 days, about 12 days, about 14 days, about 15 days, about 21 days, about 28 days, about 30 days, about 31 days, about 32 days, about 40 days, about 58 days, about 60 days, about 65 days, about 70 days, about 80 days, about 125 days, about 165 days, about 380 days, about 940 days, or even greater.

In one embodiment the half-life for the traceless linker trigger ester hydrolysis is about 0.5 hours, about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1 day, about 2 days, about 3 days, about 4 days, about 5 days, about 6 days, about 7 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 1 year, about 1.5 years, about 2 years, about 2.5 years, about 3 years, about 3.5 years, about 4, or greater than 4 years. In one aspect, the traceless linker trigger ester hydrolysis half-life is about 1 day, about 1.5 days, about 2 days, about 2.5 days, about 4 days, about 5 days, about 10 days, about 12 days, about 15 days, about 20 days, about 30 days, about 32 days, about 35 days, about 40 days, about 55 days, about 60 days, about 90 days, about 120 days, about 150 days, about 180 days, about 200 days, about 300 days, about 400 days, or even longer.

In another embodiment the half-life for the clearance of the drug delivery system, R-$R^{11}$, following release of the drug, D (e.g., D-R—$R^{11}$→R-$R^{11}$+D), from the tissue, organ, or compartment into which the drug delivery system was dosed is about 0.5 hours, about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1 day, about 2 days, about 3 days, about 4 days, about 5 days, about 6 days, about 7 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 1 year, about 1.5 years, about 2 years, about 2.5 years, about 3 years, about 3.5 years, about 4, or greater than 4 years.

Other embodiments described herein are pharmaceutical compositions comprising the drug delivery system, D-R—$R^{11}$, as described herein. In one aspect, the pharmaceutical compositions are suitable for injection or implantation in a subject in need thereof.

Pharmaceutical compositions suitable for administration by injection or implantation include sterile aqueous solutions, suspensions, or dispersions and sterile powders or lyophilates for the extemporaneous preparation of sterile injectable solutions or dispersion.

For intravenous administration, suitable carriers include phosphate buffered saline (PBS), physiological saline, Ringer's solution, or water for injection. In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, buffers, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, amino acids, sorbitol, sodium chloride, or combinations thereof in the composition. Prolonged absorption of the injectable compositions can be brought about by including in the composition an agent that delays absorption, for example, aluminum monostearate and gelatin.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers.

In addition, they may also contain other therapeutically valuable substances. Said compositions are prepared according to conventional mixing, granulating or coating methods, respectively, and contain about 0.1-75%, or contain about 1-5 0%, of the active ingredient.

Sterile injectable solutions or suspensions can be prepared by incorporating the drug delivery system in the required amount in an appropriate solvent with one or a combination of ingredients, as required, followed by filtration sterilization. Generally, solutions or suspensions are prepared by incorporating the active compound into a sterile vehicle such as sterile PBS and any excipients. In the case of sterile powders for the preparation of sterile injectable solutions, the preferred preparation methods are vacuum drying and freeze-drying which yields a powder of the active ingredient plus any additional desired ingredient from a previously sterile-filtered solution thereof.

Transmucosal or transdermal administration means are also possible. Suitable compositions for transdermal application include an effective amount of a biologically active agent with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin, eyes, or joints, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well known in the art. Such may contain solubilizers, stabilizers, tonicity enhancing agents, buffers, or preservatives.

As used herein, a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Also described herein are pharmaceutical compositions and dosage forms comprising one or more agents that reduce the rate by which the compositions described herein as active ingredients will decompose. Such agents, which are referred to herein as "stabilizers," include, but are not limited to, antioxidants such as ascorbic acid, pH buffers, or salt buffers, etc.

The effective amount of a pharmaceutical composition to be employed therapeutically will depend, for example, upon the therapeutic context and objectives. One skilled in the art will appreciate that the appropriate dosage levels for treatment will thus vary depending, in part, upon the therapeutic agent incorporated into the drug delivery system, the indication for which the drug delivery system is being used, the route of administration, and the size (body weight, body surface, or organ size) and condition (the age and general health) of the patient. Accordingly, the clinician can titer the dosage and modify the route of administration to obtain the optimal therapeutic effect.

The frequency of dosing will depend upon the pharmacokinetic parameters of the therapeutic agent incorporated into the drug delivery system being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The drug delivery system can be prepared as solutions or suspensions of micro-particles. In one aspect, the carrier is formed into microparticulate which can be administered by a standard syringe to the target tissue, e.g., administration subcutaneously, intravitreally, intra-articularly, intra tendon, or intramuscularly. Such particles may have a mean particle size distribution of between 1 μm and 5000 μm. Other aspects comprise biodegradable gauze, mesh, or sutures that have been impregnated with drug delivery systems as described herein.

In some embodiments, microparticles of the drug delivery systems described herein can be produced by emulsion polymerization, lithography, spinning, molding, spray drying, milling, extrusion, mechanical comminution, or similar procedures known in the art. In one embodiment, the drug delivery systems, carrier polymers, or hydrogels as described herein can be divided into microparticles by extrusion through mesh or screens. In one aspect, the extrusion can be repeated multiple times and/or through successively smaller meshes to achieve the desired particle distribution size.

In one embodiment, based on laser diffraction to measure particle size, the drug delivery system has a mean particle size distribution of between 1 μm and 5000 μm when suspended in an isotonic aqueous formulation buffer. In some aspects, the drug delivery system has a mean particle size distribution of between 10 μm and 1000 μm when suspended in isotonic buffer. In another aspect, the drug delivery system has a mean particle size distribution of between 50 μm and 500 μm when suspended in an isotonic aqueous buffer. In another aspect, the drug delivery system has a mean particle size distribution of between 100 μm and 300 μm when suspended in an isotonic aqueous buffer. In another aspect, the drug delivery system has a mean particle size distribution of between 200 μm and 300 μm when suspended in an isotonic aqueous buffer. In some embodiments, the mean particle size distribution comprises about 10 μm, about 50 μm, about 100 μm, about 150 μm, about 200 μm, about 250 μm, about 300 μm, about 350 μm, about 400 μm, about 450 μm, about 500 μm, about 750 μm, about 1000 μm, about 1500 μm, about 2000 μm, about 2500 μm, or about 5000 μm.

The particle sizes may be determined using standard techniques known to one of ordinary skill in the art. The exemplary techniques that can be used for measuring the particle size distributions of drug delivery system particles may include laser diffraction analysis, light scattering (e.g., dynamic light scattering), microscopic particle image analysis, elutriation, or aerosol mass spectrometry. The sample of drug delivery system particles may be measured as a dry sample or a wet sample. Any commercially available instrument for measuring particle sizes may be used, including instruments from Cilas; Brookhaven Instruments Corporation; Malvern Instruments; Horiba Scientific; or Wyatt following the recommended operating procedures according to the manufacturer's instructions.

The measured particle sizes using the techniques described herein may be expressed as a derived diameter with a normal distribution or non-normal distribution with a mean, median (e.g., mass median diameter), and mode of particle diameter sizes. The particle size distribution may be expressed as a diameter number distribution, a surface area distribution, or a particle volume distribution. The mean of the particle size distribution may be calculated and expressed in various ways, such as the volume mean diameter (D[4,3] or $d_{43}$), mean surface area diameter (D[3,2] or $d_{32}$) or the mean number particle diameter (D[1,0] or $d_{10}$). Because the particle size distribution values vary depending on the measurement methodology and how the distribution is expressed, the comparison of different mean particle size distributions must be calculated by the same methodology in order to yield an accurate comparison. For example, a sample with a measured and calculated volume mean diameter must be compared with a second sample having a measured and calculated volume mean diameter, ideally measured using the same measuring instrument under the same conditions. Thus, the specific particle size distributions described herein are not intended to be limited to any one type of method for measuring or calculating a particle size distribution (e.g., a diameter number distribution, a surface area distribution, or a particle volume distribution), but rather indicate particle size values and distributions thereof for each method of measuring particle sizes described herein.

In one embodiment drug delivery systems can be administered by injection through a needle smaller than 0.6 mm inner diameter (e.g., 20 gauge), preferably through a needle smaller than 0.3 mm inner diameter (e.g., 25 gauge), more preferably through a needle smaller than 0.25 mm inner diameter (e.g., 27 gauge), even more preferably through a needle smaller than 0.2 mm inner diameter (e.g., 28 gauge), and most preferably through a needle smaller than 0.16 mm inner diameter (e.g., 30 gauge). In one embodiment, when drug delivery systems are administered intra ocularly or intravitreally a needle small than 0.16 mm inner diameter (e.g., 30-34 gauge) is preferred. For example when a 100 μm to 300 μm particle size distribution of a drug delivery system is injected a 20 gauge needle may be optimal for delivery. Because the particle morphology is flexible, however, needle sizes narrower than the drug delivery system particle size may be used successfully.

The phrases and terms "can be administered by injection," "injectable," or "injectability" refer to a combination of factors such as a certain force applied to a plunger of a syringe containing the drug delivery systems described herein swollen in a liquid at a certain concentration (w/v) and at a certain temperature, a needle of a given inner diameter connected to the outlet of such syringe, and the time required to extrude a certain volume of the drug delivery systems from the syringe through the needle.

In one embodiment, an injectability measurement is carried out for the drug delivery system suspended in PBS or physiological saline to a concentration of about 0.1% to about 20% (w/v) including all integers within the specified percentage range.

Consequently, the drug delivery systems show the beneficial effect of a controlled release rate in respect of the released drug D-H. Preferably, a sustained release rate is obtained. Sustained release means that the administration intervals of the respective drug delivery systems described herein are expanded compared to administration of the drug in the absence of the drug delivery system. For example, drug delivery systems that are based on drugs commonly administered once or several times a day provide therapeutically effective levels for at least three days, at least one week, for at least one month, for several months, or for years.

Another embodiment described herein is a pharmaceutical composition of the drug delivery systems described herein. The pharmaceutical compositions can comprise one or more excipients, such as:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.

(iii) Preservatives and/or antimicrobials: multidose parenteral preparations may require the addition of preservatives at a sufficient concentration to minimize the risk of subjects becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

(iv) Stabilizers: Stabilization is achieved by strengthening of the protein-stabilising forces, by destabilization of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, polyethylene glycol, polyvinylpyrrolidone, protamine, or human serum albumin may be used.

(v) Anti-adsorption agents: Mainly ionic or ion-ionic surfactants or other proteins or soluble polymers are used to coat or adsorb competitively to the inner surface of the composition's container, e.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically, a monolayer of surfactant is formed at the interface just above the CMC value.

(vi) Lyophilization or cryoprotectants: During freeze- or spray drying, excipients may counteract the destabilising effects caused by hydrogen bond breaking and water removal. For this purpose, sugars and polyols may be used, but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol or sucrose are known to enhance physical stability of a lyophilized cake. Mannitol may also be combined with trehalose. Trehalose may also be combined with sorbitol or sorbitol may be used as the sole protectant. Starch or starch derivatives may also be used.

(vii) Oxidation protection agents: antioxidants such as ascorbic acid, ectoine, methionine, glutathione, monothioglycerol, morin, polyethylenimine (PEI), propyl gallate, vitamin E, chelating agents such as citric acid, EDTA, hexaphosphate, thioglycolic acid.

(viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satiagum UTC 30, aliphatic poly(hydroxy acids), such as poly(D,L- or L-lactic acid) (PLA) and poly (glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g., Pluronic™) polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(ix) Diffusion agents: modifies the permeability of connective tissue through the hydrolysis of components of the extracellular matrix in the interstitial space such as, but not limited to, hyaluronic acid, a polysaccharide found in the intercellular space of connective tissue. A spreading agent such as, but not limited to, hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

The drug delivery system may be provided as a liquid, a suspension, or as a dry composition.

In one embodiment, the drug delivery system is a dry composition. Suitable methods of drying are, for example, spray drying and lyophilization (freeze-drying). In one aspect, the drug delivery system is dried by lyophilization.

In one embodiment, the drug delivery system is sufficiently dosed in the composition to provide therapeutically effective amounts of biologically active agent for at least 12 hours in one application. In one aspect, one application of drug delivery system is sufficient for about 1 day, about 2 days, about 3 days, about 4 days, about 5 days, about 1 week, about 2 weeks, about 3 weeks, about 4 weeks, one month, 2 months, 3 months, 4 months, 6 months, 9 months, one year, 2 years, 3 years, 4 years, or even longer.

In one embodiment, the drug delivery system is provided as a single dose, meaning that the container in which it is supplied contains one pharmaceutical dose.

In another embodiment, the composition is provided as a multiple dose composition, meaning that it contains more than one therapeutic dose. Preferably, a multiple dose composition contains at least 2 doses. Such multiple dose drug delivery systems can either be used for different subjects in need thereof or is intended for use in one subject, wherein the remaining doses are stored after the application of the first dose until needed.

In another embodiment, the drug delivery system is comprised in one or more containers. For liquid or suspension compositions, the container is preferably a single chamber syringe. For dry compositions, preferably the container is a dual-chamber syringe. The dry composition is provided in a first chamber of the dual-chamber syringe and reconstitution solution is provided in a second chamber of the dual-chamber syringe.

Prior to applying the dry drug delivery system to a subject in need thereof, the dry composition is reconstituted. Reconstitution can take place in the container in which the dry drug delivery system is provided, such as in a vial, syringe, dual-chamber syringe, ampoule, and cartridge. Reconstitution is done by adding a predefined amount of reconstitution solution to the dry composition. Reconstitution solutions are sterile liquids, such as phosphate buffered saline, isotonic saline, water for injection, or other buffers, which may contain further excipients, such as preservatives and/or antimicrobials, such as, for example, benzylalcohol and cresol. Preferably, the reconstitution solution is sterile phosphate buffered saline (PBS) or physiological saline. Alternatively, the reconstitution solution is sterile water for injection.

Another embodiment is a method of preparing a reconstituted composition comprising a therapeutically effective amount of a drug delivery system, and optionally one or more pharmaceutically acceptable excipients, the method comprising the step of contacting the composition with a volume of reconstitution vehicle. The reconstituted drug delivery system may then be administered by injection or other routes.

Another embodiment is a reconstituted composition comprising a therapeutically effective amount of a drug delivery system, a reconstitution vehicle, and optionally one or more pharmaceutically acceptable excipients.

Another embodiment is a pre-filled syringe comprising a solution or a suspension comprising a therapeutically effective amount of a drug delivery system, and optionally one or more pharmaceutically acceptable excipients. In one aspect, the syringe is filled with between about 0.01 mL and about 5 mL of a drug delivery system as described herein. In one aspect, the syringe is filled with between about 0.05 mL and about 5 mL, between about 1 mL and about 2 mL, between about 0.1 mL and about 0.15 mL, between about 0.1 mL, about 0.5 mL, between about 0.15 mL and about 0.175 mL, or about 0.5 to about 5 mL. In one embodiment, the syringe is filled with 0.165 mL of a drug delivery system as described herein. In some aspects, a syringe is filled with about 0.01 mL, about 0.02 mL, about 0.03 mL, about 0.04 mL, about 0.05 mL, about 0.06 mL, about 0.07 mL, about 0.08 mL, about 0.09 mL, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.2 mL, about 1.5 mL, about 1.75 mL, about 2 mL, about 2.5 mL, about 3 mL, about 4 mL, or about 5 mL of a drug delivery system as described herein. A syringe is often filled with more than the desired dose to be administered to the patient, to take into account wastage due to "dead space" within the syringe and needle. There may also be a pre-determined amount of waste when the syringe is primed by the physician, so that it is ready to inject the patient.

In one embodiment, a syringe is filled with a dosage volume (i.e., the volume of medicament intended for delivery to the patent) of between about 0.01 mL and about 5 mL depending on the route of injection (e.g., between about 0.01 mL and about 0.1 mL, between about 0.1 mL and about 0.5 mL, between about 0.2 mL and about 2 mL, between about 0.5 mL and about 5 mL, or between about 1 mL and about 5 mL) of a drug delivery system as described herein. In one embodiment intended for intravitreal injection, a syringe is filled with a dosage volume of between about 0.01 mL and about 0.1 mL of a drug delivery system solution or suspension with a drug concentration of 1 mg/mL to 40 mg/mL as described herein. In one embodiment intended for intra-articular injection, a syringe is filled with a dosage volume of between about 0.05 mL and about 5.0 mL of a drug delivery system solution or suspension with a drug concentration of 1 mg/mL to 40 mg/mL as described herein. In one embodiment intended for subcutaneous injection, a syringe is filled with a dosage volume of between about 0.1 mL and about 5.0 mL of a drug delivery system solution or suspension with a drug concentration of 0.1 mg/mL to 40 mg/mL as described herein. In other embodiments intended for injection by other routes, a syringe is filled with a dosage volume of between about 0.01 mL and about 5.0 mL of a drug delivery system solution or suspension with a drug concentration of 0.1 mg/mL to 40 mg/mL as described herein. In some aspects, a syringe is filled with about 0.01 mL, about 0.02 mL, about 0.03 mL, about 0.04 mL, about 0.05 mL, about 0.06 mL, about 0.07 mL, about 0.08 mL, about 0.09 mL, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.2 mL, about 1.5 mL, about 1.75 mL, about 2 mL, about 2.5 mL, about 3 mL, about 4 mL, or about 5 mL of a drug delivery system as described herein for delivery to a patient in need thereof.

As the syringe contains a medicament solution, the outlet may be reversibly sealed to maintain sterility of the medicament. This sealing may be achieved by a sealing device as is known in the art, such as a luer lock or a tamper resistant seal.

Another embodiment is a kit comprising one or more pre-filled syringes comprising a solution or suspension of one or more drug delivery systems as described herein. In one embodiment, such a kit comprises a pre-filled syringe comprising drug delivery systems as described herein in a blister pack or a sealed sleeve. The blister pack or sleeve may be sterile on the inside. In one aspect, pre-filled syringes as described herein may be placed inside such blister packs or sleeves prior to undergoing sterilization, for example terminal sterilization.

Such a kit may further comprise one or more needles for administration of drug delivery systems as described herein. When the drug delivery system is to be administered intravitreally, it is typical to use a 30-gauge×½-inch needle, although 31-gauge or 32-gauge needles may be used. For intravitreal administration, 33-gauge or 34-gauge needles can alternatively be used. Such kits may further comprise instructions for use, a drug label, contraindications, warnings, or other relevant information. One embodiment described herein is a carton or package comprising one or more pre-filled syringes comprising one or more drug delivery systems as described herein contained within a blister pack, a needle, and optionally instructions for administration, a drug label, contraindications, warnings, or other relevant information.

A terminal sterilization process may be used to sterilize the syringe and such a process may use a known process such as an ethylene oxide or a hydrogen peroxide ($H_2O_2$) sterilization process. Needles to be used with the syringe may be sterilised by the same method, as may kits described herein. In one aspect, a package is exposed to the sterilising gas until the outside of the syringe is sterile. Following such a process, the outer surface of the syringe may remain sterile (whilst in its blister pack) for up to 6 months, 9 months, 12 months, 15 months, 18 months, 24 months or longer. Thus, in one embodiment, a pre-filed syringe as described herein (in its blister pack) may have a shelf life of up to 6 months, 9 months, 12 months, 15 months, 18 months, 24 months, or even longer. In one embodiment, less than one syringe in a million has detectable microbial presence on the outside of the syringe after 18 months of storage. In one aspect, the pre-filled syringe has been sterilised using ethylene oxide with a Sterility Assurance Level of at least $10^{-6}$. In another aspect, the pre-filled syringe has been sterilised using hydrogen peroxide with a Sterility Assurance Level of at least $10^{-6}$. Significant amounts of the sterilising gas should not enter the variable volume chamber of the syringe. The term "significant amounts" As used herein, refers to an amount of gas that would cause unacceptable modification of the drug delivery system solution or suspension within the variable volume chamber. In one embodiment, the sterilization process causes ≤10% (preferably ≤5%, ≤3%, ≤1%) alkylation of the drug delivery system. In one embodiment, the pre-filled syringe has been sterilised using ethylene oxide, but the outer surface of the syringe has ≤1 ppm, preferably ≤0.2 ppm ethylene oxide residue. In one embodiment, the pre-filled syringe has been sterilised using hydrogen peroxide, but the outer surface of the syringe has ≤1 ppm, preferably ≤0.2 ppm hydrogen peroxide residue. In another embodiment, the pre-filled syringe has been sterilised using ethylene oxide, and the total ethylene oxide residue found on the outside of the syringe and inside of the blister pack is ≤0.1 mg. In another embodiment, the pre-filled syringe has been sterilised using hydrogen peroxide, and the total hydrogen peroxide residue found on the outside of the syringe and inside of the blister pack is ≤0.1 mg.

Another aspect is a kit of parts. For liquid and suspension compositions, and when the administration device is simply a hypodermic syringe, the kit may comprise the syringe, a needle and a container comprising the drug delivery system composition for use with the syringe. In case of a dry composition, the container may have one chamber containing the dry drug delivery system composition, and a second chamber comprising a reconstitution solution. In one embodiment, the injection device is a hypodermic syringe adapted so the separate container with drug delivery system composition can engage with the injection device such that in use the liquid or suspension or reconstituted dry composition in the container is in fluid connection with the outlet of the injection device. Examples of administration devices include but are not limited to hypodermic syringes and pen injector devices. Particularly preferred injection devices are the pen injectors, in which case the container is a cartridge, preferably a disposable cartridge.

Another embodiment comprises a kit comprising a needle and a container containing the drug delivery system composition and optionally further containing a reconstitution solution, the container being adapted for use with the needle. In one aspect, the container is a pre-filled syringe. In another aspect, the container is dual chambered syringe.

Another embodiment is a cartridge containing a composition of drug delivery system as hereinbefore described for use with a pen injector device. The cartridge may contain a single dose or plurality of doses of drug delivery system.

In another embodiment the drug delivery system solution or suspension comprises a drug delivery system and one or more excipients, and also other biologically active agents, either in their free form or as drugs or combined with other drug delivery systems such as pegylated drugs or hydrogel linked drugs. In one aspect, such additional one or more biologically active agents is a free form drug or a second drug delivery system.

In another embodiment, one or more drug delivery systems are simultaneously administered, with each drug delivery system having either separate or related biological activities.

In an alternative embodiment, the drug delivery system is combined with a second biologically active compound in such way that the drug delivery system is administered to a subject in need thereof first, followed by the administration of the second compound. Alternatively, the drug delivery system composition is administered to a subject in need thereof after another compound has been administered to the same subject.

Another embodiment is a drug delivery system or a pharmaceutically acceptable salt thereof comprising D-R represented by Formula (I) for use as a medicament.

Another embodiment is a drug delivery system or pharmaceutically acceptable salt thereof comprising D-R represented by Formula (I) for use in the treatment of a musculoskeletal disorder.

Another embodiment is the use of drug delivery system or a pharmaceutically acceptable salt thereof comprising D-R represented by Formula (I) for the manufacture of a medicament for the treatment of a musculoskeletal disorders.

Another embodiment is a drug delivery system or a pharmaceutical composition for use in a method of treating or preventing diseases or disorders which can be treated by the biologically active moiety released from the drug delivery system.

Another embodiment is a method of manufacturing a solution or suspension composition of drug delivery system. In one embodiment, such composition is made by:

(i) admixing the drug delivery system with one or more excipients;

(ii) transferring amounts of the liquid or suspension composition equivalent to single or multiple doses into suitable containers; and (iii) sealing the containers.

Another embodiment is the method of manufacturing a dry composition of a drug delivery system. In one embodiment, such composition is made by:

(i) admixing the drug delivery system with one or more excipients;

(ii) transferring amounts equivalent to single or multiple doses into suitable containers;

(iii) drying the composition in said containers; and (iv) sealing the containers.

Suitable containers are vials, syringes, dual-chamber syringes, ampoules, and cartridges.

Another embodiment is a method for the synthesis of a drug delivery system or a pharmaceutically acceptable salt thereof as defined above. Drug delivery systems or precursors of drug delivery systems may be prepared by known methods or in accordance with the reaction sequences as described below. The starting materials used in the preparation (synthesis) of drug delivery systems or precursors thereof are known or commercially available, or can be prepared by known methods or as described below.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described.

EXAMPLES

Abbreviations

Ac Acetyl
ACN Acetonitrile
AcOH acetic acid
$Ac_2O$ acetic anhydride
aq. Aqueous
atm Atmosphere
Boc, BOC tertiary butyl carboxy
Boc-anhydride di-tert-butyl dicarbonate
$(Boc)_2O$, $(BOC)_2O$ di-tert-butyl dicarbonate
br. Broad
BSA bovine serum albumin
BuOH Butanol
CAD charged aerosol detector
calcd. Calculated
Cat, cat Catalytic
CBZ, Cbz Carbobenzyloxy
$Cu(OTf)_2$ copper(II) trifluoromethane sulfonate
d Doublet
dd doublet of doublets
DCM Dichloromethane
DIAD diisopropyl azodicarboxylate
DIPEA, DIEA N,N-diisopropylethylamine
DMAP 4,4-dimethylaminopyridine
DMF N,N-dimethylformamide
DMSO Dimethylsulfoxide
DOSY-NMR One dimensional diffusion ordered NMR
ECL Electrochemiluminescence
Elem. Anal. Elemental analysis
ELSD evaporative light scattering detector
EDC·HCl N-(3-Dimethylaminopropyl)-N'-ethylcarbodiimide hydrochloride
ESI electrospray ionization
EtOAc, AcOEt ethyl acetate
Et Ethyl
EtOH Ethanol
FCC flash column chromatography
FITC fluorescein isothiocyanate
g Grams
G Gauge
h hour(s)
HATU 2-(1H-7-azabenzotriazol-1-yl)-1,1,3,3-tetramethyl uronium hexafluorophosphate methanaminium
HC HPLC condition
HPLC high performance liquid chromatography
IPA 2-propanol
IR infrared spectroscopy
i or iso Iso
IVT, ivt Intravitreal
$K_2CO_3$ potassium carbonate
kD, kDa Kilodalton
L liter(s)
LCMS liquid chromatography-mass spectrometry
M Molar
MHz mega Hertz
m Multiplet
Me Methyl
MeCN Acetonitrile
MeOH Methanol
MES 2-(N-morpholino)ethanesulfonic acid
mg milligram(s)
µg Microgram
mM Millimolar
mm millimeter(s)
min Minutes
mL milliliter(s)
mmol Millimoles
µL Microliter
µmol Micromoles
MOPS 3-(N-morpholino)propanesulfonic acid
MS mass spectrometry
MsCl methanesulfonyl chloride
MsOH methanesulfonic acid
MWCO molecular weight cut off
m/z mass to charge ratio
N normal
NA not available
$NaBH_4$ sodium borohydride
$NaBH_3CN$ sodium cyanoborohydride
$Na(AcO)_3BH$ sodium triacetoxyborohydride
ng nanogram
$NH_4Cl$ ammonium chloride
NHS N-hydroxysuccinimide
nM nanomolar
NMR nuclear magnetic resonance
OMe methoxy
PBS phosphate buffered saline
1×PBS phosphate buffered saline, typically about 10 mM $PO_4^{3-}$
Pd/C palladium on carbon
$Pd(dppf)Cl_2$ 1,1'-bis(diphenylphosphino)ferrocene-palladium(II)dichloride
$Pd(dppf)Cl_2 \cdot CH_2Cl_2$ adduct 1,1'-bis(diphenylphosphino)ferrocene-palladium(II)dichloride dichloromethane complex
$Pd(PPh_3)_4$ tetrakis(triphenylphosphine)palladium(0)
Ph phenyl
ppm parts per million
psi pounds per square inch
rac racemic
rcf relative centrifugal force
RP reverse phase rt, RT room temperature s singlet sat. saturated SDS-page sodium dodecyl sulfate polyacrylamide gel electrophoresis SEC size exclusion chromatography SFC Supercritical Fluid Chromatography t triplet t-Bu, tBu tertiary-butyl $t_{1/2}$ half life $t_r$ or ret. time retention time TBAF tetra-n-butylammonium fluoride TBSCl, TBDMSCl tert-butyldimethylsilyl chloride TEA, $Et_3N$, $NEt_3$ triethylamine tert-tertiary TFA trifluoroacetic acid $Tf_2O$ trifluoromethanesulfonic anhydride THE tetrahydrofuran TLC Thin Layer Chromatography TMS trimethylsilyl TMSOTf trimethylsilyl trifluoromethanesulfonate Tris tris(hydroxymethyl)aminomethane Triton X-100 t-octylphenoxypolyethoxyethanol (CAS 9002-93-1)

Ts p-toluenesulfonyl

TsOH p-toluenesulfonic acid

Tween 20 polysorbate 20, Polyoxyethylene (20) sorbitan monolaurate

UPLC ultra performance liquid chromatography

UV ultraviolet

VEGF vascular endothelial growth factor v/v volume per volume w/v weight per volume w/w weight per weight The following drugs are described in these examples are abbreviated as:

D1: brolucizumab (SEQ ID NO:4);

D2: (SEQ ID NO:5);

D3: (SEQ ID NO: 6); and

D4: (SEQ ID NO:7).

METHODS

Synthesis of

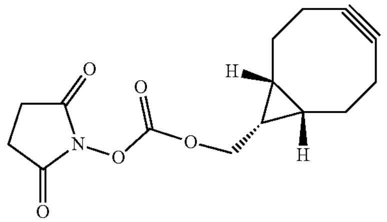 [SMILES: O=C(OC[C@@H]1[C@@H]2CCC#CCC[C@@H]21)ON1C(=O)CCC1=O]

((1R,8S,9s)-bicyclo[6.1.0]non-4-yn-9-yl)methyl (2,5-dioxopyrrolidin-1-yl) carbonate used in some following examples was described by A. M. Jawalekar, et al; *Molecules,* 2013, 18, 7346-7363.

Synthesis of

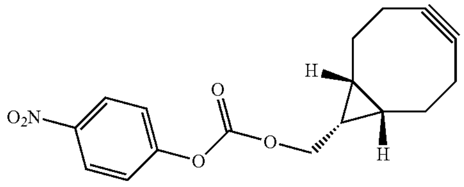 [SMILES: O=C(OC[C@@H]1[C@@H]2CCC#CCC[C@@H]21)Oc1ccc([N+](=O)[O-])cc1]

((1R,8S,9s)-bicyclo[6.1.0]non-4-yn-9-yl)methyl (4-nitrophenyl) carbonate used in some following examples was described by J. Dommerholt, et al; *Angew. Chem. Int. Ed.* 2010, 49, 9422-9425.

All other intermediates and reagents not specifically described as synthesized herein are commercially available and were used as delivered.

LCMS Methods

Method 1

Column SunFire C18 3.5 μm 3.0×30 mm; Column Temperature 40° C.; Flow 2.0 mL/min; Stop Time 2.20 min; pH 2.2; Eluent A1 0.05% TFA in Water; Eluent B1 Acetonitrile; Gradient Time (min)/% A (Eluent A1): % B (Eluent B1); 0.00/95:5; 1.70/5:95; 2.00/5:95; 2.10/95:5.

Method 2

Column AcQuity UPLC BEH C18 1.7 μm 2.1×30 mm; Column Temperature 50° C.; Flow 1.0 mL/min; Stop Time 2.00 min; pH 2.6; Eluent A1 0.1% Formic Acid in Water; Eluent B1 0.1% Formic Acid in Acetonitrile; Gradient Time (min)/% A (Eluent A1): % B (Eluent B1) 0.00/98:2; 0.10/98:2; 1.50/2:98; 1.80/2:98; 1.90/98:2; 2.00/98:2.

Method 3

Column: Kinetex 2.6 μm C18 100A (100×4.6 mm); mobile phase A (0.1% formic acid in water), B (acetonitrile); gradient (time (min)/% B): 0/5, 1/30, 3/95, 4/95, 4.1/5, 6/5.

Method 4

Column: AcQuity UPLC BEH C18 1.7 μm 2.1×30 mm; column temperature 50° C.; Flow 1.0 mL/min; Stop time: 2.00 min; pH 2.6; Eluent A1 0.1% formic acid in Water; Eluent B1 0.1% formic acid in Acetonitrile; Gradient Time (min)/% A (Eluent A1): % B (Eluent B1); 0.00/98:2; 0.10/98:2; 1.50/2:98; 1.80/2:98; 1.90/98:2; 2.00/98:2.

Method 5

Column: SunFire C18 3.5 μm 3.0×30 mm; Column Temperature 40° C.; Flow 2.0 mL/min; Stop Time 2.20 min; pH 2.2; Eluent A1 5 mM Ammonium Hydroxide in Water; Eluent B1 Acetonitrile; Gradient Time (min)/% A (Eluent A1): % B (Eluent B1); 0.00/95:5; 1.70/5:95; 2.00/5:95; 2.10/95:5.

Method 6

Column: Kinetex 2.6 m C18 100A, (100×4.60 mm); Gradient/(Time (min)/% B) 0/5, 1/30, 3/95, 4/95, 4.1/5, 6/5; mobile phase: 0.1% Formic acid in Water (A)/acetonitrile (B); Flow: 1.4 mL/min; Column Temperature: 40° C.

Method 7

Column: Synergi 2.5 μm MAX-RP 100A Mercury (100×4.6 mm); mobile phase A (0.1% formic acid in water), B (acetonitrile); gradient (time (min)/% B): 0/30, 0.5/30, 1.5/95, 2.4/95, 2.5/30, 3.0/30.

Method 8

Column: Kinetex 2.6 μm C18 100A (100×4.6 mm); mobile phase A (0.1% formic acid in water), B (acetonitrile); gradient (time (min)/% B): 0/50, 1/70, 2/100, 4/100, 4.1/50, 6/50. The ESI-MS data was recorded on an Acquity G2 Xevo-QTOF-MS. The positive ion mass spectrum was deconvoluted using MaxEnt 1 program in the MassLynx software package.

Method 9

Column: Proswift Monolith (4.6×50 mm); mobile phase A (0.1% formic acid in water), B (0.1% formic acid in acetonitrile); gradient (time (min)/% B): 0/2, 0.7/2, 2/98, 2.1/98, 2.3/2, 3.3/2. The ESI-MS data was recorded on an Acquity G2 Xevo-QTOF-MS. The positive ion mass spectrum was deconvoluted using the MaxEnt 1 program in the MassLynx software package. The deconvoluted m/z for $(M+H)^+$ was reported.

Example 1

Traceless Linkers

This example describes the synthesis of a number of traceless linkers, capable of being conjugated to both an amine-containing drug and to a carrier.

TABLE 6

Traceless Linkers L1-L11 and Traceless Linker Intermediates L12-L16

| Structure | Number |
|---|---|
| 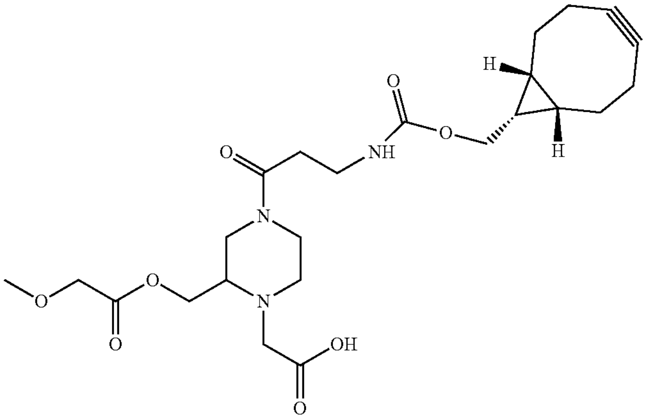 [SMILES: COCC(=O)OCC1CN(C(=O)CCNC(=O)OC[C@@H]2[C@@H]3CCC#CCC[C@@H]32)CCN1CC(=O)O] | L1 |
| 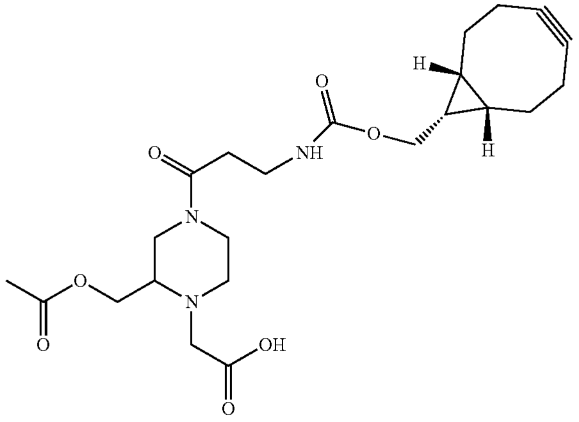 [SMILES: CC(=O)OCC1CN(C(=O)CCNC(=O)OC[C@@H]2[C@@H]3CCC#CCC[C@@H]32)CCN1CC(=O)O] | L2 |

TABLE 6-continued
Traceless Linkers L1-L11 and Traceless Linker Intermediates L12-L16
| Structure | Number |
|---|---|
| 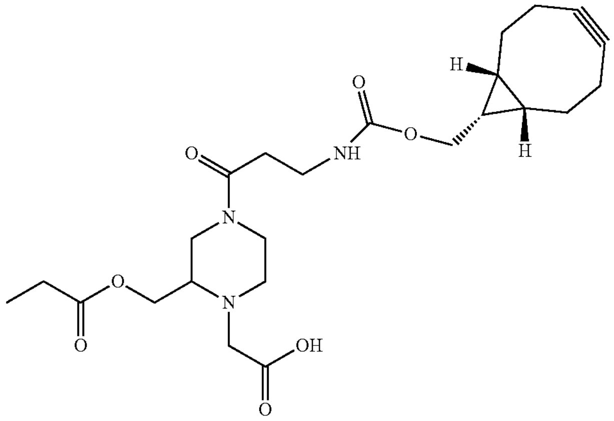 [SMILES: CCC(=O)OCC1CN(C(=O)CCNC(=O)OC[C@@H]2[C@@H]3CCC#CCC[C@@H]32)CCN1CC(=O)O] | L3 |
| 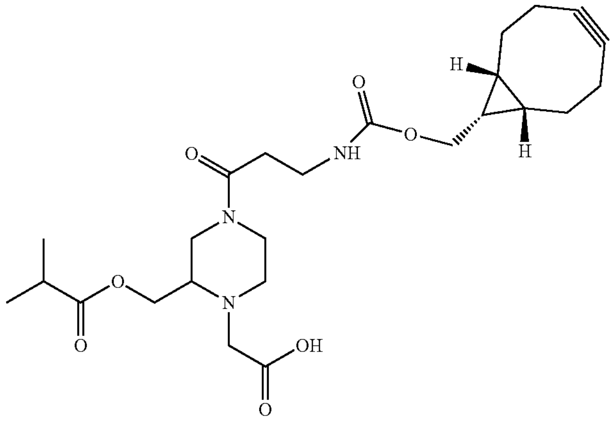 [SMILES: CC(C)C(=O)OCC1CN(C(=O)CCNC(=O)OC[C@@H]2[C@@H]3CCC#CCC[C@@H]32)CCN1CC(=O)O] | L4 |
| 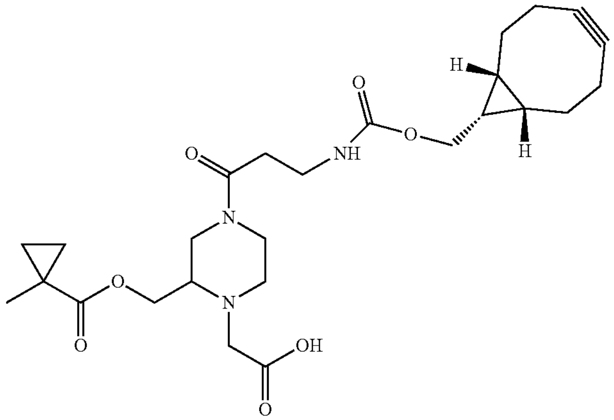 [SMILES: CC1(C(=O)OCC2CN(C(=O)CCNC(=O)OC[C@@H]3[C@@H]4CCC#CCC[C@@H]43)CCN2CC(=O)O)CC1] | L5 |

TABLE 6-continued
| Traceless Linkers L1-L11 and Traceless Linker Intermediates L12-L16 | |
|---|---|
| Structure | Number |
| 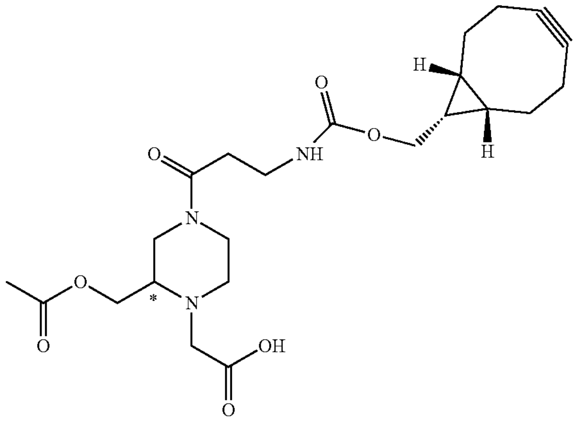 [SMILES: CC(=O)OCC1CN(C(=O)CCNC(=O)OC[C@@H]2[C@@H]3CCC#CCC[C@@H]32)CCN1CC(=O)O] | L6 |
| 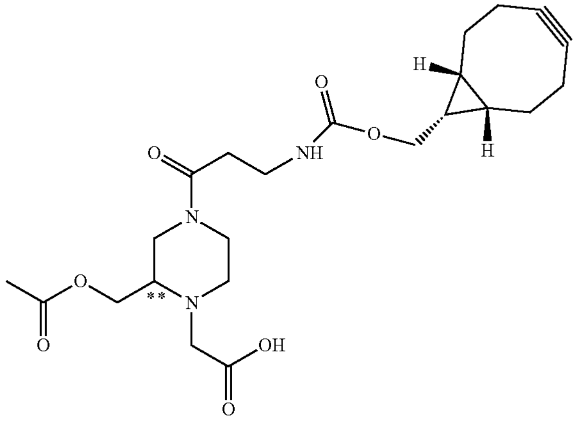 [SMILES: CC(=O)OCC1CN(C(=O)CCNC(=O)OC[C@@H]2[C@@H]3CCC#CCC[C@@H]32)CCN1CC(=O)O] | L7 |
| 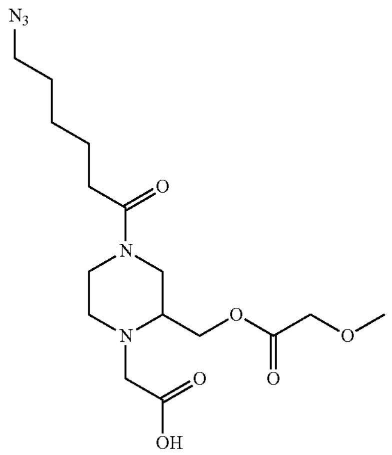 [SMILES: COCC(=O)OCC1CN(C(=O)CCCCCN=[N+]=[N-])CCN1CC(=O)O] | L8 |

TABLE 6-continued
| Traceless Linkers L1-L11 and Traceless Linker Intermediates L12-L16 | |
|---|---|
| Structure | Number |
| 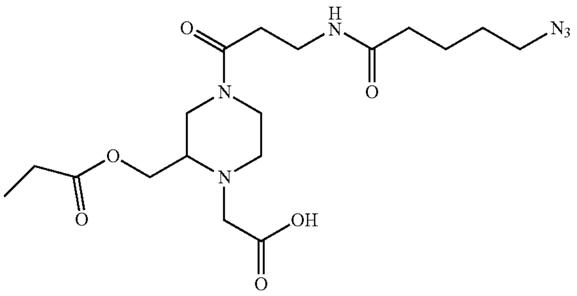 [SMILES: CCC(=O)OCC1CN(C(=O)CCNC(=O)CCCCN=[N+]=[N-])CCN1CC(=O)O] | L9 |
| 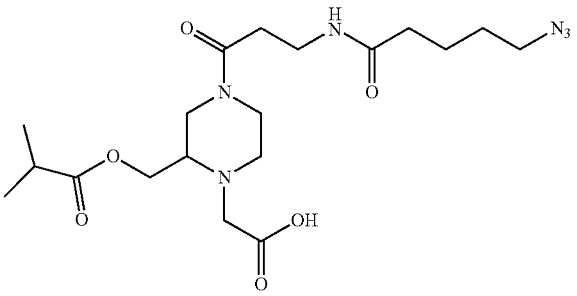 [SMILES: CC(C)C(=O)OCC1CN(C(=O)CCNC(=O)CCCCN=[N+]=[N-])CCN1CC(=O)O] | L10 |
| 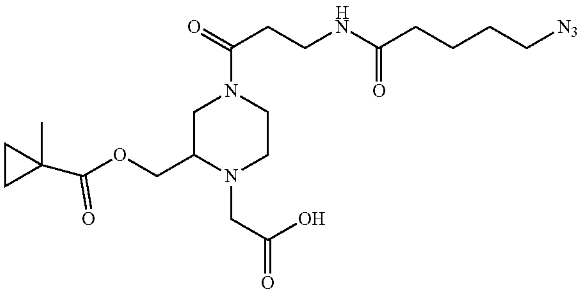 [SMILES: CC1(C(=O)OCC2CN(C(=O)CCNC(=O)CCCCN=[N+]=[N-])CCN2CC(=O)O)CC1] | L11 |
| 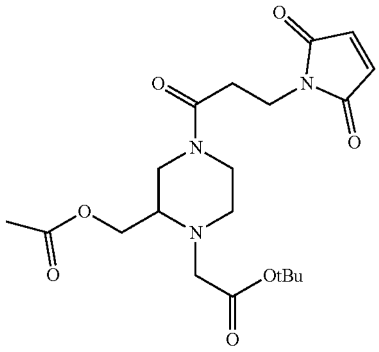 [SMILES: CC(=O)OCC1CN(C(=O)CCN2C(=O)C=CC2=O)CCN1CC(=O)OC(C)(C)C] | L12 |

TABLE 6-continued
| Traceless Linkers L1-L11 and Traceless Linker Intermediates L12-L16 | |
|---|---|
| Structure | Number |
| 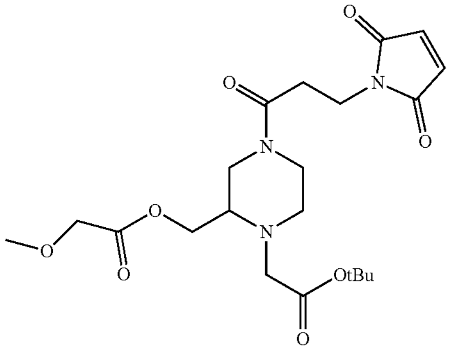 [SMILES: COCC(=O)OCC1CN(C(=O)CCN2C(=O)C=CC2=O)CCN1CC(=O)OC(C)(C)C] | L13 |
| 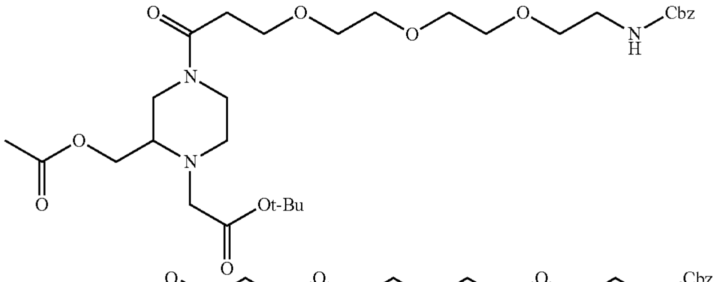 | L14 |
| 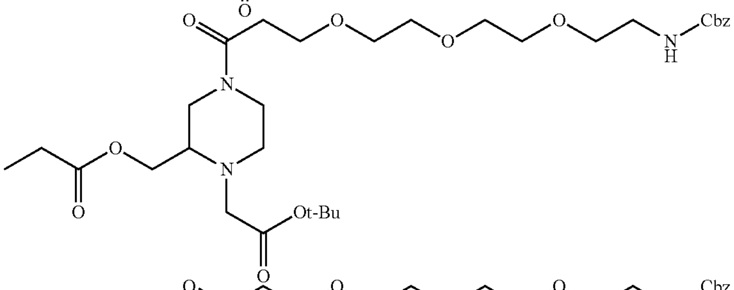 | L15 |
| 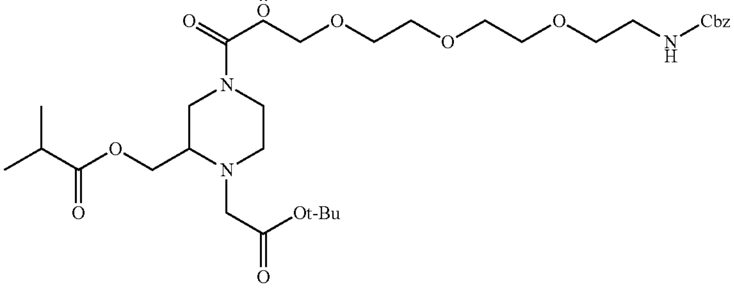 | L16 |
Synthesis of Traceless Linkers
Common Intermediate: L-INT-1c
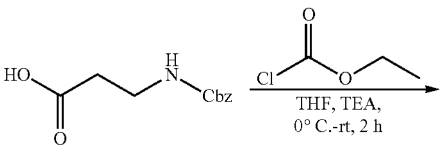
SM-1
-continued
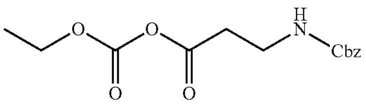
L-INT-1a
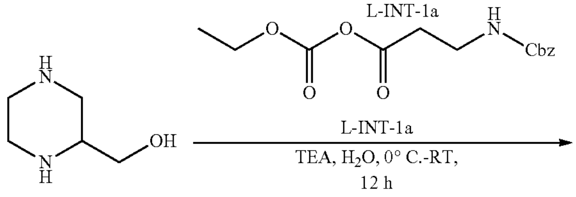
SM-2

-continued

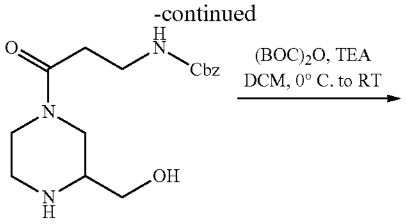

L-INT-1b

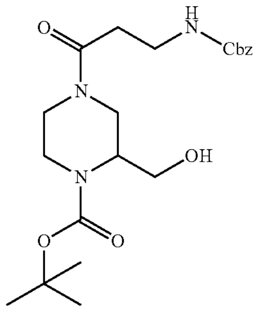

L-INT-1c

L-INT-1b. 1-(N-Cbz-beta-alanyl)-3-(hydroxymethyl) piperazine

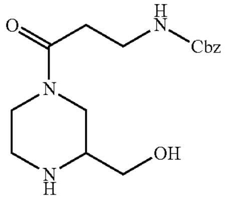 [SMILES: O=C(NCCC(=O)N1CCNC(CO)C1)OCc1ccccc1]

To a 0° C. solution of commercially available N-Cbz-beta-alanine (SM-1, 2.5 g, 11.2 mmol) in tetrahydrofuran (30 mL) was added triethylamine (1.13 g, 11.2 mmol) and ethylchloroformate (1.21 g, 11.2 mmol). The solution was stirred for 2 h at 0° C. to provide in situ formation of N-Cbz-beta-alanine ethyl carbonic anhydride (L-INT-1a). This reaction mixture was added to a solution of 2-(hydroxymethyl)piperazine (SM-2, 1.95 g, 16.8 mmol) and triethylamine (1.13 g, 11.2 mmol) in water (30 mL) and the resultant mixture was stirred 12 h at room temperature. The solution was made basic with sodium carbonate solution (2 M, 1 mL). Brine (2 mL) was added and the aqueous phase was concentrated to give a crude solid. Purification by column chromatography (basic alumina, eluted with 3-15% methanol:dichloromethane) provided L-INT-1b. MS (ESI+) m/z 322.2 (M+H).

L-INT-1c. 1-(Boc)-2-(hydroxymethyl)-4-(N-Cbz-beta-alanyl)piperazine

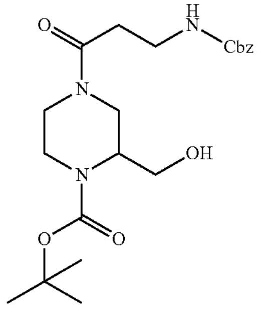 [SMILES: CC(C)(C)OC(=O)N1CCN(C(=O)CCNC(=O)OCc2ccccc2)CC1CO]

To a 0° C. solution of L-INT-1b (1 g, 3.1 mmol) in dichloromethane (20 mL) was added triethylamine (0.504 g, 4.98 mmol) and di-tert-butyl dicarbonate (611 mg, 2.8 mmol). The solution was stirred for 2 h at room temperature. The reaction mixture was treated with water and extracted with dichloromethane. The organic layer was dried (sodium sulfate) and evaporated. Purification by flash chromatography ($SiO_2$, eluted with 2:98 methanol:dichloromethane) provided L-INT-1c. MS (ESI+) m/z 422.2 (M+H).

Linker Intermediate L-INT-1

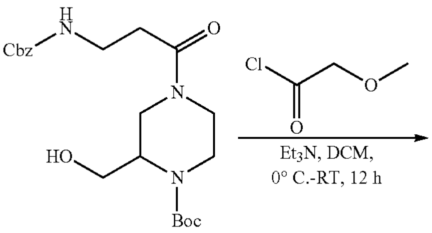

L-INT-1c

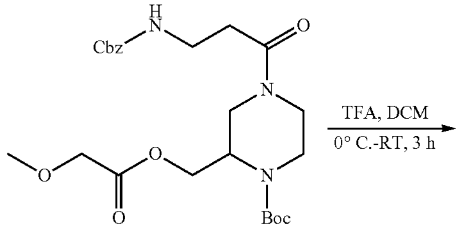

L-INT-1d

-continued

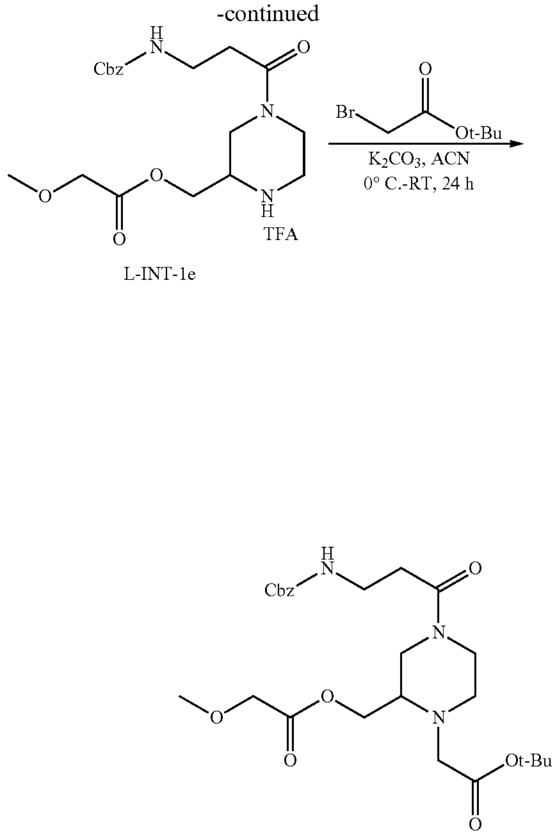

L-INT-1e

L-INT-1

L-INT-1d. 1-(Boc)-2-(2'-methoxyacetoxymethyl)-4-(N-Cbz-beta-alanyl)piperazine

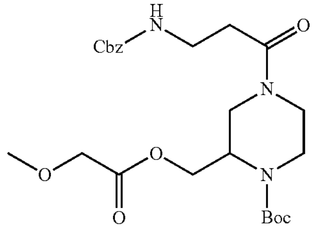 [SMILES: COCC(=O)OCC1CN(C(=O)CCNC(=O)OCc2ccccc2)CCN1C(=O)OC(C)(C)C]

To a 0° C. solution of L-INT-1c (1 g, 2.37 mmol) in dichloromethane (15 mL) was added triethylamine (0.60 g, 5.93 mmol). Methoxyacetyl chloride (307 mg, 2.85 mmol) was then added dropwise and the solution was stirred for 12 h at room temperature. The reaction mixture was treated with water and extracted with dichloromethane. The organic layer was dried (sodium sulfate) and evaporated. Purification by flash chromatography ($SiO_2$, eluted with 1-2% methanol:dichloromethane) provided L-INT-1d. MS (ESI+) m/z 494.2 (M+H).

L-INT-1e. 1-(N-Cbz-beta-alanyl)-3-(2'-methoxyacetoxymethyl)piperazine, trifluoroacetic acid salt

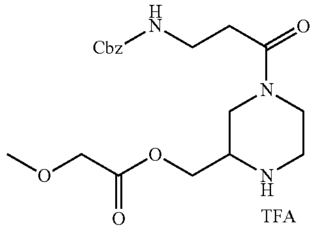 [SMILES: COCC(=O)OCC1CN(C(=O)CCNC(=O)OCc2ccccc2)CCN1]

To a 0° C. solution of L-INT-1d (1 g, 2.02 mmol) in dichloromethane (26 mL) was added trifluoroacetic acid (7 mL). The solution was stirred for 3 h at room temperature. The reaction mixture was concentrated, washed with pentane and dried under high vacuum to provide the trifluoroacetic acid salt L-INT-1e. MS (ESI+) m/z 394 (M+H).

L-INT-1. 2-(2'-methoxyacetoxymethyl)-4-(N-Cbz-beta-alanyl)-1-piperazineacetic acid t-butyl ester

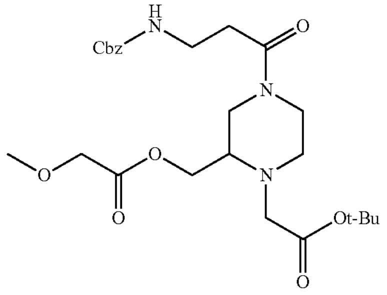 [SMILES: COCC(=O)OCC1CN(C(=O)CCNC(=O)OCc2ccccc2)CCN1CC(=O)OC(C)(C)C]

To a 0° C. mixture of L-INT-1e (1.0 g, 2.54 mmol) and potassium carbonate (1.05 g, 7.63 mmol) in acetonitrile (25 mL) was dropwise added tert-butyl bromoacetate (0.744 g, 3.82 mmol). The solution was stirred for 24 h at room temperature. The reaction mixture was treated with water and extracted with ethyl acetate. The organic layer was dried (sodium sulfate) and evaporated. Purification by flash chromatography ($SiO_2$, eluted with methanol dichloromethane) provided L-INT-1 as a colorless sticky solid. LCMS (method 8): retention time=3.43 min; MS (ESI+) m/z 508.3 (M+H). $^1$H NMR (400 MHz, CDCl3) 7.35-7.28 (m, 5H), 5.58-5.52 (m, 1H), 5.08 (s, 2H), 4.38-4.22 (i, 1H), 4.20-4.08 (m, 1H), 4.10-4.00 (m, 3H), 4.00-3.90 (m, 1H), 3.70-3.60 (m, 1H), 3.60-3.54 (, 1H), 3.50-3.49 (d, J=4, 4H), 3.45 (s, 3H), 3.42-3.38 (m, 1H), 3.33 (s, 1H), 3.32-3.29 (m, 1H), 3.28-3.20 (i, 1H), 3.18-3.10 (i, 1H), 3.10-3.00 (i, 1H), 2.86-2.72 (i, 2H), 2.53-2.51 (t, J=4, 2H), 1.46 (s, 9H).

Species shown in Table 7 were prepared using methods analogous to those used in the synthesis of L-INT-1.

TABLE 7

| Exemplary Traceless Linker Species | | | |
|---|---|---|---|
| Structure, Name | number | LCMS: [M + H]; retention time; method | $^1$H NMR (400 MHz, $CDCl_3$) |
| 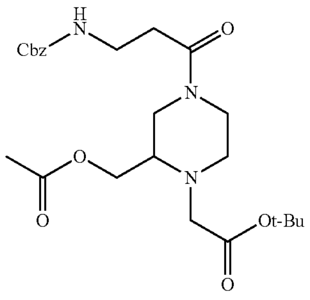 2-(acetoxymethyl)-4-(N-Cbz-beta-alanyl)-1-piperazineacetic acid t-butyl ester | L-INT-2 | 478.3; 3.46 min; 8 | 7.35-7.31 (m, 5H), 5.56-5.55 (m, 1H), 5.08 (s, 2H), 4.28-4.10 (m, 2H), 4.10-3.92 (m, 2H), 3.68-3.55 (m, 1H), 3.48 (s, 3H), 3.46-3.42 (m, 1H), 3.41-3.40 (d, J = 4, 1H), 3.33-3.28 (m, 2H), 3.28-3.15 (m, 1H), 3.10-2.98 (m, 2H), 2.88-2.76 (m, 2H), 2.53-2.51 (t, J = 4, 2H), 2.09-2.07 (d, J = 8, 3H), 1.45 (s, 9H) |
| 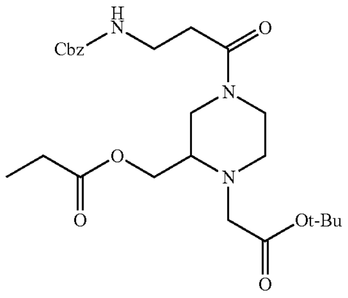 2-(propanoyloxymethyl)-4-(N-Cbz-beta-alanyl)-1-piperazineacetic acid t-butyl ester | L-INT-3 | 492.3; 3.61 min; 8 | 7.35-7.26 (m, 5H), 5.56-5.55 (m, 1H), 5.08 (s, 2H), 4.28-3.94 (m, 4H), 3.52-3.39 (m, 4H), 3.34-3.20 (m, 3H), 3.12-2.94 (m, 2H), 2.81-2.76 (m, 2H), 2.53-2.50 (m, 2H), 2.38-2.33 (m, 2H), 1.45 (s, 9H), 1.17-1.12 (m, 3H). |
| 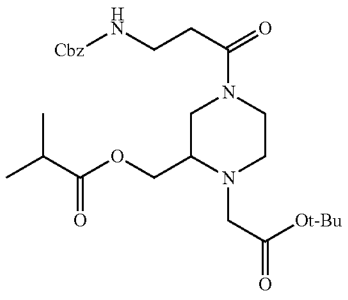 2-(isobutanoyloxymethyl)-4-(N-Cbz-beta-alanyl)-1-piperazineacetic acid t-butyl ester | L-INT-4 | 506.3; 3.80 min; 8 | 7.35-7.30 (m, 5H), 5.75-5.54 (t, J = 4, 1H), 5.08 (s, 2H), 4.26-3.93 (m, 3H), 3.64-3.48 (m, 3H), 3.43-3.19 (m, 4H), 3.09-2.99 (m, 2H), 2.80-2.76 (m, 2H), 2.75-2.51 (m, 3H), 1.45 (s, 9H), 1.18-1.16 (d, J = 4, 6H) |

L-INT-5. 2-(1'-methylcyclopropylcarbonyloxymethyl)-4-(N-Cbz-beta-alanyl)-1-piperazineacetic acid t-butyl ester

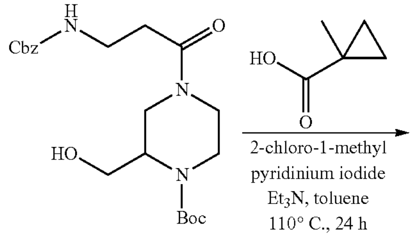

L-INT-1c

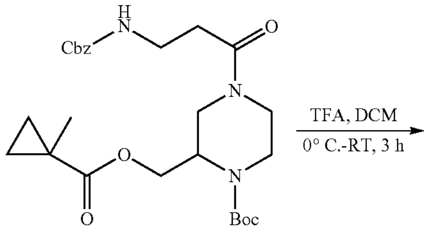

L-INT-5a

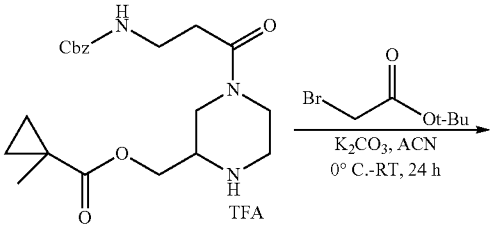

L-INT-5b

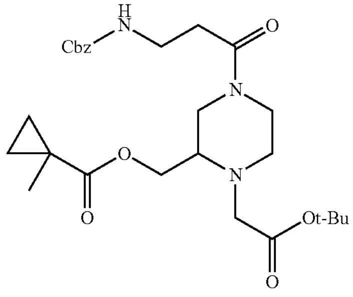

L-INT-5

L-INT-5a. 1-(Boc)-2-(1'-methylcyclopropylcarbonyloxymethyl)-4-(N-Cbz-beta-alanyl)piperazine

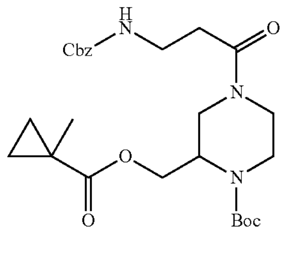 [SMILES: CC(C)(C)OC(=O)N1CCN(C(=O)CCNC(=O)OCc2ccccc2)CC1COC(=O)C1(C)CC1]

To a solution of L-INT-1c (1.0 g, 2.37 mmol), 1-methylcyclopropane carboxylic acid (0.475 g, 4.75 mmol) and 2-chloro-1-methyl-pyridinium iodide (1.21 g, 4.75 mmol) in toluene (20 mL) was added triethylamine (5.0 mL) and the resultant reaction was stirred 24 h at 110° C. The reaction mixture was treated with water and extracted with ethyl acetate. The organic phase was washed with brine, dried (sodium sulfate) and evaporated. Purification by flash chromatography ($SiO_2$, eluted with 1-2% methanol:dichloromethane) provided L-INT-5a. MS (ESI+) m/z 504.2 (M+H).

L-INT-5. 2-(1'-methylcyclopropylcarbonyloxymethyl)-4-(N-Cbz-beta-alanyl)-1-piperazineacetic acid t-butyl ester

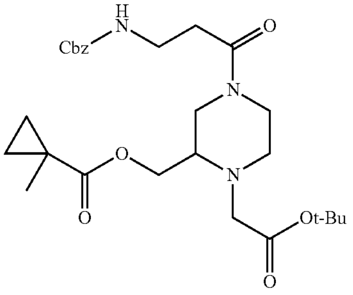 [SMILES: CC(C)(C)OC(=O)CN1CCN(C(=O)CCNC(=O)OCc2ccccc2)CC1COC(=O)C1(C)CC1]

L-INT-5 was prepared in two steps from L-INT-5a following the general methods described for the synthesis of L-INT-1e and L-INT-1. L-INT-5: LCMS (method 8): retention time=3.84 min; MS (ESI+) m/z 518.3 $^1H$ NMR (400 MHz, $CDCl_3$) 7.35-7.30 (m, 5H), 5.5 (s 1H), 5.08 (s, 2H), 4.28-4.12 (m, 2H), 4.06-3.88 (m, 2H), 3.67-3.49 (m, 3H), 3.41-3.28 (m, 3H), 3.26-3.17 (m, 1H), 3.12-3.05 (m, 1H), 3.03-2.90 (m, 1H), 2.78-2.74 (m, 2H), 2.53-2.50 (t, J=8, 2H), 1.45 (s, 9H), 1.29 (s, 3H), 1.25-1.20 (m, 2H), 0.73-0.68 (m, 2H).

L-INT-6 and L-INT-7. Chiral separation of 2-(acetoxymethyl)-4-(N-Cbz-beta-alanyl)-1-piperazineacetic acid t-butyl ester

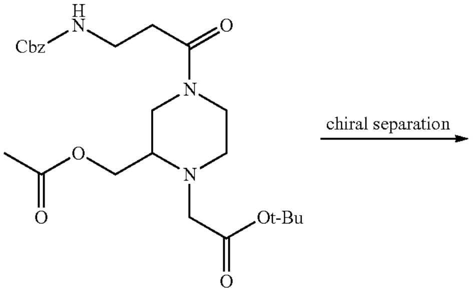

L-INT-2

-continued

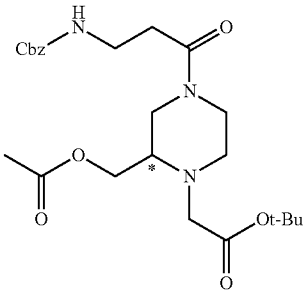

L-INT-6

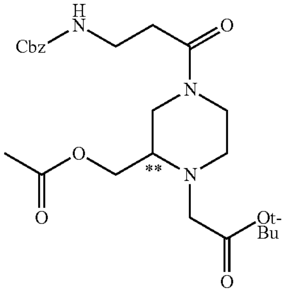

L-INT-7

The individual enantiomers of L-INT-2 were isolated by preparative chiral HPLC purification of L-INT-2 (Phenomenex Lux Amylose-2 column, 5 m, 250 mm×21.2 mm), eluting with 20 mL/min of mobile phase with the following composition (isocratic): 55% n-hexane, 45% 70:30 ethanol: isopropanol with 0.1% diethylamine. The product containing fractions were evaporated, dissolved in chloroform, washed with water, dried (sodium sulfate), and evaporated to provide stereoisomers L-INT-6 and L-INT-7.

L-INT-6: LCMS (method 8): retention time=1.93 min; MS (ESI+) m/z 478.3 (M+H). Chiral HPLC (method below): retention time=8.018 min; 98.3% purity).

L-INT-7: LCMS (method 8): retention time=1.92 min; MS (ESI+) m/z 478.3 (M+H). Chiral HPLC (method below): retention time=9.694 min; 94.4% purity).

Chiral HPLC method: Column: Phenomenex Lux Amylose-2, 5 μm, 250 mm×4.60 mm; column temperature 25° C.; Flow 1.0 mL/min; mobile phase: A=hexane, B=ethanol: methanol 1:1; elution:isocratic 30:70 A:B.

Traceless Linkers; L1-L7

-continued

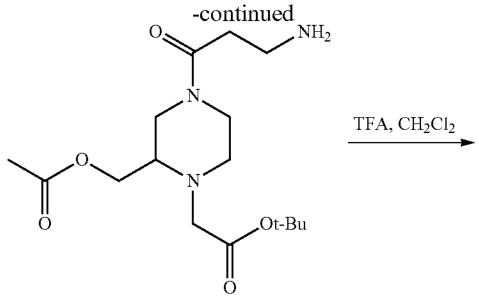

L-2a

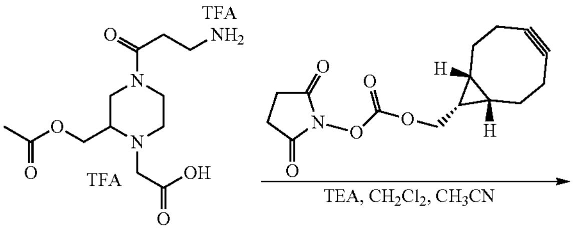

L-2b

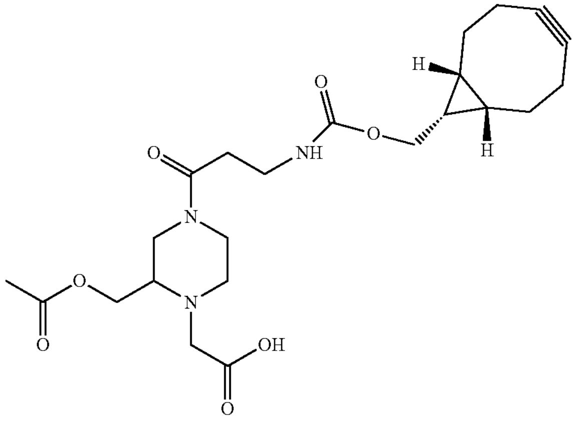

L-2

L-2a. 2-(acetoxymethyl)-4-(beta-alanyl)-1-piperazineacetic acid t-butyl ester

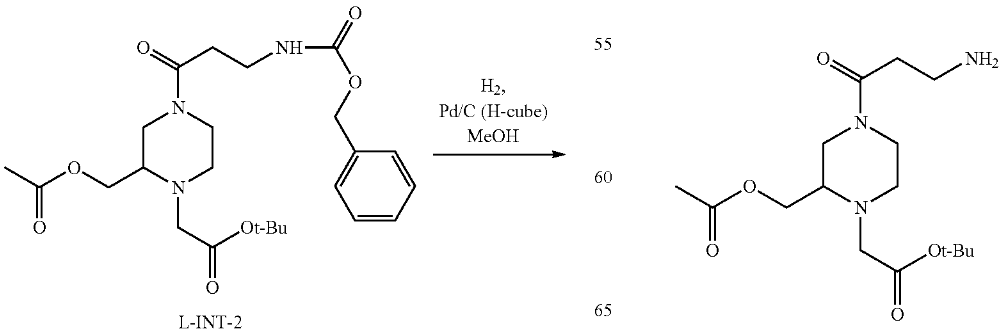

L-INT-2

L-INT-2 (185.5 mg, 0.39 mmol) was dissolved in methanol (12 mL) and subjected to flow hydrogenolysis (palladium on carbon cartridge, 5 atm $H_2$, 35° C., 1 h at 1 mL/min flow-rate). The solution was evaporated to provide the title compound L-2a. LCMS (method 1): retention time=0.72 min; MS (ESI+) m/z 344.1 (M+H).

L-2b: 2-(acetoxymethyl)-4-(beta-alanyl)-1-piperazineacetic acid, bis trifluoroacetic acid salt

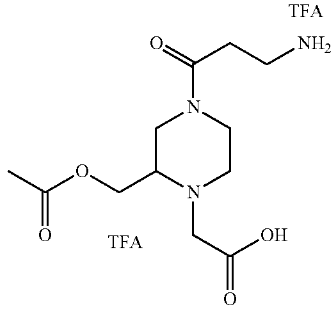 [SMILES: CC(=O)OCC1CN(C(=O)CCN)CCN1CC(=O)O]

L-2a (123.2 mg, 0.36 mmol) was dissolved in dichloromethane (5 mL) and trifluoroacetic acid (1 mL). The reaction was stirred at room temperature overnight, then evaporated to provide crude title material (L-2b). LCMS (method 1): retention time=0.10 min; MS (ESI+) m/z 288.0 (M+H).

L2. 2-(acetoxymethyl)-4-(N-(((1R,8S,9s)-bicyclo[6.1.0]non-4-yn-9-yl)methoxycarbonyl)-beta-alanyl)-1-piperazineacetic acid

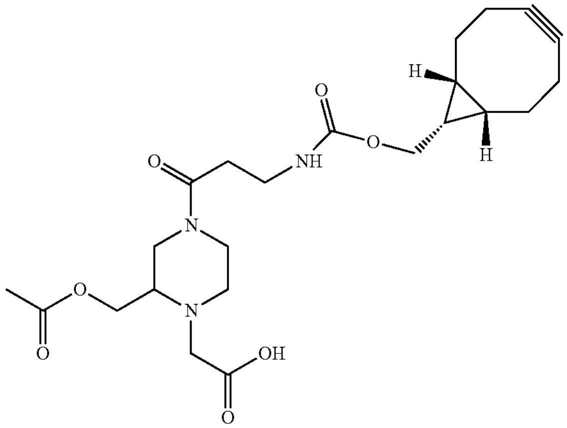 [SMILES: CC(=O)OCC1CN(C(=O)CCNC(=O)OC[C@@H]2[C@@H]3CCC#CCC[C@@H]32)CCN1CC(=O)O]

Crude L-2b (163 mg, 0.57 mmol) was taken up in dichloromethane and acetonitrile to provide a faintly cloudy mixture. Addition of triethylamine (0.40 mL, 2.84 mmol) and ((1R,8S,9s)-bicyclo[6.1.0]non-4-yn-9-yl)methyl (2,5-dioxopyrrolidin-1-yl) carbonate (182 mg, 0.63 mmol) resulted in a solution, which was evaporated after 0.5 h. The crude material was dissolved in 6 mL 3:1 acetonitrile:water and purified by HPLC (Column: Waters XBridge BEH 5 μm 19×150 mm; method: 15-30% acetonitrile 10 min gradient (10 mM ammonium hydroxide) in water 30 mL/min). The fractions were evaporated, flash frozen and lyophilized to provide L2. LCMS (method 1): retention time=0.97 min; MS (ESI+) m/z 464.1 (M+H). $^1$H-NMR ($CD_3OD$, ppm) (sample contains trace residual triethylamine): 4.17 (m, 4H); 4.00 (m, 1H), 3.75 (m, 1H), 3.5-3.32 (m, 5H), 3.06 (m, 1H), 2.91 (m, 1H), 2.79 (m, 1H), 2.60 (t, 2H), 2.19 (m, 6H), 2.05 (m, 3H), 1.59 (m, 2H), 1.38 (m, 1H), 0.96 (m, 2H).

Species shown in Table 8 were prepared using methods analogous to those used in the synthesis of L2.

TABLE 8

Exemplary Traceless Linker Species

| Structure | Number (starting intermediate) | LCMS: [M + H]; retention time; method | $^1$H-NMR (400 MHz, $CD_3OD$) |
|---|---|---|---|
| 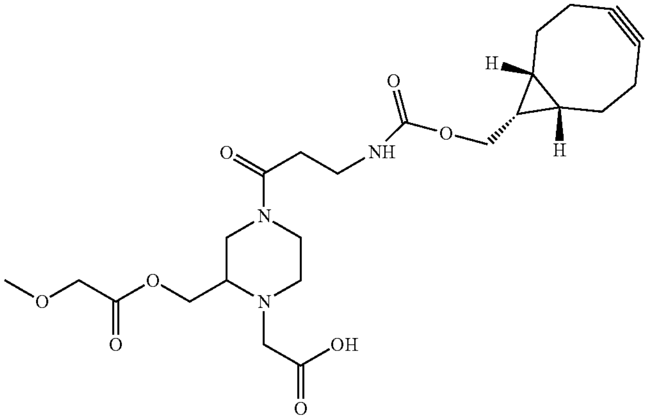 2-(2′-methoxyacetoxymethyl)-4-(N-(((1R,8S,9s)-bicyclo[6.1.0]non-4-yn-9-yl)methoxycarbonyl)-beta-alanyl)-1-piperazineacetic acid | L1 (L-INT-1) | 494.1; 0.98 min; 1 | 4.25 (m, 2H); 4.14 (m, 4H); 4.0-3.44 (m, 5H), 3.42 (s, 3H), 3.3-3.1 (m, 2H), 2.96 (m, 1H), 2.83 (m, 1H), 2.69 (m, 1H), 2.62 (m, 2H), 2.21 (m, 6H), 1.61 (m, 2H), 1.37 (m, 1H), 0.93 (m, 2H) |

TABLE 8-continued

Exemplary Traceless Linker Species

| Structure | Number (starting intermediate) | LCMS: [M + H]; retention time; method | $^1$H-NMR (400 MHz, $CD_3OD$) |
|---|---|---|---|
| 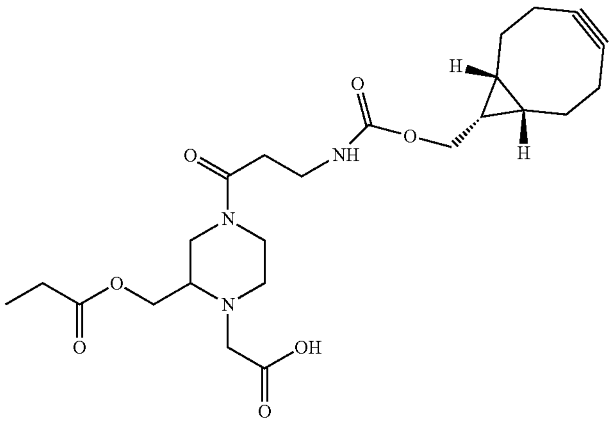 2-(propanoyloxymethyl)-4-(N-(((1R,8S,9s)-bicyclo[6.1.0]non-4-yn-9-yl)methoxycarbonyl)-beta-alanyl)-1-piperazineacetic acid | L3 (L-INT-3) | 478.2; 1.03 min; 1 | 4.17 (m, 3H); 3.99 (dd, 1H), 3.76 (dd, 1H), 3.47 (m, 2H), 3.37 (M, 2H), 3.06 (dd, 1H), 2.91 (m, 1H), 2.79 (m, 1H), 2.60 (t, 2H), 2.36 (m, 2H), 2.19 (m, 6H), 1.59 (m, 2H), 1.38 (m, 1H), 1.12 (t, 3H), 0.96 (m, 2H) |
| 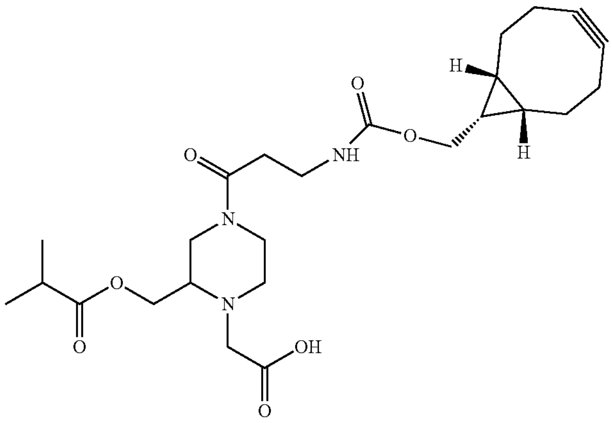 2-(isobutanoyloxymethyl)-4-(N-(((1R,8S,9s)-bicyclo[6.1.0]non-4-yn-9-yl)methoxycarbonyl)-beta-alanyl)-1-piperazineacetic acid | L4 (L-INT-4) | 492.7; 0.82 min; 2 | 4.17 (m, 3H); 3.99 (dd, 1H), 3.76 (dd, 1H), 3.41 (m, 4H), 3.06 (dd, 1H), 2.90 (m, 1H), 2.79 (m, 1H), 2.58 (m, 3H), 2.19 (m, 6H), 1.60 (m, 2H), 1.37 (m, 1H), 1.16 (d, 6H), 0.96 (t, 2H) |

TABLE 8-continued

Exemplary Traceless Linker Species

| Structure | Number (starting intermediate) | LCMS: [M + H]; retention time; method | $^1$H-NMR (400 MHz, $CD_3OD$) |
|---|---|---|---|
| 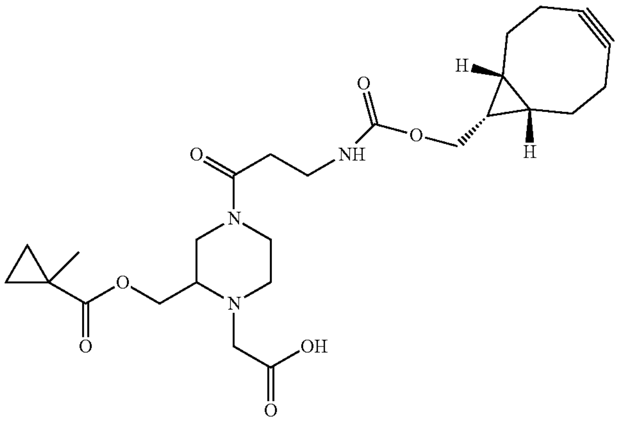 2-(1′-methylcyclopropylcarbonyloxymethyl)-4-(N-(((1R,8S,9s)-bicyclo[6.1.0]non-4-yn-9-yl)methoxycarbonyl)-beta-alanyl)-1-piperazineacetic acid | L5 (L-INT-5) | 504.2; 1.09 min; 1 | 4.16 (m, 4H); 3.99 (m, 1H), 3.76 (m, 1H), 3.5-3.35 (m, 5H), 3.06 (m, 1H), 2.93 (m, 1H), 2.88 (dt, 1H), 2.77 (m, 1H), 2.61 (m, 2H), 2.19 (m, 6H), 1.60 (m, 2H), 1.38 (m, 1H), 1.29 (s, 3H), 1.22 (d, 2H), 0.93 (t, 2H), 0.73 (dq, 2H) |
| 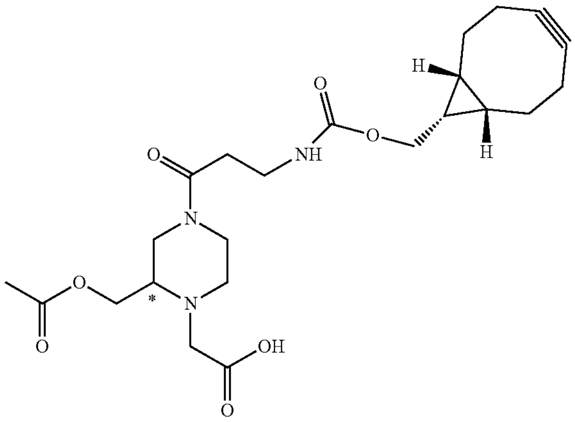 Isomer 1. 2-(acetoxymethyl)-4-(N-(((1R,8S,9s)-bicyclo[6.1.0]non-4-yn-9-yl)methoxycarbonyl)-beta-alanyl)-1-piperazineacetic acid | L6 (L-INT-6) | 464.2; 0.95 min; 1 | Used as a crude, no NMR |

TABLE 8-continued

Exemplary Traceless Linker Species

| Structure | Number (starting intermediate) | LCMS: [M + H]; retention time; method | $^1$H-NMR (400 MHz, $CD_3OD$) |
|---|---|---|---|
| 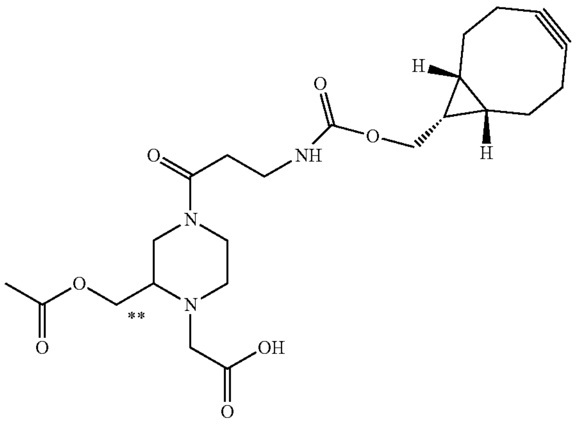 Isomer 2. 2-(acetoxymethyl)-4-(N-(((1R,8S,9s)-bicyclo[6.1.0]non-4-yn-9-yl)methoxycarbonyl)-beta-alanyl)-1-piperazineacetic acid | L7 (L-INT-7) | 464.2; 0.96 min; 1 | Used as a crude, no NMR |

Traceless linker L8. 2-(2'-methoxyacetoxymethyl)-4-(6'-azidohexanoyl)-1-piperazineacetic acid

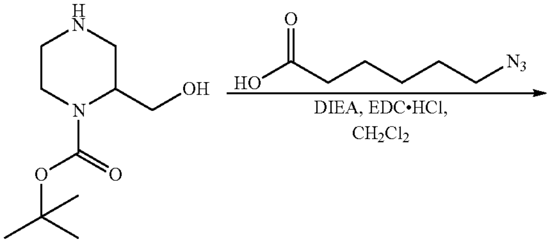

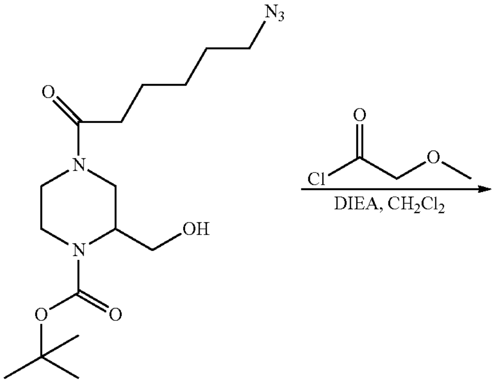

L-8a

-continued

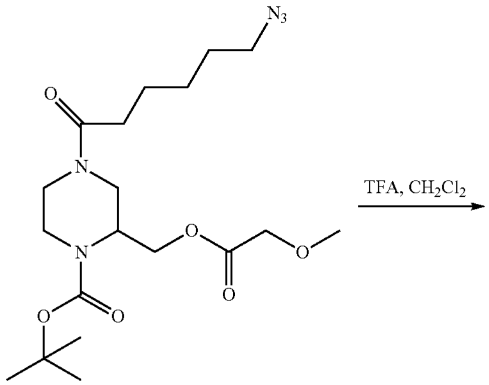

L-8b

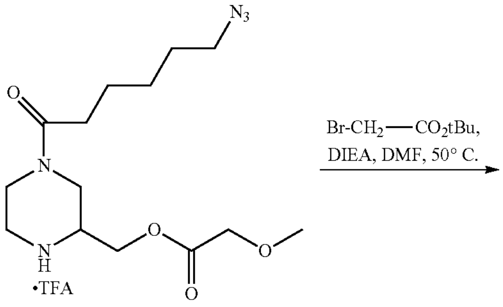

L-8c

-continued

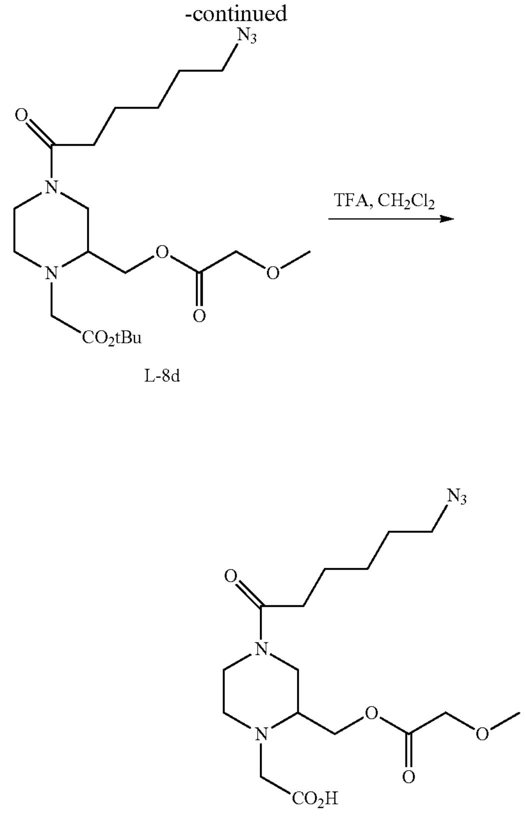

L-8d

L8

L-8a. 1-(Boc)-2-(hydroxymethyl)-4-(6'-azido-hexanoyl)piperazine

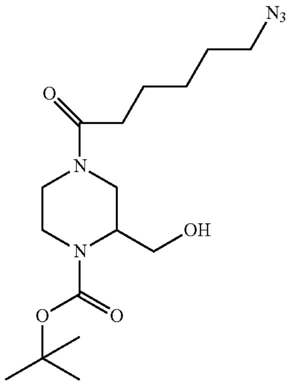 [SMILES: CC(C)(C)OC(=O)N1CCN(C(=O)CCCCCN=[N+]=[N-])CC1CO]

6-azidohexanoic acid (743 mg, 4.73 mmol) and N-(3-dimethylaminopropyl)-N'-ethylcarbodiimide hydrochloride (1.0 g, 5.22 mmol) were weighed into a round-bottomed flask and dissolved in dichloromethane (20 mL). After 5 min, solid tert-butyl 2-(hydroxymethyl)piperazine-1-carboxylate (0.98 g, 4.53 mmol) and diisopropylethylamine (1.0 mL, 5.73 mmol) were added and the solution was stored at room temperature overnight. The next day, the reaction mixture was diluted with 100 mL dichloromethane and washed with 1 M HCl (2×50 mL), 1 M NaOH (1×50 mL), and brine (1×50 mL). The organic phase was concentrated to provide L-8a. MS (ESI+) m/z 356.3 (M+H).

L-8b. 1-(Boc)-2-(2'-methoxyacetoxymethyl)-4-(6"-azidohexanoyl)piperazine

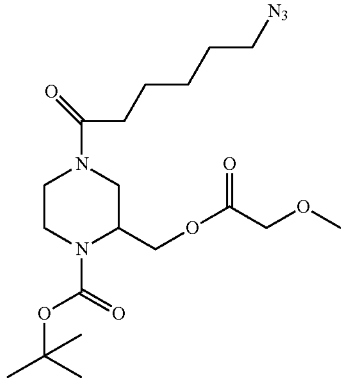 [SMILES: COCC(=O)OCC1CN(C(=O)CCCCCN=[N+]=[N-])CCN1C(=O)OC(C)(C)C]

L-8a (959 mg, 2.70 mmol) was dissolved in dichloromethane (12 mL) in a round-bottomed flask. A stir bar and diisopropylethylamine (1 mL, 5.73 mmol) were added, followed by 2-methoxyacetyl chloride (0.32 mL, 3.51 mmol), and the flask was capped. The reaction was stirred at room temperature. After 6 h, 100 μL additional 2-methoxyacetyl chloride was added. After 30 min, the reaction mixture was diluted with 90 mL ethyl acetate and washed with 1 M HCl (2×25 mL) and brine (1×20 mL). The organic phase was concentrated using a rotoevaporator. The product was purified by flash column chromatography on silica with an ethyl acetate:heptanes gradient. Product containing fractions were combined and concentrated to provide L-8b. MS (ESI+) m/z=428.3 (M+H).

L-8c. 1-(6'-azidohexanoyl)-3-(2"-methoxyacetoxymethyl)piperazine, trifluoroacetic acid salt

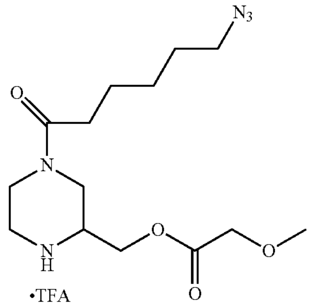 [SMILES: COCC(=O)OCC1CN(C(=O)CCCCCN=[N+]=[N-])CCN1]

L-8b (846 mg, 1.979 mmol) was dissolved in trifluoroacetic acid (10 mL, 130 mmol) and dichloromethane (10 mL). The solution was stirred at room temperature. After 1 h, the solvents were removed using a rotoevaporator and the product dried under vacuum to provide L-8c. MS (ESI+) m/z 328.2 (M+H).

L-8d. 2-(2'-methoxyacetoxymethyl)-4-(6"-azido-hexanoyl)-1-piperazineacetic acid t-butyl ester

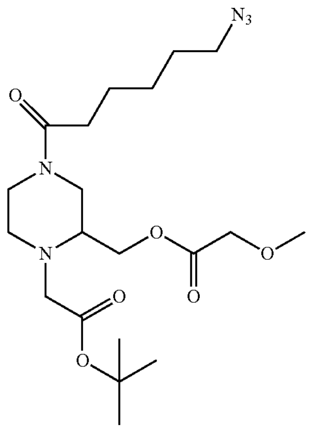 [SMILES: COCC(=O)OCC1CN(C(=O)CCCCCN=[N+]=[N-])CCN1CC(=O)OC(C)(C)C]

L-8c (439 mg, 0.994 mmol) was dissolved in dimethylformamide (5 mL) in a glass vial with a stirbar. t-Butyl bromoacetate (0.220 mL, 1.491 mmol) and diisopropylethylamine (0.868 mL, 4.97 mmol) were added, and the vial was capped. The reaction was stirred at 50° C. overnight. The next day, the reaction mixture was removed from the heat source and stored at −20° C. until purification the following day. The reaction mixture was purified without extractive work up by flash column chromatography on silica with a heptane:ethyl acetate gradient. Product containing fractions were combined, and concentrated to provide L-8d. MS (ESI−) m/z=486.5 (M+formate).

L8. 2-(2'-methoxyacetoxymethyl)-4-(6"-azido-hexanoyl)-1-piperazineacetic acid

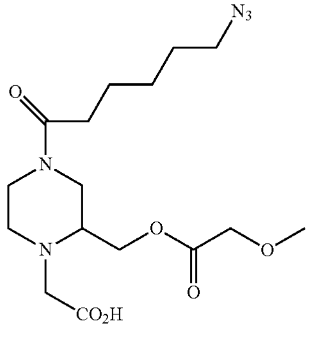 [SMILES: COCC(=O)OCC1CN(C(=O)CCCCCN=[N+]=[N-])CCN1CC(=O)O]

L-8d (150 mg, 0.317 mmol) was dissolved in dichloromethane (5 mL) and trifluoroacetic acid (5 mL) and the reaction was stirred at room temperature overnight. The next day, the solution was concentrated using a rotoevaporator and the residue was redissolved in 4 mL acetonitrile. The solution was filtered and purified by preparative reverse phase HPLC with mass directed fraction collection (method below). Product containing fractions were pooled, frozen, and lyophilized to provide L8. MS (ESI+) m/z=386.5 (M+H). Preparative HPLC conditions: Waters Sunfire C18; particle size: 5 μm; column size: 30×50 mm; eluent/gradient: 10% $CH_3CN/H_2O$/0.7 min, 10-30% $CH_3CN/H_2O$/3.5 min, 30-95% $CH_3CN/H_2O$ 0.5 min ($CH_3CN$ and $H_2O$ containing 0.1% TFA); flow rate: 75 mL/min; column temperature: room temperature; collection m/z: +385.

Traceless Linkers: L9-L11

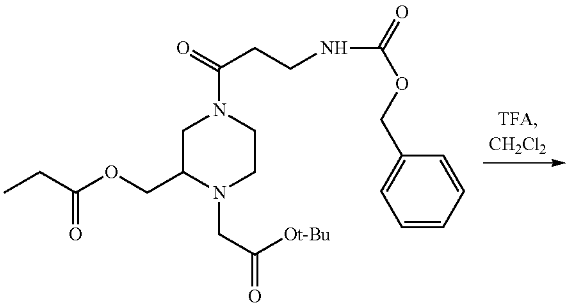

L-INT-3

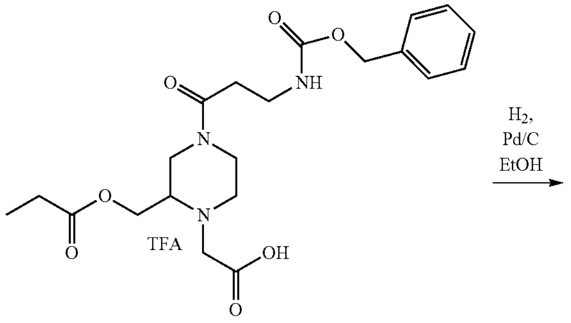

L-9a

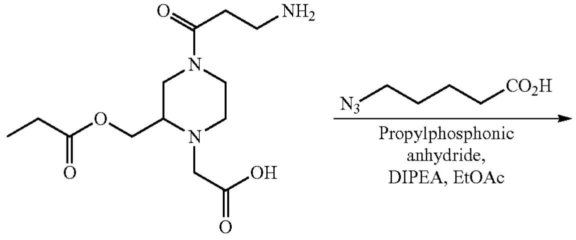

L-9b

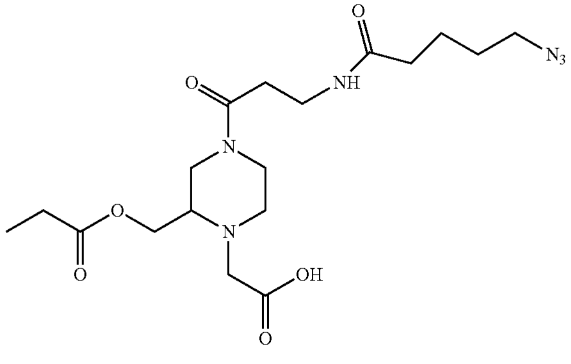

L9

L-9a. 2-(propanoyloxymethyl)-4-(N-Cbz-beta-alanyl)-1-piperazineacetic acid, trifluoroacetic acid salt

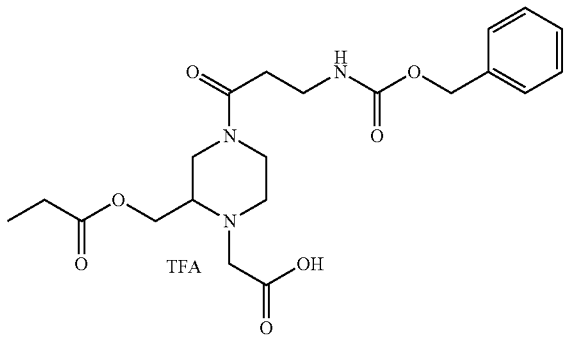 [SMILES: CCC(=O)OCC1CN(C(=O)CCNC(=O)OCc2ccccc2)CCN1CC(=O)O]

L-INT-3 (250 mg, 0.51 mmol) was dissolved in dichloromethane (5 mL) at 0° C., then treated with trifluoroacetic acid (2.5 mL) and stirred at room temperature 6 h under argon. The reaction was evaporated, washed with pentane and dried to provide crude L-9a as a trifluoroacetic acid salt. LCMS (method 5): retention time=0.262 min; MS (ESI+) m/z 436.2 (M+H).

L-9b. 2-(propanoyloxymethyl)-4-(beta-alanyl)-1-piperazineacetic acid

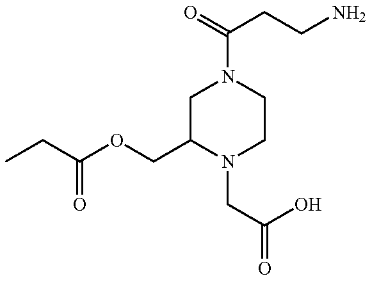 [SMILES: CCC(=O)OCC1CN(C(=O)CCN)CCN1CC(=O)O]

L-9a (250 mg, 0.57 mmol) was dissolved in ethanol (5 mL), to which was added 10% palladium on carbon (25 mg). The solution was stirred under a balloon of hydrogen gas for 6 h and then filtered through Celite©, washing with ethanol. The combined filtrates were evaporated to provide compound L-9b. LCMS (method 5): retention time=0.774 min; MS (ESI+) m/z 302.2 (M+H).

L9

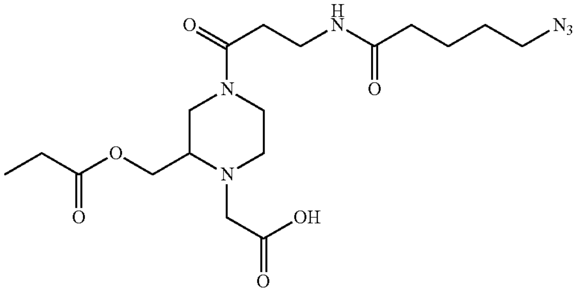 [SMILES: CCC(=O)OCC1CN(C(=O)CCNC(=O)CCCCN=[N+]=[N-])CCN1CC(=O)O]

L-9b (100 mg, 0.33 mmol) and 5-azidopentanoic acid (57 mg, 0.40 mmol) in ethyl acetate (5 mL) at 0° C. were treated with diisopropylethylamine (107 mg, 0.83 mmol) and propylphosphonic anhydride (50% solution in ethyl acetate, 158 mg, 0.50 mmol). The reaction was stirred at room temperature 16 h under argon, then quenched with water and evaporated. Initial flash chromatography ($SiO_2$, 10% methanol:dichloromethane) was followed by preparative HPLC (column: zorbax C-18 4.6×150 mm; Mobile phase A=: methanol (1:1) 0.01% TFA in water, mobile phase B=acetonitrile:methanol (1:1); time=0 min: 30% B; 1 min: 70% B; 6 min: 100% B; 1 mL/min) to provide L9. LCMS (method 5): retention time=0.18 min; MS (ESI+) m/z 427.1 (M+H). $^1$H-NMR ($CD_3OD$, ppm) (all assignments provisional) 4.23-4.17 (m, 2H), 4.16-3.98 (m, 1H), 3.78-3.62 (m, 1H), 3.54 (s, 2H), 3.46-3.43 (t, J=4, 3H), 3.26-3.20 (m, 1H), 3.18-3.05 (m, 1H), 3.03-2.76 (m, 2H), 2.64-2.61 (t, J=8, 2H), 2.43-2.36 (m, 2H), 2.24-2.21 (t, J=8, 2H), 1.75-1.58 (m, 4H), 1.15-1.12 (t, J=8, 3H).

Species shown in Table 9 were prepared using methods analogous to those used in the synthesis of L-9:

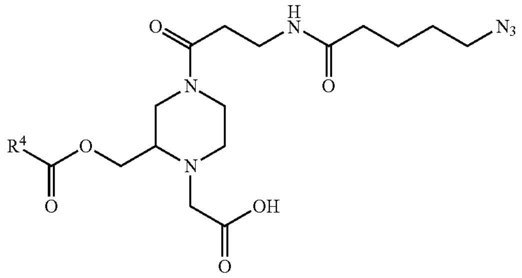

TABLE 9

| Exemplary Traceless Linker Species | | | |
|---|---|---|---|
| $R^4$, Name | Number (starting intermediate) | LCMS: [M + H]; retention time; method | $^1$H-NMR (300 MHz, $CD_3OD$) |
| $R^4$ = $(CH_3)_2CH$— 2-(isobutanoyloxymethyl)-4-(N-(5'-azidopentanoyl)-beta-alanyl)-1-piperazineacetic acid | L10 (L-INT-4) | 441.1 0.16 min 5 | 4.21-4.15 (m, 2H), 4.04-3.84 (t, J = 16, 1H), 3.81-3.73 (m, 1H), 3.55 (s, 2H), 3.49-3.45 (t, J = 8, 3H), 3.34 (s, 1H), 3.27-3.22 (m, 1H), 3.14-3.10 (m, 2H), 2.99-2.80 (m, 2H), 2.70-2.57 (m, 3H), 1.72-1.58 (m, 4H), 1.19-1.17 (d, J = 8, 6H). |

TABLE 9-continued

| Exemplary Traceless Linker Species | | | |
|---|---|---|---|
| $R^4$, Name | Number (starting intermediate) | LCMS: [M + H]; retention time; method | $^1$H-NMR (300 MHz, $CD_3OD$) |
| $R^4$ = 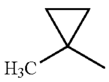 2-(1′-methylcyclo-propylcarbonyloxy-methyl)-4-(N-(5″-azidopentanoyl)-beta-alanyl)-1-piperazineacetic acid | L11 (L-INT-5) | 453.2 0.21 min 5 | 4.21-4.16 (dd, J = 16.4, 2H), 4.05-3.99 (t, J = 12, 1H), 3.83-3.72 (m, 1H), 3.56 (s, 2H), 3.49-3.45 (t, J = 8, 3H), 3.28-3.20 (m, 1H), 3.18-3.04 (m, 1H), 3.02-2.76 (m, 2H), 2.72-2.54 (m, 2H), 2.24-2.21 (t, J = 8, 2H), 1.72-1.56 (m, 5H), 1.13 (s, 3H), 1.26-1.21 (m, 2H), 1.07-0.90 (m, 1H), 0.76-0.74 (t, J = 4, 2H) |

Traceless Linkers: L12 and L13

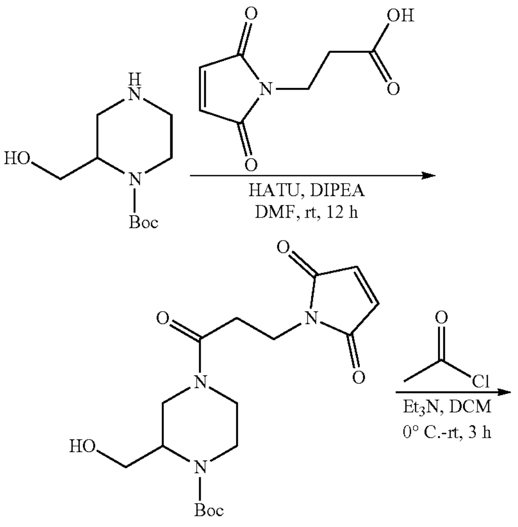

L-12a

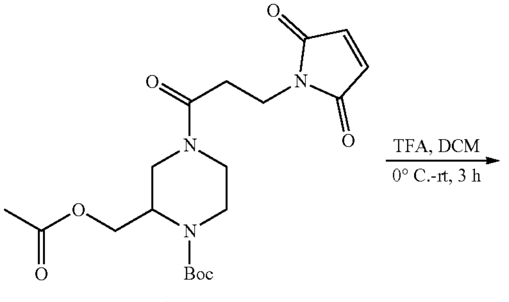

L-12b

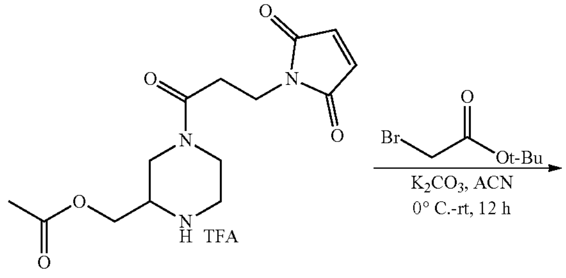

L-12c

-continued

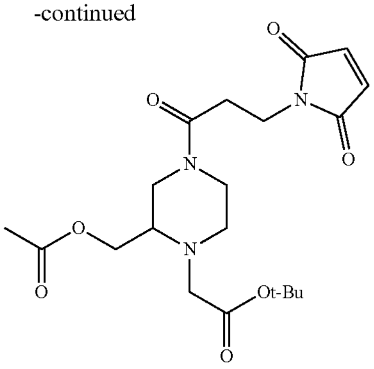

L12

L-12a. 1-(Boc)-2-(hydroxymethyl)-4-(N-maleoyl-beta-alanyl)piperazine

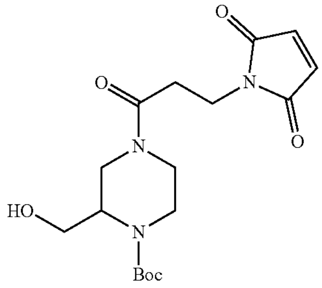 [SMILES: CC(C)(C)OC(=O)N1CCN(C(=O)CCN2C(=O)C=CC2=O)CC1CO]

tert-Butyl 2-(hydroxymethyl)piperazine-1-carboxylate (200 mg, 0.93 mmol) was dissolved in dichloromethane (10 mL) at 0° C. Diisopropylethylamine (359 mg, 2.78 mmol) and HATU (422 mg, 1.11 mmol) were added and the solution was stirred 15 min at 0° C. 3-maleimidopropionic acid (187 mg, 1.11 mmol) was added, and then the reaction was stirred 12 h at room temperature under argon. The reaction was diluted with water and extracted with dichloromethane. The organic layer was washed with brine, dried over sodium sulfate and concentrated. Purification by flash chromatography (neutral alumina, 2% methanol:ethyl acetate provided the title material L-12a. LCMS (method 6): retention time=2.87 min.

L-12b. 1-(Boc)-2-(acetoxymethyl)-4-(N-maleoyl-beta-alanyl)piperazine

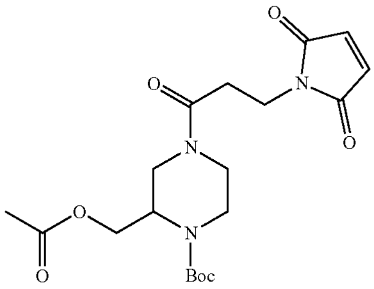 [SMILES: CC(=O)OCC1CN(C(=O)CCN2C(=O)C=CC2=O)CCN1C(=O)OC(C)(C)C]

To L-12a (300 mg, 0.82 mmol) and triethylamine (330 mg, 3.27 mmol) in dichloromethane (4 mL) at 0° C. under argon was dropwise added acetyl chloride (125 mg, 1.64 mmol). The reaction was stirred at room temperature for 3 h, then treated with water and extracted with dichloromethane. The organic layer was dried (sodium sulfate), concentrated and purified by flash chromatography (neutral alumina, 2% methanol:ethyl acetate) to provide the title material L-12b. LCMS (method 6): retention time=3.2 min.

L-12c. 1-(N-maleoyl-beta-alanyl)-3-(acetoxymethyl) piperazine, trifluoroacetic acid salt

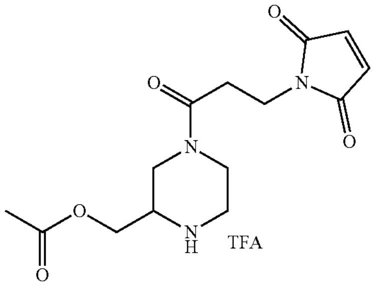 [SMILES: CC(=O)OCC1CN(C(=O)CCN2C(=O)C=CC2=O)CCN1]

L-12b (200 mg, 0.49 mmol) was dissolved in dichloromethane (5 mL) at 0° C., then treated dropwise with trifluoroacetic acid (0.4 mL) and stirred at room temperature 3 h under argon. The reaction was evaporated, washed with pentane and dried to provide crude title material L-12c. LCMS (method 6): retention time=1.709 min; MS (ESI+) m/z 310 (M+H).

L12. 2-(acetoxymethyl)-4-(N-maleoyl-beta-alanyl)-1-piperazineacetic acid t-butyl ester

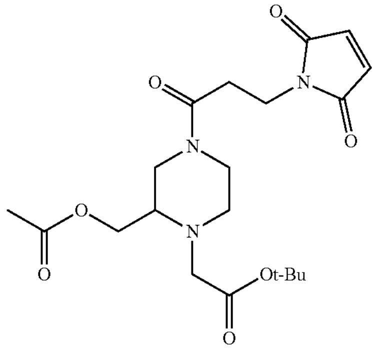 [SMILES: CC(=O)OCC1CN(C(=O)CCN2C(=O)C=CC2=O)CCN1CC(=O)OC(C)(C)C]

To L-12c (140 mg, 0.45 mmol) and potassium carbonate (156 mg, 1.13 mmol) in acetonitrile (5 mL) at 0° C. was dropwise added tert-butyl bromoacetate (100 mg, 0.54 mmol). The reaction was warmed to 10-15° C., then allowed to stir for 12 h at room temperature under argon. The reaction was diluted with water and extracted with ethyl acetate. The organic layer was dried (sodium sulfate), concentrated and purified by preparative HPLC (column: zorbax eclipse XDB C18, 21.2×150 mm, 5 μm; Mobile phase A=water, mobile phase B=acetonitrile; time=0 min: 30% B; 2 min: 40% B; 10 min: 60% B) to provide L12. LCMS (method 6): retention time=3.08 min; MS (ESI+) m/z 424 (M+H). $^1$H-NMR ($CDCl_3$, ppm) 6.69 (s, 2H), 4.25-4.14 (m, 2H), 4.09-3.96 (m, 2H), 3.88-3.83 (t, J=9, 2H), 3.65-3.54 (m, 1H), 3.46-3.33 (m, 2H), 3.31-3.17 (m, 2H), 3.05-2.98 (m, 2H), 2.84-2.75 (m, 2H), 2.68-2.63 (t, J=9, 2H), 2.09-2.07 (d, J=6, 3H), 1.45 (s, 9H).

L13 was prepared using methods analogous to those used in the synthesis of L12:

L13. 2-(2'-methoxyacetoxymethyl)-4-(N-maleoyl-beta-alanyl)-1-piperazineacetic acid t-butyl ester (1-(2-(tert-butoxy)-2-oxoethyl)-4-(3-(maleimidyl) propanoyl)piperazin-2-yl)methyl 2-methoxyacetate

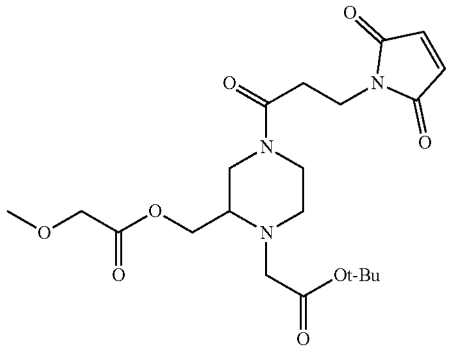 [SMILES: COCC(=O)OCC1CN(C(=O)CCN2C(=O)C=CC2=O)CCN1CC(=O)OC(C)(C)C]

L13. LCMS (method 6): retention time=3.04 min; MS (ESI+) m/z 454.5 (M+H). $^1$H-NMR ($CDCl_3$, ppm) 6.70 (s, 2H), 4.40-4.24 (m, 1H), 4.20-4.10 (m, 1H), 4.07-4.60 (d, J=4, 2H), 4.02-3.94 (m, 1H), 3.87-3.83 (t, J=8, 2H), 3.70-3.60 (m, 1H), 3.68-3.60 (m, 1H), 3.58-3.51 (m, 1H), 3.45 (s, 3H), 3.41-3.39 (d, J=8, 1H), 3.36-3.32 (s, 1H), 3.32-3.28 (s, 1H), 3.18-3.10 (m, 1H), 3.04-2.97 (m, 1H), 2.83-2.81 (t, J=4, 1H), 2.79-2.75 (m, 1H), 2.67-2.64 (t, J=8, 2H), 1.46 (s, 9H).

Traceless Linkers; L14-L16

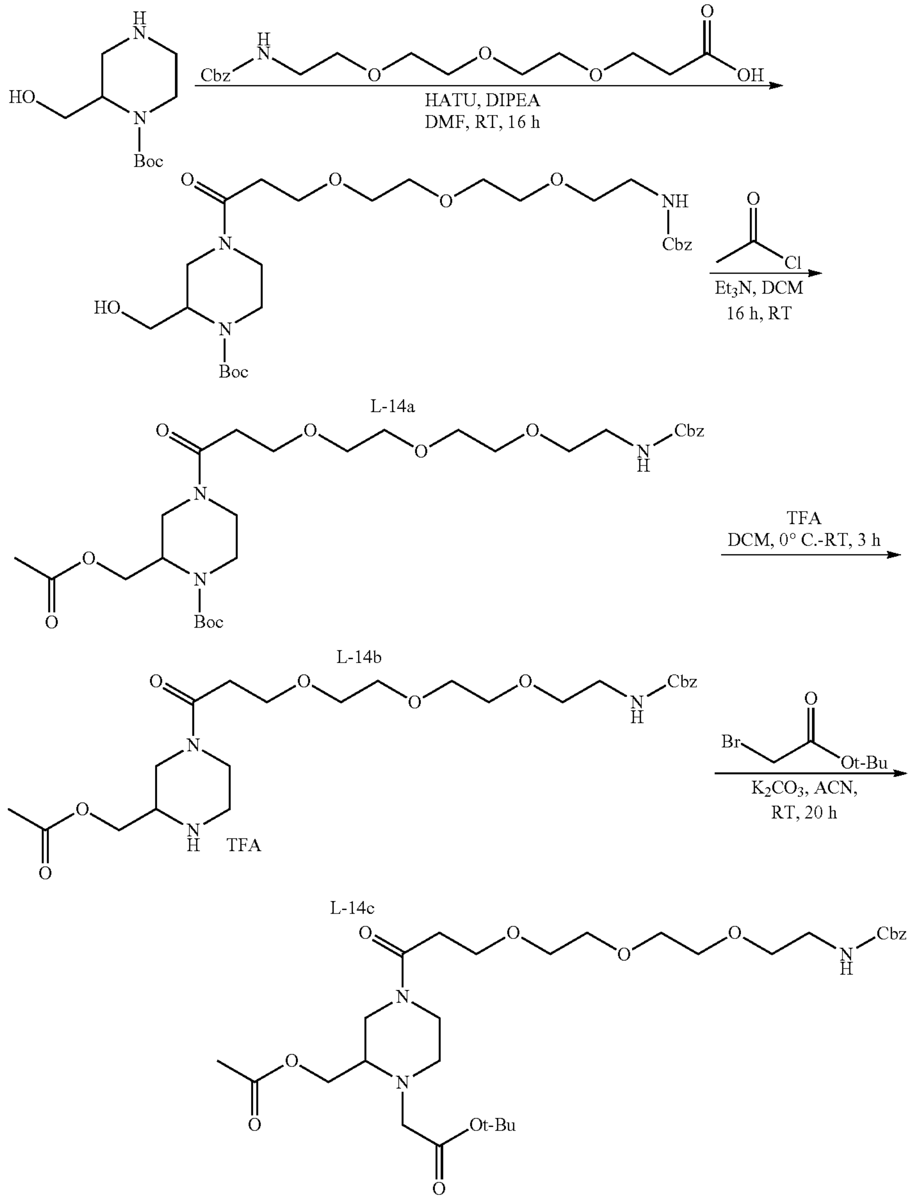

L-14

L14a. 1-(Boc)-2-(hydroxymethyl)-4-(3'-(2"-(2'''-(2''''-((N-Cbz)-amino)ethoxy)ethoxy)ethoxy)propanoyl)piperazine

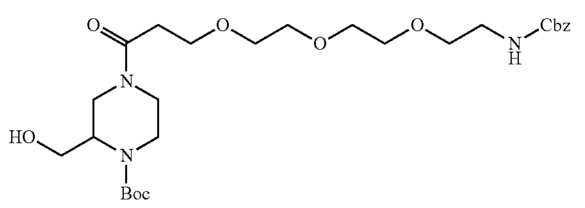 [SMILES: CC(C)(C)OC(=O)N1CCN(C(=O)CCOCCOCCOCCNC(=O)OCc2ccccc2)CC1CO]

To tert-butyl 2-(hydroxymethyl)piperazine-1-carboxylate (1.0 g, 4.63 mmol) dissolved in dichloromethane (20 mL) at 0° C. was added diisopropylethylamine (1.79 g, 13.9 mmol) and HATU (2.10 g, 5.55 mmol). The solution was stirred 15 min at 0° C. 3-(2'-(2"-(2'''-((N-Cbz)-amino)ethoxy)ethoxy)ethoxy)propanoic acid (1.64 g, 4.63 mmol) was added and the reaction was stirred 16 h at room temperature under argon. The reaction was diluted with water and extracted with ethyl acetate. The organic layer was washed with brine, dried over sodium sulfate and concentrated. Purification by flash chromatography ($SiO_2$, 1-4% methanol:dichloromethane) provided the title material L-14a. LCMS (method 5): retention time=1.27 min; MS (ESI+) m/z 554.3 (M+H).

L-14b. 1-(Boc)-2-(acetoxymethyl)-4-(3'-(2"-(2'"-(2""-((N-Cbz)-amino)ethoxy)ethoxy)ethoxy)propanoyl)piperazine

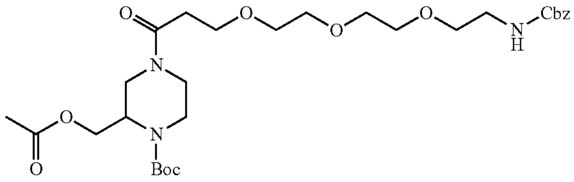 [SMILES: CC(=O)OCC1CN(C(=O)CCOCCOCCOCCNC(=O)OCc2ccccc2)CCN1C(=O)OC(C)(C)C]

To L-14a (500 mg, 0.90 mmol) and triethylamine (228 mg, 2.26 mmol) dissolved in dichloromethane (20 mL) at 0° C. was dropwise added acetyl chloride (83 mg, 1.08 mmol). The reaction was stirred at room temperature under argon for 16 h. The reaction was diluted with water and extracted with dichloromethane. The combined organic layer was dried over sodium sulfate and concentrated, then purified by flash chromatography ($SiO_2$, 1-4% methanol:dichloromethane) to provide the title material L-14b. LCMS (method 7): retention time=1.54 min; MS (ESI+) m/z 595.8 (M+H).

L-14c. 1-(3'-(2"-(2'"-(2""-((N-Cbz)-amino)ethoxy)ethoxy)ethoxy)propanoyl)-3-(acetoxymethyl)piperazine, trifluoroacetic acid salt

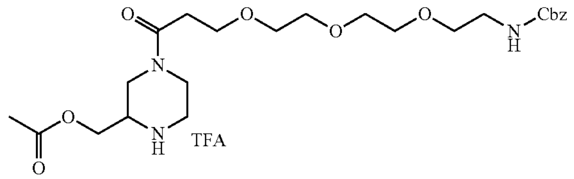 [SMILES: CC(=O)OCC1CN(C(=O)CCOCCOCCOCCNC(=O)OCc2ccccc2)CCN1]

L-14b (500 mg, 0.84 mmol) was dissolved in dichloromethane (10 mL) at 0° C., then treated dropwise with trifluoroacetic acid (3 mL) and stirred at room temperature 3 h under argon. The reaction was evaporated, washed with pentane and dried to provide crude title material L-14c, which was carried into the next reaction without further purification or analysis.

L14. 2-(acetoxymethyl)-4-(3'-(2"-(2'"-(2""-((N-Cbz)-amino)ethoxy)ethoxy)ethoxy)propanoyl)-1-piperazineacetic acid t-butyl ester

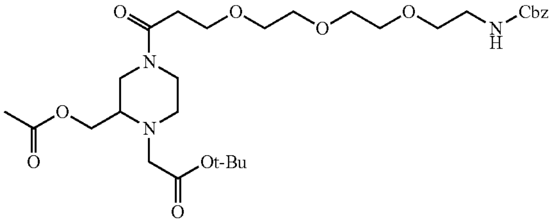 [SMILES: CC(=O)OCC1CN(C(=O)CCOCCOCCOCCNC(=O)OCc2ccccc2)CCN1CC(=O)OC(C)(C)C]

To L-14c (500 mg, 1.0 mmol) and potassium carbonate (418 mg, 3.03 mmol) in acetonitrile (10 mL) at 0° C. was dropwise added tert-butyl bromoacetate (295 mg, 1.51 mmol). The reaction was stirred for 20 h at room temperature under argon. The reaction was diluted with water and extracted with ethyl acetate. The organic layer was dried (sodium sulfate), concentrated and purified by an initial flash chromatography ($SiO_2$, 1-5% methanol:dichloromethane), followed by preparative HPLC (column: zorbax eclipse XDB C18, 4.6×150 mm, 5 μm; Mobile phase A=0.01% TFA in water, mobile phase B=acetonitrile:methanol (1:1), 1 mL/min; time=0 min: 30% B; 1 min: 70% B; 6 min: 100% B) to provide L14. LCMS (method 5): retention time=3.43 min; MS (ESI+) m/z 610.35 (M+H). $^1$H-NMR ($CDCl_3$, ppm) 7.36-7.31 (m, 5H), 5.49 (s, 1H), 5.09 (s, 2H), 4.26-4.16 (m, 1H), 4.07-3.98 (m, 1H), 3.78-3.74 (t, J=6, 2H), 3.60-3.53 (m, 11H), 3.39-3.32 (m, 4H), 2.84-2.72 (m, 2H), 2.61-2.57 (t, J=3, 2H), 2.08-2.06 (d, J=6, 2H), 1.45 (s, 9H).

Species shown in Table 10 were prepared using methods analogous to those used in the synthesis of L14:

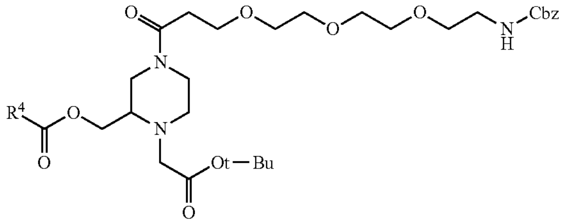

TABLE 10

| Exemplary Traceless Linker Species | | | |
|---|---|---|---|
| $R^4$, Name | Number | LCMS: [M + H]; Retention Time; Method | $^1$H-NMR (300 MHz, $CDCl_3$) |
| $R^4$ = $CH_3CH_2$— 2-(propanoyloxymethyl)-4-(3'-(2"-(2'"-(2""-((N-Cbz)-amino)ethoxy)ethoxy)ethoxy) propanoyl)-1-piperazineacetic acid t-butyl ester | L15 | 624.35; 3.60 min; 5 | 7.36-7.30 (m, 5H), 5.41 (s 1H), 5.09 (s, 2H), 4.28-3.96 (m, 3H), 3.78-3.74 (t, J = 6, 3H), 3.60-3.53 (m, 12H), 3.43-3.22 (m, 6H), 3.10-2.92 (m, 2H), 2.81-2.74 (m, 2H), 2.61-2.56 (t, J = 9, 2H), 2.39-20 (m, 2H), 1.63 (s, 3H), 1.45 (s, 9H), 1.16-1.10 (t, J = 6, 3H). |

TABLE 10-continued

| Exemplary Traceless Linker Species | | | |
|---|---|---|---|
| $R^4$, Name | Number | LCMS: [M + H]; Retention Time; Method | $^1$H-NMR (300 MHz, $CDCl_3$) |
| $R^4 = (CH_3)_2CH—$ 2-(isobutanoyloxymethyl)-4-(3'-(2''-(2'''-(2''''-((N-Cbz)-amino)ethoxy)ethoxy)ethoxy) propanoyl)-1-piperazineacetic acid t-butyl ester | L16 | 638.35; 3.60 min; 5 | 7.36-7.30 (m, 5H), 4.95 (s, 1H), 5.10 (s, 2H), 4.26-4.12 (m, 2H), 4.08-3.96 (m, 2H), 3.81-3.76 (m, 3H), 3.61 (s, 8H), 3.57-3.54 (t, J = 4, 3H), 3.41-3.19 (m, 6H), 3.11-3.04 (m, 1H), 3.02-2.88 (m, 1H), 2.84-2.72 (m, 2H), 2.60-2.57 (m, 3H), 1.45 (s, 9H), 1.18-1.16 (d, J = 8, 6H). |

TABLE 11

| Exemplary Traceless Linker Synthetic Intermediates | | |
|---|---|---|
| Structure | Number | Analogous compounds |
| 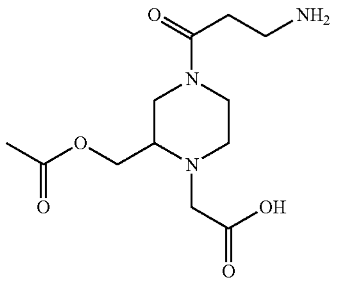 [SMILES: CC(=O)OCC1CN(C(=O)CCN)CCN1CC(=O)O] | L-2b | L-1b, L-3b, L-4b, L-5b, L-6b, L-7b |
| 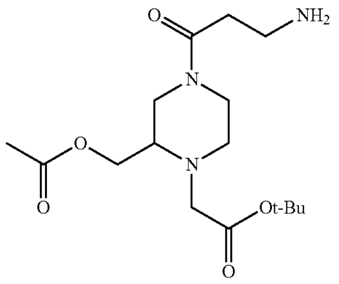 [SMILES: CC(=O)OCC1CN(C(=O)CCN)CCN1CC(=O)OC(C)(C)C] | L-2a | L-1a, L-3a, L-4a, L-5a, L-6a, L-7a |
| 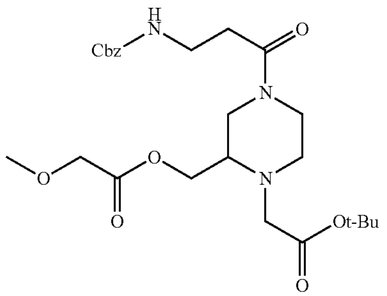 [SMILES: COCC(=O)OCC1CN(C(=O)CCNC(=O)OCc2ccccc2)CCN1CC(=O)OC(C)(C)C] | L-INT-1 | L-INT-2, L-INT-3, L-INT-4 |
| 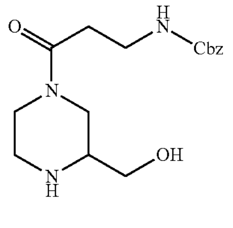 [SMILES: O=C(NCCC(=O)N1CCNC(CO)C1)OCc1ccccc1] | L-INT-1b | L-INT-2b, L-INT-3b, L-INT-4b |

TABLE 11-continued
| Exemplary Traceless Linker Synthetic Intermediates | | |
|---|---|---|
| Structure | Number | Analogous compounds |
| 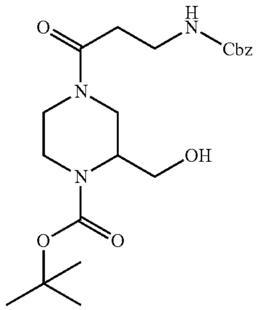 [SMILES: CC(C)(C)OC(=O)N1CCN(C(=O)CCNC(=O)OCc2ccccc2)CC1CO] | L-INT-1c | L-INT-2c, L-INT-3c, L-INT-4c |
| 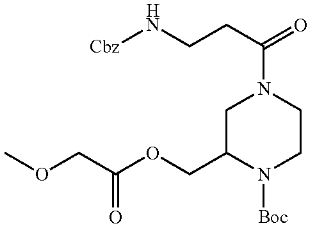 [SMILES: COCC(=O)OCC1CN(C(=O)CCNC(=O)OCc2ccccc2)CCN1C(=O)OC(C)(C)C] | L-INT-1d | L-INT-2c, L-INT-3c, L-INT-4c |
| 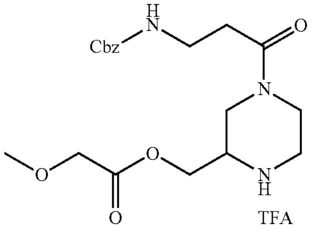 [SMILES: COCC(=O)OCC1CN(C(=O)CCNC(=O)OCc2ccccc2)CCN1] | L-INT-1e | L-INT-2c, L-INT-3c, L-INT-4c |
| 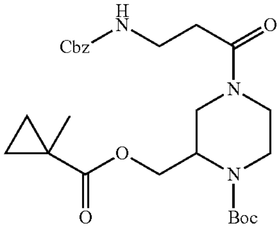 [SMILES: CC(C)(C)OC(=O)N1CCN(C(=O)CCNC(=O)OCc2ccccc2)CC1COC(=O)C1(C)CC1] | L-INT-5a | |
| 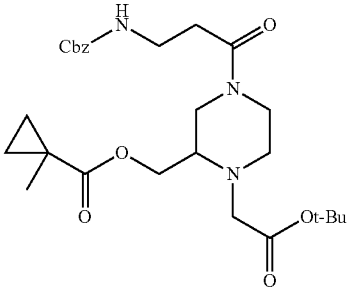 [SMILES: CC(C)(C)OC(=O)CN1CCN(C(=O)CCNC(=O)OCc2ccccc2)CC1COC(=O)C1(C)CC1] | L-INT-5b | |

TABLE 11-continued
| Exemplary Traceless Linker Synthetic Intermediates | | |
|---|---|---|
| Structure | Number | Analogous compounds |
| 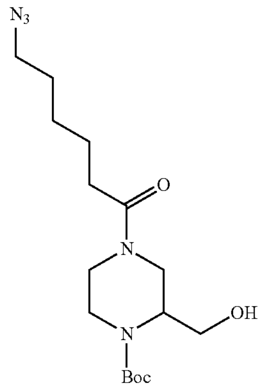 [SMILES: CC(C)(C)OC(=O)N1CCN(C(=O)CCCCCN=[N+]=[N-])CC1CO] | L-8a | |
| 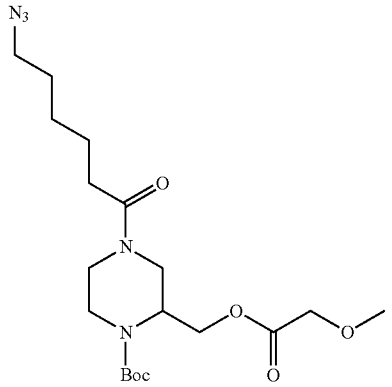 [SMILES: COCC(=O)OCC1CN(C(=O)CCCCCN=[N+]=[N-])CCN1C(=O)OC(C)(C)C] | L-8b | |
| 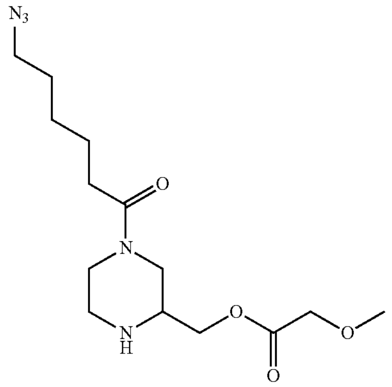 [SMILES: COCC(=O)OCC1CN(C(=O)CCCCCN=[N+]=[N-])CCN1] | L-8c | |

TABLE 11-continued
| Exemplary Traceless Linker Synthetic Intermediates | | |
|---|---|---|
| Structure | Number | Analogous compounds |
| 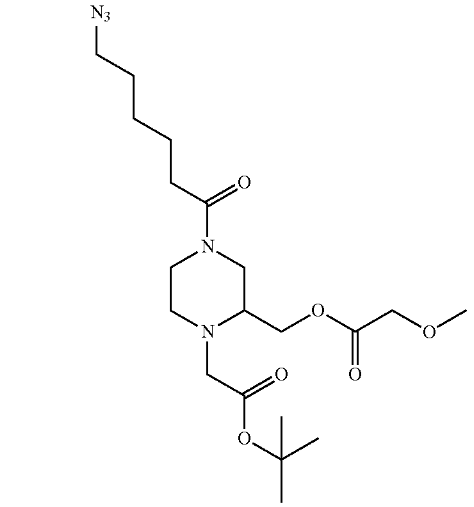 [SMILES: COCC(=O)OCC1CN(C(=O)CCCCCN=[N+]=[N-])CCN1CC(=O)OC(C)(C)C] | L-8d | |
| 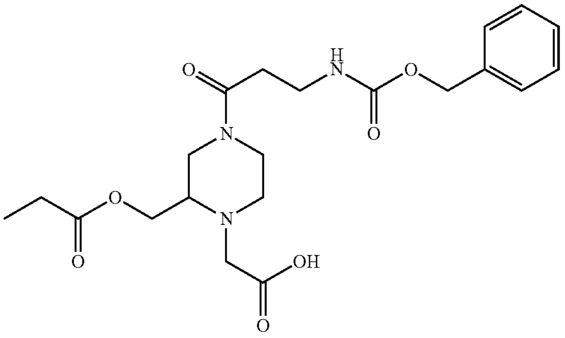 [SMILES: CCC(=O)OCC1CN(C(=O)CCNC(=O)OCc2ccccc2)CCN1CC(=O)O] | L-9a | L-10a, L-11a |
| 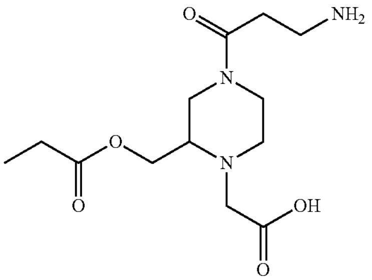 [SMILES: CCC(=O)OCC1CN(C(=O)CCN)CCN1CC(=O)O] | L-9b | L-10b, L-11b |
| 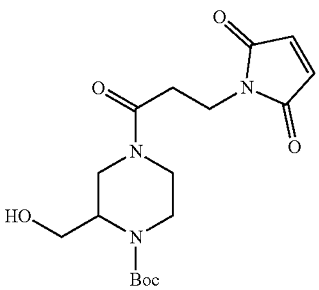 [SMILES: CC(C)(C)OC(=O)N1CCN(C(=O)CCN2C(=O)C=CC2=O)CC1CO] | L-12a | L-13a |

TABLE 11-continued
Exemplary Traceless Linker Synthetic Intermediates
| Structure | Number | Analogous compounds |
|---|---|---|
| 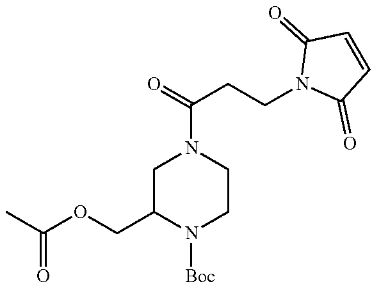 [SMILES: CC(=O)OCC1CN(C(=O)CCN2C(=O)C=CC2=O)CCN1C(=O)OC(C)(C)C] | L-12b | L-13b |
| 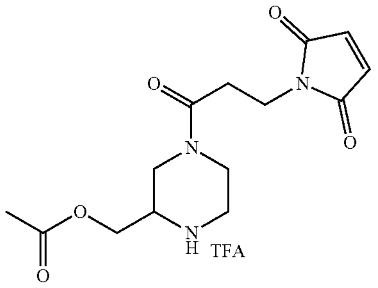 [SMILES: CC(=O)OCC1CN(C(=O)CCN2C(=O)C=CC2=O)CCN1] | L-12c | L-13c |
| 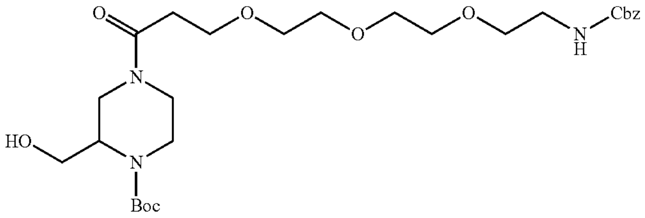 [SMILES: CC(C)(C)OC(=O)N1CCN(C(=O)CCOCCOCCOCCNC(=O)OCc2ccccc2)CC1CO] | L-14a | L-15a, L-16a |
| 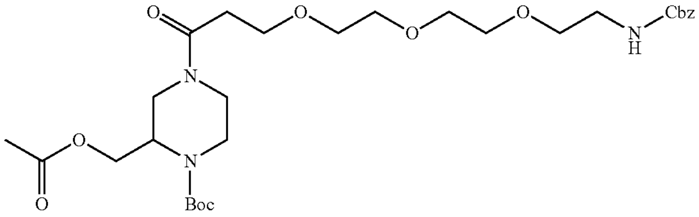 [SMILES: CC(=O)OCC1CN(C(=O)CCOCCOCCOCCNC(=O)OCc2ccccc2)CCN1C(=O)OC(C)(C)C] | L-14b | L-15b, L-16b |
| 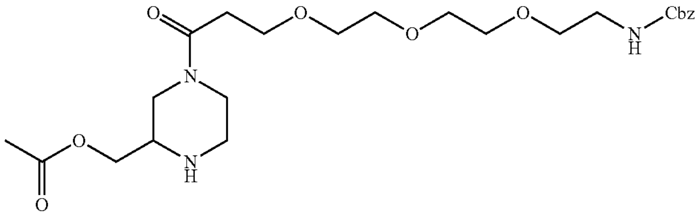 [SMILES: CC(=O)OCC1CN(C(=O)CCOCCOCCOCCNC(=O)OCc2ccccc2)CCN1] | L-15c | L-15c, L-16c |

Example 2

Adducts of Traceless Linkers with Biologically Active Moieties

This example describes the synthesis of a number of traceless linker-drug adducts, which are also capable of being conjugated to a carrier.

TABLE 12

Exemplary Traceless Linker-Drug Adducts

| Number | Structure | Traceless linker | drug |
|---|---|---|---|
| L1D1 | 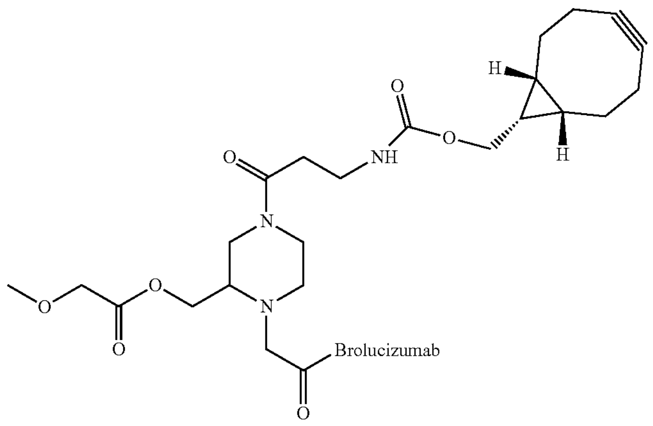 | L1 | Brolucizumab = D1 |
| L2D1 | 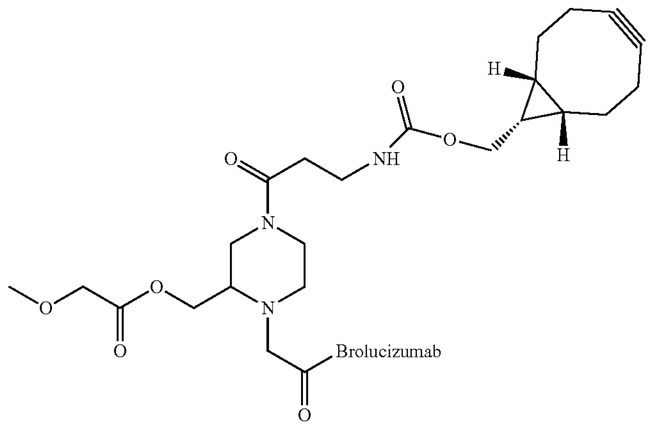 | L2 | Brolucizumab = D1 |
| L3D1 | 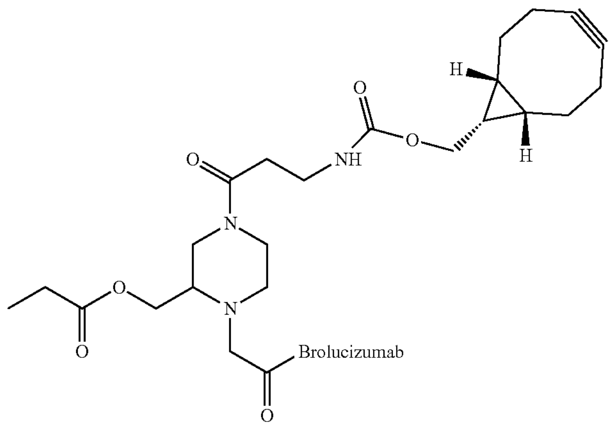 | L3 | Brolucizumab = D1 |

TABLE 12-continued
Exemplary Traceless Linker-Drug Adducts
| Number | Structure | Traceless linker | drug |
|---|---|---|---|
| L4D1 | 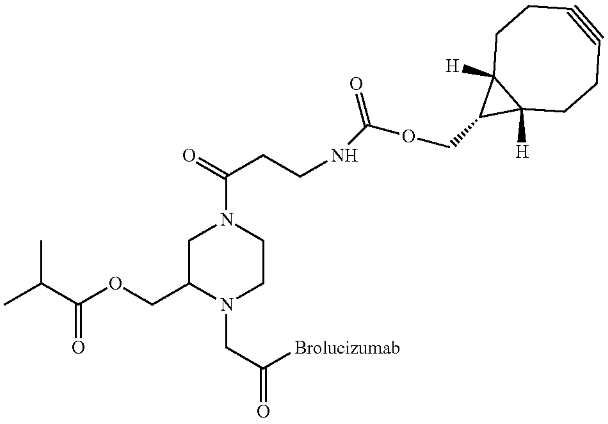 | L4 | Brolucizumab = D1 |
| L5D1 | 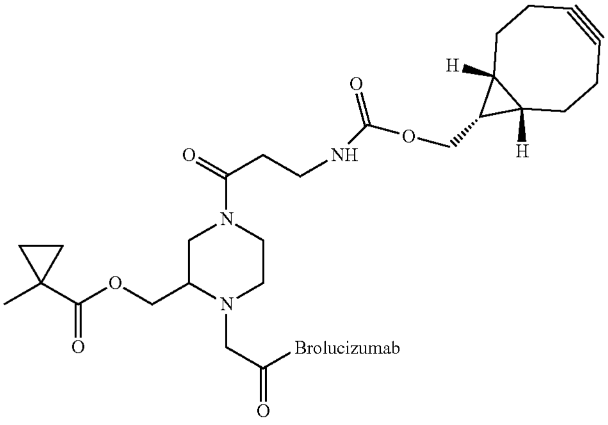 | L5 | Brolucizumab = D1 |
| L1D2 | 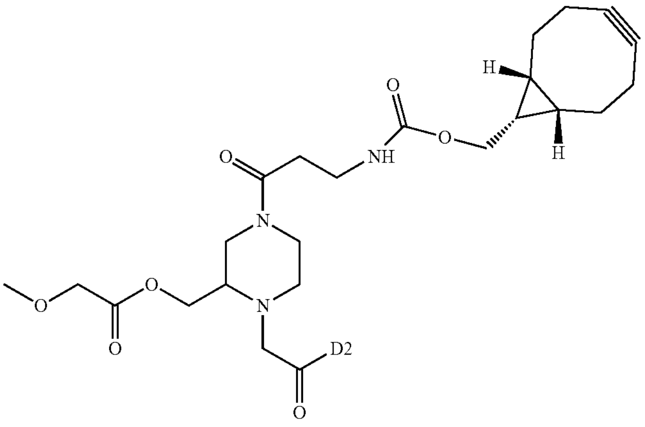 | L1 | D1 |

TABLE 12-continued
| Exemplary Traceless Linker-Drug Adducts | | | |
|---|---|---|---|
| Number | Structure | Traceless linker | drug |
| L1D3 | 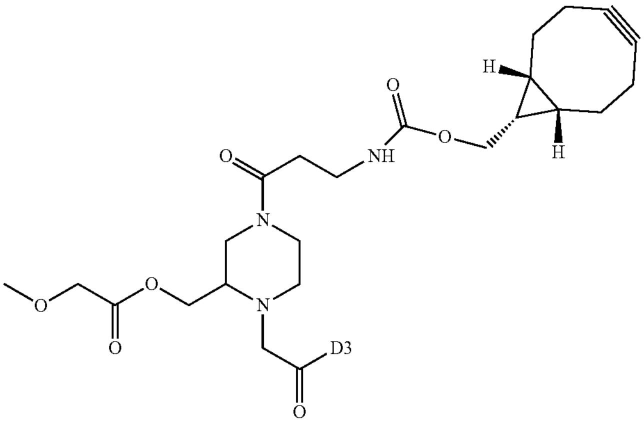 | L1 | D3 |
| L2D2 | 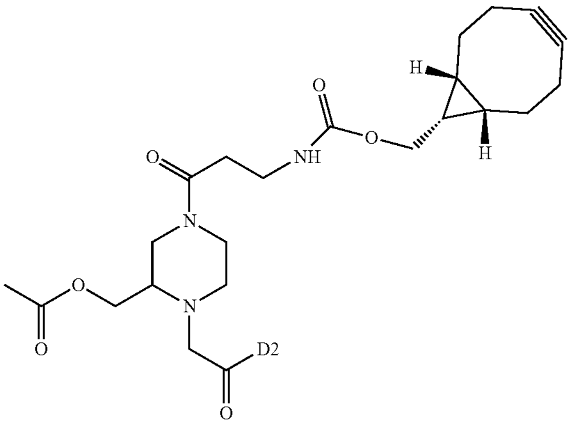 | L2 | D2 |
| L5D2 | 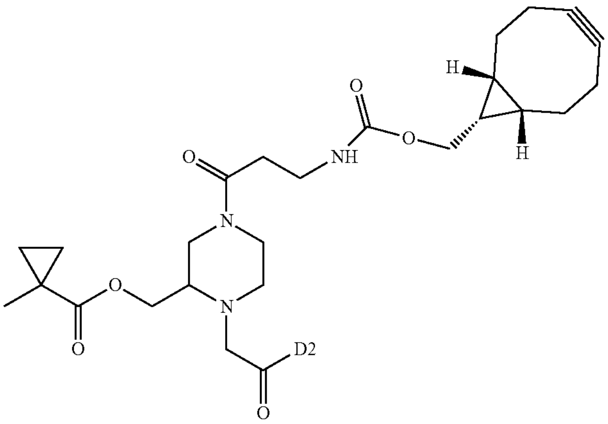 | L5 | D2 |

TABLE 12-continued
| Exemplary Traceless Linker-Drug Adducts | | | |
|---|---|---|---|
| Number | Structure | Traceless linker | drug |
| L8D4 | 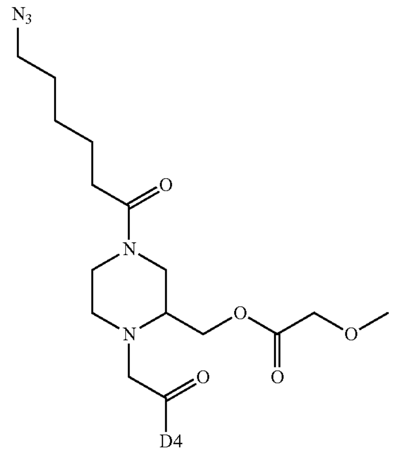 | L8 | D4 |
Synthesis of Adducts
Acylation of biologically active moieties with a traceless linker:
L4-NHS. 2-(isobutanoyloxymethyl)-4-(N-(((1R',8'S, 9's)-bicyclo[6.1.0]non-4'-yn-9'-yl)methoxycarbonyl)-beta-alanyl)-1-piperazineacetic acid N-hydroxysuccinimidyl ester
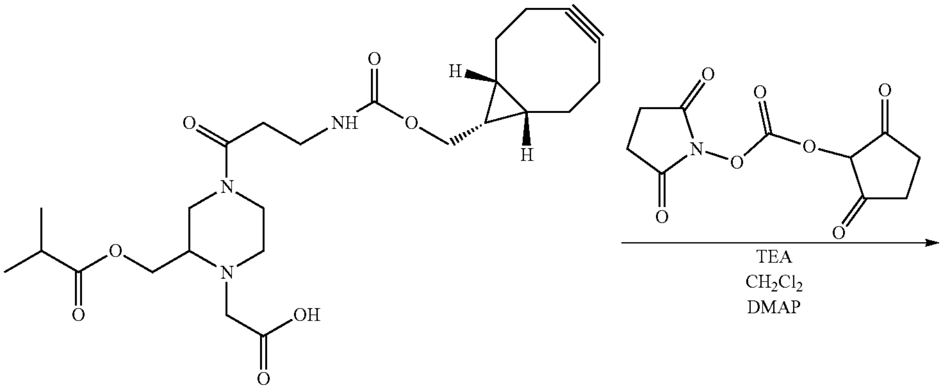
L-4

-continued

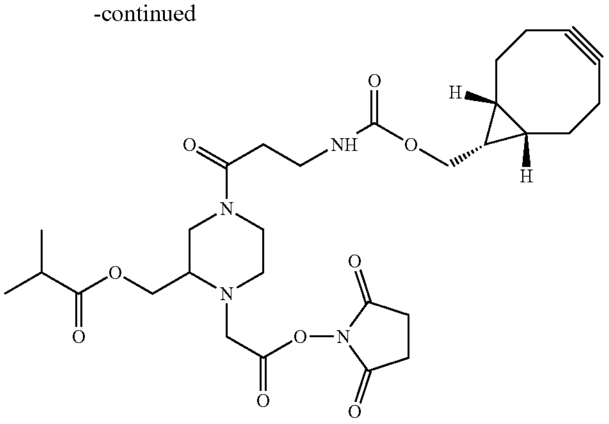

L4-NHS

A suspension of L4 (22 mg, 0.045 mmol) in dichloromethane (5 mL) was treated with triethylamine (0.0062 mL, 0.045 mmol), dimethylaminopyridine (0.55 mg, 0.0045 mmol) and N, N'-disuccinimidyl carbonate (10.9 mg, 0.043 mmol) and was stirred for 2 h at room temperature, then evaporated and immediately used as is without further purification. LCMS (method 1): retention time=1.33 min; MS (ESI+) m/z 589.6 (M+H).

The species in Table 13 were prepared using methods analogous to those used in the synthesis of L4-NHS.

TABLE 13

Exemplary Activated Traceless Linker Species

| Structure | Number (starting intermediate) | Name | MS (ESI+) m/z (M + H) retention time; method |
|---|---|---|---|
| 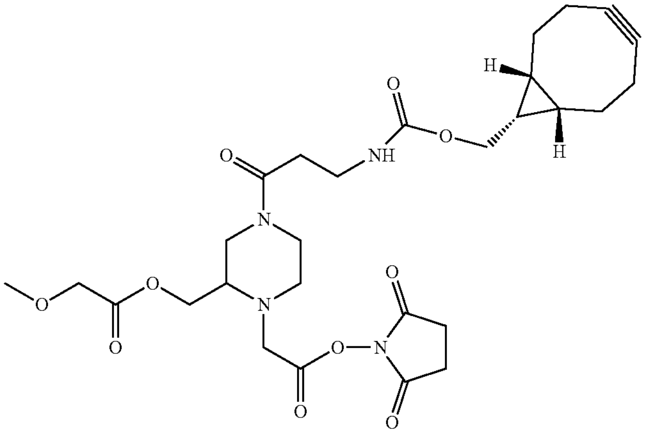 [SMILES: COCC(=O)OCC1CN(C(=O)CCNC(=O)OC[C@@H]2[C@@H]3CCC#CCC[C@@H]32)CCN1CC(=O)ON1C(=O)CCC1=O] | L1-NHS (L1) | 2-(2'-methoxyacetoxymethyl)-4-(N-(((1"R,8"S,9"s)-bicyclo[6.1.0]non-4"-yn-9"-yl)methoxycarbonyl)-beta-alanyl)-1-piperazineacetic acid N-hydroxysuccinimidyl ester | 591.4; 0.87 min; 2 |
| 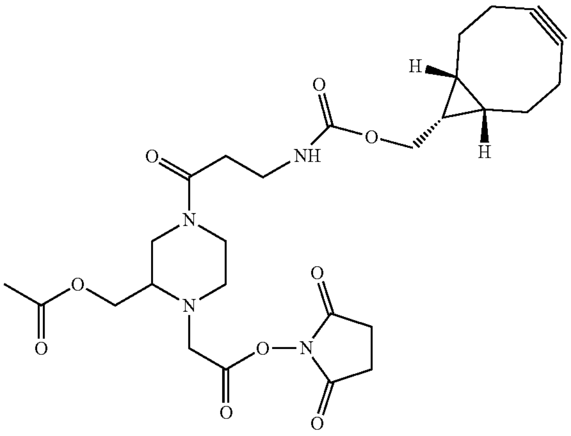 [SMILES: CC(=O)OCC1CN(C(=O)CCNC(=O)OC[C@@H]2[C@@H]3CCC#CCC[C@@H]32)CCN1CC(=O)ON1C(=O)CCC1=O] | L2-NHS (L2) | 2-(acetoxymethyl)-4-(N-(((1'-R,8'S,9's)-bicyclo[6.1.0]non-4'-yn-9'-yl)methoxycarbonyl)-beta-alanyl)-1-piperazineacetic acid N-hydroxysuccinimidyl ester | 561.4; 0.87 min; 2 |

TABLE 13-continued

| | | | |
|---|---|---|---|
| 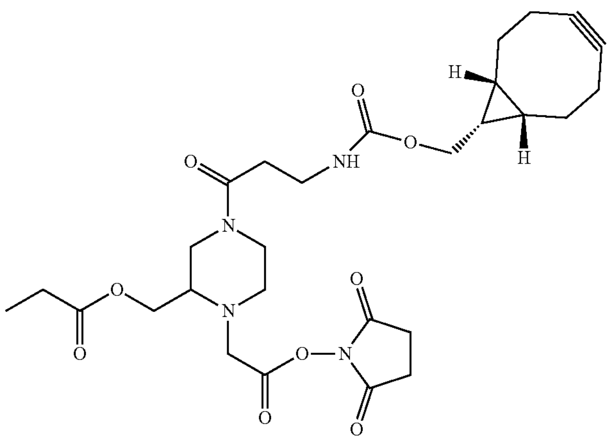 [SMILES: CCC(=O)OCC1CN(C(=O)CCNC(=O)OC[C@@H]2[C@@H]3CCC#CCC[C@@H]32)CCN1CC(=O)ON1C(=O)CCC1=O] | L3-NHS (L3) | 2-(propanoyloxymethyl)-4-(N-(((1'R,8'S,9's)-bicyclo[6.1.0]non-4'-yn-9'-yl)methoxycarbonyl)-beta-alanyl)-1-piperazineacetic acid N-hydroxysuccinimidyl ester | 575.5; 0.91 min; 4 |
| 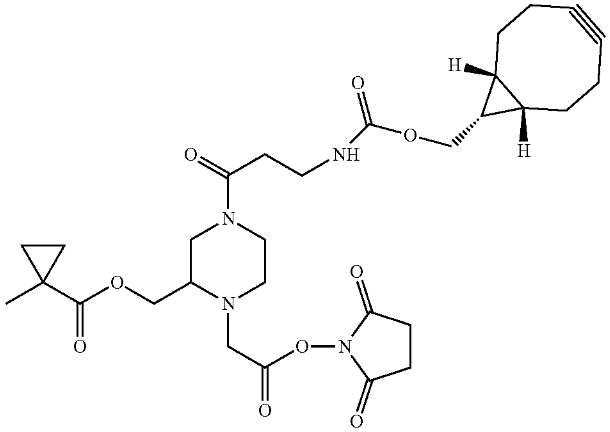 [SMILES: CC1(C(=O)OCC2CN(C(=O)CCNC(=O)OC[C@@H]3[C@@H]4CCC#CCC[C@@H]43)CCN2CC(=O)ON2C(=O)CCC2=O)CC1] | L5-NHS (L5) | 2-(1'-methylcyclopropylcarbonyloxymethyl)-4-(N-(((1"R,8"S,9"s)-bicyclo[6.1.0]non-4"-yn-9"-yl)methoxycarbonyl)-beta-alanyl)-1-piperazineacetic acid N-hydroxysuccinimidyl ester | 601.4; 0.99 min; 4 |

L4-Brolucizumab (L4D1b)

Brolicizumab +

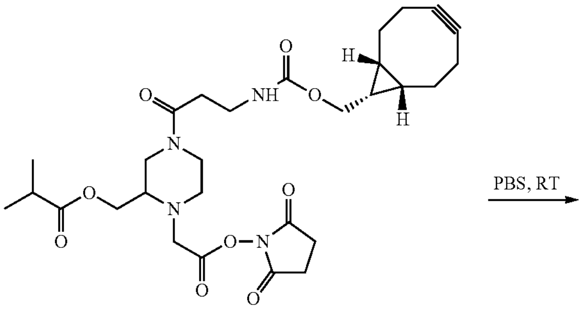

L4-NHS

-continued

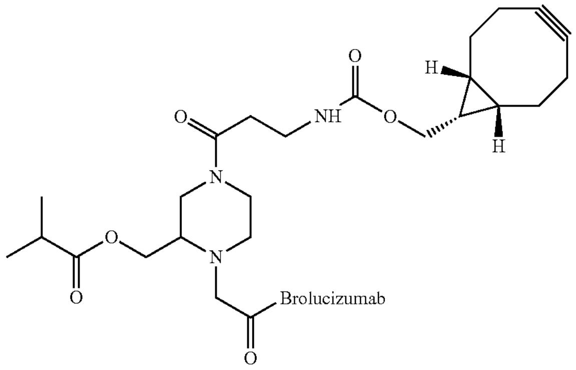

L4D1

A 60 mg/mL solution of brolucizumab (10 mL, 0.023 mmol) in a buffer consisting of 20 mM trisodium citrate dihydrate, 125 mM sodium chloride, 0.01 mg/mL Tween 20, at pH 6.25, was diluted with 1×PBS (10 mL, pH 7.4) to provide a 30 mg/mL solution, which was then treated slowly with a 38 mM solution of L4-NHS in DMSO (0.65 mL, 0.023 mmol), vortexed, and held at room temperature for 1 h. Purification by ultracentrifugation (Vivaspin concentrators, 10 kDa MWCO), washing with 1×PBS (4 times) removed residual small molecule impurities, resulting in a mixture of L4D1 and unmodified brolucizumab (D1). MS (method 9) deconvoluted m/z 26312 (brolucizumab, M+H); deconvoluted m/z 26786 (L4D1, M+H, expected MW=MW (brolucizumab)+473).

An important analytical parameter is determination of ratio of (unmodified brolucizumab, n=0):(mono-acylated brolucizumab, n=1):(poly-acylated brolucizumab, n>1). Comparison of relative peak heights for the various species in a mass spectrum allows an estimate of the product ratio to be made, but this ratio might not be accurate, as the various products may not have similar molar response factors in MS analysis. In this example: MS analysis indicated a product ratio of [(n=0):(n=1):(n=2)]~5:1:0 (method 9).

An additional method for estimating the ratio of reaction products utilizes SEC (size exclusion chromatography) or SDS-PAGE (sodium dodecyl sulfate polyacrylamide gel electrophoresis) analysis of derivatized reaction products; derivitization is required in order to achieve separation of the reaction products.

L4D1b Derivatization Reaction

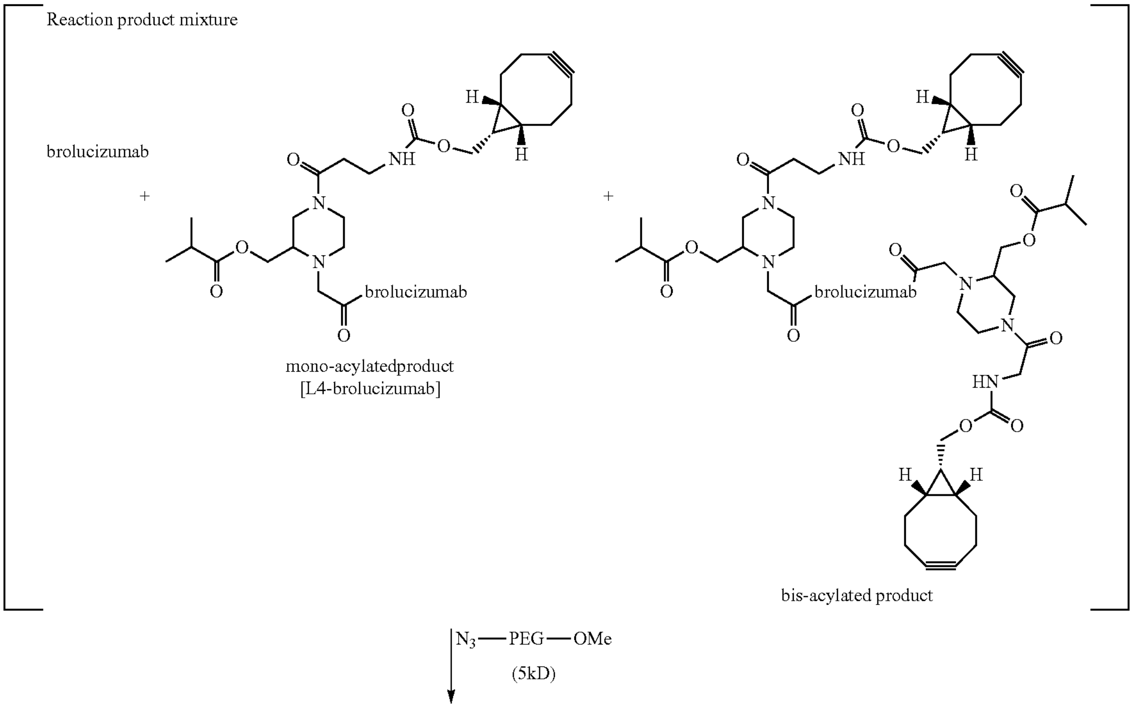

-continued

Derivatized reaction product mixture for analysis brolucizumab +

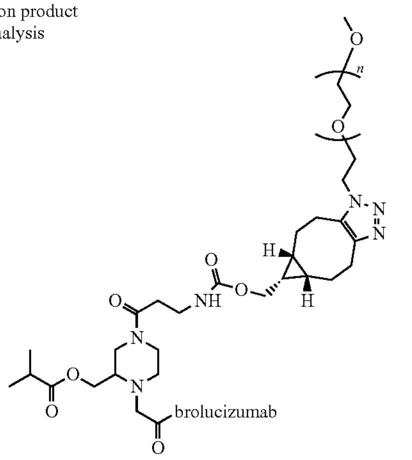

PEGylayted mono-acylated product

+

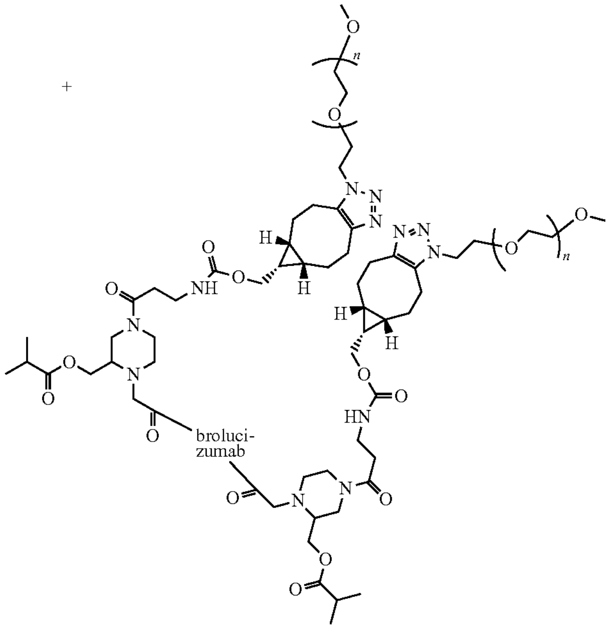

PEGylayted bis-acylated product

An aliquot from the reaction solution of 30 mg/mL L4D1b reaction mixture (0.005 mL, 0.0057 μmol) was treated with a $M_n$~5 kDa methoxy-PEG-azide (Sigma-Aldrich, 689475, 10 μL of a 100 mg/mL solution in 1×PBS, 0.20 μmol), vortexed, then shaken at 37° C. for 45 min.

Analysis of L4D1b-derivative

SEC: (Column: Agilent AdvanceBioSEC 300A 2.7 μm 4.6×150 mm; Mobile phase: 150 mM potassium phosphate in water with 5% isopropanol (isocratic); Fast method: 0.2 mL/min for 13 min; Slow method: 0.1 mL/min for 25 min; Detection: 210 nm). L4D1b-derivative determination of ratio of (unmodified brolucizumab, n=0, retention time=12.74 min (slow method)):(mono-acylated brolucizumab, n=1, retention time=11.26 min (slow method)):(bis-acylated brolucizumab, n=2, retention time=10.36 min (slow method))=[(n=0):(n=1):(n=2)]=81:18:1.

SDS-Page: (MOPS running buffer; NuPage® Novex© 4-12% Bis-Tris Gels; Coomassie Blue stain; Bio-Rad ChemiDoc imager; Image Lab 5.2.1 analysis software): L4D1b-derivative determination of ratio of (unmodified brolucizumab, n=0):(mono-acylated brolucizumab, n=1) (poly-acylated brolucizumab, n=2)=[(n=0):(n=1):(n=2)] ~67:33:trace.

Adducts shown in Table 14 and Table 15 were prepared using methods analogous to those used in the synthesis of L4D1b. The reaction conditions used to prepare the adducts are specified in Table 14; characteristics of the adducts are described in Table 15.

TABLE 14

| Exemplary D-R Adducts. Reaction conditions | | | | | | |
|---|---|---|---|---|---|---|
| Number | Study | Used to prepare conjugate | conc. Of protein in reaction (mg/mL) | Buffer | Equivalents of activated linker added to the reaction; linker-NHS used | Temperature and time of reaction |
| L1D1 | In vitro release 8.1 | C1 | 30 | D | 2.0; L1-NHS | RT, 30 h |
| L2D1a | In vitro release 8.1 | C2a | 30 | D | 2.0; L2-NHS | RT 2 h |
| L2D1b | In vivo release 9.1 | C2b | 30 | D | 2.1; L2-NHS | RT, 2 h |
| L3D1a | In vitro release 8.1 | C3a | 30 | D | 2.0; L3-NHS | RT, 2 h |
| L3D1b | | C3b | 30 | D | 1.0; L3-NHS | RT, 2 h |
| L3D1c | | C6 | 30 | D | 1.1; L3-NHS | RT, 1 h |
| L4D1a | In vitro release 8.1 | C4a | 30 | D | 2.0; L4-NHS | RT, 1 h |
| L4D1b | | C4b | 30 | D | 1.0; L4-NHS | RT, 1 h |
| L4D1c | | C7 | 30 | D | 1.1; L4-NHS | RT, 16 h |
| L4D1d | | C14, C15 | 60 | E | 0.8; L4-NHS | RT, 1.5 h |
| L5D1 | | C5 | 30 | D | 1.6; L5-NHS | RT, 16 h |
| L1D2a | | C8 | 5.1 | A | 2.1; L1-NHS | RT, 2 h |
| L1D2b | In vitro release 8.2 | C10 | 9.1 | C | 2.1; L1-NHS | RT, 3 h |
| L2D2 | In vitro release 8.2 | C11 | 9.1 | C | 2.1; L2-NHS | RT, 1 h |
| L5D2 | In vitro release 8.2 | C12 | 9.1 | C | 2.1; L5-NHS | RT, 2 h |
| L1D3 | | C9 | 5.1 | B | 2.1; L1-NHS | RT, 3 h |

Reaction buffer A: (1:2.2) = (20 mM sodium phosphate, 40 mM sodium chloride, pH6.5):(1 × PBS, pH 7.4)

Reaction buffer B: (1:2) = (7 mM succinate, pH5):(1X PBS, pH 7.4)

Reaction buffer C: (1.25:1) = (20 mM sodium phosphate, 40 mM sodium chloride, pH6.5):(1 × PBS, pH 7.4)

Reaction buffer D: (1:1) = (20 mM trisodium citrate dihydrate, 125 mM sodium chloride, 0.01 mg/mL Tween20, pH6.25):(1 × PBS, pH 7.4)

Reaction buffer E: 20 mM trisodium citrate dihydrate, 125 mM sodium chloride, 0.01 mg/mL Tween20, pH6.25

TABLE 15

| Exemplary D-R Adducts. Adduct characterization. | | | | | | |
|---|---|---|---|---|---|---|
| Number | Study | Used to prepare conjugate | MS (method 9) m/z (mono-acylated product) | MS product ratio (n = 0:n = 1:n = 2) (method 9) | SEC product ratio (n = 0:n = 1:n = 2) | SDS-Page product ratio (n = 0:n = 1:n = 2) |
| L1D1 | In vitro release 8.1 | C1 | 26788.5 | 2:1:trace | NA | NA |
| L2D1a | In vitro release 8.1 | C2a | 26758.5 | 3:2:trace | NA | NA |
| L3D1a | In vitro release 8.1 | C3a | 26772.5 | 3:1:trace | NA | NA |
| L3D1b | | C3b | 26773.0 | 5:1:0 | 78:20:2 | 68:32:0 |
| L3D1c | | C6 | NA | NA | 89:11:0 | NA |
| L4D1a | | C4a | 26786.5 | 2:1:trace | NA | NA |
| L4D1b | | C4b | 26786.0 | 5:1:0 | 81:18:1 | 67:33:0 |
| L4D1c | | C7 | 26786.0 | NA | 90:10:0 | NA |
| L4D1d | | C14, C15 | 26787.0 | 5:1:0 | 84:16:trace | NA |
| L5D1 | | C5 | NA | NA | 83:17:0 | NA |
| L1D2a | | C8 | ND | ND | NA | 48:42:10 |
| L1D2b | In vitro release 8.2 | C10 | ND | ND | NA | 73:27:0 |
| L2D2 | In vitro release 8.2 | C11 | ND | ND | NA | 60:40:0 |
| L5D2 | In vitro release 8.2 | C12 | ND | ND | NA | 80:20:0 |

NA: not measured.

ND: Products of D2 reactions with linkers do not ionize well and cannot be detected using QTOF technology as configured unless present in high concentration.

L8D4
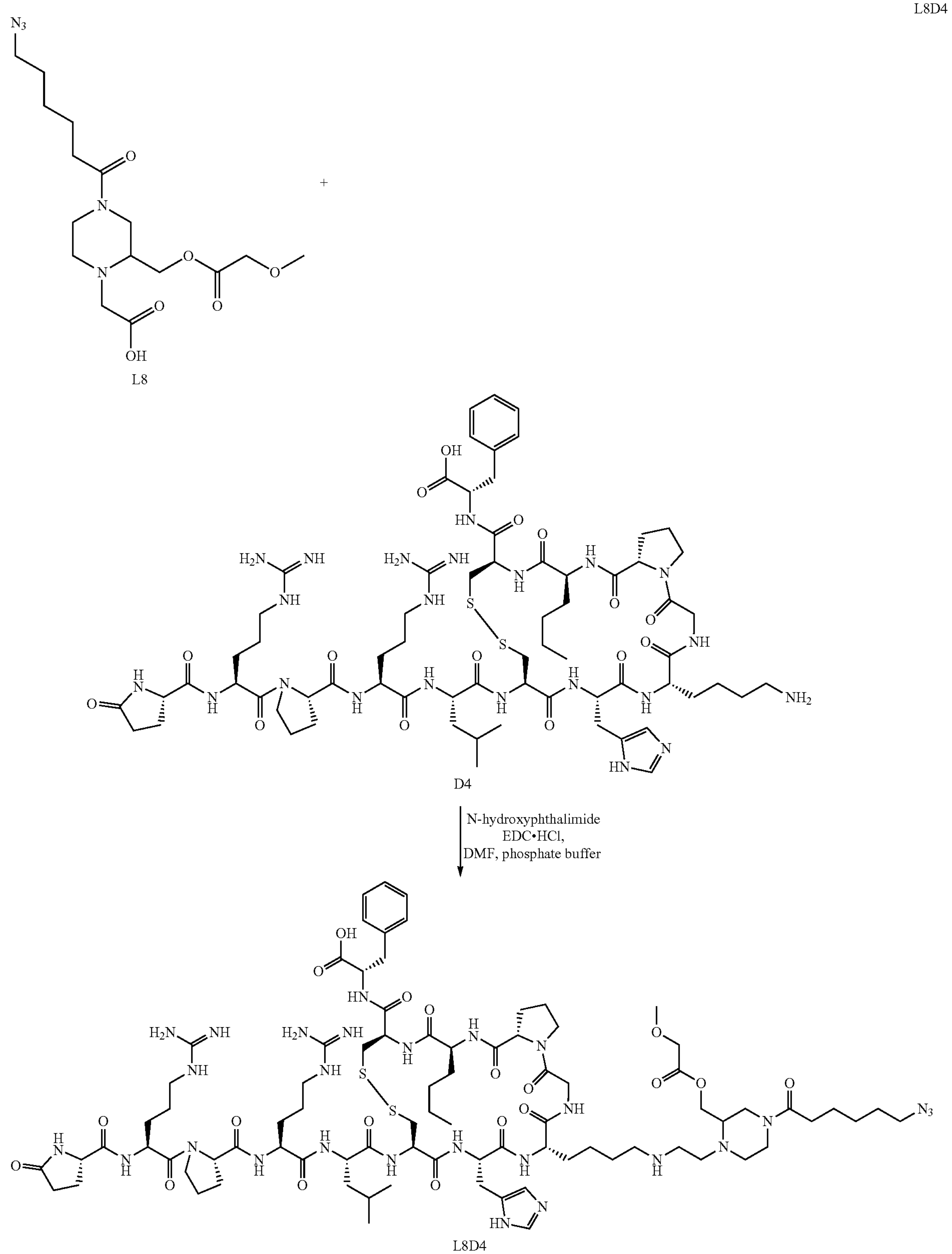
L8
D4
L8D4
L8 (43.4 mg, 0.113 mmol) was dissolved in dimethylformamide (2.55 mL), followed by EDC·HCl (21.2 mg, 0.111 mmol) and N-hydroxyphthalimide (18.6 mg, 0.114 mmol). The solution was stirred at room temperature overnight (~16 hr). To this solution was added D4 (35 mg, 0.02 mmol) dissolved in 1.5 mL dimethylformamide and 1.5 mL of 100 mM phosphate buffer (pH 6.5). After 2 h, the reaction was diluted with 4 mL of acetonitrile, filtered, and purified by preparative reverse phase HPLC with mass directed fraction collection (method below). Product containing fractions were pooled, frozen, and lyophilized to provide L8D4. MS (ESI+) m/z=952.5 $(M+2H)^{2+}$.

Preparative HPLC conditions: Waters XSelect CSH OBD; particle size: 5 μm; column size: 19×150 mm; eluent/gradient: 24% $CH_3CN/H_2O$/1.65 min, 24-34% $CH_3CN/H_2O$/8.35 min ($CH_3CN$ and $H_2O$ containing 0.1% TFA); flow rate: 30 mL/min; column temperature: room temperature; collection m/z: +951.7.

Example 3

Functionalization of Hyaluronic Acid

This example describes the synthesis of a functionalized hyaluronic acid, which may itself be a carrier or may also be reacted with a crosslinking moiety to form a hydrogel.

Synthesis of Hyaluronic Acid Intermediate [HA-N3]

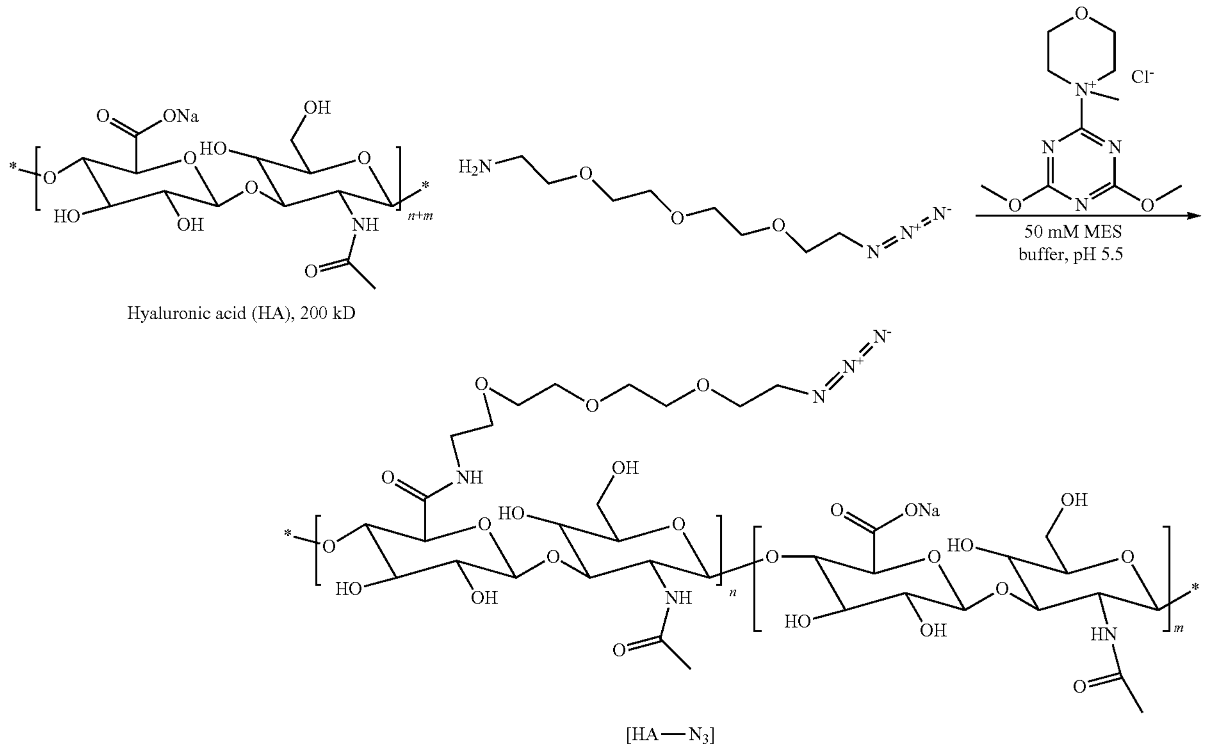

Hyaluronic acid (HA), 200 kD

[HA—N3]

Hyaluronic acid sodium salt is a linear polymer consisting of repeating dimeric units of glucuronic acid and N-acetyl-galactosamine, with a repeating unit molecular weight of 401.3 Da. In this example the moles of hyaluronic acid reported refers to the moles of repeating unit and the equivalents of reagents used in the reaction with hyaluronic acid are reported relative to the moles of hyaluronic acid repeating unit. The average molecular weight of the polymer determines the average number of repeat units per polymer strand. Hyaluronic acid sodium salt labeled by the supplier, Lifecore Biomedical (HA200K, Chaska, MN) as having a nominal average molecular weight of 200 kDa may vary from batch to batch in the range of 151-300 kDa, as determined by viscometry. In this example, such a molecule of hyaluronic acid sodium salt with an assumed nominal average molecular weight of 200 kDa would have an average length of approximately 500 monomer units.

Synthesis of [HA-N3]-23%

A solution of hyaluronic acid, sodium salt (nominal average molecular weight 200 kD; 250.1 mg, 0.623 mmol; Lifecore Biomedical, LLC; product number HA200K) was fully dissolved in 25 mL of MES buffer (50 mM, pH 5.5). To this solution was added 4-(4',6'-dimethoxy-1',3',5'-triazin-2'-yl)-4-methylmorpholin-4-ium chloride (DMTMM, 295 mg, 1.07 mmol, 1.71 eq), followed after 5 min by addition of 11-azido-3,6,9-trioxaundecan-1-amine (N3-PEG3-NH2, 196 mg, 0.90 mmol). The reaction was stirred overnight, then diluted with 25 mL of 0.25 M NaCl solution and purified by tangential flow filtration.

Tangential flow filtration was carried out using a 30 kDa MWCO Vivaflow-50R hydrosart cartridge from Sartorius, eluting with 400 mL of 0.25 M NaCl solution, then 400 mL of water.

The product was flash frozen and lyophilized to provide the title material [HA-N3]-23%.

$^1H$ NMR (400 MHz, D20) δ 4.45 (bs, 2H), 4.0-3.1 (m, 15.5H), 1.95 (s, 3H). DOSY-NMR. One dimensional diffusion ordered NMR spectra (DOSY) were collected using the stimulated echo with one spoil gradient pulse sequence (stegp1s1d) on a Bruker AVANCE III 400 MHz (for $^1H$) instrument with 5 mm DCH cryoprobe. The diffusion time and the diffusion gradient time were set to 50 ms and 4 ms, respectively. Two spectra were collected with gradient strength (gpz6) set to 2% and 95%. Comparison of the two spectra showed no differences apart from the solvent peak, indicating no small molecule impurities were present in the polymer.

Elem. Anal: C: 40.05%; H: 5.67%; N: 5.70%.

The degree of substitution of the [HA-N3] is defined as the % of repeat units in which the carboxylate moiety has undergone reaction to give the depicted amide. Elemental analysis was used to determine the degree of substitution. The [% C/% N] ratio determined by elemental analysis of a purified sample is entered into the following formula to provide the degree of substitution. Where y=[(% C)/(% N)]) then:

$$\text{Degree of substitution} = 100\times\frac{\frac{14\times 12.01}{14.01\times y}-1}{4-\frac{8\times 12.01}{14.01\times y}}$$

In this example, the degree of substitution (DS) of [HA-N3] was 23%.

This 200 kDa hyaluronic acid, functionalized with 23% of the azide linker is labeled [HA-N3]-23%.

In the rest of the examples, a 200 kDa hyaluronic acid, functionalized with X % of the azide linker is labeled [HA-N3]-X %.

The species in Table 16 were prepared and characterized using methods analogous to those used in the synthesis of [HA-N3]-23%. We find that the degree of substitution achieved depends on the given stock of DMTMM reagent used and can be idiosyncratic. In general, for a given stock of DMTMM, the degree of substitution increases as the number of equivalents of DMTMM used increases, and the degree of substitution decreases as the number of equivalents of DMTMM used decreases. Some of the [HA-N3] intermediates were purified by dialysis instead of tangential flow filtration ([HA-N3]-23% b, [HA-N3]-37%). In these cases, a crude reaction mixture was filled into a regenerated cellulose dialysis membrane (MWCO 1-25 kD), and dialyzed 1-3 days against 0.25 M-1 M NaCl, with several changes of the dialysis solution, followed by 1-3 day's dialysis against deionized water, also with multiple changes of the dialysis solution. Upon completion, the sample was removed from the dialysis tubing, flash-frozen, and lyophilized.

TABLE 16

Exemplary Functionalized Hyaluronic Acid Species

| Hyaluronic acid derivative | DS | Equivalents of DMTMM/N3-PEG3-NH2 used in reaction | Elemental analysis |
|---|---|---|---|
| [HA-N3]-15% | 15% | 1.66/1.42 | C: 39.80<br>H: 5.52<br>N: 4.93 |
| [HA-N3]-22% | 22% | 1.65/1.42 | C: 39.89<br>H: 5.76<br>N: 5.53 |
| [HA-N3]-23% | 23% | 1.71/1.44 | C: 40.05<br>H: 5.67<br>N: 5.70 |
| [HA-N3]-23%b | 23% | 4.08/3.04 | C: 36.93<br>H: 5.97<br>N: 5.18 |
| [HA-N3]-23%c | 23% | 1.60/1.02 | C: 36.85<br>H: 6.44<br>N: 5.19 |
| [HA-N3]-26% | 26% | 1.90/1.44 | C: 39.78<br>H: 5.72<br>N: 5.92 |
| [HA-N3]-33% | 33% | 1.75/1.43 | C: 40.60<br>H: 5.97<br>N: 6.63 |
| [HA-N3]-37% | 37% | 3.84/2.88 | C: 39.87<br>H: 5.92<br>N: 6.82 |

Example 4

Preparation of PEG Polymers, XL-1-XL-10

This example describes the synthesis of crosslinkers that may be reacted with other functionalized polymers to form hydrogels.

PEG-Based Cross-Linking Polymers

General structure 1

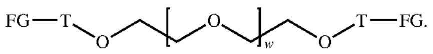

General structure 2

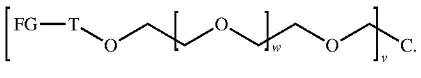

TABLE 17

Exemplary Crosslinking Species

| Number | General structure | FG | T | v | $M_n$ ~ starting PEG (Da) |
|---|---|---|---|---|---|
| XL-1 | 1 | 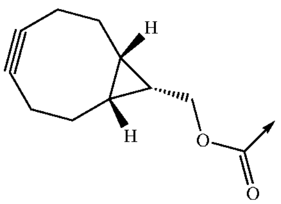 | 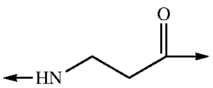 | NA | 2000<br>(w ~ 45) |

TABLE 17-continued
Exemplary Crosslinking Species
| Number | General structure | FG | T | v | $M_n$ ~ starting PEG (Da) |
|---|---|---|---|---|---|
| XL-2 | 1 | 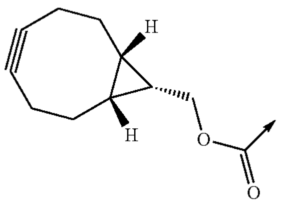 | 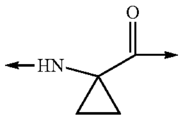 | NA | 2000 (w ~ 45) |
| XL-3 | 1 | 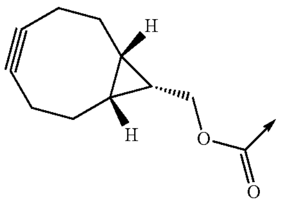 | 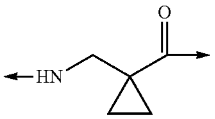 | NA | 2000 (w ~ 45) |
| XL-4 | 1 | 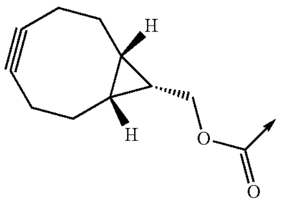 | 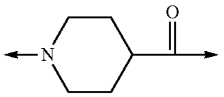 | NA | 2000 (w ~ 45) |
| XL-5 | 1 | 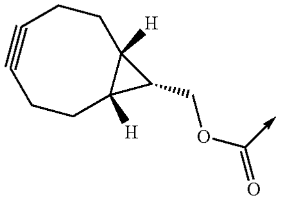 | 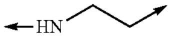 | NA | 2000 (w ~ 45) |
| XL-6 | 2 | 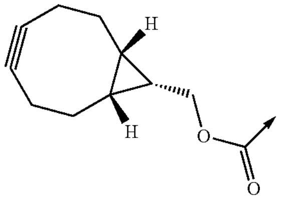 | 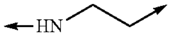 | 4 | 10000 (w ~ 57) |
| XL-7 (commercial product) | 2 | $N_3$ | $-CH_2CH_2-$ | 4 | 10000 (w ~ 57) |
| XL-9 | 1 | 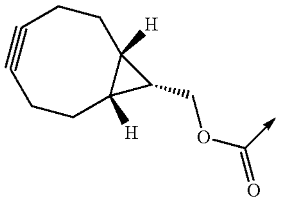 | 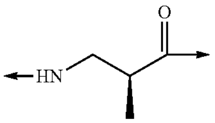 | NA | 2000 (w ~ 45) |

TABLE 17-continued

| Exemplary Crosslinking Species | | | | | |
|---|---|---|---|---|---|
| Number | General structure | FG | T | v | $M_n$ ~ starting PEG (Da) |
| XL-10 | 1 | 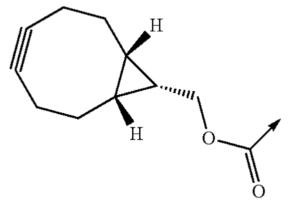 | 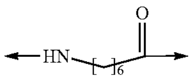 | NA | 2000 (w ~ 45) |

The structure of XL-8:

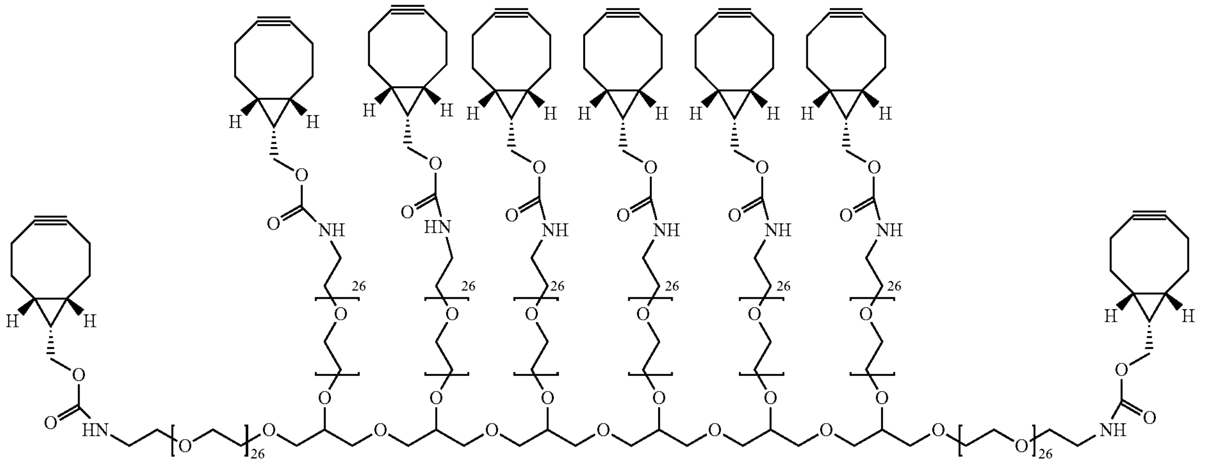

MW of starting PEG: $M_n$~10,000 kDa.

Synthesis of PEG-Based Cross-Linking Polymers

Degree of substitution is an important parameter for PEG-derived cross-linkers and is defined as the percentage of PEG end groups substituted with the desired introduced functional group. Degree of substitution was determined using $^1$H-NMR to compare the integration of a methylene group specific to the PEG end group to the integration of protons specific to the introduced functional group. For XL-1-XL-6, the methylene group specific to the PEG moiety was the ester or carbamate methylene [—(C═O)—O—C$\underline{H}_2$—], which was compared to the integration of protons in the bicyclo[6.1.0]non-4-yne moiety. Degree of substitution=((moles introduced functional group by $^1$H-NMR)/(moles PEG end group by $^1$H-NMR))×100.

XL-1. PEG(2000)-bis-[3-(((((1R,8S,9s)-bicyclo[6.1.0]non-4-yn-9-yl)methoxy)carbonyl)amino)propanoate]

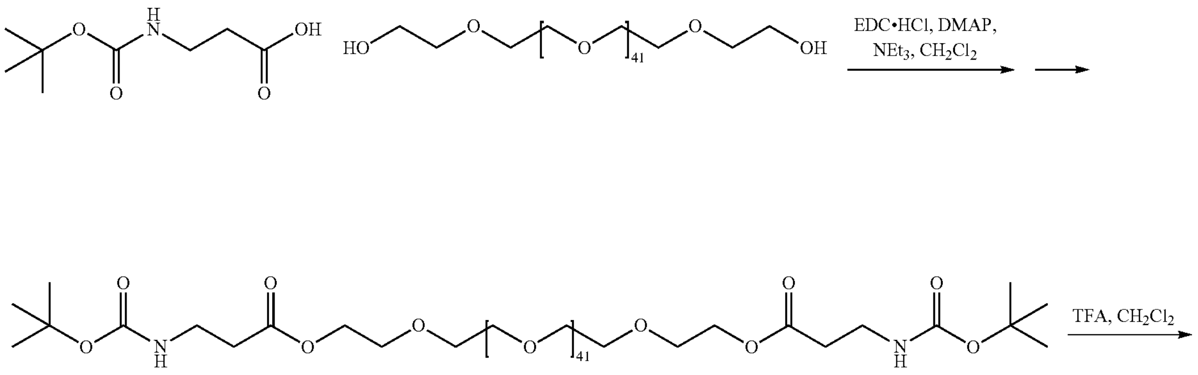

XL-1a

-continued

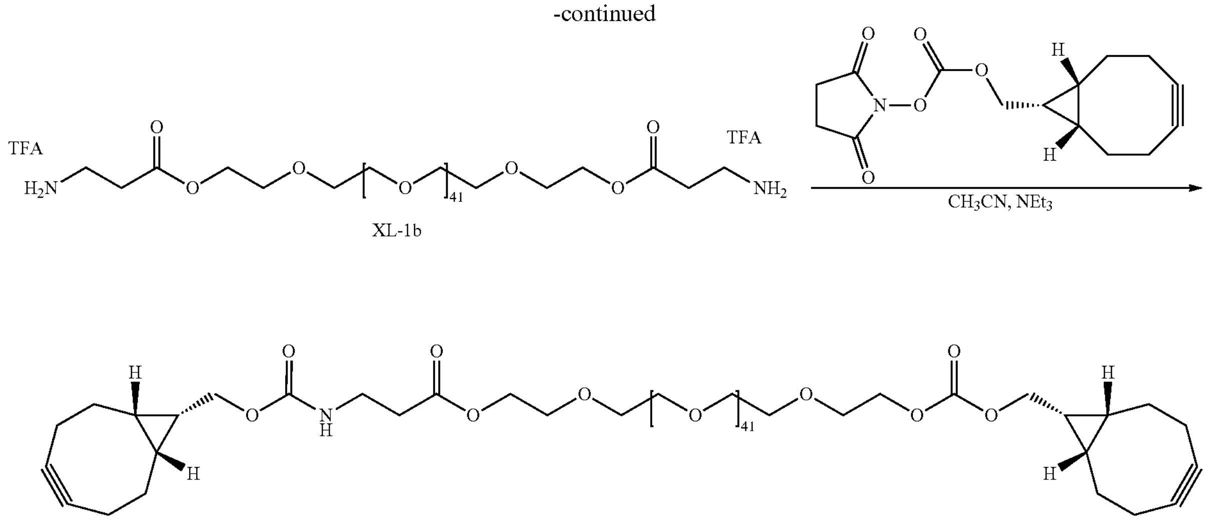

XL-1b

XL-1

XL-1a. PEG(2000)-bis-[3-((tert-butoxycarbonyl) amino)propanoate]

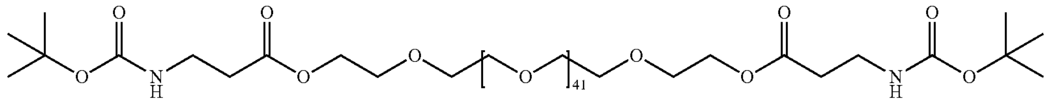

3-((tert-butoxycarbonyl)amino)propanoic acid (1.892 g, 10.00 mmol) and $M_n$~2 kDa PEG (5 g, 2.500 mmol) were dissolved in 50 mL dichloromethane. Dimethylaminopyridine (0.153 g, 1.250 mmol) and EDC·HCl (1.922 g, 10.03 mmol) were added and the reaction mixture was stirred at room temperature overnight. The crude product was purified by flash column chromatography on silica with a 0-15% dichloromethane. methanol gradient. The product containing fractions were combined and reduced to dryness to provide XL-1a. $^{1}$H NMR (400 MHz, methanol-d4) δ 4.23 (m, 4H), 3.70 (m, 4H), 3.63 (br s, 167H), 2.52 (m, 4H), 1.43 (br s, 18H).

XL-1b. PEG(2000)-bis-[3-(amino)propanoate], bis-trifluoroacetic acid

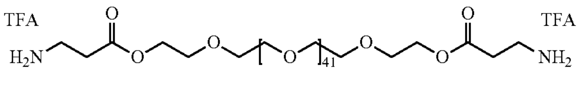

XL-1a (600 mg, 0.261 mmol) was dissolved in dichloromethane (6 mL). Trifluoroacetic acid was added (2 mL) and the reaction mixture was stirred at room temperature overnight. The solvent was removed under reduced pressure. The crude product was triturated with $Et_2O$ twice, then dried under vacuum to provide XL-1b. $^{1}$H NMR (400 MHz, methanol-d4) δ 4.33 (m, 4H), 3.73 (m, 4H), 3.64 (br s, 183H), 2.80 (m, 4H).

XL-1-1. PEG(2000)-bis-[3-(((((1R,8S,9s)-bicyclo [6.1.0]non-4-yn-9-yl)methoxy)carbonyl)amino)propanoate]

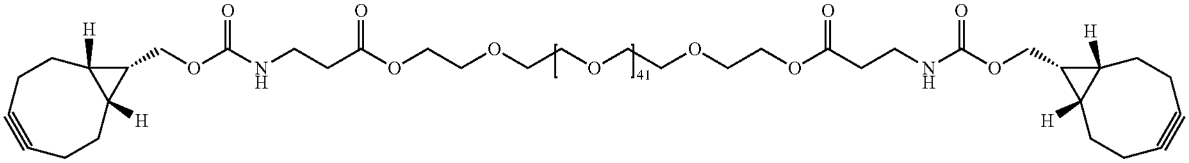

XL-1b (200 mg, 0.086 mmol) was dissolved in acetonitrile (3 mL). Triethylamine (0.599 mL, 4.30 mmol) was added, followed by ((1R,8S,9s)-bicyclo[6.1.0]non-4-yn-9-yl)methyl (2,5-dioxopyrrolidin-1-yl) carbonate (200 mg, 0.688 mmol) and the reaction mixture was stirred at room temperature for 4 h. The reaction mixture was directly purified by preparative reverse phase HPLC with ELSD triggered fraction collection (method below). The product containing fractions were pooled, frozen and lyophilized to provide XL-1-1. For storage purposes, XL-1-1 was kept as an acetonitrile, DMSO, or methanol solution in a freezer. Analytical HPLC-CAD (method below): retention time=11.93 min. $^1$H NMR (400 MHz, methanol-d4) δ 4.23 (m, 4H), 4.14 (m, 4H), 3.63 (br s, 175H), 2.54 (m, 4H), 2.22 (m, 12H), 1.60 (m, 4H), 1.37 (m, 2H), 0.94 (m, 4H).

Preparative HPLC conditions: Waters XBridge C18; particle size: 5 μm; column size: 19×250 mm; eluent/gradient: 5% $CH_3CN/H_2O$/0.5 min, 5-95% $CH_3CN/H_2O$/12.5 min, 95% $CH_3CN/H_2O$/3 min; flow rate: 30 mL/min; column temperature: room temperature.

Analytical HPLC-CAD conditions: Waters XBridge BEH300 C18; particle size: 3.5 μm; column size: 4.6×100 mm; eluent/gradient: 2% $CH_3CN/H_2O$/0.5 min, 2-98% $CH_3CN/H_2O$/17.5 min ($CH_3CN$ containing 0.05% TFA and $H_2O$ containing 0.1% TFA); flow rate: 1 mL/min; column temperature: 50° C.

Analytical HPLC-CAD conditions (method 10): Waters ACQUITY BEH C18; particle size: 1.7 μm; pore size: 130A; column size: 2.1×50 mm; eluent/gradient: 5% $CH_3CN/H_2O$/1.2 min, 5-95% $CH_3CN/H_2O$/1.8 min ($CH_3CN$ containing 0.1% TFA and $H_2O$ containing 0.1% TFA); flow rate: 1 mL/min; column temperature: 45° C.

Alternatively, the reaction mixture was directly purified by flash chromatography ($SiO_2$, 0-10% methanol:dichloroethane) to provide the less pure batch XL-1-2.

The species in Table 18 were prepared using methods analogous to those used in the synthesis of XL-1 (except for XL-1-2):

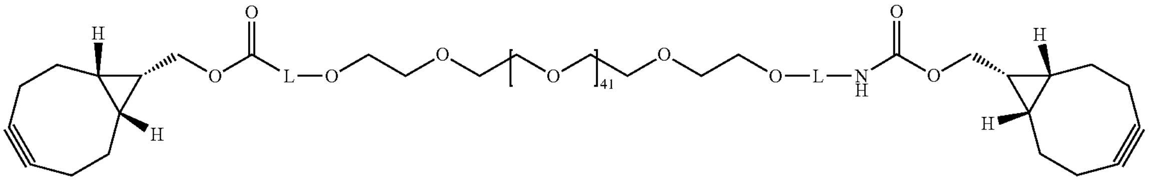

TABLE 18

Exemplary PEG-based Cross-Linking Polymers

| Number | T | Number of PEG-end groups substituted with functional group | Anal HPLC (CAD) Retention time (min) | $^1$H NMR (400 MHz, methanol-$d_4$) |
|---|---|---|---|---|
| XL-1-1 | 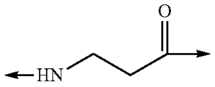 | 2 of 2 100% | 11.93 min | δ 4.23 (m, 4H), 4.14 (m, 4H), 3.63 (br s, 175H), 2.54 (m, 4H), 2.22 (m, 12H), 1.60 (m, 4H), 1.37 (m, 2H), 0.94 (m, 4H) |
| XL-1-2 | 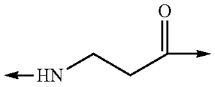 | (1.5-1.8) of 2 75% | NA | δ 4.23 (m, 4H), 4.14 (m, 3.3H), 3.63 (br s, 156H), 2.55 (m, 4H), 2.21 (m, 9.6H), 1.60 (m, 3.6H), 0.94 (m, 3.9H) |
| XL-2 | 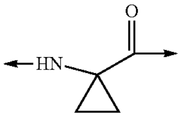 | 2 of 2 100% | 12.20 min | δ 4.23 (m, 8H), 3.63 (br s, 180H), 2.23 (m, 12H), 1.61 (m, 4H), 1.48 (m, 4H), 1.39 (m, 2H), 1.15 (m, 4H), 0.95 (m, 4H). |
| XL-3 | 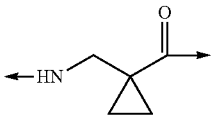 | 2 of 2 100% | 12.93 min | δ 4.19 (m, 8H), 3.85-3.43 (m, 192H), 3.36 (br s, 4H), 2.22 (m, 12H), 1.60 (m, 4H), 1.38 (m, 2H), 1.19 (m, 4H), 0.95 (m, 8H). |
| XL-4 | 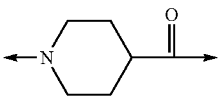 | 2 of 2 100% | 13.25 min | δ 4.22 (m, 8H), 4.02 (m, 4H), 3.84-3.43 (m, 194H), 3.00 (br s, 4H), 2.60 (m, 2H), 2.23 (m, 12H), 1.91 (m, 4H), 1.61 (m, 8H), 1.42 (m, 2H), 0.97 (m, 4H). |

TABLE 18-continued

Exemplary PEG-based Cross-Linking Polymers

| Number | T | Number of PEG-end groups substituted with functional group | Anal HPLC (CAD) Retention time (min) | $^1$H NMR (400 MHz, methanol-$d_4$) |
|---|---|---|---|---|
| XL-9 | 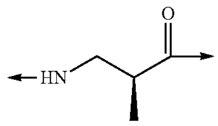 | 2 of 2 100% | 1.85 min (method 10) | δ 4.29-4.19 (m, 4H), 4.14 (d, J = 8.1 Hz, 4H), 3.87-3.41 (m, 179H), 3.28-3.18 (m, 3H), 2.78-2.62 (m, 2H), 2.37-2.06 (m, 12H), 1.72-1.51 (m, 4H), 1.47-1.31 (m, 2H), 1.21-1.09 (m, 6H), 1.04-0.87 (m, 4H). |
| XL-10 | 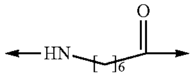 | 2 of 2 100% | 1.96 min (method 10) | δ 4.25-4.18 (m, 4H), 4.13 (d, J = 8.3 Hz, 4H), 3.85-3.40 (m, 178H), 3.09 (t, J = 7.0 Hz, 4H), 2.34 (t, J = 7.5 Hz, 4H), 2.31-2.09 (m, 11H), 1.72-1.54 (m, 8H), 1.54-1.44 (m, 4H), 1.44-1.25 (m, 11H), 1.03-0.85 (m, 4H). |

Intermediates Used in the Synthesis of PEG-Based Cross-Linking Polymers:

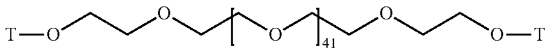

TABLE 19

Exemplary PEG-based Cross-Linking Polymers

| Number | T | Number of PEG-end groups substituted with functional group | $^1$H NMR (400 MHz) |
|---|---|---|---|
| XL-2a | 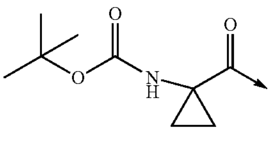 | 2 of 2 100% | (chloroform-d) δ 4.23 (m, 4H), 3.64 (br s, 165H), 1.52 (br m, 4H), 1.45 (br s, 18H), 1.16 (br m, 4H). |
| XL-3a | 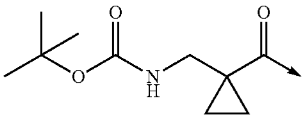 | 2 of 2 100% | (methanol-d4) δ 4.23 (m, 4H), 3.83-3.41 (m, 18H), 1.44 (br s, 18H) 1.17 (m, 4H), 0.94 (m, 4H). |
| XL-4a | 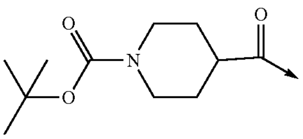 | 2 of 2 100% | (methanol-d4) δ 4.23 (m, 4H), 3.95 (m, 4H), 3.85-3.41 (m, 180H), 2.92 (br s, 4H), 2.57 (m, 2H), 1.89 (m, 4H), 1.56 (m, 4H), 1.45 (m, 18H). |
| XL-9a | 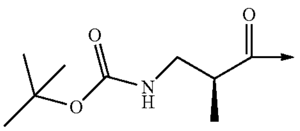 | 2 of 2 100% | (methanol-$d_4$) δ 4.31-4.17 (m, 4H), 3.83-3.44 (m, 179H), 3.27-3.15 (m, 4H), 2.72-2.61 (m, 2H), 1.50-1.39 (m, 18H), 1.14 (d, J = 7.2 Hz, 6H). |

TABLE 19-continued

Exemplary PEG-based Cross-Linking Polymers

| Number | T | Number of PEG-end groups substituted with functional group | $^1$H NMR (400 MHz) |
|---|---|---|---|
| XL-10a | 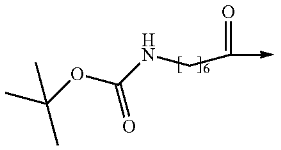 | 2 of 2 100% | (methanol-$d_4$) δ 4.27-4.15 (m, 4H), 3.83-3.44 (m, 180H), 3.04-2.99 (m, 4H), 2.34 (t, J = 7.3 Hz, 4H), 1.68-1.57 (m, 4H), 1.55-1.40 (m, 22H), 1.39-1.27 (m, 9H). |
| XL-2b | 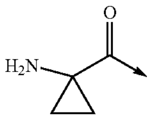 Bis-TFA salt | 2 of 2 100% | (chloroform-d) δ 4.23 (m, 4H), 3.64 (br s, 165H), 1.55 (br m, 4H), 1.19 (br m, 4H). |
| XL-3b | 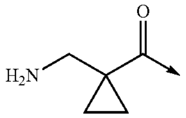 Bis-TFA salt | 2 of 2 100% | (methanol-d4) δ 4.33 (m, 4H), 3.88-3.42 (m, 184H), 2.91 (br m, 4H), 3.22 (br s, 2H), 1.41 (m, 4H), 1.15 (m, 4H), |
| XL-4b | 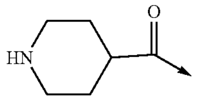 Bis-TFA salt | 2 of 2 100% | (methanol-d4) δ 4.30 (m, 4H), 3.85-3.54 (m, 178H), 3.99 (m, 4H), 3.15, (m, 4H), 2.79 (m, 2H), 2.14 (m, 4H), 1.95 (m, 4H). |
| XL-9b | 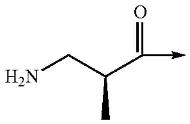 Bis-TFA Salt | 2 of 2 100% | (methanol-$d_4$) δ 4.56-4.43 (m, 2H), 4.32-4.20 (m, 2H), 3.92-3.41 (m, 180H), 3.25-3.12 (m, 4H), 2.99-2.84 (m, 2H), 1.28 (d, J = 7.0 Hz, 6H). |
| XL-10b | 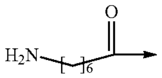 Bis-TFA Salt | 2 of 2 100% | (methanol-$d_4$) δ 4.25-4.19 (m, 4H), 4.10-3.41 (m, 180H), 3.04-2.90 (m, 4H), 2.44-2.30 (m, 4H), 1.77-1.55 (m, 8H), 1.54-1.33 (m, 8H). |

XL-5. PEG(2000)-bis-[3-(((((1R,8S,9s)-bicyclo [6.1.0]non-4-yn-9-yl)methylcarbamoyl]

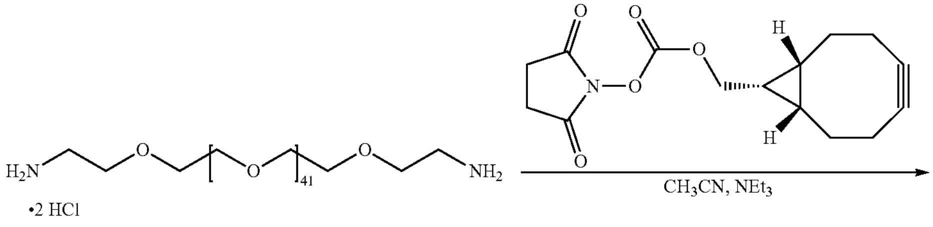

-continued

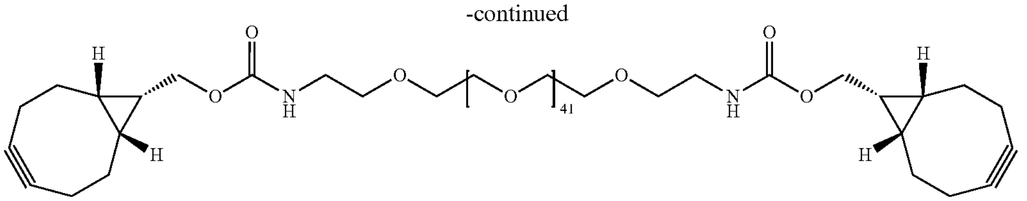

XL-5

$M_n$~2 kDa PEG diamine hydrochloride (JenKem Technology, 300 mg, 0.148 mmol) was dissolved in acetonitrile (3 mL). Triethylamine (0.413 mL, 2.96 mmol) was added, followed by ((1R,8S,9s)-bicyclo[6.1.0]non-4-yn-9-yl) methyl (2,5-dioxopyrrolidin-1-yl) carbonate (345 mg, 1.184 mmol) and the reaction mixture was stirred at room temperature for 4 h. The reaction mixture was directly purified by preparative reverse phase HPLC with ELSD triggered fraction collection (method below). The product containing fractions were pooled, frozen and lyophilized to provide XL-5. For storage purposes, XL-5 was kept as an acetonitrile, DMSO, or methanol solution in a freezer. Analytical HPLC-CAD (method below): retention time=11.85 min. $^1$H NMR (400 MHz, methanol-d4) δ 4.14 (m, 4H), 3.63 (br s, 186H), 3.54 (m, 4H), 2.22 (m, 12H), 1.61 (m, 4H), 1.38 (m, 2H), 0.94 (m, 4H).

Preparative HPLC conditions: Waters XBridge C18; particle size: 5 μm; column size: 19×250 mm; eluent/gradient: 5% $CH_3CN/H_2O$/0.5 min, 5-95% $CH_3CN/H_2O$/12.5 min, 95% $CH_3CN/H_2O$/3 min; flow rate: 30 mL/min; column temperature: room temperature.

Analytical HPLC-CAD conditions: Waters XBridge BEH300 C18; particle size: 3.5 μm; column size: 4.6×100 mm; eluent/gradient: 2% $CH_3CN/H_2O$/0.5 min, 2-98% $CH_3CN/H_2O$/17.5 min ($CH_3CN$ containing 0.05% TFA and $H_2O$ containing 0.1% TFA); flow rate: 1 mL/min; column temperature: 50 C.

XL-6. PEG(10000)-tetra-[3-(((((1R,8S,9s)-bicyclo[6.1.0]non-4-yn-9-yl)methylcarbamoyl]

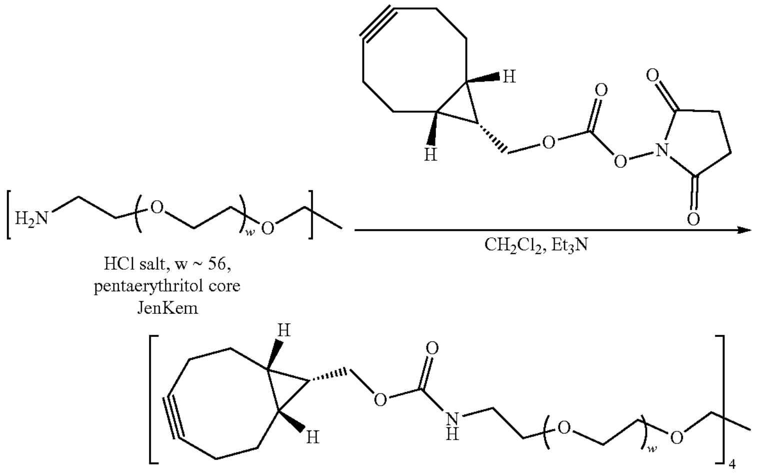

XL-6

$M_n$~10 kDa 4-arm PEG amine hydrochloride (pentaerythritol core, JenKem Technology, 500 mg, 0.05 mmol) was dissolved in dichloromethane (15 mL). Triethylamine (0.554 mL, 4.00 mmol) was added, followed by ((1R,8S,9s)-bicyclo[6.1.0]non-4-yn-9-yl)methyl (2,5-dioxopyrrolidin-1-yl) carbonate (175 mg, 0.600 mmol) and the reaction mixture was stirred at room temperature overnight. The reaction mixture was directly purified by dialysis against methanol using a 2 kDa MWCO Spectra/Por 6 regenerated cellulose dialysis membrane (Spectrum, Inc.). For analysis and utilization in further reactions, XL-6 was isolated by concentration using a roto evaporator. For storage purposes the compound was kept as a methanol solution at room temperature. $^1$H NMR (400 MHz, methanol-d4) δ 4.14 (m, 8H), 3.63 (br s, 995H), 2.22 (m, 24H), 1.61 (m, 8H), 1.38 (m, 4H), 0.94 (m, 8H).

XL-8

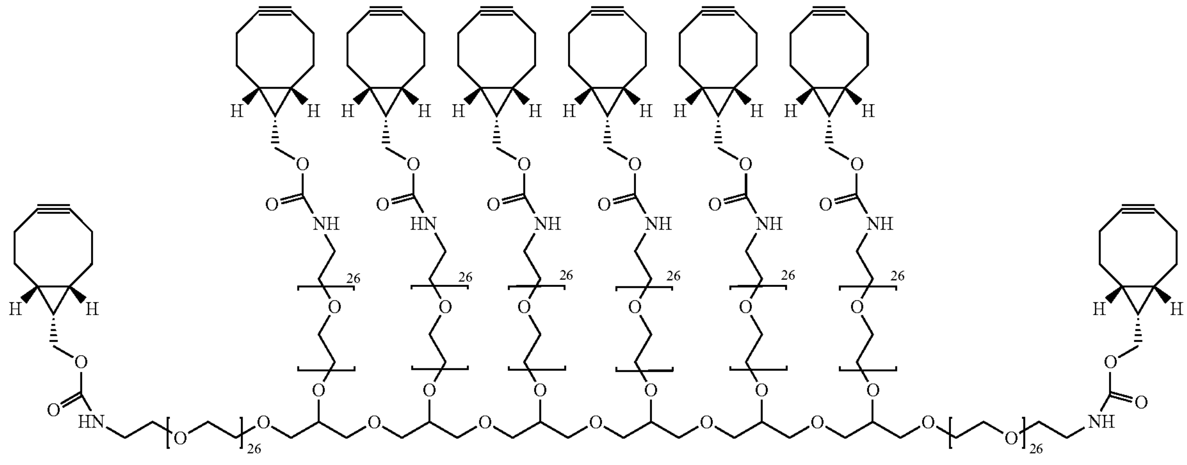

$M_n$~10 kDa 8-arm PEG amine hydrochloride (hexaglycerol core, JenKem Technology, 800 mg, 0.08 mmol) was dissolved in dichloromethane (5 mL). Triethylamine (0.887 mL, 6.40 mmol) was added, followed by ((1R,8S,9s)-bicyclo[6.1.0]non-4-yn-9-yl)methyl (2,5-dioxopyrrolidin-1-yl) carbonate (807 mg, 2.56 mmol) and the reaction mixture was stirred at room temperature for 5 h. The reaction mixture was concentrated using a rotoevaporator, then dissolved in methanol and purified by dialysis against methanol using a 2 kDa MWCO Spectra/Por 6 regenerated cellulose dialysis membrane (Spectrum, Inc.). For analysis and utilization in further reactions, XL-8 was isolated by concentration using rotoevaporator, however for storage purposes XL-8 was kept as a methanol solution at room temperature. $^1$H NMR (400 MHz, methanol-d4) δ 4.14 (m, 16H), 3.63 (br s, 935H), 2.23 (m, 48H), 1.61 (m, 16H), 1.38 (m, 8H), 0.95 (m, 16H).

Example 5

This example describes the synthesis of hydrogels prepared by reacting appropriately functionalized polymers with crosslinkers.

Synthesis of Hyaluronic Acid Hydrogel: H1a

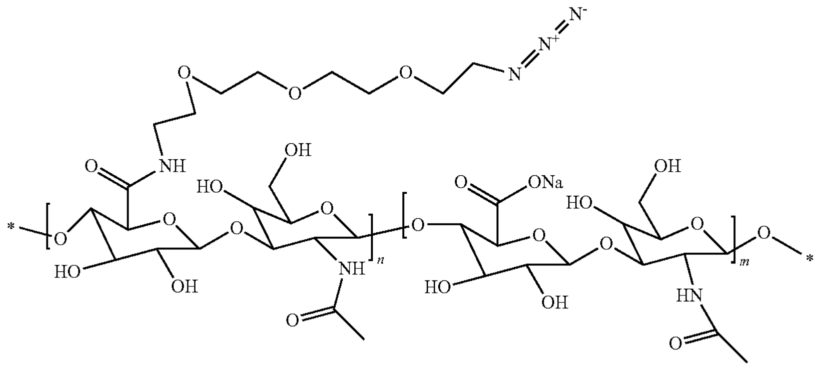

[HA—N3]-23% b

+

-continued

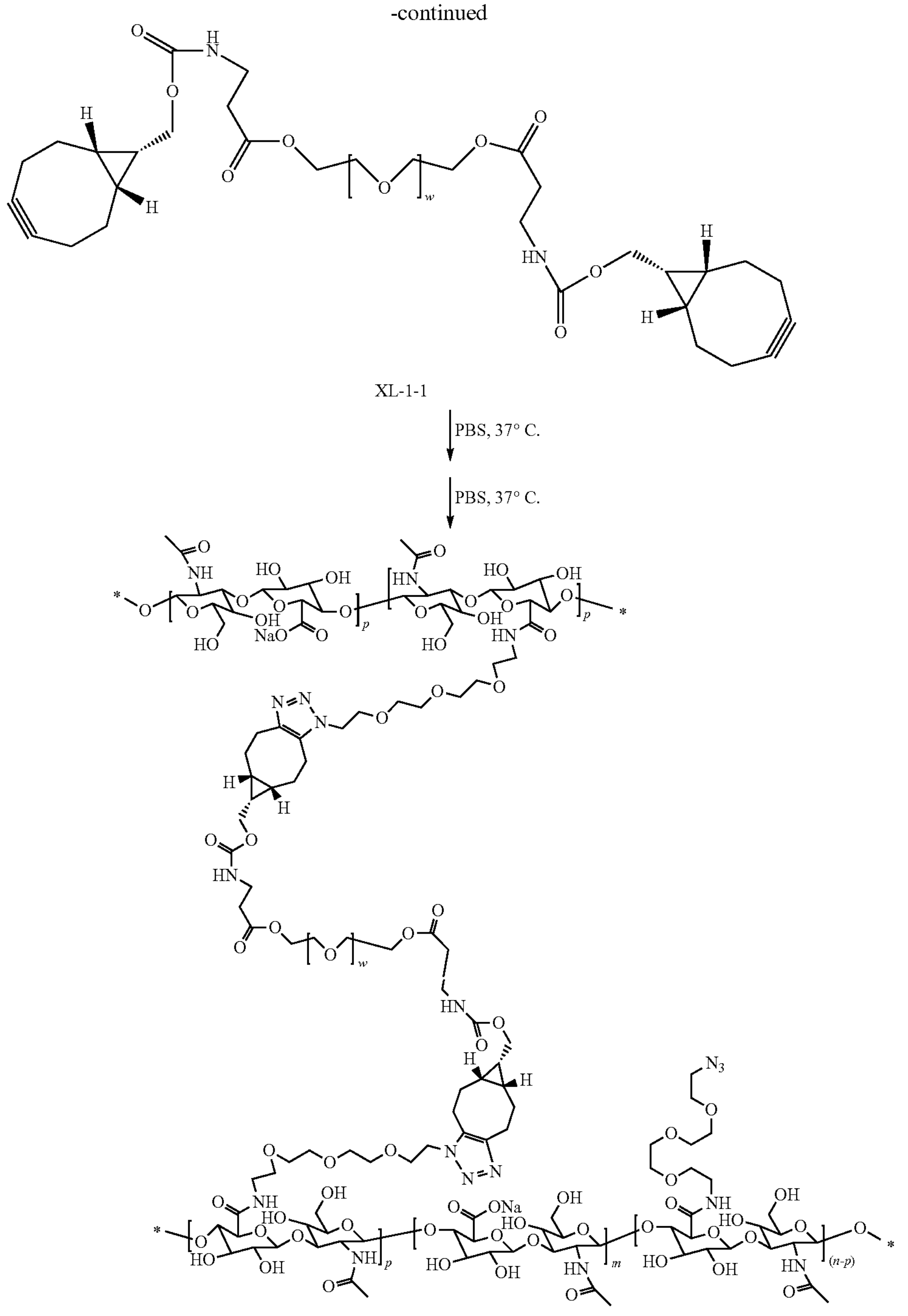

H1a

[HA-N3]-23% b (60 mg, 136 μmol, degree of substitution=23%) was dissolved in 3.8 mL sterile 1×PBS buffer, pH 7.4 at room temperature over 30 min in a 5 mL Eppendorf tube. The molecular weight of the unsubstituted carboxylate sodium salt repeat dimer unit is 401.3 Da. The MW of the azidylated repeat dimer unit is 579.6 Da. The average MW of a dimer unit for the sodium salt form of [HA-N3]-23% b is 442.3 Da=((401.3×0.77)+(579.6×0.23)). Using the average MW of a sodium salt dimer unit, the total moles of repeat dimer unit is 136 μmol and the number of moles of azidylated repeat dimer unit is 31 μmol.

To this solution was added a 50 mg/mL solution of XL-1-1 (0.215 mL, 4.30 μmol of reagent assuming a MW of 2500 Da, 8.60 μmol of reactive functionality). This resulted in a solution which was 1.5% w/v with respect to [HA-N3]-23% b and where 6.3% of the [HA-N3]-22% b repeat units were predicted to be cross-linked by the XL-1-1] ((8.60 μmol [XL-1-1-reactive functionality]/136 μmol [HA-units)×100=6.3%).

The mixture was vortexed briefly to mix, then distributed into two 3 mL syringes, which were capped and held at 37°

C. overnight to provide Ha. Visual inspection (inversion test) showed successful gelation.

Preparation of Hyaluronic Acid-Based Hydrogel Particles

H1a, 2 mL, was forced through a 100 mesh stainless steel screen disc into a 5 mL syringe, yielding coarse gel particles. To this syringe 1 mL of 1×PBS was added, followed by vortexing to mix. The syringe was held at room temperature for 6 h to allow swelling of the hydrogel. This resulted in a mixture that was 1.0% with respect to [HA-N3]-23% b. The swollen, coarse gel particles of $H_1a$ were forced 20 times through a 200-mesh stainless steel screen disc, yielding fine gel particles as the final product.

The hyaluronic acid-based hydrogels (and corresponding hydrogel particles) listed in Table 20 were prepared analogously to Ha. A hydrogel is defined by the [HA-N3] component used and its concentration in the crosslinking reaction, as well as by the PEG crosslinker used and the degree with which it is expected to form cross-links to the back bone polymer (% cross-link).

TABLE 20

Exemplary Hyaluronic Acid-based Hydrogels

| Number | [HA-$N_3$]-X% | Conc of [HA-N3] in Hydrogel Reaction | XL-m | % cross-link in hydrogel |
|---|---|---|---|---|
| H1a | [HA-$N_3$]-23%b | 1.5% | XL-1-1 | 6.3 |
| H1b | [HA-$N_3$]-23%b | 1.0% | XL-1-1 | 4.5 |
| H1c | [HA-$N_3$]-37% | 1.0% | XL-1-1 | 5.3 |
| H1e | [HA-$N_3$]-22% | 1.4% | XL-1-1 | 6.3 |
| H1f | [HA-$N_3$]-23%b | 1.0% | XL-1-1 | 5.9 |
| H2 | [HA-$N_3$]-23% | 1.4% | XL-2 | 6.4 |
| H5 | [HA-$N_3$]-26% | 1.4% | XL-5 | 6.3 |
| H6 | [HA-$N_3$]-37% | 1.8% | XL-6 | 5.6 |
| H7 | [HA-$N_3$]-23%c | 1.5% | XL-9 | 6.1 |
| H8 | [HA-$N_3$]-23%c | 1.5% | XL-10 | 6.2 |

Example 6

Synthesis of Hydrogel-Drug Conjugates

This example describes the synthesis of hydrogel-drug conjugates, in which the drug is conjugated to the carrier via a traceless linker.

When preparing samples for in vivo dosing, all manipulations of materials or solutions that were not capped took place in a laminar flow hood under aseptic conditions. All consumables used were previously unopened and were labeled “sterile.”

C4b (H1a-L4D1)

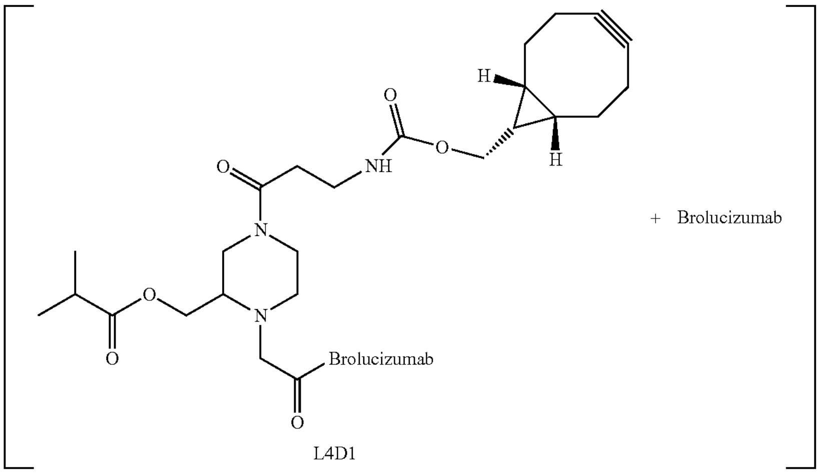

+

-continued
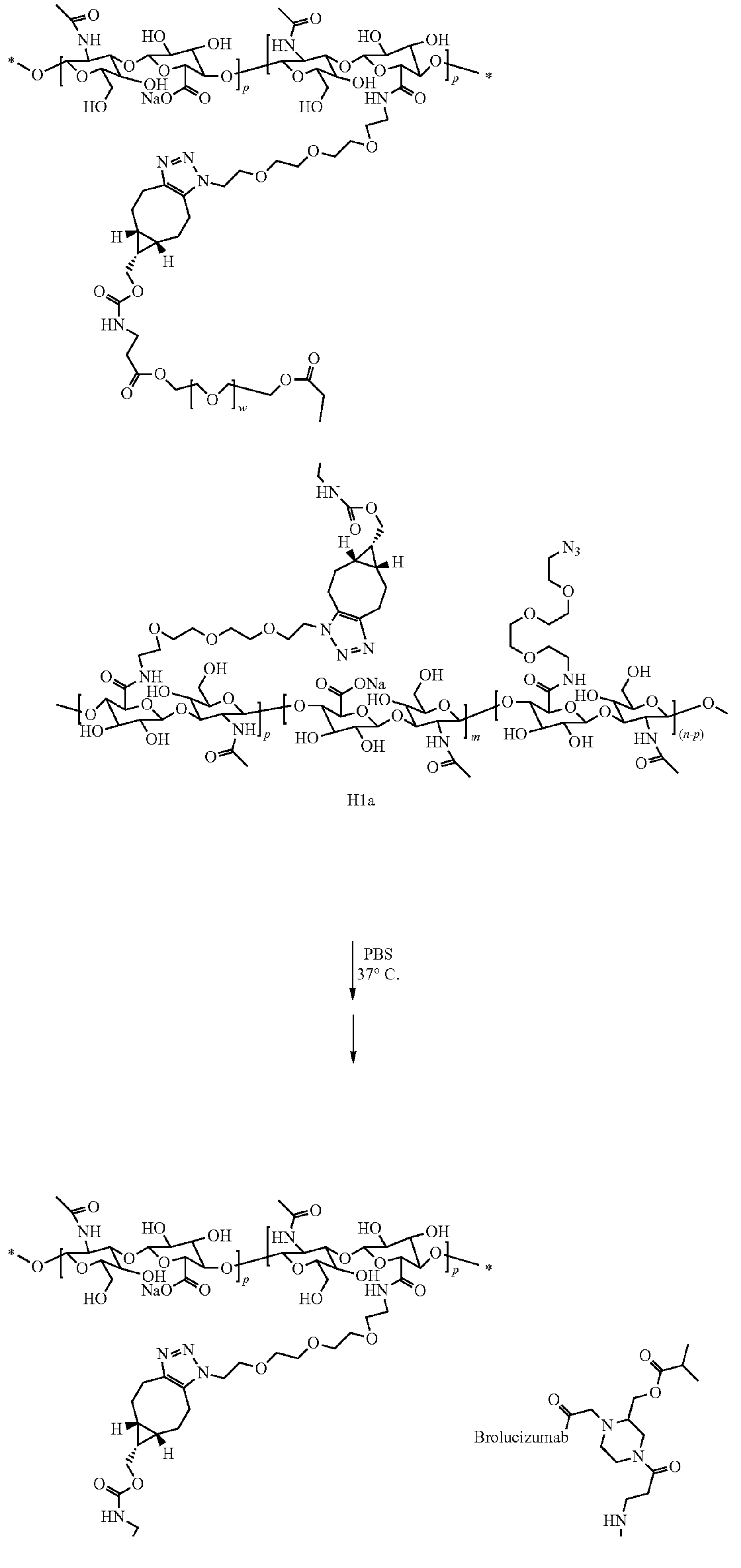

-continued

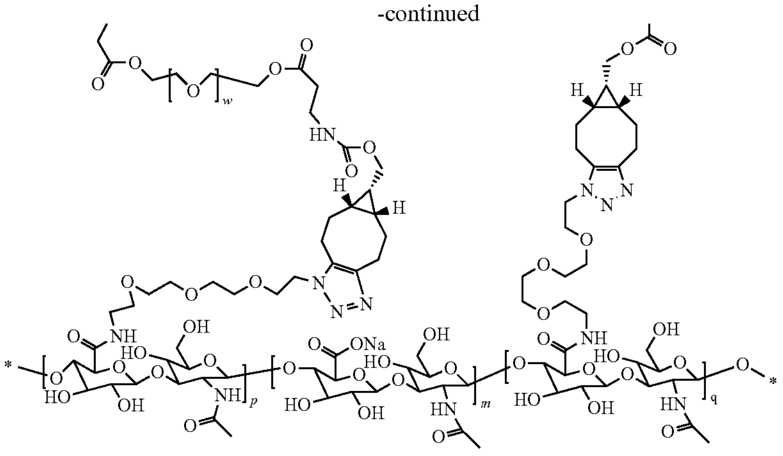

C4b

Hydrogel particle suspension of H1a (2.5 mL, 10 mg/mL, 23 mM total dimer repeat unit) was treated with a solution of L4D1b (14.5 mL of 42 mg/mL solution in 1×PBS), vortexed and held at 37° C. overnight. The reaction tube was centrifuged (1000 rcf, 5 min) and the supernatant was removed from the tube using a needle and syringe. Fresh 1×PBS (10-15 mL) was added to the tube, which was shaken to resuspend the gel. Centrifugation, removal of supernatant, and dilution with fresh buffer was repeated. The washing continued until no brolucizumab was detected in the supernatant (Nanodrop spectrophotometer used for detection of absorbance at 280 nm, ~65 mL PBS wash in total). The remaining hydrogel pellet, [C4b], was transferred into a syringe for storage and dispensing.

A key descriptor of hydrogel-drug conjugates is the amount of drug loaded per volume of hydrogel (=drug loading). When the drug is a protein, there are several methods to determine the loading.

Protein loading of the hydrogel was determined by forced release of the conjugated protein from a known volume of hydrogel, followed by quantification of the released protein. In this example, 37.3 μg of [C4b] was weighed into a reaction tube (this corresponds to 37.3 μL of sample, under the assumption that the density of this hydrogel ~1 g/mL). The sample was treated with 1 M Tris HCl buffer, pH 9.5 (1 mL), vortexed and shaken at 37° C. for 48 h (or until the measured concentration reached a steady state). The concentration of released drug (brolucizumab) was measured (Nanodrop spectrophotometer) to be 0.48 mg/mL in this sample, corresponding to 13.35 mg brolucizumab/mL of hydrogel in [C4b] ((0.048 mg/mL/0.0373 mL)×(1.0373 mL total volume)=13.35 mg/mL). This analysis was carried out in triplicate. The average determined protein loading for [C4b] prior to dilution was 13.9 mg of brolucizumab/mL of hydrogel.

An alternate method of determining protein loading relies on difference calculations. In this method, the measured (Nanodrop spectrophotometer) brolucizumab recovered in the hydrogel washes is subtracted from the known total added protein (for example: brolucizumab+L4D1). The difference gives the brolucizumab loading based on the volume of total hydrogel.

The hydrogels in Table 21 were prepared using methods analogous to those used in the synthesis of C4b.

TABLE 21

Exemplary Hydrogel-Drug Conjugates

| Number | Study | Linker-drug adduct used | Hydrogel used | Drug loading (mg/mL) | Analytical method |
|---|---|---|---|---|---|
| C1a | In vitro release Example 8.1 | L1D1 | H1c | 12.0 | Difference |
| C2a | In vitro release Example 8.1 | L2D1a | H1c | 14.1 | Difference |
| C2b | In vivo study Example 9.1 | L2D1b | H1b | 10.2 | Difference |
| C3a | In vitro release Example 8.1 | L3D1a | H1c | 15.0 | Difference |
| C3b | | L3D1b | H1a | 11.4 | Forced release |
| C6 | | L3D1c | H2 | 21.7 | Forced release |
| C4a | In vitro release Example 8.1 | L4D1a | H1c | 18.5 | Difference |
| C4b | | L4D1b | H1a | 13.9 | Forced release |
| C7 | | L4D1c | H2 | 17.0 | Forced release |
| C5 | | L5D1 | H1e | 11.1 | Forced release |
| C8 | | L1D2a | H6 | 17.2 | Forced release |
| C10 | In vitro release Example 8.2 | L1D2b | H5 | 13.2 | Difference |
| C11 | In vitro release Example 8.2 | L2D2 | H5 | 12.5 | Difference |
| C12 | In vitro release Example 8.2 | L5D2 | H5 | 10.6 | Difference |
| C9 | | L1D3 | H6 | 3.2 | Forced release |
| C14 | | L4D1d | H7 | 14.7 | Forced release |
| C15 | | L4D1d | H8 | 15.6 | Forced release |

The hydrogel-drug conjugate may be diluted with 1×PBS to attain the desired final drug concentration for dosing. The amount of 1×PBS to be added can be calculated by the following equation: (PBS diluent (mL))=[(total drug (mg)/desired drug loading (mg/mL)]−(initial volume of conjugate (mL)).

Conjugate C4b (2 mL hydrogel conjugate, 13.9 mg/mL brolucizumab, total brolucizumab=27.8 mg) prepared as described above was diluted by addition of 1×PBS (0.8 mL). The syringe was capped and shaken vigorously to homogenize. This resulted in a total sample volume of 2.8 mL with protein loading=27.8 mg brolucizumab/2.8 mL=9.93 mg/mL brolucizumab.

Conjugate C4b was dispensed for dosing in 0.5 mL insulin syringes with attached 30G needles, by removing the plunger and backfilling with the desired volume of C4b.

The hydrogel-drug conjugates were stored at 4° C.

Synthesis of Hydrogel Drug Conjugate: C13 temperature for 1 h to allow swelling of the gel. The swollen, coarse gel particles were forced 20 times through a 200 mesh stainless steel screen disc, yielding fine gel particles.

The fine gel particle suspension (in a capped syringe) was centrifuged for 5 min at 2000 rcf to pellet the gel. The supernatant was removed using a needle and syringe, and the pellet was washed with cold 1×PBS, pH 6.5, as follows to remove unconjugated species from the gel. The suspension was centrifuged at 2000 rcf for 5 min to pellet the gel. The supernatant was removed from the syringe using a needle

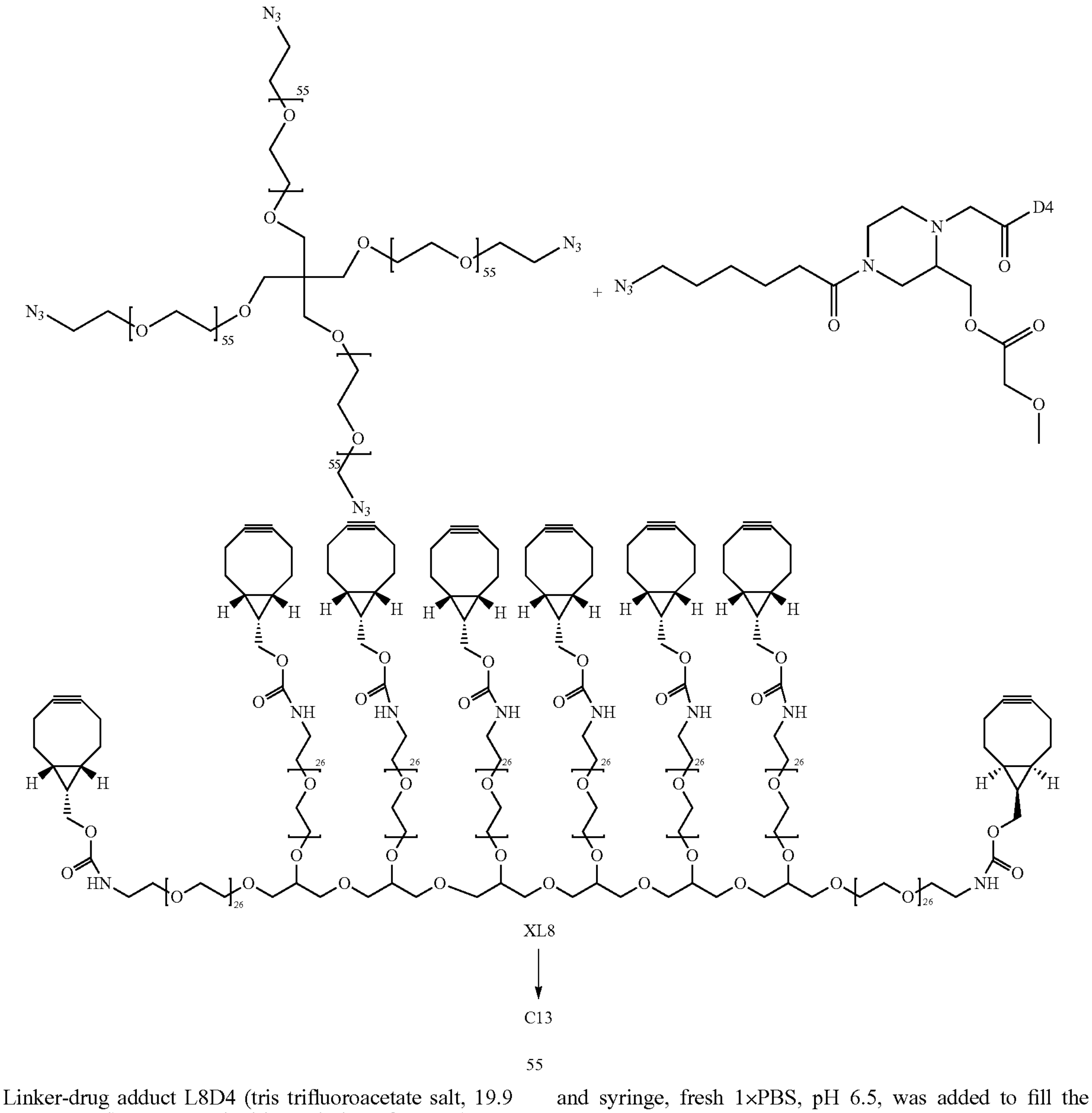

XL8

C13

Linker-drug adduct L8D4 (tris trifluoroacetate salt, 19.9 mg, 8.86 μmol) was treated with a solution of XL-8 (0.157 mL of a 200 mg/mL solution in DMSO), shaken and held for 80 min, at which time HPLC analysis showed complete conjugation of L8D4 to XL-8. To this solution was added a solution of XL-7 (0.154 mL of a 200 mg/mL solution in DMSO). The reaction was shaken and held at room temperature for 4 h.

The bulk gel was forced through a 100 mesh stainless steel screen disc into a 3 mL syringe, yielding coarse gel particles. To this syringe 2 mL of DMSO was added, followed by vortexing to mix. The syringe was held at room and syringe, fresh 1×PBS, pH 6.5, was added to fill the syringe, and the capped syringe was shaken to resuspend the gel. Centrifugation, removal of supernatant, and dilution with fresh buffer was repeated four additional times. After the final centrifugation and removal of buffer the supernatant was tested for endotoxin and the washed gel pellet was diluted with 1×PBS, pH 6.5, to a final total volume of 1.4 mL. The diluted particle suspension was vortexed to mix and the product, C13 was stored at 4° C.

The concentration of D4 in C13 (assuming 100% conjugation) was 10.3 mg/mL.

Example 7

This example describes the preparation of a series of model traceless linker-drug conjugates, in which the model "drug" is a low molecular weight amine-containing compound, most frequently, p-methoxybenzylamine. Compounds M1-M27 are not conjugated to a polymer, hydrogel or other carrier. In vitro release studies of the low molecular weight amine-containing compound from compounds M1-M27 allowed evaluation of a number of different release triggers.

TABLE 22

| Model Compounds | |
|---|---|
| Structure | Number |
| 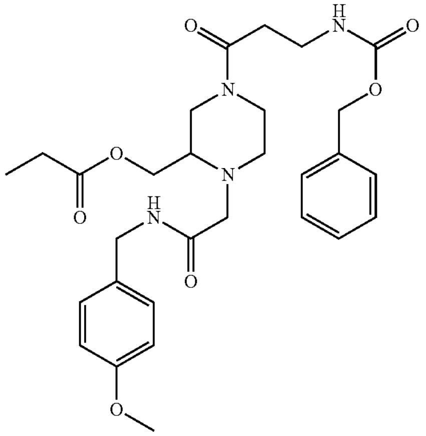 [SMILES: CCC(=O)OCC1CN(C(=O)CCNC(=O)OCc2ccccc2)CCN1CC(=O)NCc1ccc(OC)cc1] | M1 |
| 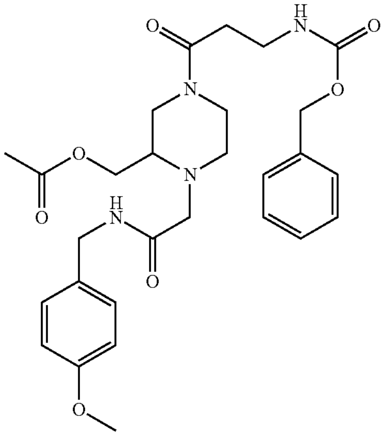 [SMILES: COc1ccc(CNC(=O)CN2CCN(C(=O)CCNC(=O)OCc3ccccc3)CC2COC(C)=O)cc1] | M2 |
| 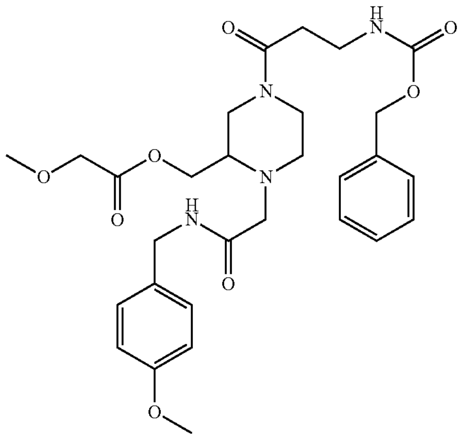 [SMILES: COCC(=O)OCC1CN(C(=O)CCNC(=O)OCc2ccccc2)CCN1CC(=O)NCc1ccc(OC)cc1] | M3 |

TABLE 22-continued
| Model Compounds | |
|---|---|
| Structure | Number |
| 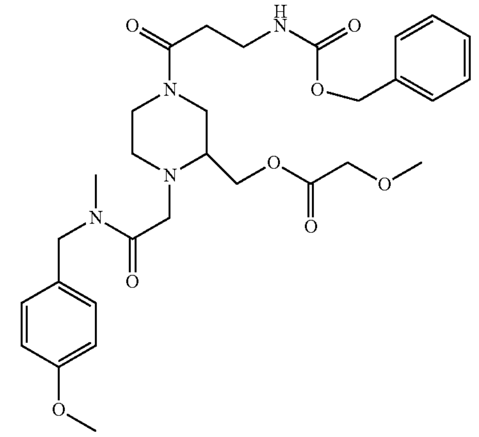 [SMILES: COCC(=O)OCC1CN(C(=O)CCNC(=O)OCc2ccccc2)CCN1CC(=O)N(C)Cc1ccc(OC)cc1] | M4 |
| 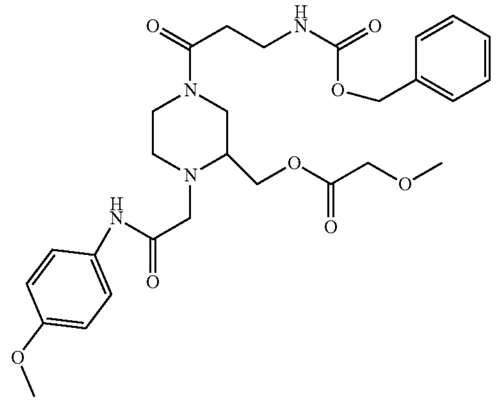 [SMILES: COCC(=O)OCC1CN(C(=O)CCNC(=O)OCc2ccccc2)CCN1CC(=O)Nc1ccc(OC)cc1] | M5 |
| General structure for M1-M5<br>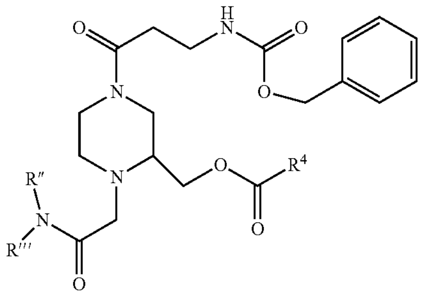 | M1-M5 |
| 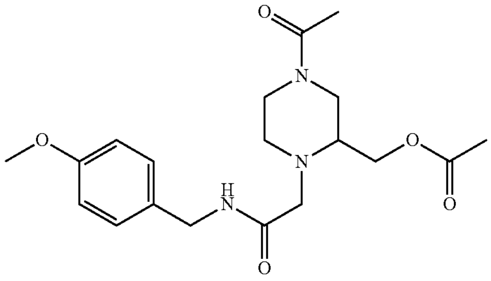 [SMILES: COc1ccc(CNC(=O)CN2CCN(C(C)=O)CC2COC(C)=O)cc1] | M6 |

TABLE 22-continued
| Model Compounds | |
|---|---|
| Structure | Number |
| 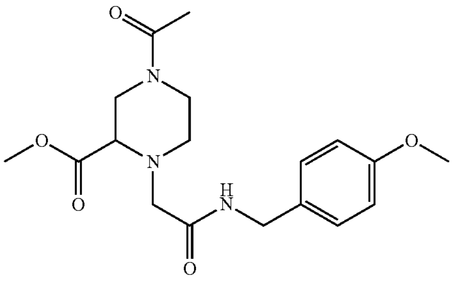 | M7 |
| 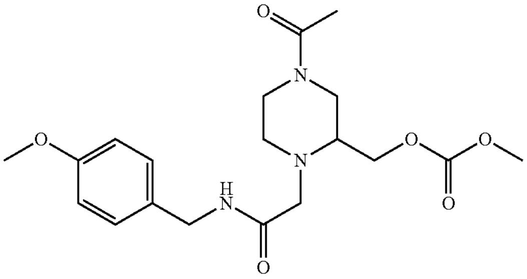 | M8 |
| 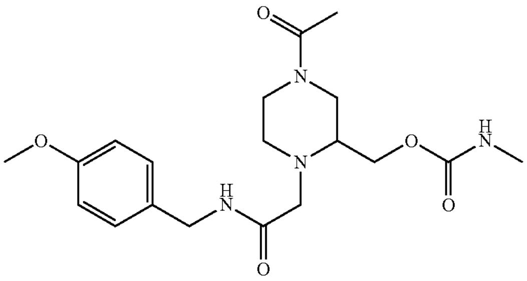 | M9 |
| 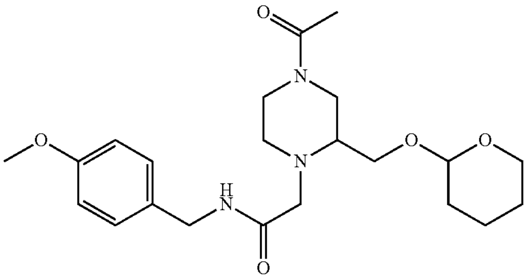 [SMILES: COc1ccc(CNC(=O)CN2CCN(C(C)=O)CC2COC2CCCCO2)cc1] | M10 |
| 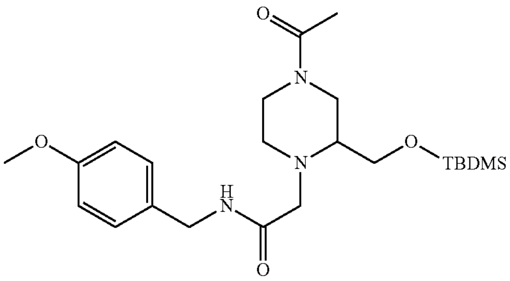 | M11 |

TABLE 22-continued
| Model Compounds | |
|---|---|
| Structure | Number |
| 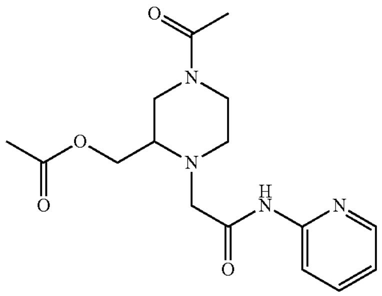 [SMILES: CC(=O)OCC1CN(C(C)=O)CCN1CC(=O)Nc1ccccn1] | M17 |
| 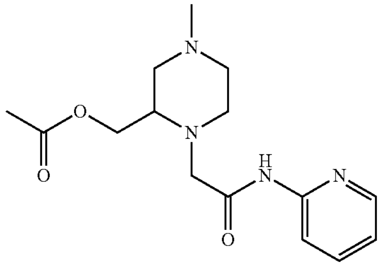 [SMILES: CC(=O)OCC1CN(C)CCN1CC(=O)Nc1ccccn1] | M18 |
| 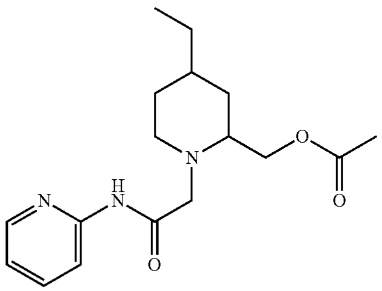 [SMILES: CCC1CCN(CC(=O)Nc2ccccn2)C(COC(C)=O)C1] | M19 |
| 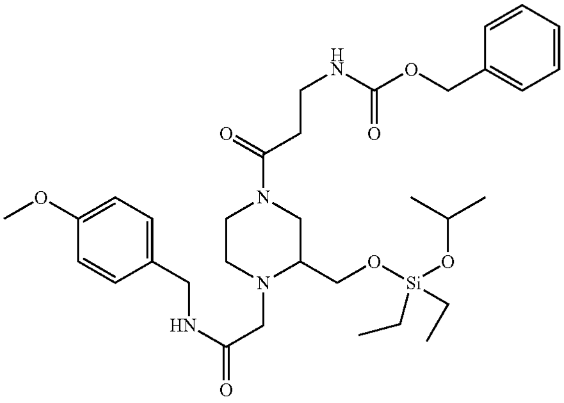 [SMILES: CC[Si](CC)(OCC1CN(C(=O)CCNC(=O)OCc2ccccc2)CCN1CC(=O)NCc1ccc(OC)cc1)OC(C)C] | M20 |

TABLE 22-continued
| Model Compounds | |
|---|---|
| Structure | Number |
| 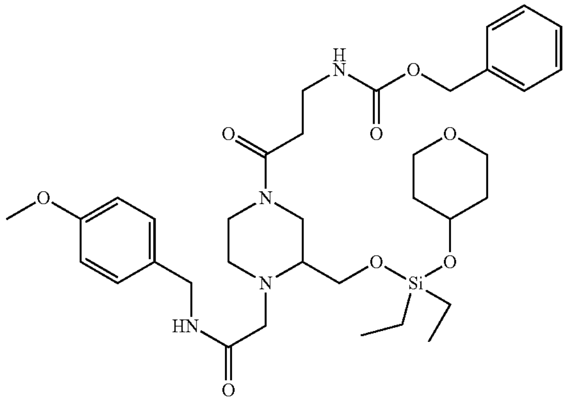 [SMILES: CC[Si](CC)(OCC1CN(C(=O)CCNC(=O)OCc2ccccc2)CCN1CC(=O)NCc1ccc(OC)cc1)OC1CCOCC1] | M21 |
| 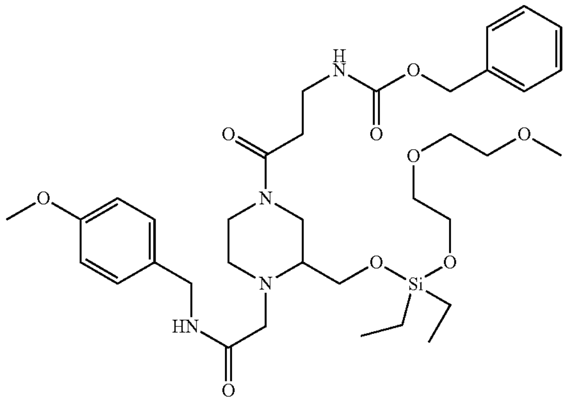 | M22 |
| 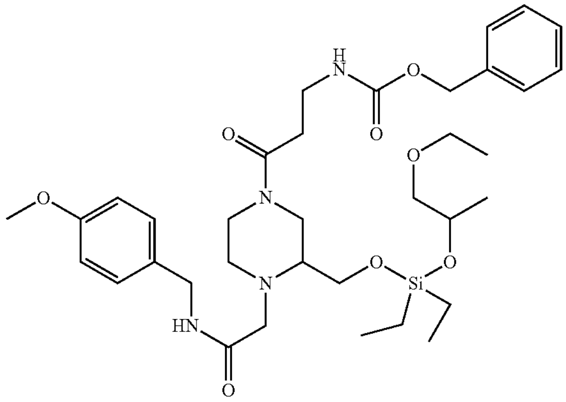 [SMILES: CCOCC(C)O[Si](CC)(CC)OCC1CN(C(=O)CCNC(=O)OCc2ccccc2)CCN1CC(=O)NCc1ccc(OC)cc1] | M23 |

TABLE 22-continued
| Model Compounds | |
|---|---|
| Structure | Number |
| 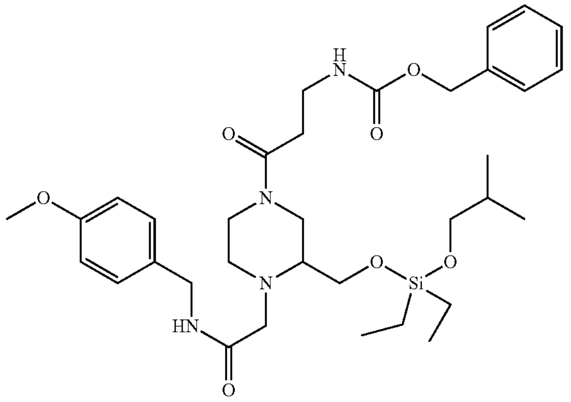 [SMILES: CC[Si](CC)(OCC(C)C)OCC1CN(C(=O)CCNC(=O)OCc2ccccc2)CCN1CC(=O)NCc1ccc(OC)cc1] | M24 |
| 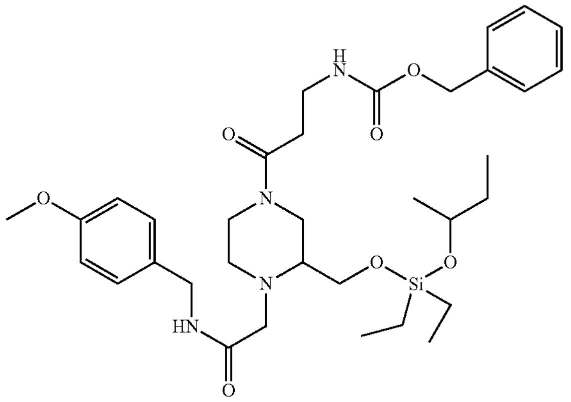 [SMILES: CCC(C)O[Si](CC)(CC)OCC1CN(C(=O)CCNC(=O)OCc2ccccc2)CCN1CC(=O)NCc1ccc(OC)cc1] | M25 |
| 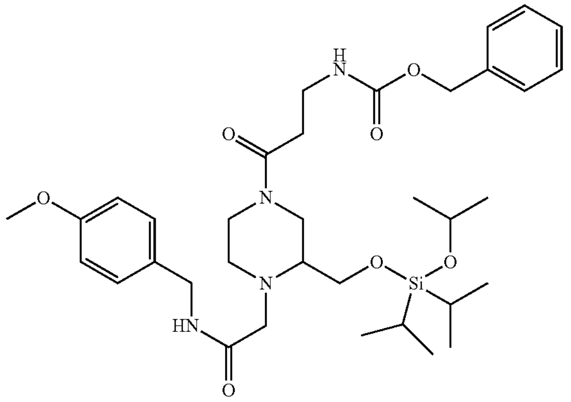 [SMILES: COc1ccc(CNC(=O)CN2CCN(C(=O)CCNC(=O)OCc3ccccc3)CC2CO[Si](OC(C)C)(C(C)C)C(C)C)cc1] | M26 |

TABLE 22-continued
| Model Compounds | |
|---|---|
| Structure | Number |
| 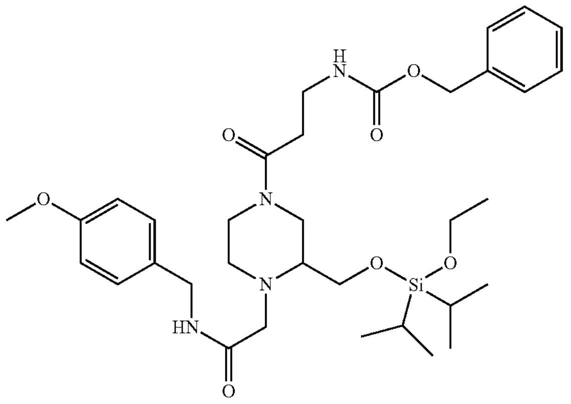 [SMILES: CCO[Si](OCC1CN(C(=O)CCNC(=O)OCc2ccccc2)CCN1CC(=O)NCc1ccc(OC)cc1)(C(C)C)C(C)C] | M27 |
| General structure for M20-M27: 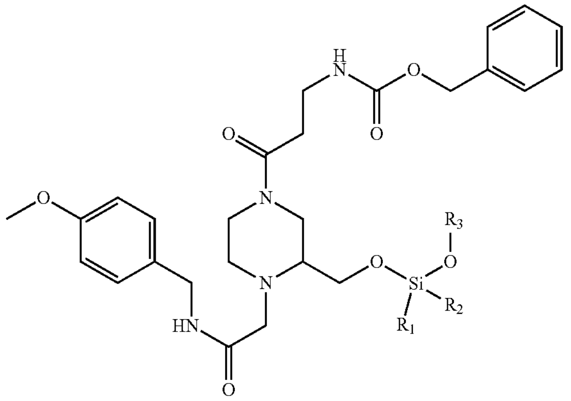 | M20-M27 |
Synthesis of Model Compounds
M1. (4-(3'-(((benzyloxy)carbonyl)amino)propanoyl)-1-(2"-((4'"-methoxybenzyl)amino)-2"-oxoethyl)piperazin-2-yl)methyl propionate
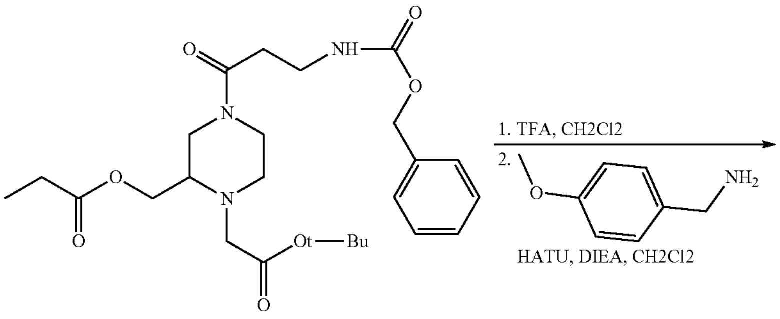
L-INT-3

-continued

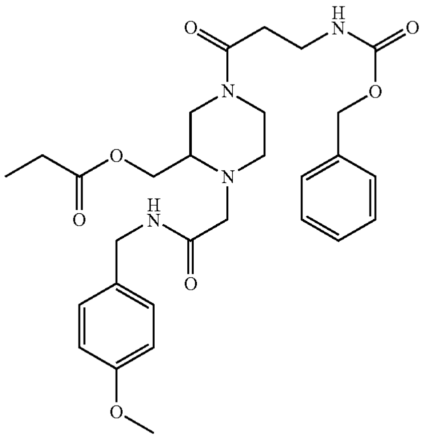

M1

M1. (4-(3'-(((benzyloxy)carbonyl)amino)propanoyl)-1-(2"-((4'"-methoxybenzyl)amino)-2"-oxoethyl)piperazin-2-yl)methyl propionate

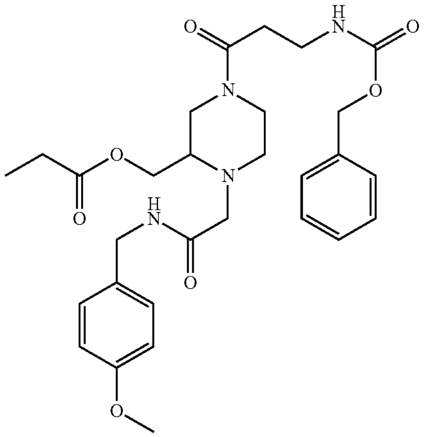 [SMILES: CCC(=O)OCC1CN(C(=O)CCNC(=O)OCc2ccccc2)CCN1CC(=O)NCc1ccc(OC)cc1]

A solution of L-INT-3 (61.7 mg, 0.13 mmol) in dichloromethane (3 mL) was treated with trifluoroacetic acid (1 mL) and stirred overnight at room temperature, then evaporated. The crude intermediate was dissolved in dichloromethane (3 mL) and treated with diisopropylethylamine (0.066 mL, 0.38 mmol), HATU (57.3 mg, 0.15 mmol) and p-methoxybenzylamine (0.017 mL, 0.13 mmol), stirred for 1 h, then evaporated. Purification by flash chromatography ($SiO_2$, 0-15% methanol:dichloromethane) provided M1. LCMS (method 1): retention time=1.16 min; MS (ESI+) m/z 555.2 (M+H). $^1$H-NMR (400 MHz, $CDCl_3$) 7.25 (m, 5H), 7.12 (m, 2H), 6.80 (m, 2H), 5.43 (m, 1H), 5.01 (m, 2H), 4.33 (d, 2H), 4.02 (tdt, 2H), 3.73 (s, 3H), 3.55-3.2 (m, 7H), 3.09 (m, 1H), 2.72 (m, 2H), 2.41 (dq, 3H), 2.18 (m, 2H), 1.04 (dt, 3H).

M2. (4-(3'-(((benzyloxy)carbonyl)amino)propanoyl)-1-(2"-((4'"-methoxybenzyl)amino)-2"-oxoethyl)piperazin-2-yl)methyl acetate

M2

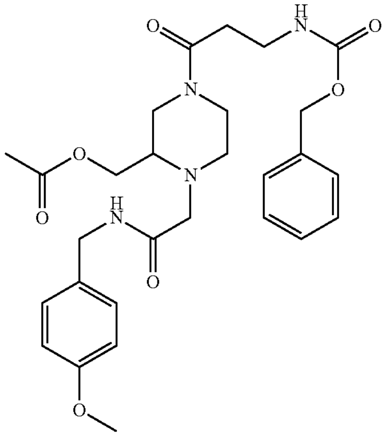

M2 was prepared from intermediate (L-INT-2) using methods analogous to those used to synthesize M1. LCMS (method 1): retention time=1.10 min: MS (ESI+) m/z 541.1 (M+H). NMR (400 MHz, $CDCl_3$) 7.35 (m, 5H), 7.20 (m, 2H), 6.88 (m, 2H), 5.53 (m, 1H), 5.09 (m, 2H), 4.41 (d, 2H), 4.10 (tdt, 2H), 3.81 (s, 3H), 3.55-3.2 (m, 7H), 3.17 (dd, 1H), 2.79 (m, 2H), 2.49 (dq, 3H), 2.0 (m, 3H).

M3. (4-(3'-(((benzyloxy)carbonyl)amino)propanoyl)-1-(2"-((4"'-methoxybenzyl)amino)-2"-oxoethyl)piperazin-2-yl)methyl methoxyacetate

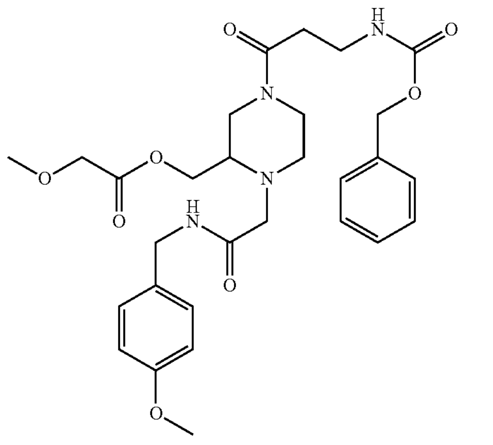 [SMILES: COCC(=O)OCC1CN(C(=O)CCNC(=O)OCc2ccccc2)CCN1CC(=O)NCc1ccc(OC)cc1]

M3 was prepared from intermediate (L-INT-1) using methods analogous to those used to synthesize M1. LCMS (method 1): retention time=1.11 min MS (ESI+) m/z 571.2 (M+H). NMR (400 MHz, $CDCl_3$) 7.37 (m, 5H), 7.21 (m, 2H), 6.90 (m, 2H), 5.49 (m, 1H), 5.10 (m, 2H), 4.42 (d, 2H), 4.23 (tdd, 2H), 3.83 (s, 3H), 3.55-3.2 (m, 9H), 3.20 (dd, 1H), 2.83 (d, 2H), 2.52 (m, 3H).

M4. (4-(3'-(((benzyloxy)carbonyl)amino)propanoyl)-1-(2"-((4"'-methoxybenzyl)(methyl)amino)-2"-oxoethyl)piperazin-2-yl)methyl 2-methoxyacetate

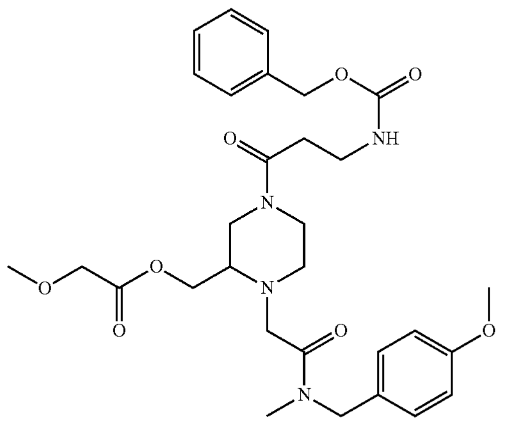

M4 was prepared from intermediate (L-INT-1) using methods analogous to those used to synthesize M1, except substituting N-methyl-p-methoxybenzylamine for p-methoxybenzylamine. LCMS (method 1): retention time=1.04 min MS (ESI+) m/z 585.2 (M+H). NMR (400 MHz, $CDCl_3$) 7.35 (m, 5H), 7.20 (m, 2H), 6.80 (m, 2H), 5.43 (m, 1H), 5.13 (m, 2H), 4.7-3.9 (m, 7H), 3.82 (m, 3H), 3.8-3.2 (m, 10H), 2.8 (m, 3H), 2.7 (m, 3H), 2.6 (m, 2H).

M5. (4-(3'-(((benzyloxy)carbonyl)amino)propanoyl)-1-(2"-((4"'-methoxyphenyl)amino)-2"-oxoethyl)piperazin-2-yl)methyl 2""-methoxyacetate

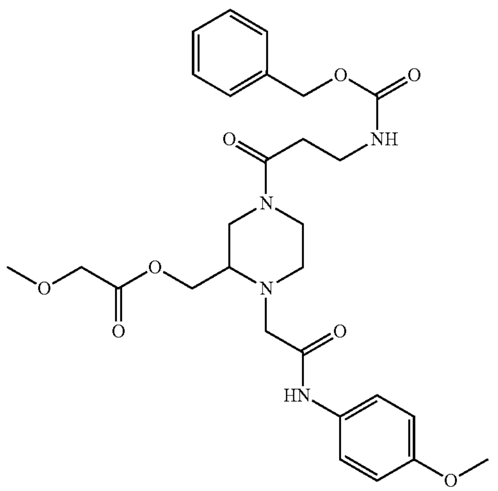

M5 was prepared from intermediate (L-INT-1) using methods analogous to those used to synthesize M1, except substituting 4-methoxyaniline for p-methoxybenzylamine. LCMS (method 1): retention time=1.14 min MS (ESI+) m/z 557.1 (M+H). NMR (400 MHz, $CDCl_3$) 8.7 (br s, 1H), 7.4 (d, 2H), 7.37 (m, 5H), 6.8 (m, 2H), 5.5 (m, 1H), 5.1 (m, 2H), 4.3 (m, 2H), 4.0 (m, 2H), 3.8 (s, 4H), 3.7-3.2 (m, 11H), 3.2 (m, 1H), 2.8 (m, 2H), 2.5 (m, 2H), 2.18 (m, 3H).

M6. (4-acetyl-1-(2-((4-methoxybenzyl)amino)-2-oxoethyl)piperazin-2-yl)methyl acetate

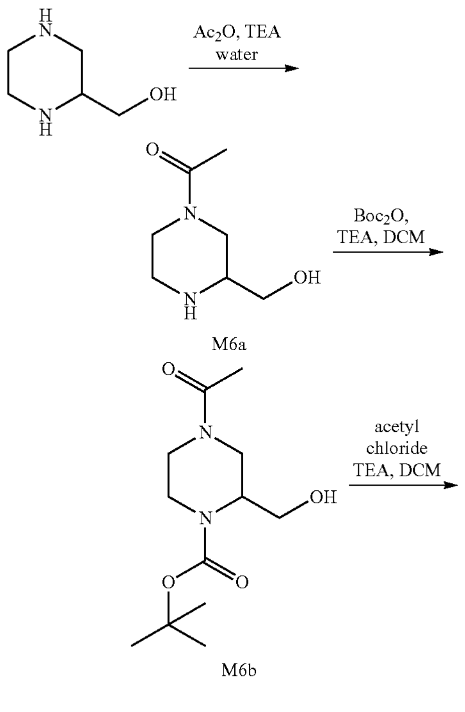

M6a

M6b

-continued

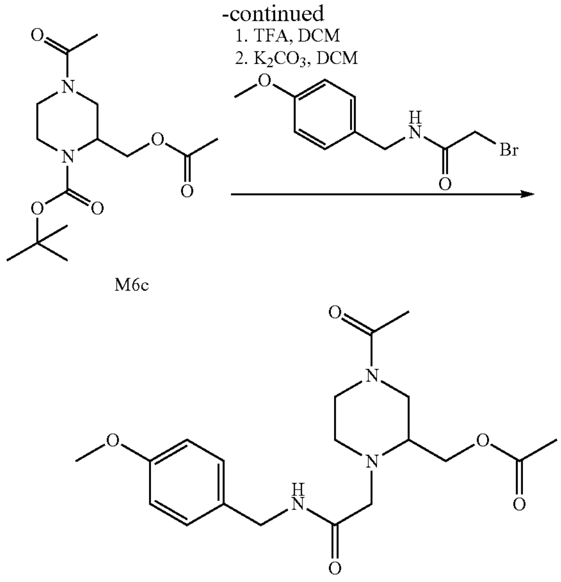

M6c

M6

M6a. 1-N-acetyl-3-hydroxymethylpiperazine

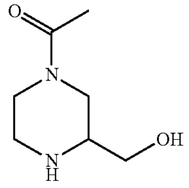

A solution of 2-(hydroxymethyl)piperazine (2 g, 17.2 mmol) in water (25 mL) at 0° C. under argon was treated dropwise with triethylamine (3.5 mL, 25 mmol), stirred for 10 min, then treated dropwise with a solution of acetic anhydride (1.64 mL, 17.3 mmol) in water (15 mL). The reaction was stirred 2 h at RT, then treated with 2 M sodium carbonate (10 mL) and saturated sodium chloride (20 mL). The aqueous was evaporated and the residue purified by flash chromatography (basic alumina, 3% methanol:dichloromethane) to provide M6a. MS (ESI+) m/z 159.0 (M+H).

M6b. tert-butyl 4-acetyl-2-(hydroxymethyl)piperazine-1-carboxylate

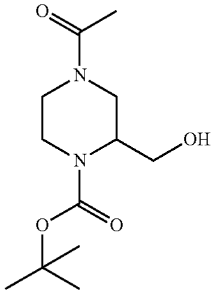 [SMILES: CC(=O)N1CCN(C(=O)OC(C)(C)C)C(CO)C1]

A solution of M6a (1.4 g, 8.84 mmol) in dichloromethane (20 mL) at 0° C. under argon was treated dropwise with triethylamine (1.78 g, 17.6 mmol), stirred for 10 min, then treated dropwise with di-tert-butyl dicarbonate (2.12 g, 9.73 mmol). The reaction was stirred 12 h at RT, then diluted with dichloromethane, washed with brine, dried over sodium sulfate and evaporated. Purification by flash chromatography (basic alumina, 3% methanol:dichloromethane) provided M6b. MS (ESI+) m/z 259.0 (M+H).

M6c. tert-butyl 2-(acetoxymethyl)-4-acetylpiperazine-1-carboxylate

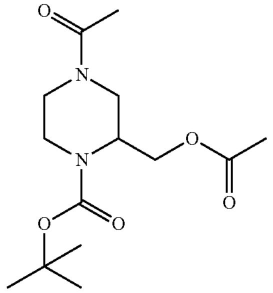 [SMILES: CC(=O)OCC1CN(C(C)=O)CCN1C(=O)OC(C)(C)C]

A solution of M6b (0.20 g, 0.77 mmol) in dichloromethane (5 mL) at 0° C. under argon was treated dropwise with triethylamine (0.20 g, 1.94 mmol), stirred for 10 min, then treated dropwise with acetyl chloride (0.072 g, 0.93 mmol). The reaction was stirred 4 h at RT, then diluted with DCM, washed with brine, dried over sodium sulfate and evaporated. Purification by flash chromatography (basic alumina, 3% methanol:dichloromethane) provided M6c. MS (ESI+) m/z 301.1 (M+H).

M6. (4-acetyl-1-(2'-((4"-methoxybenzyl)amino)-2'-oxoethyl)piperazin-2-yl)methyl acetate

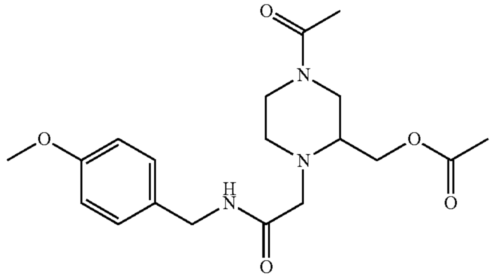 [SMILES: COc1ccc(CNC(=O)CN2CCN(C(C)=O)CC2COC(C)=O)cc1]

A solution of M6c (0.15 g, 0.49 mmol) in dichloromethane (5 mL) at 0° C. under argon was treated dropwise with trifluoroacetic acid (2.0 mL), and was stirred 4 h at RT, then evaporated. This material was dissolved in acetonitrile (10 mL) and held at 0° C. under argon, then treated with potassium carbonate (0.414 g, 2.99 mmol) and 2-bromo-N-(4-methoxybenzyl)acetamide (0.232 g, 0.89 mmol). The reaction was stirred 12 h at RT, then evaporated. The crude mixture was extracted with dichloromethane, which was washed with brine, dried over sodium sulfate and evaporated. Purification by flash chromatography (basic alumina, 5% methanol:dichloromethane), followed by preparative HPLC (Column: Zorbax Eclipse XDB C18 (150×21.5 mm*5 mm); mobile phase: A=water, B=acetonitrile; gradient: 0-2 min: 10% B; 2-8 min: 20% B; 8 min-end: 40% B;)

provided M6. LCMS (method 8): retention time=2.67 min; MS (ESI+) m/z 378.2 (M+H).

M7. methyl 4-acetyl-1-(2'-((4"-methoxybenzyl) amino)-2'-oxoethyl)piperazine-2-carboxylate

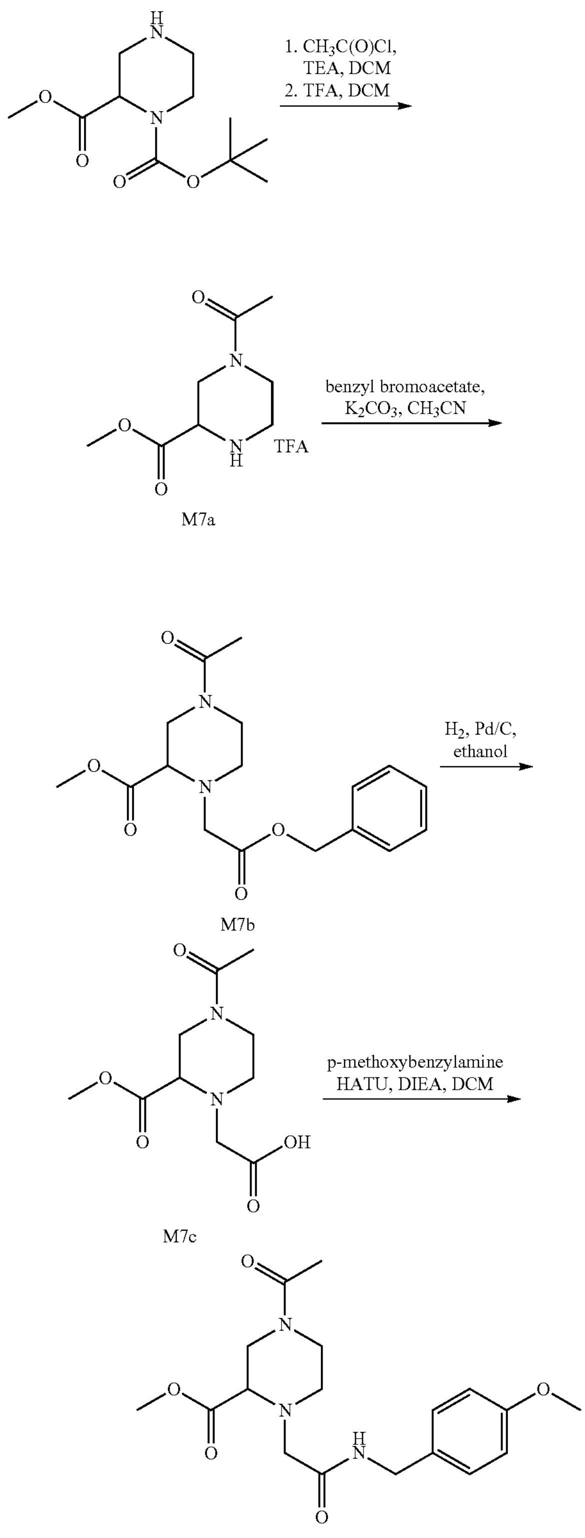

M7a. methyl 4-acetylpiperazine-2-carboxylate, trifluoroacetic acid salt

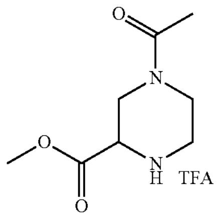

A solution of 1-(tert-butyl) 2-methyl piperazine-1,2-dicarboxylate (0.20 g, 0.82 mmol) and triethylamine (0.33 g, 3.27 mmol) in dichloromethane (4 mL) at 0° C. under argon was treated dropwise with acetyl chloride (0.125 mg, 25 mmol), then stirred 2 h at RT. The reaction was diluted with water, extracted with dichloromethane, and the organic phase dried over sodium sulfate and evaporated. Purification by flash chromatography (basic alumina, 2% methanol:ethyl acetate) provided the intermediate product: MS (ESI+) m/z 287 (M+H). This material was dissolved in dichloromethane (5 mL) at 0° C. and was treated dropwise with trifluoroacetic acid, then stirred 3 h at RT. The reaction mixture was evaporated, washed with pentane and dried, to provide M7a, as the trifluoroacetic acid salt which was used with no further purification. MS (ESI+) m/z 187 (M+H).

M7b. methyl 4-acetyl-1-(2'-(benzyloxy)-2'-oxoethyl) piperazine-2-carboxylate

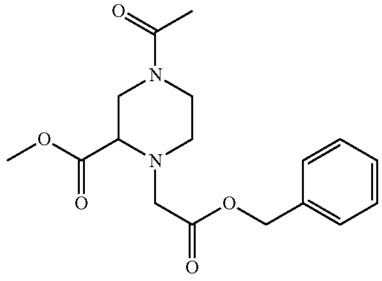 [SMILES: COC(=O)C1CN(C(C)=O)CCN1CC(=O)OCc1ccccc1]

A mixture of M7a (0.16 g, 0.86 mmol) and potassium carbonate (0.30 mg, 2.15 mmol) in acetonitrile (5 mL) at 0° C. under argon was treated dropwise with benzyl bromoacetate (0.234 mg, 1.03 mmol), allowed to come slowly to RT, then stirred 12 h at RT. The reaction was diluted with water, extracted with ethylacetate, and the organic phase dried over sodium sulfate and evaporated. Purification by flash chromatography (neutral alumina, 1% methanol:ethylacetate) provided M7b. MS (ESI+) m/z 335 (M+H).

M7c. 2-(4'-acetyl-2'-(methoxycarbonyl)piperazin-1'-yl)acetic acid

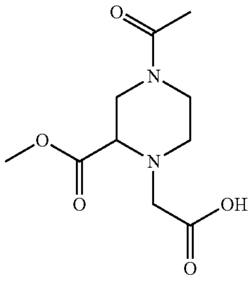 [SMILES: COC(=O)C1CN(C(C)=O)CCN1CC(=O)O]

To a solution of M7b (0.285 g, 0.85 mmol) was added 10% palladium on carbon (0.02 g), then stirred under balloon hydrogen-pressure for 12 h at RT. The reaction was filtered through Celite, washed with methanol, dried over sodium sulfate and evaporated. M7c was used without further purification. MS (ESI+) m/z 245 (M+H).

M7. Methyl 4-acetyl-1-(2'-((4"-methoxybenzyl) amino)-2'-oxoethyl)piperazine-2-carboxylate

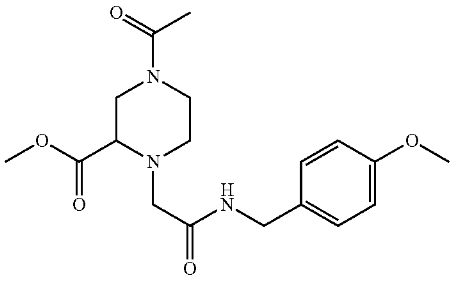

A solution of M7c (0.21 g, 0.86 mmol) in dichloromethane (5 mL) at 0° C. under argon was treated with diisopropylethylamine (0.275 g, 2.14 mmol) and HATU (0.39 g, 1.03 mmol), then after 15 min with 4-methoxybenzylamine (0.117 g, 0.86 mmol). The reaction was stirred 12 h at RT, then treated with water and extracted with dichloromethane, which was washed with brine, dried over sodium sulfate and evaporated. Purification by preparative HPLC (Column: XBridge (150×19 mm); mobile phase: A=(0.01% TFA in water), B=acetonitrile; gradient: 0-2 min: 20% B; 2-8 min: 20% B; 8 min-end: 80% B) provided M7. LCMS (method 3): retention time=2.85 min; MS (ESI+) m/z 364 (M+H).

M8. (4-acetyl-1-(2'-((4"-methoxybenzyl)amino)-2'-oxoethyl)piperazin-2-yl)methyl methyl carbonate

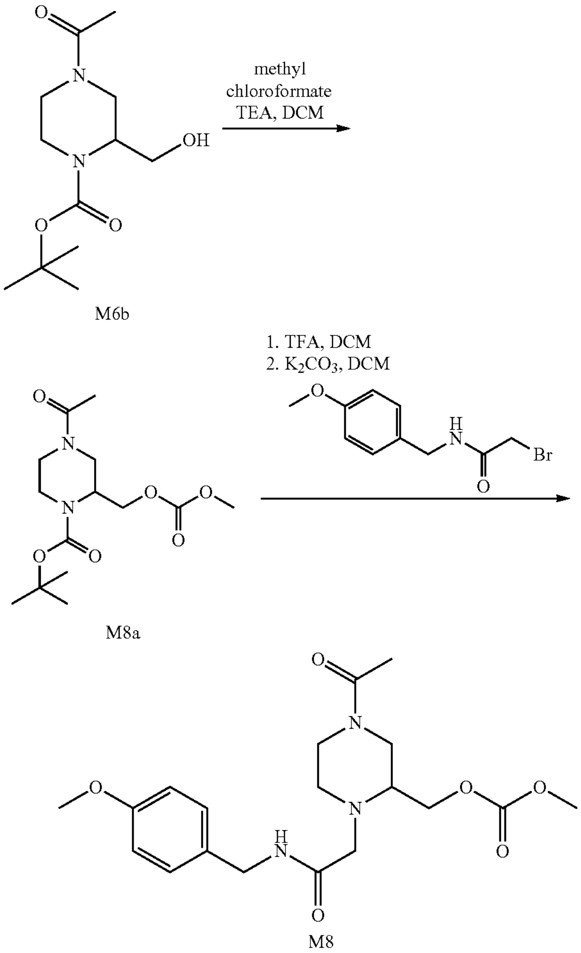

M8a (4-acetyl-1-(tert-butoxycarboxyl)piperazin-2-yl)methyl methylcarbonate

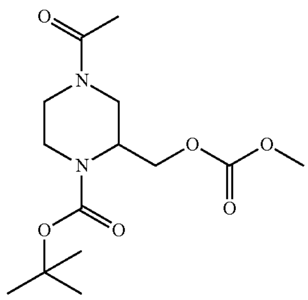 [SMILES: COC(=O)OCC1CN(C(C)=O)CCN1C(=O)OC(C)(C)C]

A solution of M6b (0.30 g, 1.16 mmol) in dichloromethane (5 mL) at 0° C. under argon was treated dropwise with triethylamine (0.20 g, 1.94 mmol), stirred for 10 min, then treated dropwise with methyl chloroformate (0.54 g, 5.8 mmol). The reaction was stirred 72 h at RT, then diluted with dichloromethane, washed with brine, dried over sodium sulfate and evaporated. Purification by flash chromatography (basic alumina, 3% methanol:dichloromethane) provided M8a. MS (ESI+) m/z 317.1 (M+H).

M8. (4-acetyl-1-(2'-((4"-methoxybenzyl)amino)-2'-oxoethyl)piperazin-2-yl)methyl methyl carbonate

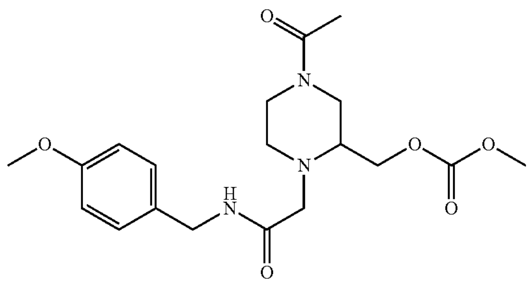

A solution of M8a (0.09 g, 0.28 mmol) in dichloromethane (5 mL) at 0° C. under argon was treated dropwise with trifluoroacetic acid (2.0 mL), and was stirred 4 h at RT, then evaporated. This material was dissolved in acetonitrile (10 mL) and held at 0° C. under argon, then treated with potassium carbonate (0.23 g, 1.66 mmol) and 2-bromo-N-(4-methoxybenzyl)acetamide (0.128 g, 0.49 mmol). The reaction was stirred 12 h at RT, then evaporated. The crude mixture was extracted with dichloromethane, which was washed with brine, dried over sodium sulfate and evaporated. Purification by flash chromatography (basic alumina, 5% methanol:dichloromethane), followed by preparative HPLC (Column: Zorbax Eclipse XDB C18 (150×21.5 mm*5 mm); mobile phase: A=water, B=acetonitrile; gradient: 0-2 min: 10% B; 2-10 min: 20% B; 10 min-end: 50% B;) provided M8. LCMS (method 7): retention time=0.24 min; MS (ESI+) m/z 394.2 (M+H).

M9. 1-(4'-acetyl-1'-(2"-((4'"-methoxybenzyl)amino)-2"-oxoethyl)piperazin-2'-yl)methyl N-methylcarbamate

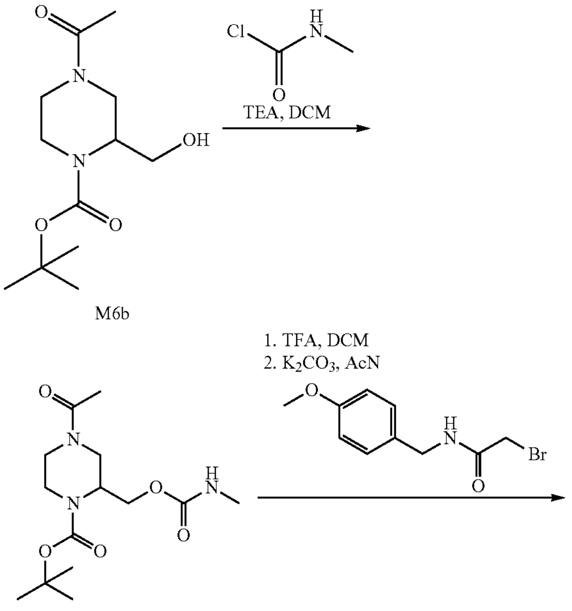

M6b

M9a

-continued

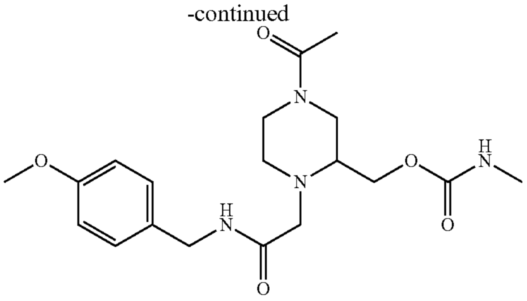

M9

M9a. 1-(4'-acetyl-1'-(tert-butoxycarbonyl)piperazin-2'-yl)methyl N-methylcarbamate

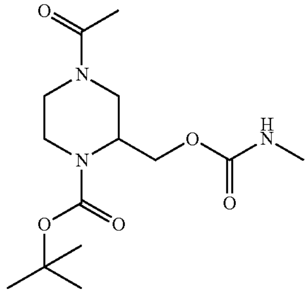 [SMILES: CNC(=O)OCC1CN(C(C)=O)CCN1C(=O)OC(C)(C)C]

A solution of M6b (0.30 g, 1.16 mmol) in dichloromethane (5 mL) at 0° C. under argon was treated dropwise with triethylamine (0.30 mg, 2.90 mmol) and stirred for 10 min. Methylcarbamic chloride (0.11 g, 1.27 mmol) was added and the reaction was stirred 72 h at RT. The reaction was diluted with dichloromethane, washed with brine, dried over sodium sulfate and evaporated. Purification by flash chromatography (basic alumina, 3% methanol:ethyl acetate) provided M9a. MS (ESI+) m/z 316.1 (M+H).

M9. 1-(4'-acetyl-1'-(2"-((4'"-methoxybenzyl)amino)-2"-oxoethyl)piperazin-2'-yl)methyl N-methylcarbamate

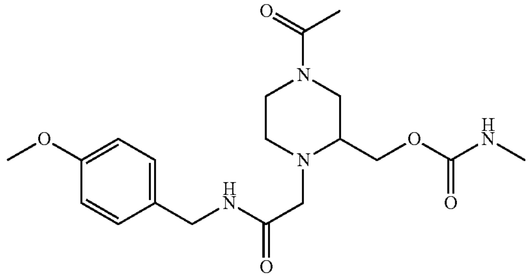

A solution of M9a (0.12 g, 0.38 mmol) in dichloromethane (5 mL) at 0° C. under argon was treated dropwise with trifluoroacetic acid (2.0 mL), and was stirred 4 h at RT, then evaporated and used without further purification. MS (ESI+) m/z 216.1 (M+H). This material was dissolved in acetonitrile (10 mL) and held at 0° C. under argon, then treated with potassium carbonate (0.385 g, 2.78 mmol) and 2-bromo-N-

(4-methoxybenzyl)acetamide (0.215 g, 0.83 mmol). The reaction was stirred 12 h at RT, then evaporated. The crude mixture was extracted with dichloromethane, which was washed with brine, dried over sodium sulfate and evaporated. Purification by flash chromatography (basic alumina, 5% methanol:dichloromethane), followed by preparative HPLC (Column: Zorbax Eclipse XDB C18 (150×21.5 mm*5 mm); mobile phase: A=water, B=acetonitrile; gradient: 0-2 min: 10% B; 2-8 min: 20% B; 8 min-end: 50% B) provided M9. LCMS (method 3): retention time=2.61 min; MS (ESI+) m/z 393.2 (M+H).

M10. 2-(4'-acetyl-2'-(((tetrahydro-2"H-pyran-2"-yl)oxy)methyl)piperazin-1'-yl)-N-(4'"-methoxybenzyl)acetamide

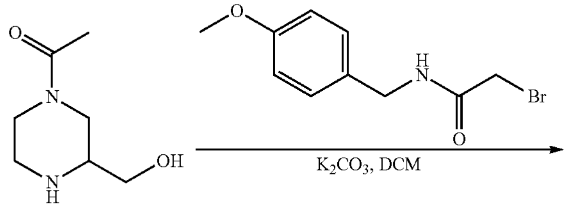

M6a

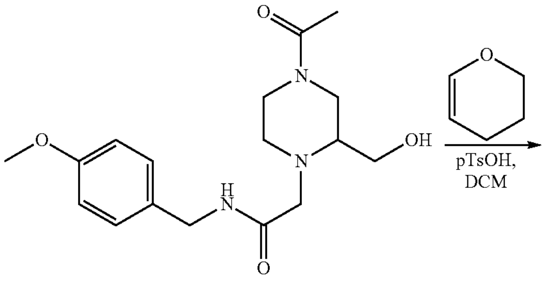

M10a

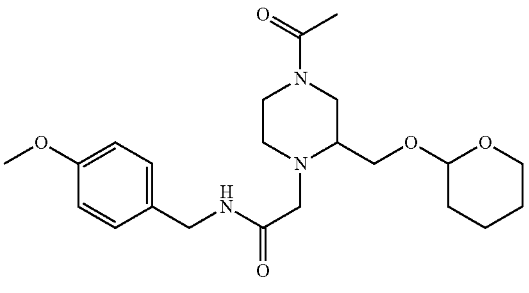

M10

M10a. 2-(4'-acetyl-2'-(hydroxymethyl)piperazin-1'-yl)-N-(4"-methoxybenzyl)acetamide

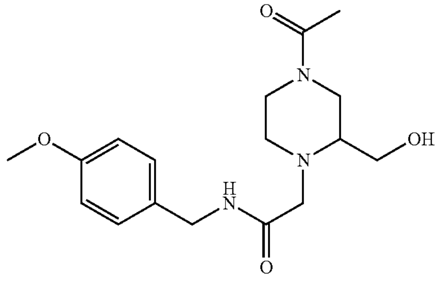 [SMILES: COc1ccc(CNC(=O)CN2CCN(C(C)=O)CC2CO)cc1]

A solution of M6a (1.0 g, 6.32 mmol) in acetonitrile (20 mL) was held at 0° C. under argon, then treated with potassium carbonate (2.62 g, 19.0 mmol) and 2-bromo-N-(4'-methoxybenzyl)acetamide (1.4 g, 5.68 mmol). The reaction was stirred 16 h at RT, then treated with water, extracted with ethyl acetate, and the combined organic layer was dried over sodium sulfate and evaporated. Purification by flash chromatography ($SiO_2$, 1-2% methanol:dichloromethane) provided M10a. LCMS (method 8): retention time=2.61 min; MS (ESI+) m/z 336.3 (M+H).

M10. 2-(4'-acetyl-2'-(((tetrahydro-2"H-pyran-2"-yl)oxy)methyl)piperazin-1'-yl)-N-(4'"-methoxybenzyl)acetamide

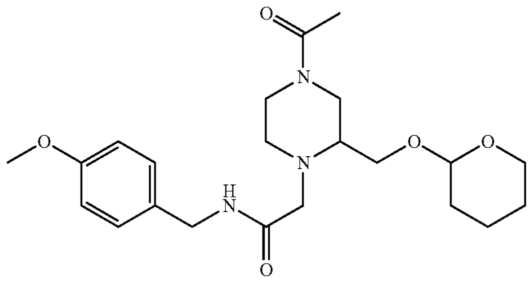 [SMILES: COc1ccc(CNC(=O)CN2CCN(C(C)=O)CC2COC2CCCCO2)cc1]

A solution of M10a (0.10 g, 0.30 mmol) in dichloromethane (5 mL) at 0° C. under argon was treated with 3,4-dihydro-2H-pyran (0.05 g, 0.60 mmol), then p-toluenesulfonic acid (0.030 g, 0.89 mmol) was added in portions and the reaction was stirred 4 h at RT. The reaction was treated with saturated aqueous sodium bicarbonate and extracted with dichloromethane, which was washed with brine, dried over sodium sulfate and evaporated. Purification by flash chromatography ($SiO_2$, 1-2% methanol:dichloromethane) provided M10. LCMS (method 8): retention time=2.78 min; MS (ESI+) m/z 420.3 (M+H).

M11. 2-(4'-acetyl-2'-(((tert-butyldimethylsilyl)oxy) methyl)piperazin-1'-yl)-N-(4'''-methoxybenzyl)acetamide

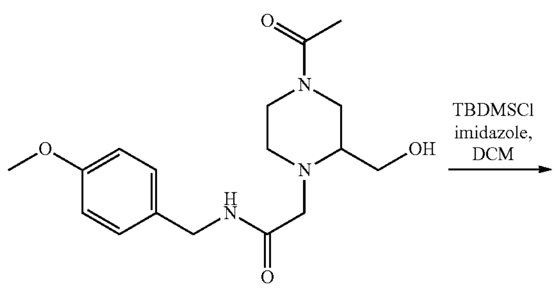

M10a

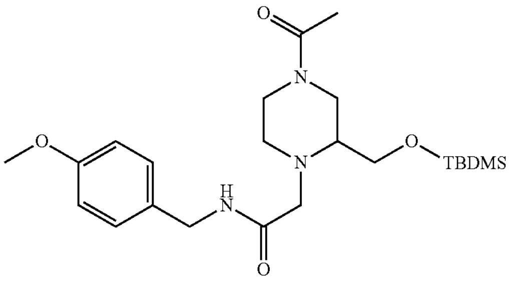

M11

M11. 2-(4'-acetyl-2'-(((tert-butyldimethylsilyl)oxy) methyl)piperazin-1'-yl)-N-(4'''-methoxybenzyl)acetamide

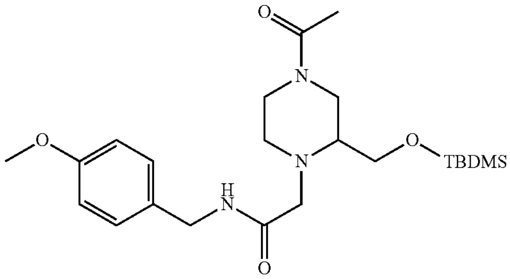

A solution of M10a (0.10 g, 0.30 mmol) in dichloromethane (5 mL) at 0° C. under argon was treated with imidazole (0.061 g, 0.89 mmol), then tert-butyldimethylchlorosilane (0.054 g, 0.36 mmol) was added drop-wise and the reaction was stirred 2 h at RT. The reaction was treated with saturated aqueous ammonium chloride and extracted with dichloromethane, which was washed with brine, dried over sodium sulfate and evaporated. Purification by preparative HPLC (Column: Zorbax Eclipse XDB C18 (150×21.5 mm*5 mm); mobile phase: A=water, B=acetonitrile; gradient: 0-2 min: 30% B; 2-8 min: 40% B; 8 min-end: 90% B;) provided M11. LCMS (method 8): retention time=3.48 min; MS (ESI+) m/z 450.3 (M+H).

M17. 1-(4'-acetyl-1'-(2''-oxo-2''-(pyridin-2'''-ylamino)ethyl)piperazin-2'-yl)methyl acetate

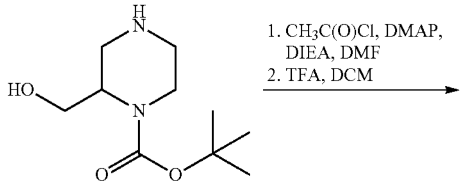

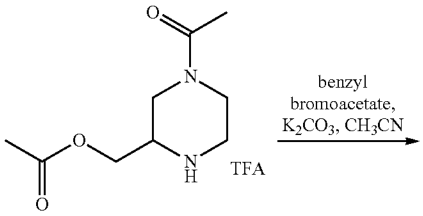

M17a

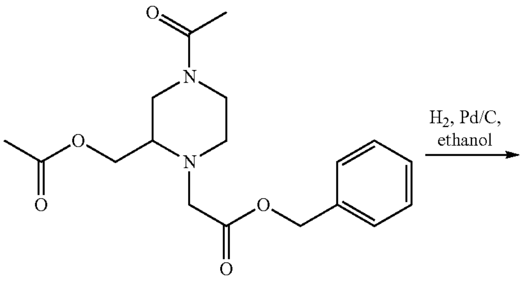

M17b

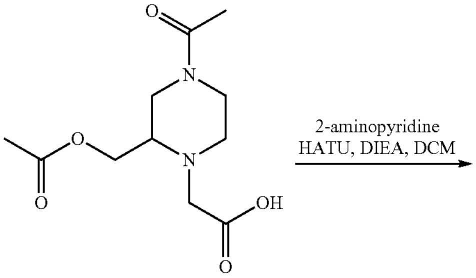

M17c

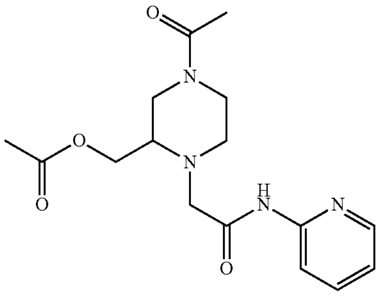

M17

M17a 1-(4'-acetylpiperazin-2'-yl)methyl acetate, trifluoroacetic acid salt

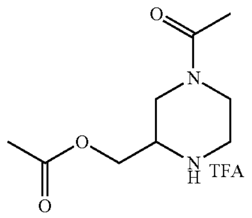

To a solution of tert-butyl 2-(hydroxymethyl)piperazine-1-carboxylate (0.70 g, 3.23 mmol) in DMF (7 mL) at 0° C. under argon was added diisopropylethylamine (1.65 mL, 2.76 mmol), 4-dimethylaminopyridine (0.007 g) and acetyl chloride (0.57 mL, 8.09 mmol), and stirred 16 h at RT. The reaction was treated with water and extracted with ethyl acetate. The combined organic layers were washed with water and brine, dried over sodium sulfate and evaporated. Purification by flash chromatography (basic alumina, 50% ethyl acetate:hexane) provided the intermediate compound that was used without further purification. MS (ESI+) m/z 323 (M+Na). This material was dissolved in dichloromethane (2 mL) at 0° C. and was treated with trifluoroacetic acid (1 mL), and was stirred 16 h at RT, then evaporated. The residue was washed with pentane and dried under high vacuum to provide M17a, as the trifluoroacetic acid salt which was used without further purification. MS (ESI+) m/z 201 (M+H).

M17b. benzyl 2-(2'-(acetoxymethyl)-4'-acetylpiperazin-1'-yl)acetate

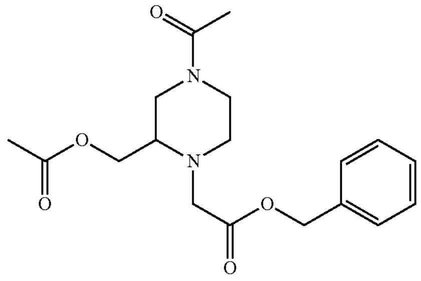 [SMILES: CC(=O)OCC1CN(C(C)=O)CCN1CC(=O)OCc1ccccc1]

A solution of M17a (0.75 g, 3.73 mmol) in acetonitrile (8 mL) under argon was treated with potassium carbonate (1.54 g, 11.9 mmol) and benzyl 2-bromoacetate (0.59 mL, 3.73 mmol) and stirred 16 h at RT. The reaction was concentrated and purified by flash chromatography (basic alumina, 1% methanol:dichloromethane) to provide M17b. MS (ESI+) m/z 349 (M+H).

M17c. 2-(2'-(acetoxymethyl)-4'-acetylpiperazin-1'-yl)acetic acid

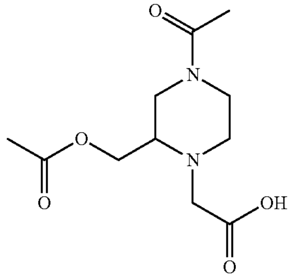 [SMILES: CC(=O)OCC1CN(C(C)=O)CCN1CC(=O)O]

To a solution of M17b (0.30 g, 0.86 mmol) in ethanol (6 mL) was added 5% palladium on carbon (0.060 g) and the reaction was stirred under balloon pressure hydrogen for 16 h. The reaction was concentrated and purified by preparative HPLC (Column: Zorbax Eclipse XDB C18 (150×21.5 mm*5 mm); mobile phase: A=water, B=acetonitrile; gradient: 0-2 min: 10% B; 2-10 min: 20% B; 10 min-end: 40% B) to provide M17c. MS (ESI+) m/z 259 (M+H).

M17. 1-(4'-acetyl-1'-(2"-oxo-2"-(pyridin-2'"-ylamino)ethyl)piperazin-2'-yl)methyl acetate

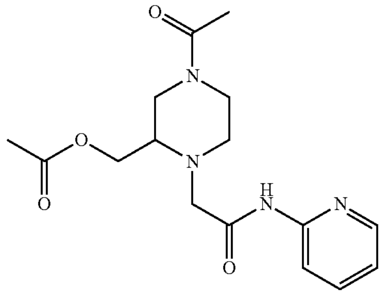 [SMILES: CC(=O)OCC1CN(C(C)=O)CCN1CC(=O)Nc1ccccn1]

To a solution of M17c (0.070 g, 0.27 mmol) in dichloromethane (1 mL) under argon was added diisopropylethylamine (0.039 mL, 0.81 mmol), HATU (0.35 g, 0.90 mmol) and 2-aminopyridine (0.028 g, 0.29 mmol) and stirred 16 h at RT. The reaction was treated with water and extracted with dichloromethane. The combined organic layers were washed with brine and evaporated. Purification by preparative HPLC (Column: Zorbax Eclipse XDB C18 (150×21.5 mm*5 mm); mobile phase: A=water, B=acetonitrile; gradient: 0-2 min: 10% B; 2-6 min: 20% B; 6 min-end: 70% B) provided M17. LCMS (method 3): retention time=2.35 min; MS (ESI+) m/z 335.2 (M+H).

M18. 1-(4'-methyl-1'-(2"-oxo-2"-(pyridin-2'"-ylamino)ethyl)piperazin-2'-yl)methyl acetate

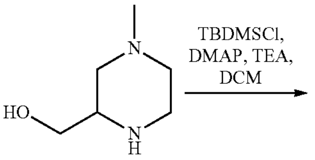

-continued

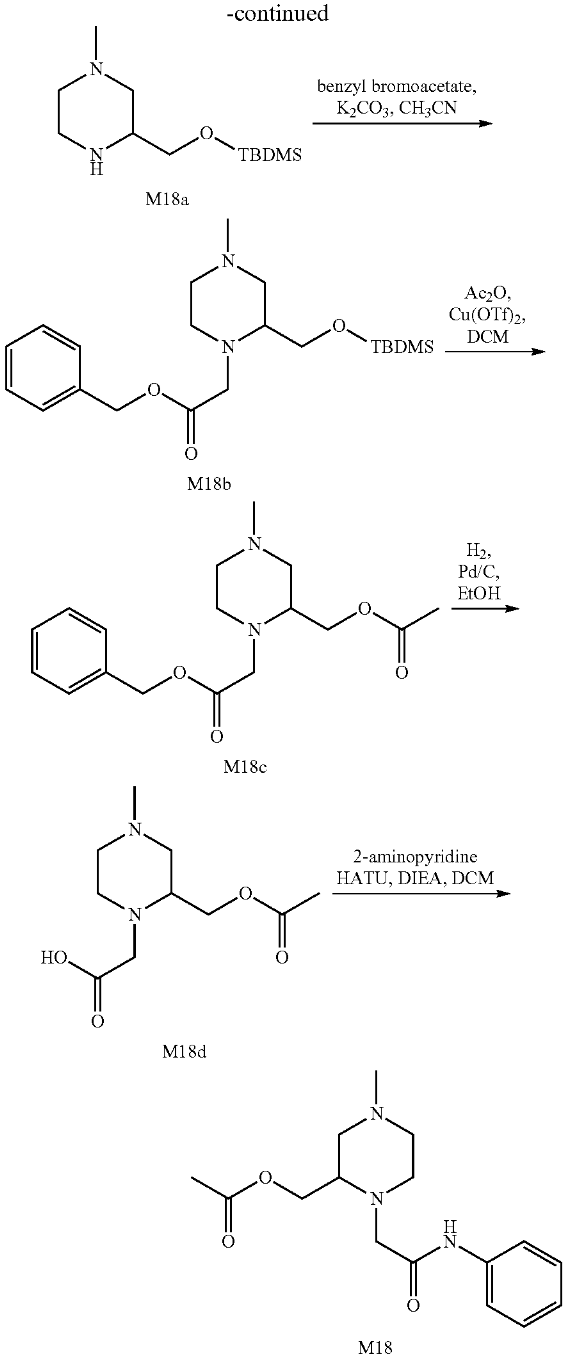

M18a. 3-(((tert-butyldimethylsilyl)oxy)methyl)-1-methylpiperazine

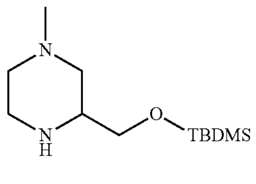

To a solution of (4-methylpiperazin-2-yl)methanol (0.60 g, 4.6 mmol) in dichloromethane (7 mL) under argon was added triethylamine (1.08 mL, 7.82 mmol), 4-dimethylaminopyridine (0.01 g), then dropwise, a solution of tert-butyldimethylchorosilane (1 g, 6.91 mmol) in dichloromethane (20 mL), and stirred 16 h at RT. Additional triethylamine (0.6 eq) and tert-butyldimethylchorosilane (0.6 eq) were added to the solution, which was stirred 2 h at RT. The reaction was treated with water and extracted with dichloromethane. The combined organic layers were dried over sodium sulfate and evaporated. Purification by flash chromatography (basic alumina, 1% methanol:dichloromethane) provided M18a. MS (ESI+) m/z 245 (M+H).

M18c. benzyl 2-(2'-(acetoxymethyl)-4'-methylpiperazin-1'-yl)acetate

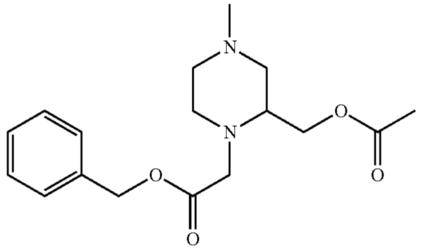 [SMILES: CC(=O)OCC1CN(C)CCN1CC(=O)OCc1ccccc1]

A solution of M18a (1.2 g, 4.91 mmol) in acetonitrile (12 mL) under argon was treated with potassium carbonate (1.69 g, 12.3 mmol) and benzyl 2-bromoacetate (0.7 mL, 4.42 mmol) and stirred 16 h at RT. The reaction was treated with water and extracted with ethyl acetate. The combined organic layers were washed with water, dried over sodium sulfate and concentrated. Purification by flash chromatography (basic alumina, 1% methanol:dichloromethane) provided intermediate M18b. To a solution of M18b (0.49 g, 1.25 mmol) in de-gassed (with argon) dichloromethane (12 mL) was added copper(II) trifluoromethane sulfonate (0.45 g, 1.25 mmol). This mixture was again degassed (10 min), followed by addition of acetic anhydride (0.31 g, 3.0 mmol), a third degassing (10 min) and stirred under argon for 48 h at RT. The reaction was treated with saturated aqueous sodium bicarbonate and extracted with dichloromethane. The combined organic layers were washed with brine, dried over sodium sulfate and concentrated. Purification by flash chromatography (neutral alumina, 0.25% methanol:dichloromethane) provided M18c. MS (ESI+) m/z 321 (M+H)

M18d. 2-(2'-(acetoxymethyl)-4'-methylpiperazin-1'-yl)acetic acid

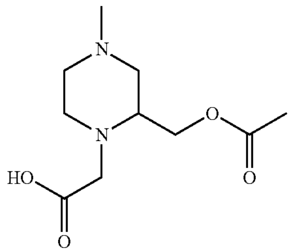 [SMILES: CC(=O)OCC1CN(C)CCN1CC(=O)O]

To a solution of M18c (0.225 g, 0.70 mmol) in ethanol (5 mL) was added 5% palladium on carbon (0.045 g) and the reaction was stirred under balloon pressure hydrogen for 5 h. The reaction was filtered through Celite, the filtrate was dried over sodium sulfate and concentrated to provide M18d which was used without further purification. MS (ESI+) m/z 231.2 (M+H)

M18. 1-(4'-methyl-1'-(2"-oxo-2"-(pyridin-2'"-ylamino)ethyl)piperazin-2'-yl)methyl acetate

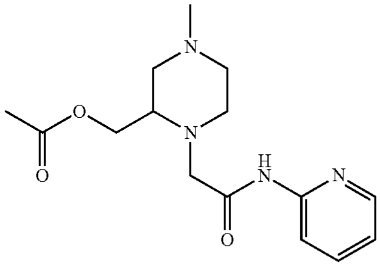 [SMILES: CC(=O)OCC1CN(C)CCN1CC(=O)Nc1ccccn1]

To a solution of M18d (0.060 g, 0.26 mmol) in dichloromethane (5 mL) at 0° C. under argon was added diisopropylethylamine (0.10 g, 0.78 mmol) and HATU (0.146 g, 0.39 mmol). The solution was stirred 10 min, then 2-aminopyridine (0.029 g, 0.31 mmol) was added. The reaction was stirred 16 h at RT then treated with water and extracted with dichloromethane. The combined organic layers were washed with brine, dried over sodium sulfate and evaporated. Purification by flash chromatography ($SiO_2$, 10-12% methanol:dichloromethane), followed by preparative HPLC (Column: XBridge (150×19 mm); mobile phase: A=(0.1% TFA in water), B=(CAN: methanol); gradient: 0-2 min: 10% B; 2-8 min: 20% B; 8 min-end: 50% B) provided M18. LCMS (method 8): retention time=2.12 min; MS (ESI+) m/z 307.1 (M+H).

M19. 1-(4'-ethyl-1'-(2"-oxo-2"-(pyridin-2"'-ylamino)ethyl)piperidin-2'-yl)methyl acetate

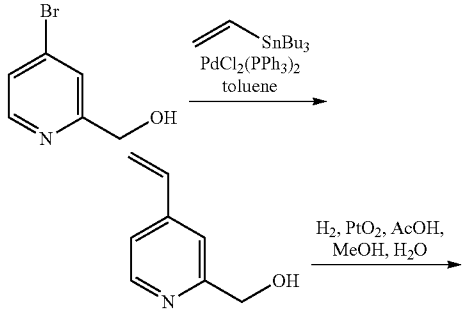

M19a

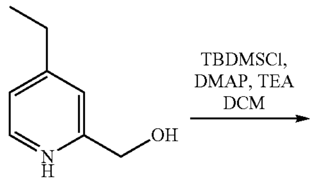

M19b

-continued

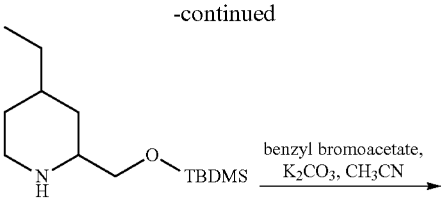

M19c

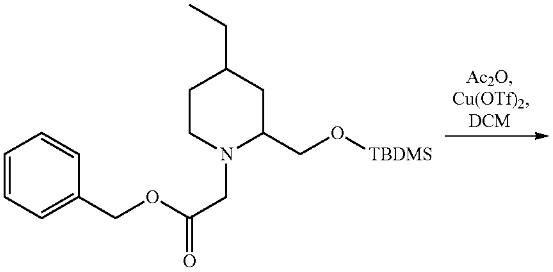

M19d

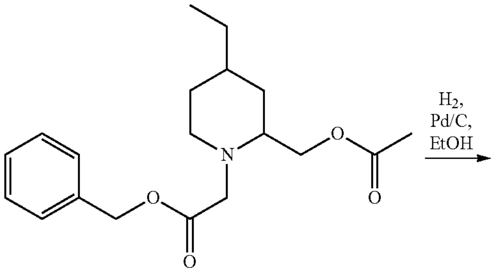

M19e

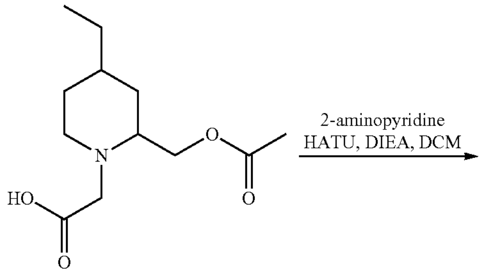

M19f

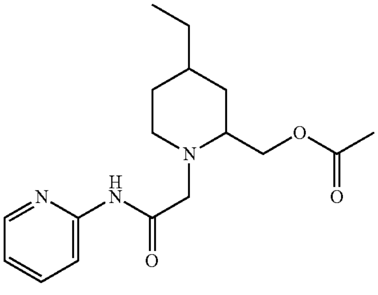

M19

M19b. 1-(4'-ethylpiperidin-2'-yl)methanol

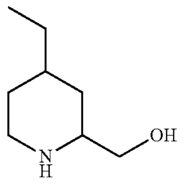

To a solution of 1-(4'-bromopyridin-2'-yl)methanol (2 g, 10.6 mmol) in degassed toluene (20 mL) was added tributylvinyl tin (4.44 g, 16.0 mmol) and $PdCl_2(PPh_3)_2$ (0.746 g, 1.06 mmol), followed by a second 10 min degassing. The reaction was stirred under argon for 18 h at 50° C., then treated with additional portions of tributylvinyl tin (0.5 eq) and $PdCl_2(PPh_3)_2$ (0.05 eq), followed by stirring 18 h at 80° C. The reaction was evaporated. Purification by flash chromatography ($SiO_2$, 30% ethyl acetate:hexane) provided intermediate M19a. A mixture of M19a (1.4 g, 10.4 mmol), platinum oxide (0.941 g, 4.15 mmol) and acetic acid (0.622 g, 10.4 mmol) in methanol (54 mL) and water (36 mL) was kept in a Parr shaker for 36 h at 80 psi hydrogen pressure. The reaction was filtered through Celite© and concentrated. The residue was treated with water and extracted with ethyl acetate. The aqueous layer was concentrated to provide M19b, which was used without further purification. MS (ESI+) m/z 144 (M+H).

M19c. 2-(((tert-butyldimethylsilyl)oxy)methyl)-4-ethylpiperidine

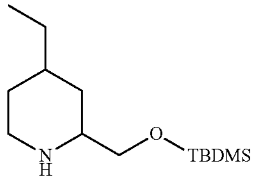

To a solution of M19b (0.4 g, 2.79 mmol) in dichloromethane (8 mL) was added triethylamine (0.85 g, 8.4 mmol), 4-dimethylaminopyridine (0.01 g), then dropwise, a solution of tert-butyldimethylchorosilane (1.26 g, 8.4 mmol) in dichloromethane (4 mL), and stirred 16 h at RT. The reaction was treated with water and extracted with dichloromethane. The combined organic layers were dried over sodium sulfate and evaporated. Purification by flash chromatography (neutral alumina, 10% ethyl acetate:hexane) provided M19c. MS (ESI+) m/z 258.6 (M+H).

M19e. benzyl 2-(2'-(acetoxymethyl)-4'-ethylpiperidin-1'-yl)acetate

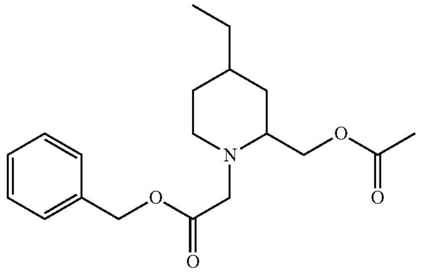 [SMILES: CCC1CCN(CC(=O)OCc2ccccc2)C(COC(C)=O)C1]

A solution of M19c (0.50 g, 1.94 mmol) and potassium carbonate (0.67 g, 4.86 mmol) in acetonitrile (10 mL) at 0° C. under argon was treated dropwise with benzyl 2-bromoacetate (0.53 g, 2.33 mmol) and stirred 6 h at RT. The reaction was treated with saturated aqueous ammonium chloride and extracted with ethyl acetate. The combined organic layers were washed with brine, dried over sodium sulfate and concentrated. Purification by flash chromatography ($SiO_2$, 10% ethyl acetate:hexane) provided intermediate M19d. To a solution of M19d (0.30 g, 0.74 mmol) in de-gassed (with argon) dichloromethane (12 mL) was added copper(II) trifluoromethane sulfonate (0.267 g, 0.74 mmol). This mixture was again degassed (10 min), followed by addition of acetic anhydride (0.18 g, 1.78 mmol), a third degassing (10 min) and stirred for 24 h at RT under argon. The reaction was treated with saturated aqueous sodium bicarbonate and extracted with dichloromethane. The combined organic layers were washed with brine, dried over sodium sulfate and concentrated. Purification by flash chromatography ($SiO_2$, 15% ethyl acetate hexane) provided M19e. MS (ESI+) m/z 334.0 (M+H).

M19f. 2-(2'-(acetoxymethyl)-4'-ethylpiperidin-1'-yl) acetic acid

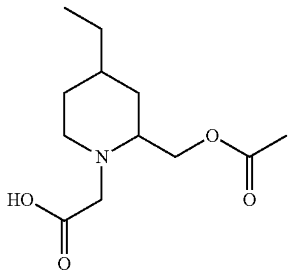 [SMILES: CCC1CCN(CC(=O)O)C(COC(C)=O)C1]

To a solution of M19e (0.40 g, 1.2 mmol) in ethanol (8 mL) was added 5% palladium on carbon (0.08 g) and the reaction was stirred under balloon pressure hydrogen for 5 h. The reaction was filtered through Celite©. The filtrate was dried over sodium sulfate and concentrated to provide M19f which was used without further purification. MS (ESI+) m/z 244.1 (M+H).

M19. 1-(4'-ethyl-1'-(2"-oxo-2"-(pyridin-2'"-ylamino) ethyl)piperidin-2"-yl)methyl acetate

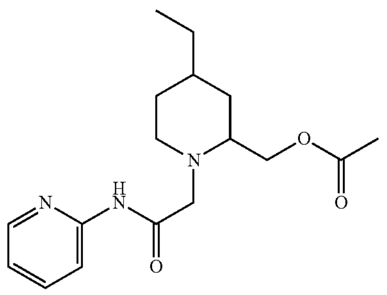 [SMILES: CCC1CCN(CC(=O)Nc2ccccn2)C(COC(C)=O)C1]

To a solution of M19f (0.10 g, 0.41 mmol) in dichloromethane (5 mL) at 0° C. under argon was added diisopropylethylamine (0.16 g, 1.23 mmol) and HATU (0.187 g, 0.39 mmol). The solution was stirred 15 min, then 2-aminopyridine (0.046 g, 0.49 mmol) was added. The reaction was stirred 16 h at RT then treated with water and extracted with dichloromethane. The combined organic layers were washed with brine, dried over sodium sulfate and evaporated. Purification by flash chromatography ($SiO_2$, 25-30% ethyl acetate:hexane) provided M19. LCMS (method 8): retention time=2.58 min; MS (ESI+) m/z 320.5 (M+H).

M20. Benzyl N-(3-(3'-(((diethyl(isopropoxy)silyl) oxy)methyl)-4'-(2"-((4'"-methoxybenzyl)amino)-2"-oxoethyl)piperazin-1'-yl)-3-oxopropyl)carbamate

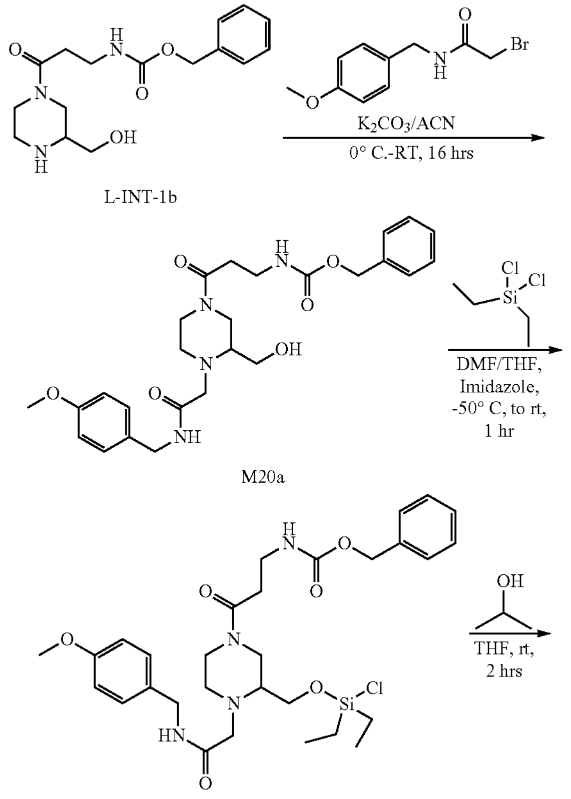

L-INT-1b

M20a

M20b

-continued

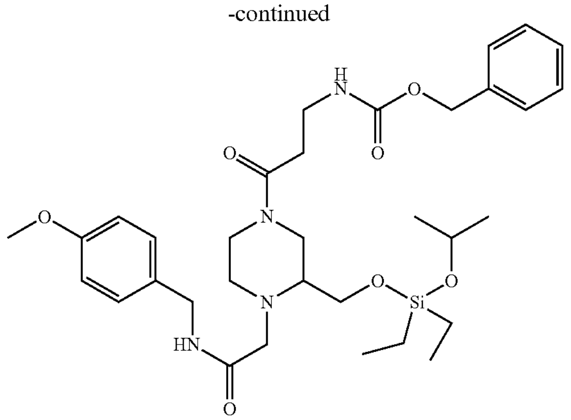

M20

M20a. Benzyl (3-(3-(hydroxymethyl)-4-(2-((4-methoxybenzyl)amino)-2-oxoethyl)piperazin-1-yl)-3-oxopropyl)carbamate

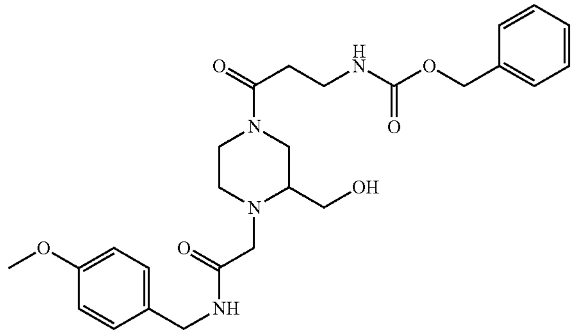 [SMILES: COc1ccc(CNC(=O)CN2CCN(C(=O)CCNC(=O)OCc3ccccc3)CC2CO)cc1]

L-INT-1b (342 mg, 1.065 mmol) was dissolved in acetonitrile (5 mL), and cooled to 0° C. The reaction was treated with potassium carbonate (402 mg, 2.91 mmol) and 2-bromo-N-(4-methoxybenzyl)acetamide (250 mg, 0.969 mmol) stirred at RT overnight. The reaction mixture was treated with water and extracted with ethyl acetate. The organic phase was washed with brine, dried (sodium sulfate) and evaporated. Purification by flash chromatography ($SiO_2$, eluted with 0-10% methanol:dichloromethane) provided M20a. LCMS (method 1): retention time=0.91 min; MS (ESI+) m/z 499.4 (M+H).

M20b. Benzyl N-(3-(3'-(((chlorodiethylsilyl)oxy) methyl)-4'-(2"-((4'"-methoxybenzyl)amino)-2"-oxoethyl)piperazin-1'-yl)-3-oxopropyl)carbamate

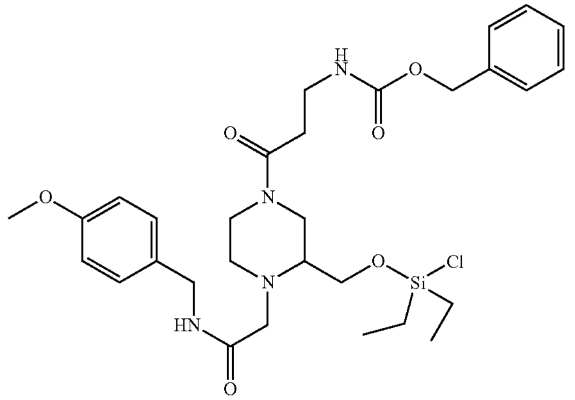 [SMILES: CC[Si](Cl)(CC)OCC1CN(C(=O)CCNC(=O)OCc2ccccc2)CCN1CC(=O)NCc1ccc(OC)cc1]

M20a (40 mg, 0.080 mmol) and imidazole (273 mg, 4.01 mmol) were dissolved in tetrahydrofuran (2 mL) at RT, and added dropwise over a few minutes to a solution of dichlorodiethylsilane (0.120 mL, 0.802 mmol) in dimethylformamide (1 mL) and tetrahydrofuran (1 mL) at ~−50° C. The resulting solution was removed from the cold bath and stirred at rt for 1 hr to provide M20b, which was used without further purification. LCMS (method 5): retention time=1.13 min; MS (ESI+) m/z 601.3 (M+H for hydrolyzed M20b).

M20. Benzyl N-(3-(3'-(((diethyl(isopropoxy)silyl) oxy)methyl)-4'-(2'''-((4''''-methoxybenzyl)amino)-2''-oxoethyl)piperazin-1-yl)-3-oxopropyl)carbamate

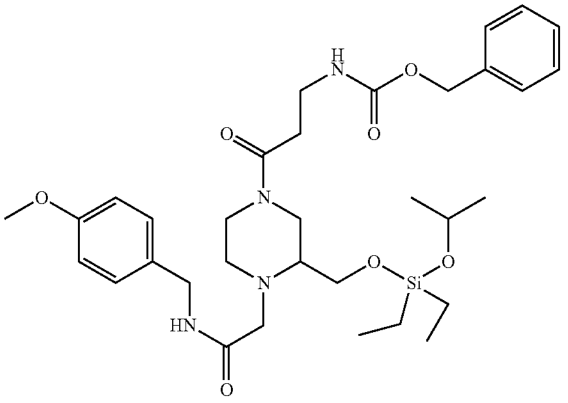 [SMILES: CC[Si](CC)(OCC1CN(C(=O)CCNC(=O)OCc2ccccc2)CCN1CC(=O)NCc1ccc(OC)cc1)OC(C)C]

2-Propanol (0.061 mL, 0.802 mmol) was added dropwise at RT to the solution of crude M20b in DMF/THF prepared above. The solution was stirred at RT for 2 h and then concentrated. Purification by preparative HPLC (column: Waters XBridge 5 μm 30×50 mm; method: 45% to 70% acetonitrile/$H_2O$ with 10 mM $NH_4OH$ over 3.5 min gradient at 75 mL/min) yielded fractions which were concentrated, flash-frozen and lyophilized to provide M20. LCMS (method 5): retention time=1.35 min; MS (ESI+) m/z 643.3 (M+H). $^1$H-NMR ($CD_3OD$, ppm): δ: 7.25-7.39 (m, 5H), 7.22 (d, J=8.7 Hz, 2H), 6.85-6.90 (m, 2H), 5.06 (d, J=1.3 Hz, 2H), 4.27-4.42 (m, 2H), 4.08-4.12 (m, 1H), 3.70-3.84 (m, 5H), 3.61-3.66 (m, 1H), 3.44-3.55 (m, 1H), 3.34-3.43 (m, 4H), 3.03-3.19 (m, 2H), 2.74-2.85 (m, 1H), 2.39-2.66 (m, 4H), 1.15 (d, J=6.0 Hz, 6H), 0.92-0.98 (m, 6H), 0.52-0.63 (m, 4H).

The species in Table 23 were prepared using methods analogous to those used in the synthesis of M20:

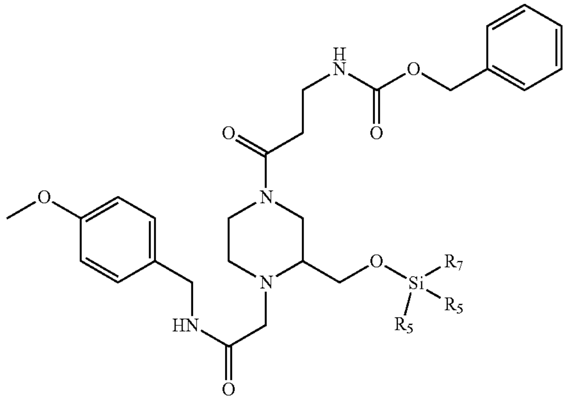

TABLE 23

| Model Compounds | | | |
|---|---|---|---|
| $R_5$<br>$R_7$<br>Name | Number (intermediates used) | LCMS: $[M + H]^+$; retention time; (method) | $^1$H-NMR (400 MHz, $CD_3OD$) |
| $R_7$ = 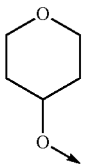<br>$R_5$ = Et<br>benzyl N-(3-(3′-(((diethyl((tetra-hydro-2″H-pyran-4″-yl)oxy)silyl) oxy)methyl)-4′-(2‴-((4⁗-methoxybenzyl) amino)-2‴-oxoethyl) piperazin-1′-yl)-3-oxopropyl) carbamate | M21 (M20a, M20b) | 685.5; 1.43 min; (5) | 7.25-7.40 (m, 5H), 7.22 (d, J = 8.7 Hz, 2H), 6.85-6.91 (m, 2H), 5.06 (d, J = 1.3 Hz, 2H), 4.27-4.41 (m, 2H), 3.93-4.04 (m, 1H), 3.87 (dt, J = 11.7, 4.5 Hz, 2H), 3.71-3.83 (m, 5H), 3.61-3.66 (m, 1H), 3.34-3.52 (m, 7H), 3.02-3.20 (m, 2H), 2.74-2.85 (m, 1H), 2.42-2.69 (m, 4H), 1.75-1.86 (m, 2H), 1.47-1.57 (m, 2H), 0.96 (t, J = 7.9 Hz, 6H), 0.54-0.65 (m, 4H). |

TABLE 23-continued

| Model Compounds | | | |
|---|---|---|---|
| $R_5$<br>$R_7$<br>Name | Number (intermediates used) | LCMS: $[M + H]^+$; retention time; (method) | $^1$H-NMR (400 MHz, $CD_3OD$) |
| $R_7$ = 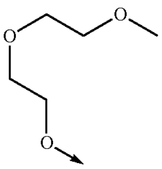<br>$R_5$ = Et<br>benzyl N-(3-(3′-(((diethyl(2″-(2‴-methoxyethoxy)ethan-1″-yl)oxysilyl)oxy)methyl)-4′-(2⁗-((4′′′′′-methoxybenzyl)amino)-2⁗-oxoethyl)piperazin-1′-yl)-3-oxopropyl)carbamate | M22 (M20a, M20b) | 703.5; 1.41; (5) | 7.26-7.37 (m, 5H), 7.18-7.25 (m, 2H), 6.87 (d, J = 8.7 Hz, 2H), 5.06 (s, 2H), 4.27-4.43 (m, 2H), 3.65-4.11 (m, 7H), 3.45-3.65 (m, 6H), 3.32-3.44 (m, 9H), 3.08-3.20 (m, 2H), 2.73-2.85 (m, 1H), 2.52-2.67 (m, 3H), 2.39-2.49 (m, 1H), 0.87-1.03 (m, 6H), 0.49-0.68 (m, 4H) |
| $R_7$ = 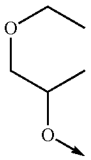<br>$R_5$ = Et<br>benzyl N-(3-(3′-(((diethyl(1‴-ethoxypropan-2″-yl)oxysilyl)oxy) methyl)-4′-(2‴-((4⁗-methoxy-benzyl)amino)-2‴-oxoethyl) piperazin-1′-yl)-3-oxopropyl) carbamate | M23 (M20a, M20b) | 687.6; 1.55; (5) | 7.25-7.37 (m, 5H), 7.22 (d, J = 8.6 Hz, 2H), 6.85-6.90 (m, 2H), 5.01-5.15 (m, 2H), 4.29-4.41 (m, 2H), 4.01-4.10 (m, 1H), 3.58-3.92 (m, 7H), 3.32-3.58 (m, 8H), 3.05-3.19 (m, 2H), 2.73-2.85 (m, 1H), 2.41-2.66 (m, 4H), 1.31-1.37 (m, 1H), 1.11-1.18 (m, 5H), 0.90-0.99 (m, 6H), 0.54-0.65 (m, 4H) |
| $R_7$ = 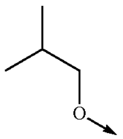<br>$R_5$ = Et<br>benzyl N-(3-(3′-(((diethyl(isobutoxy) silyl)oxy)methyl)-4′-(2″-((4‴-methoxybenzyl) amino)-2″-oxoethyl)piperazin-1′-yl)-3-oxopropyl) carbamate | M24 (M20a, M20b) | 657.4; 1.44; (5) | 7.25-7.39 (m, 5H), 7.18-7.25 (m, 2H), 6.84-6.90 (m, 2H), 5.06 (s, 2H), 4.28-4.41 (m, 2H), 3.68-3.84 (m, 5H), 3.50-3.68 (m, 2H), 3.32-3.50 (m, 7H), 3.02-3.19 (m, 2H), 2.72-2.85 (m, 1H), 2.39-2.71 (m, 4H), 1.58-1.75 (m, 1H), 0.81-1.05 (m, 11H), 0.50-0.64 (m, 4H) |

TABLE 23-continued

| Model Compounds | | | |
|---|---|---|---|
| $R_5$<br>$R_7$<br>Name | Number (intermediates used) | LCMS: $[M + H]^+$; retention time; (method) | $^1$H-NMR (400 MHz, $CD_3OD$) |
| $R_7$ = 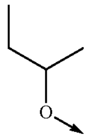<br>$R_5$ = Et<br>benzyl N-(3-(3′-(((sec-butoxydiethylsilyl)oxy)methyl)-4′-(2″-((4‴-methoxy-benzyl)amino)-2″-oxoethyl)piperazin-1′-yl)-3-oxopropyl)carbamate | M25 (M20a, M20b) | 657.4; 1.42; (5) | 7.25-7.38 (m, 5H), 7.22 (d, J = 8.7 Hz, 2H), 6.84-6.90 (m, 2H), 5.06 (d, J = 1.3 Hz, 2H), 4.28-4.41 (m, 2H), 3.69-3.90 (m, 6H), 3.44-3.69 (m, 3H), 3.35-3.40 (m, 3H), 3.02-3.18 (m, 2H), 2.74-2.85 (m, 1H), 2.41-2.69 (m, 4H), 1.36-1.52 (m, 2H), 1.13 (d, J = 6.1 Hz, 3H), 0.93-0.98 (m, 6H), 0.86-0.90 (m, 3H), 0.55-0.61 (m, 4H). |
| $R_7$ = OiPr<br>$R_5$ = iPr<br>benzyl N-(3-(3'-(((isopropoxydiisopropylsilyl)oxy)methyl)-4'-(2''-((4'''-methoxybenzyl)amino)-2''-oxoethyl)piperazin-1'-yl)-3-oxopropyl)carbamate | M26 (M20a, dichlorodiisopropylsilane) | 671.4; 1.51; (1) | 7.31 (m, 5H), 7.22 (d, 2H), 6.92 (m, 2H), 6.86 (m, 1H), 5.05 (d, 2H), 4.35 (m, 2H), 4.13 (m, 2H), 3.4-3.90 (m, 10H), 3.37 (m, 4H), 3.08 (m, 2H), 2.78 (m, 1H), 2.60 (m, 3H), 2.44 (m, 1H), 0.5-1.3 (m, 20H) |
| $R_7$ = OEt<br>$R_5$ = iPr<br>benzyl N-(3-(3'-(((ethoxydiisopropylsilyl)oxy)methyl)-4'-(2''-((4'''-methoxybenzyl)amino)-2''-oxoethyl)piperazin-1'-yl)-3-oxopropyl)carbamate | M27 (M20a, dichlorodiisopropylsilane) | 657.4; 1.63; (5) | 7.31 (m, 5H), 7.21 (d, 2H), 6.86 (m, 1H), 5.05 (s, 2H), 4.35 (m, 2H), 4.3 (m, 0.5H), 4.13 (m, 2H), 3.4-3.90 (m, 11H), 3.37 (m, 4H), 3.09 (m, 2H), 2.65 (m, 1H), 2.57 (m, 3H), 2.45 (m, 1H), 1.09 (m, 18H) |

TABLE 24

| Model Compound Synthetic Intermediates | |
|---|---|
| Structure | Number |
| 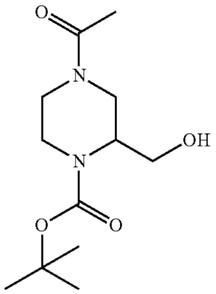 [SMILES: CC(=O)N1CCN(C(=O)OC(C)(C)C)C(CO)C1] | M6b |

TABLE 24-continued

| Model Compound Synthetic Intermediates | |
|---|---|
| Structure | Number |
| 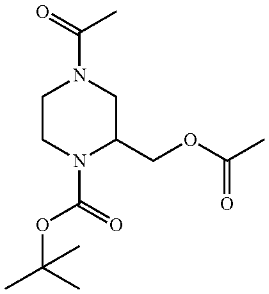 [SMILES: CC(=O)OCC1CN(C(C)=O)CCN1C(=O)OC(C)(C)C] | M6c |

TABLE 24-continued
| Model Compound Synthetic Intermediates | |
|---|---|
| Structure | Number |
| 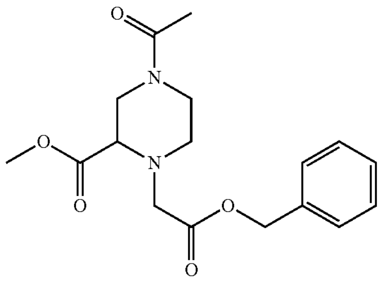 [SMILES: COC(=O)C1CN(C(C)=O)CCN1CC(=O)OCc1ccccc1] | M7b |
| 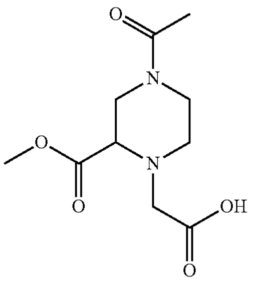 [SMILES: COC(=O)C1CN(C(C)=O)CCN1CC(=O)O] | M7c |
| 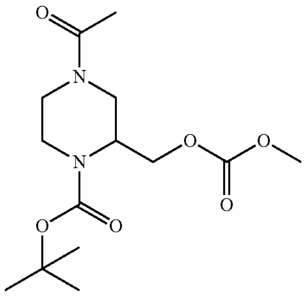 [SMILES: COC(=O)OCC1CN(C(C)=O)CCN1C(=O)OC(C)(C)C] | M8a |
| 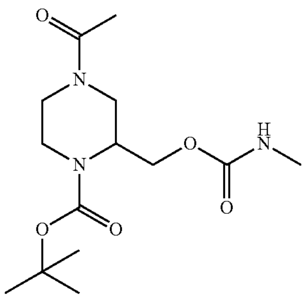 [SMILES: CNC(=O)OCC1CN(C(C)=O)CCN1C(=O)OC(C)(C)C] | M9a |
TABLE 24-continued
| Model Compound Synthetic Intermediates | |
|---|---|
| Structure | Number |
| 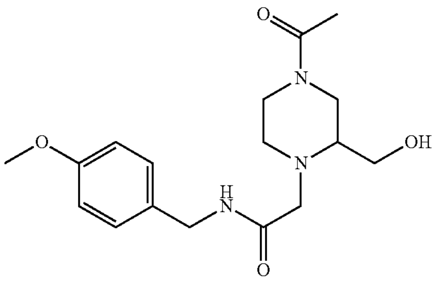 [SMILES: COc1ccc(CNC(=O)CN2CCN(C(C)=O)CC2CO)cc1] | M10a |
| 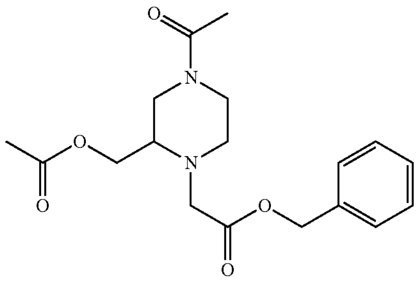 [SMILES: CC(=O)OCC1CN(C(C)=O)CCN1CC(=O)OCc1ccccc1] | M17b |
| 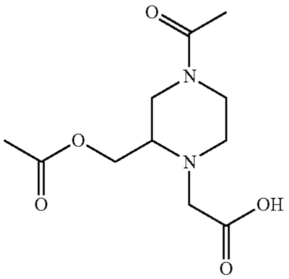 [SMILES: CC(=O)OCC1CN(C(C)=O)CCN1CC(=O)O] | M17c |
| 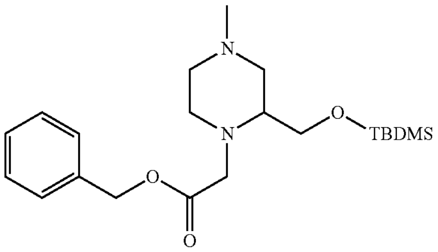 | M18b |

TABLE 24-continued
| Model Compound Synthetic Intermediates | |
|---|---|
| Structure | Number |
| 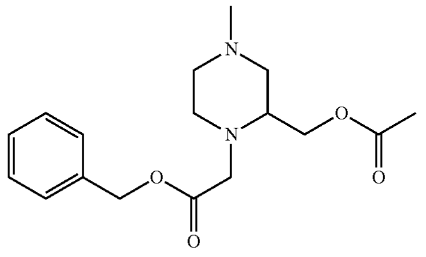 [SMILES: CC(=O)OCC1CN(C)CCN1CC(=O)OCc1ccccc1] | M18c |
| 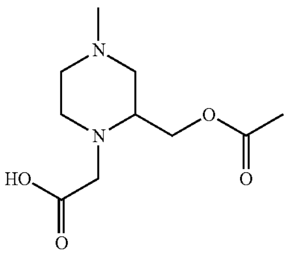 [SMILES: CC(=O)OCC1CN(C)CCN1CC(=O)O] | M18d |
| 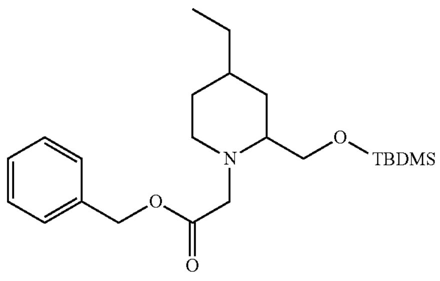 | M19d |
TABLE 24-continued
| Model Compound Synthetic Intermediates | |
|---|---|
| Structure | Number |
| 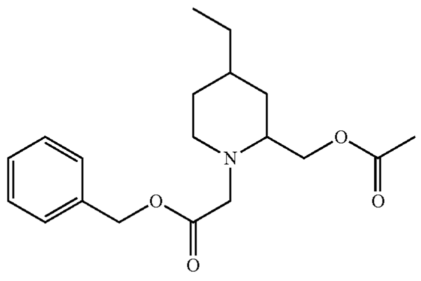 [SMILES: CCC1CCN(CC(=O)OCc2ccccc2)C(COC(C)=O)C1] | M19e |
| 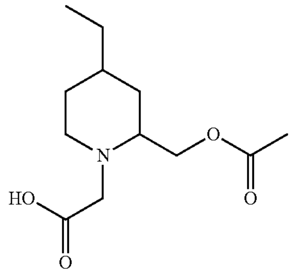 [SMILES: CCC1CCN(CC(=O)O)C(COC(C)=O)C1] | M19f |
| 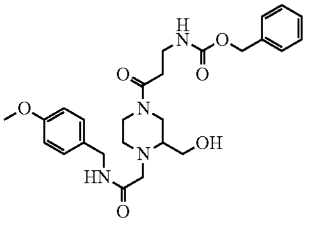 [SMILES: COc1ccc(CNC(=O)CN2CCN(C(=O)CCNC(=O)OCc3ccccc3)CC2CO)cc1] | M20a |
| 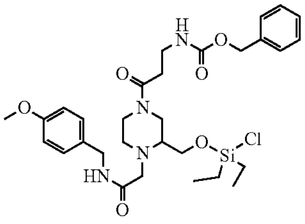 [SMILES: CC[Si](Cl)(CC)OCC1CN(C(=O)CCNC(=O)OCc2ccccc2)CCN1CC(=O)NCc1ccc(OC)cc1] | M20b |

Example 8

In Vitro Drug Release Studies 8-1. Release of Brolucizumab from Hydrogel-Drug Conjugates

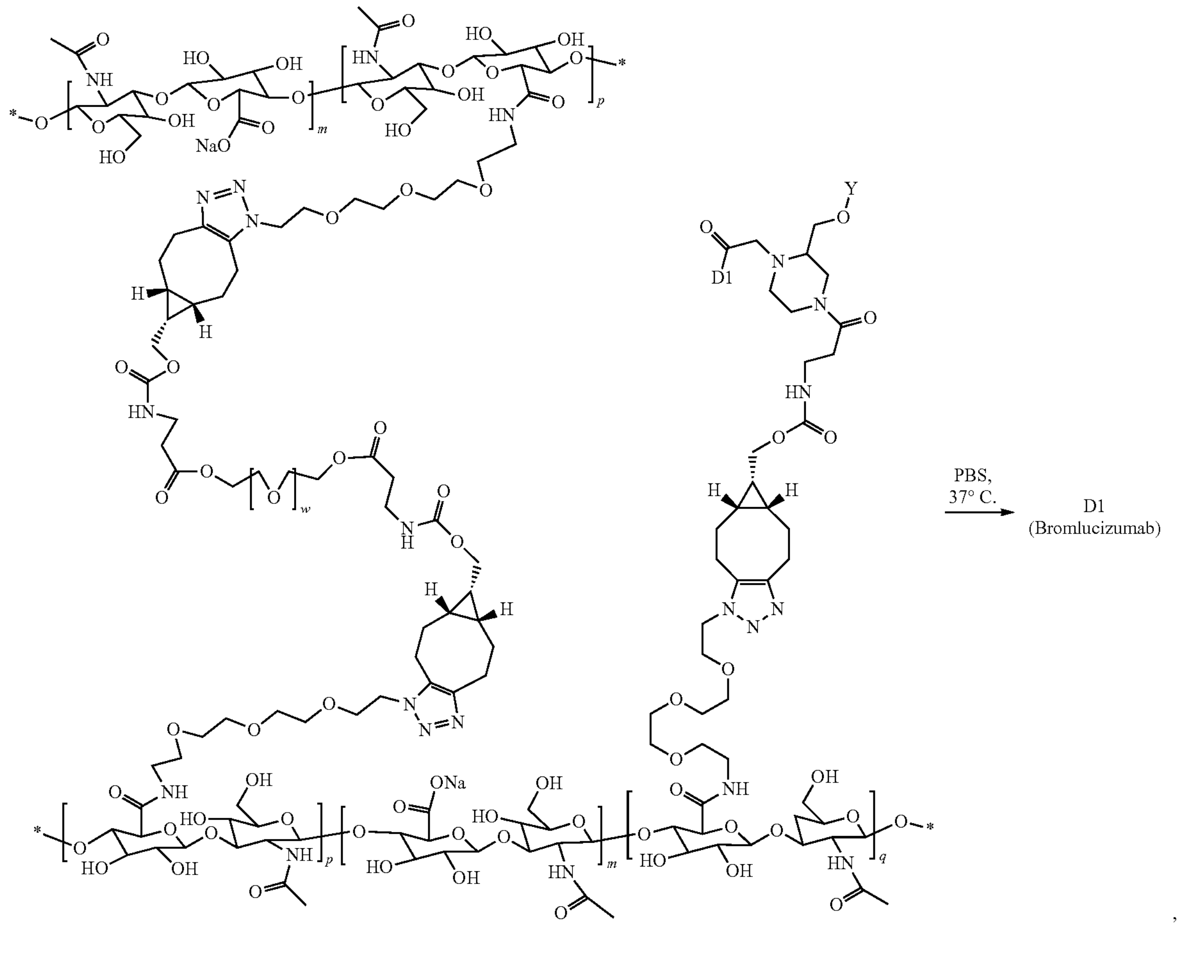

where Y is selected from Table 2, above.

Figure 4A:
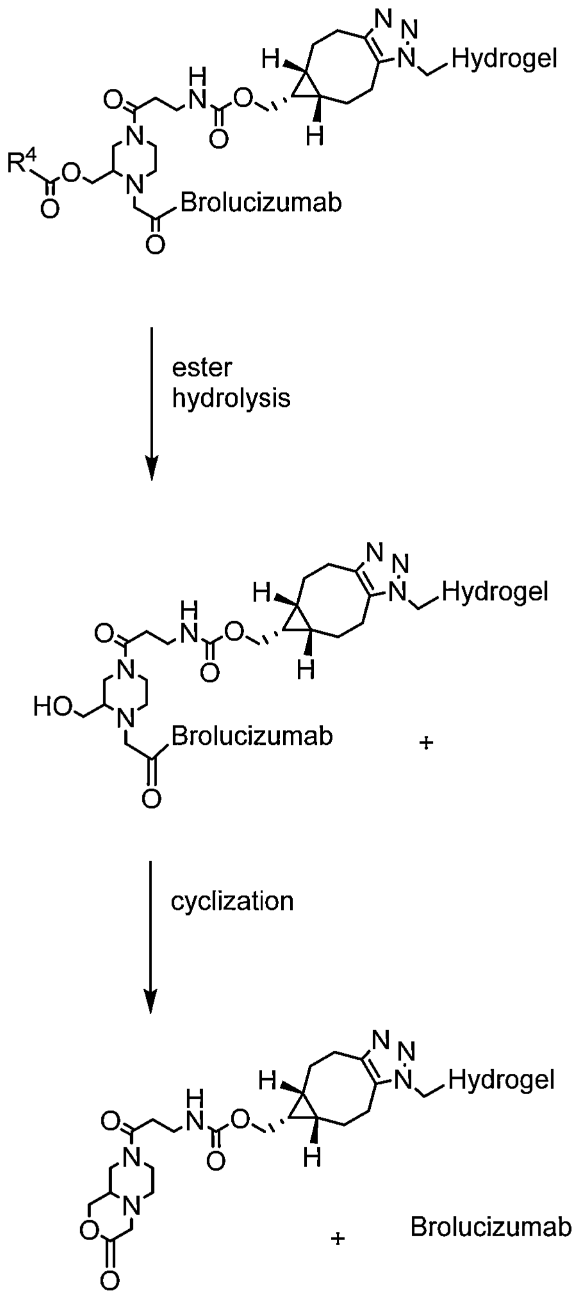
FIG. 4A (illustrating Example 8.1) shows an example of the in vitro release of brolucizumab from a hydrogel conjugate.

Release of brolucizumab from hydrogel conjugates C1a, C2a, C3a, and C4a occurs as depicted in FIG. 4A. In this study a series of hydrogel-brolucizumab-conjugates was held in 1×PBS at 37° C. to assess the release of drug following the traceless linker cleavage reaction. These reactions were sampled at various timepoints and analyzed to determine the concentration of released brolucizumab in the supernatant.

Each hydrogel (approximately 50 μL; exact amount determined by weighing, assumed density of hydrogel=1 g/mL) was added into a Transwell© insert (Corning, Inc; polycarbonate membrane, 10 μm thickness, 6.5 mm diameter, 0.4 μm pore size). Wells of the plate were filled with 1 mL 1×PBS and the hydrogel-containing inserts were placed into the wells. Three wells were prepared for each hydrogel sample. The plate was securely capped and held at 37° C. in a humid environment.

Samples of collection buffer were removed from the wells at various timepoints for up to 180 days. At each timepoint and for each well, the Transwell© insert was removed from the well and the entire volume of collection buffer was transferred to a clean tube and weighed, then a timepoint sample was removed from the collection buffer (0.10 mL) and stored at 4° C. until final analysis. The collection buffer was replenished with 1×PBS to restore the collection buffer volume to 1 mL and then the collection buffer was returned to the well. The insert was then placed back in its well and the plate returned to the incubator.

Figure 4B:
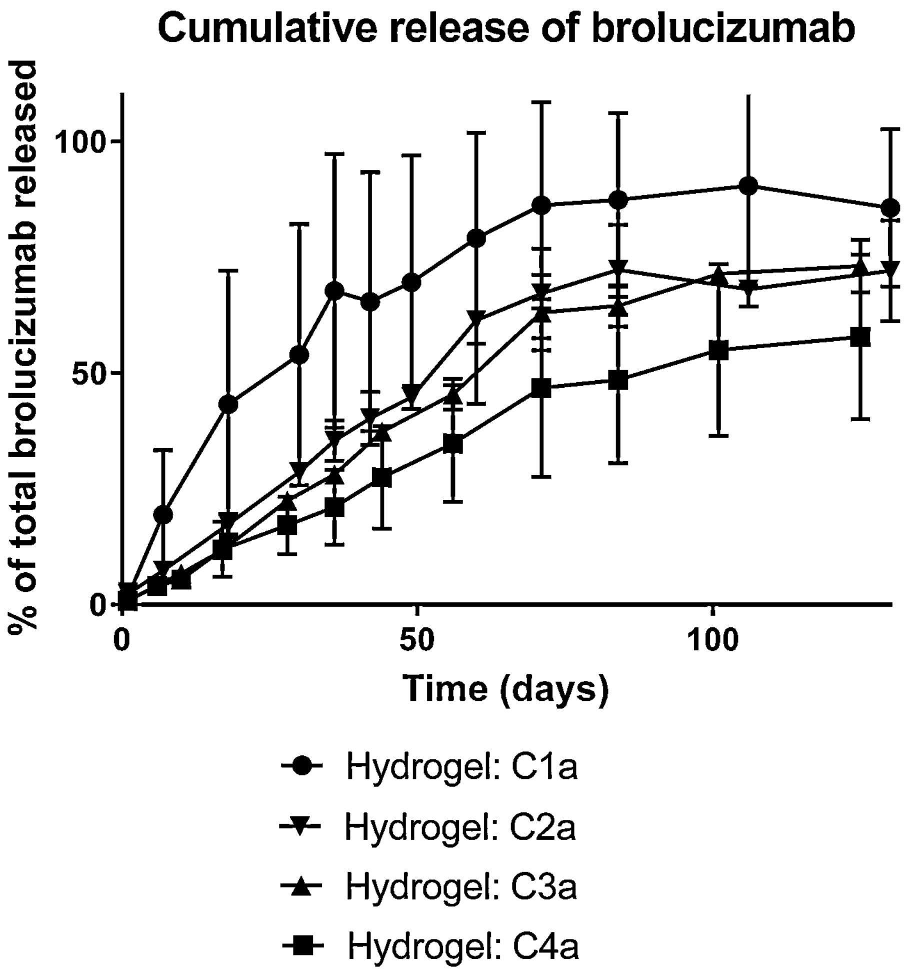

At the completion of the study, the protein concentration of the timepoint samples (which represents the protein concentration in each well at the timepoint) was determined using a protein assay kit (DC™ Protein Assay Kit II, BioRad 5000112) with a standard curve generated from brolucizumab. Each timepoint sample was analyzed in duplicate and the results were averaged. The total amount of protein in a given well at a given timepoint was calculated by multiplying the protein concentration at the timepoint by the measured volume (assuming density of 1 g/mL). The amount of protein removed from a given well at a given timepoint was calculated by multiplying the protein concentration at the timepoint by the volume removed (0.10 mL). The cumulative brolucizumab released from each hydrogel into each well up to that timepoint was calculated by adding the total amount of brolucizumab in the well at each timepoint to the cumulative amount of brolucizumab removed from that well at each timepoint prior to that timepoint. The cumulative percent of protein released from conjugates C1a, C2a, C3a, and C4a up until a given timepoint is shown in FIG. 4B. The cumulative percent of brolucizumab released is calculated by dividing the cumulative brolucizumab released at a given timepoint by the total brolucizumab present in the initial hydrogel sample and multiplying by 100. The data is normalized by setting the amount of measured released drug which has reached the plateau value as 100%. As evident from FIG. 4B, release of brolucizumab from the carrier is sustained over a period of months and the rate of release is influenced by the structure of the traceless linker used in the conjugate.

Concentration of Protein in a Well at Timepoint t:

$$[P](t)$$

Total Volume in a Well at Timepoint t:

$$V(t)$$

Total Protein in a Well at Timepoint t:

$$P_{well}(t)=[P](t)\times V(t)$$

Protein Removed from a Well at Timepoint t:

$$R(t)=[P](t)\times 0.1\ \text{mL}$$

Cumulative Protein Released from Hydrogel Until Timepoint t:

$$P_{cum}(t)=P_{well}(t)+\Sigma_{i=0}^{t-1}R(t)$$

8-2. Release of D2 from Hydrogel-Drug Conjugates

In vitro release assays were performed in 6.5 mm Transwell© inserts (8 μm pore size, Corning). A 100 μL aliquot of drug-linked HA hydrogel was added to each Transwell insert along with 100 μL bovine synovial fluid (BSF, from Bioreclamation IVT, supplemented with the following antimicrobial agents: 100 U/mL penicillin, 100 μg/mL streptomycin (Life Technologies) and 1% Fungizone (Life Technologies)) or 100 μL PBS. The total initial volume of gel and release media in the insert was 200 μL. 900 μL of either BSF (plus antimicrobial agents) or PBS was pipetted into the wells of a Transwell plate, the hydrogel-containing inserts were placed in the wells, and the plate was incubated in a humidified incubator at 37° C., 5% $CO_2$ (two inserts were prepared for each hydrogel sample). At each time point, the Transwell inserts were transferred to a new well filled with 1000 μL fresh BSF (plus antimicrobial agents) or PBS and the contents of the old well were removed and stored at −80° C. until assaying.

Figure 5A:
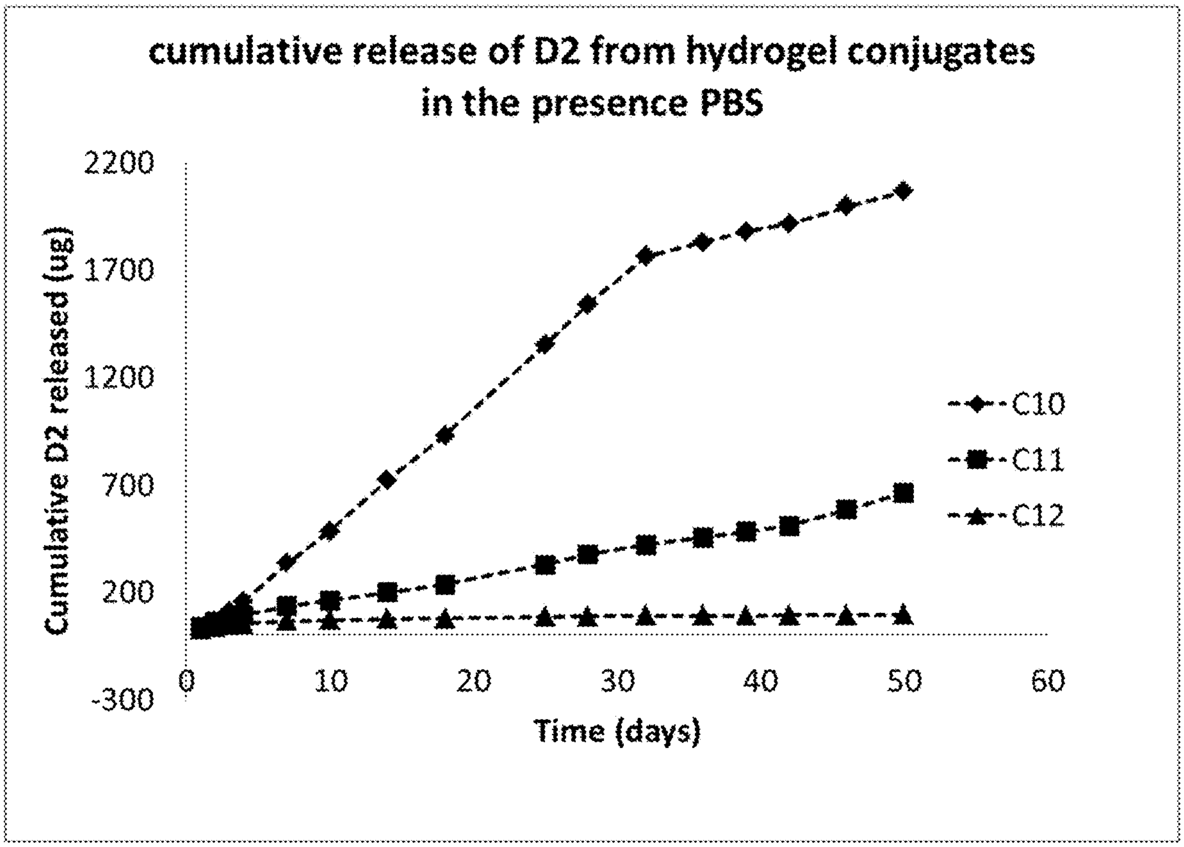
FIG. 5A (illustrating Example 8.2) shows the in vitro release of D2 from a hydrogel conjugate, comparing release from traceless linkers L1, L2, and L5 into PBS buffer.
Figure 5B:
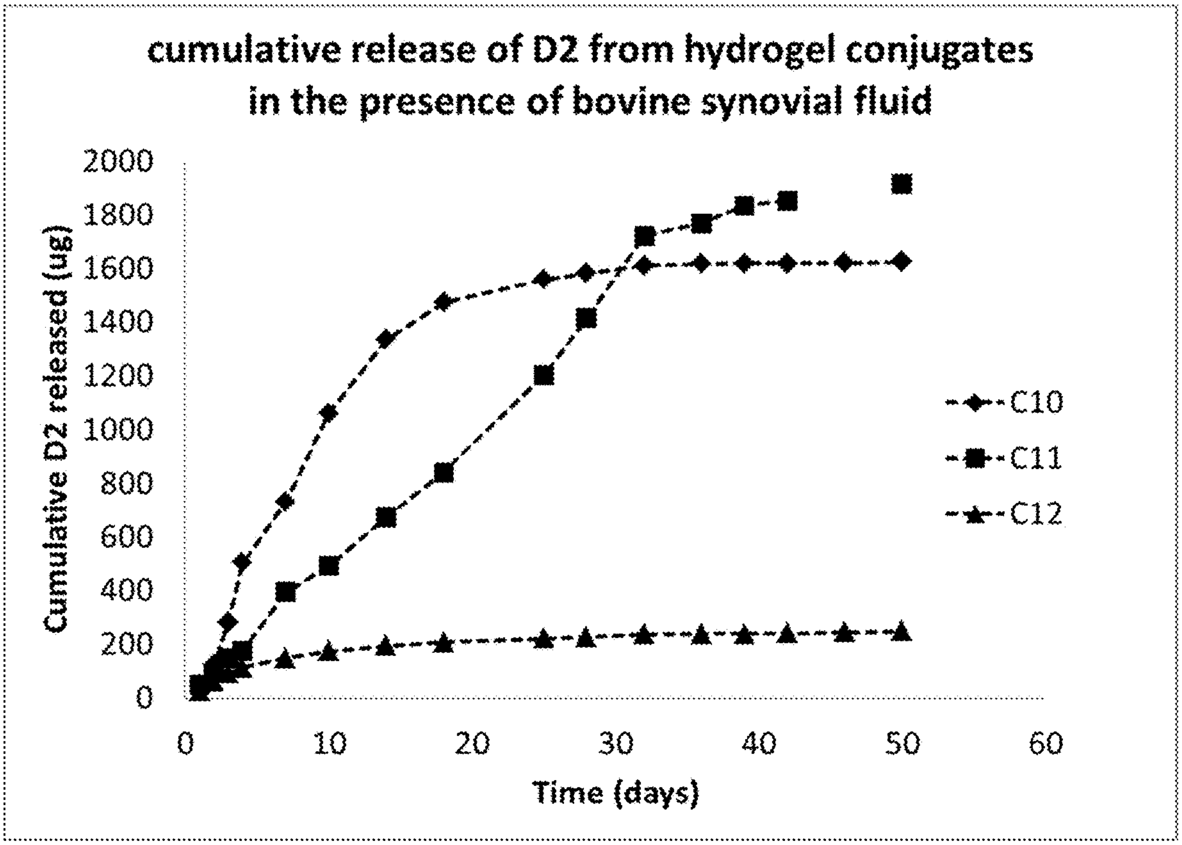
FIG. 5B shows the in vitro release of D2 from a hydrogel conjugate, comparing release from traceless linkers L1, L2, and L5 into bovine synovial fluid (BSF).

Quantification of the D2 released was determined by sandwich ELISA. The protocol was similar to the one described in the human IGF-1 DuoSet Elisa development system (R&D systems) with the following modifications: for the plate preparation, 96-well format plates (Costar) were coated with Capture antibody (Novartis) diluted in BupH Carbonate-Bicarbonate Buffer Pack (Thermoscientific) and incubated overnight at 4° C. All other reagents were from R&D systems except BSA (Sigma), wash buffer KPL (Kirkegaard & Perry) and blocking solution KPL milk diluent/blocking (Kirkegaard & Perry). Detection antibody was incubated for 1.5 h. The cumulative amount of protein released from the hydrogels C10, C11, and C12 during incubation with PBS or BSF is shown in FIG. 5. The amount of protein released in the well at a given timepoint was calculated by multiplying the protein concentration in the release media (BSF or PBS) at the timepoint by the total volume of release medium (1.1 mL). The cumulative protein released from each hydrogel up to a given timepoint was calculated by adding the amount of protein released at that timepoint (average value from the two wells for each hydrogel) to the cumulative amount of protein released at each timepoint prior to that timepoint. As evident from FIG. 5, release of D2 from the carrier is sustained over a period of weeks and the rate of release is influenced by the structure of the traceless linker used in the conjugate.

Figure 9:
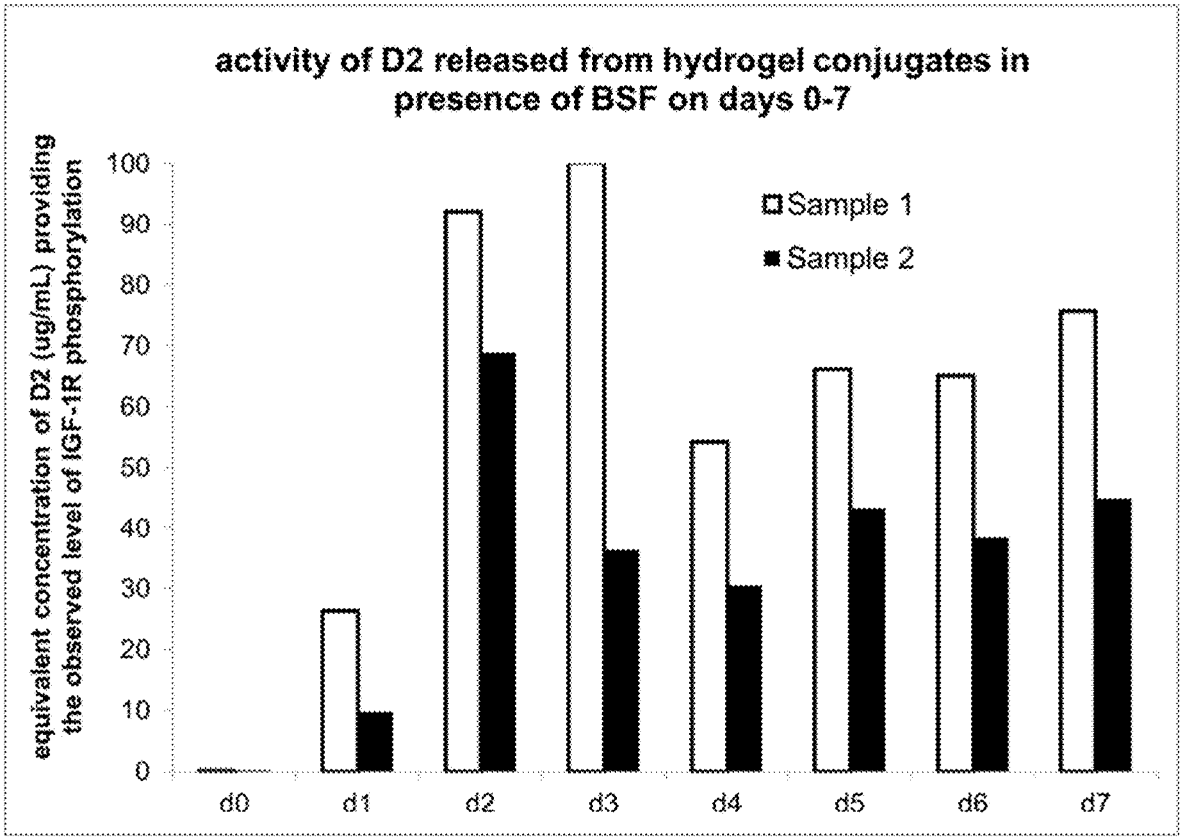
FIG. 9 (illustrating Example 8.2) shows the activity of D2 released in vitro from a hydrogel into bovine synovial fluid (daily sampling).

D2 is a drug that causes phosphorylation of the IGF1 receptor in NIH3T3 cells overexpressing the human IGF-1 receptor. Biological activity of the D2 released was assessed by quantifying the phosphorylation of the IGF1 receptor caused when NIH3T3 cells overexpressing the human IGF-1 receptor were incubated with the drug-containing release media from the individual time points (collected as described above). The level of IGF-1 receptor phosphorylation was determined by lysing the cells and subjecting the lysates to ELISA. Cells were seeded at 6000 cells/well (96-well plate format) in DMEM high glucose, 10% FCS, 1% sodium pyruvate, 2 mM L-glutamine, 10 mM HEPES, 100 U/mL penicillin, and 100 μg/mL streptomycin, and incubated overnight at 37° C. in a humidified incubator with 5% $CO_2$. Cells were then serum-starved in starvation media (DMEM high glucose, 0.1% BSA, 1% sodium pyruvate, 2 mM L-glutamine, 10 mM HEPES, 100 U/mL penicillin, 100 μg/mL streptomycin) for 1.5 h at 37° C., 5% $CO_2$ before being incubated with fresh D2 standards or the drug-containing release media for 1 h at 37° C., 5% $CO_2$. The drug-containing release media was diluted with starvation medium prior to addition to the cells in order to achieve a D2 concentration in the range of the standard curve, assuming no loss of activity. The appropriate dilution factor for each sample was determined based on the D2 concentration in the release media that had previously been measured by sandwich ELISA using the method described in the above paragraph. Cells were lysed in 1×Tris-buffered saline (50 mM Tris HCl, pH 7.5, 150 mM NaCl), 1% Triton X-100, 5 mM EDTA, 1×protease phosphatase inhibitor (Thermoscientific) for 30-45 min on a horizontal shaker at 4° C. The samples were stored overnight at −80° C. IGF-1R phosphorylation levels were analyzed by ELISA using the DuoSet IC human phosphor-IGF-1R (R&D systems) with the following modifications: the capture antibody (R&D MAB391) was diluted to 4 ug/ml in PBS, wells were washed with 300 ul/well of PBS-Tween (Millipore, 524653), wells were blocked with 200 ul/well 1% BSA in PBS, phosphorylation was detected using an antibody HRP-anti-phosphotyrosine (R&D, HAM1676) and the luminescent signal was detected with a chemiluminescence substrate (Pierce, 37069). The equivalent concentration of fresh D2 required to achieve the measured IGF-1R phosphorylation level in cells treated with released D2 was interpolated from a standard curve, and then corrected for dilution. The resulting values, shown in FIG. 9 for D2 released from conjugate C8 into BSF release media, represent the equivalent concentration of fresh D2 that would provide the observed level of IGF-1R phosphorylation in cells. As evident from FIG. 9, release of biologically active D2 from conjugate C8 is sustained over a period of seven days.

8-3. Release of D4 from Linker-Drug Adduct: L8D4
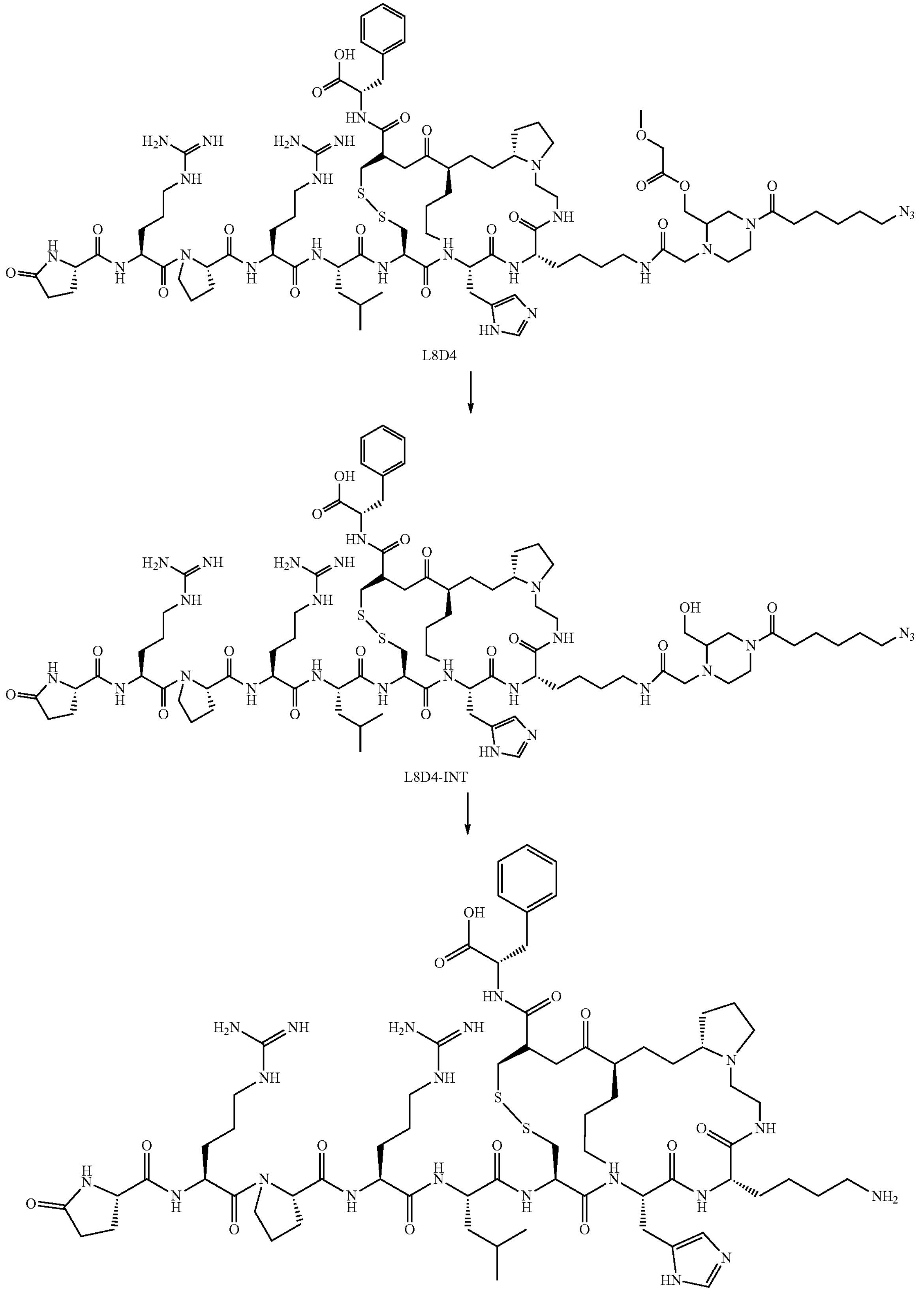
D4

A 1 mg/mL solution of L8D4 was prepared in 1×PBS. The pH of the adduct solution was measured and found to be 6.9. The solution was placed in a 40° C. Thermomixer with shaking at 600 rpm. Aliquots were removed for HPLC analysis at the following timepoints after dissolution: 0 h, 2 h, 4 h, 21.5 h, 28.5 h, 43.5 h, 67.5 h, 100.5h, 180.5 h, and 266.5 h.

Figure 6:
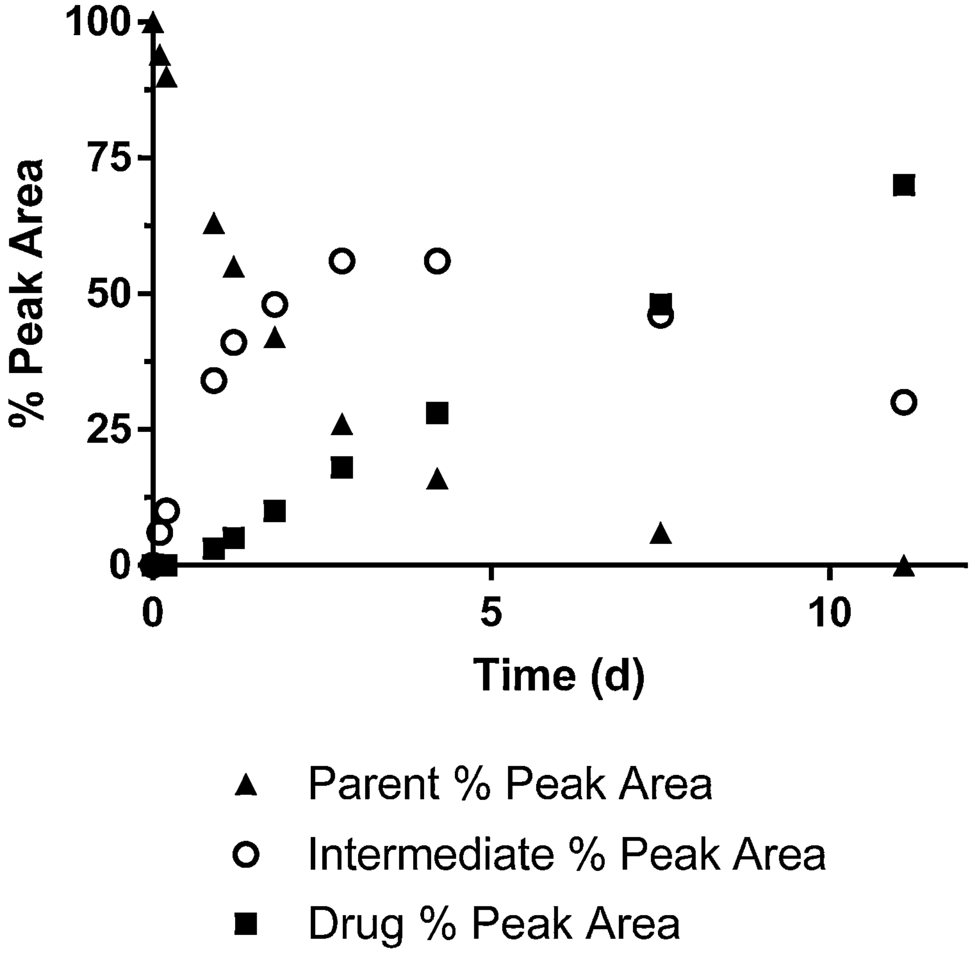
FIG. 6 (illustrating example 8.3) shows the in vitro release of D4 from a traceless linker, illustrating loss of parent, appearance, and subsequent disappearance of intermediate and release of D4.

The composition of the solution was evaluated at each timepoint by HPLC (method below). Parent (L8D4, m/z=+952.2 for $(M+2H)^{2+}$), intermediate (L8D4-INT, m/z=+916.4 for $(M+2H)^{2+}$), and released drug (D4, m/z=+1537.9 for M+H) peaks were assigned by MS detection, and the relative amounts of each species were determined by integration of the peaks from the chromatogram generated using UV absorbance at 214 nm. The percentage of each species present in the solution was calculated by dividing the respective peak area (either L8D4, L8D4-INT or D4) by the sum of the three peak areas for L8D4, L8D4-INT, and D4 and multiplying the result by 100. The percent of each species present in the solution was plotted versus time (FIG. 6) and the half-life of degradation for the parent L8D4 (1 day) and the half-life of release for D4 (8 days) were estimated using curve-fitting software assuming first order kinetics of release and degradation. As evident from FIG. 6, release of D4 from the traceless linker is sustained over a period of 11 days. The reaction products observed are consistent with the traceless linker cleavage mechanism shown in FIG. 1.

Analytical HPLC-MS conditions: ACQUITY UPLC BEH C18; particle size: 1.7 μm; column size: 2.1×50 mm; eluent/gradient: 2-98% $CH_3CN/H_2O$/4.4 min ($CH_3CN$ containing 0.1% formic acid and $H_2O$ containing 0.1% formic acid); flow rate: 1.0 mL/min; column temperature: 50° C.

8-4a. Release Study Protocol for M1-M19 Model Traceless Linker-Drug Conjugates In Vitro In this study a series of model traceless linker-drug conjugates, in which the drug is a low molecular weight amine-containing compound, was held in 1×PBS at 37° C. These reactions were sampled at various timepoints and analyzed to determine concentration of remaining starting compound, as well as concentration of the released amine-containing drug (p-methoxybenzylamine, 2-amino-pyridine, p-methoxyaniline, or N-methyl-p-methoxybenzylamine). Half-lives for the parent degradation and the half-lives of release for the amine-containing drug were calculated.

Method for Estimation of Amine-Containing Drug Release Rates from M1-M19

Each compound M1-M19 was prepared as a 0.1 M stock solution in DMF, as were a set of standard solutions for the released amine-containing drug (4-methoxybenzylamine, 2-aminopyridine, p-methoxyaniline, and N-methyl-p-methoxybenzylamine). A 35 μL aliquot of each solution was added to 3.465 mL of PBS to obtain 1 mM solutions of each conjugate or amine-containing drug. A 150 μL aliquot of each 1 mM solution was dispensed into LCMS vials with a polypropylene insert; 2 vials were prepared for each compound at each time point.

The vials were incubated at 37° C. At each time point (e.g., 0, 1, 5, 7, 14, 21, 28, 35, 49, and 56 days), two vials of each conjugate were removed from the incubator and frozen at −20° C. to avoid further hydrolysis. All samples were thawed and analyzed in one batch after completion of the release study using the analytical HPLC method described below. Each sample was analyzed twice. Control solutions of the amine-containing drugs were prepared prior to analysis and were analyzed as is without prior incubation at 37° C.

Analytical HPLC-MS Conditions for Study 8.4a

HPLC: Thermo Accela HPLC and Autosampler; Autosampler Tray Temperature: 8° C.; Injection Volume: 20 μL; Column: Phenomenex Kinetex C18, 2.1×50 mm, 2.6 μm. Column Temperature: Ambient; Mobile Phases: A=0.1% formic acid in water; B=0.1% formic acid in acetonitrile; Flow Rate: 200 μL/min. Gradient (time/% B): 0/0, 3/0, 10/80, 15/80, 15.1/0, 18/0.

UV: Thermo Accela PDA; Scan Range: 200-400 nm; Wavelength Step: 1 nm; Sample Rate: 20 Hz; Filter Bandwidth: 9 nm; MS: Thermo LTQ XL; Ionization Mode: ESI; Spray Voltage: 0 V at time 0-1 minutes then switched to 4 kV; Capillary Temperature: 250° C.; Divert Valve: LC eluate to waste at time 0-1 minutes then flow diverted MS; Mass Range: 120-800 Da.

The composition of the solution was evaluated at each timepoint using HPLC. Parent, intermediate and released amine-containing drug peaks were assigned by MS detection, and the relative amounts of each species were determined by integration of the peaks from the chromatogram generated using UV absorbance detection at 272 nm. The mean peak area for each compound M1-M19 on Day 0 was assigned a normalized value of 100. For the standard of the amine-containing drug being released (e.g., p-methoxybenzylamine) the mean peak area of each standard was assigned a normalized value of 100. The absolute area under curve for each species detected were compared with these values. Run-to-run peak area reproducibility was typically within 20% on strong signal and considerably worse on weak signals, so normalized signals above 100 likely correspond to values at or approaching 100 (likely 90-100, within experimental error). The percentage of parent and amine-containing drug present in the solution were calculated by dividing the relevant peak area by the mean area that was assigned a normalized value of 100 for the same species and multiplying the result by 100. The percentage of parent and amine-containing drug present in the solution was plotted versus time and the half-life of degradation for the parent and the half-life of release for the amine-containing drug were estimated using curve-fitting software assuming first order kinetics. Calculated half-lives rounded to the nearest whole day, are reported in Table 25.

8-4b. M20-M27 In Vitro Release Study

In this study, a series of model traceless linker-drug conjugates M20-M27 was held in aqueous solution at 37° C. These reactions were sampled at various timepoints and analyzed to determine the concentration of remaining starting compound. The analytical method was not optimized to determine concentration of the amine-containing drug. Half-life of degradation for the parent was calculated.

Method for Estimation of Conjugate Degradation Rates for M20-M27

Each compound M20-M27 was prepared as a 0.1 M stock solution in DMF. A 35 μL aliquot of each solution was added to 3.465 mL of 2:1 DMF:PBS (for compound M24: 3:1 DMF:PBS) to obtain 1 mM solutions of each compound M20-M27. The reaction vials were held at 37° C. At each time point (e.g., 0, 1, 3, 8, 14, 21, 28, 35, 49, 56, 70, 92 days) analytical samples were prepared by collecting 150 μL from each 1 mM solution and diluting with 75 μL DMF. Two analytical samples were collected from each reaction vial at each time point and stored at 4° C. All samples were analyzed in one batch after completion of the release study. Each sample was analyzed twice using an analytical HPLC method described below.

The composition of the reaction solution was evaluated at each timepoint using HPLC. Compound M20-M27 peaks were assigned by MS detection, and the integration of the peak from the chromatogram generated using UV absorbance detection at 272 nm was determined. The mean peak area for each compound M20-M27 on Day 0 was assigned a normalized value of 100. The absolute area under the curve at each timepoint was compared with these values. Run-to-run peak area reproducibility was typically within 2000 on strong signal and considerably worse on weak signals, so normalized signals above 100 likely correspond to values at or approaching 100 (likely 90-100, within experimental error). The percentage of compounds M20-M27 remaining in the solution were calculated by dividing the relevant peak area by the mean area that was assigned a normalized value of 100 and multiplying the result by 100. The percentage of compound M20-M27 present in the solution was plotted versus time and the half-life of degradation was estimated using curve-fitting software assuming first order kinetics. Calculated half-lives rounded to the nearest whole day, are reported in Table 25.

Analytical HPLC-MS Conditions for Study 8.4b.

All settings the same as for analytical HPLC-MS conditions for study 8.4a except the following: Mobile Phases: A=5 mM ammonium hydroxide in water; B=5 mM ammonium hydroxide in acetonitrile; Flow Rate: 400 μL/min: Gradient (time/% B): 0/10, 0.5/10, 4/80, 8/80, 8.1/10, 12/10. Divert valve switched at 0.5 minutes after sample injection.

TABLE 25

Release Study Results for M1-M27

| Name | Calculated stability $t_{1/2}$, parent (d) | Calculated release $t_{1/2}$, of amine-containing drug (d) |
|---|---|---|
| M1 | 37 | 59 |
| M2 | 23 | 65 |
| M3 | 2 | 12 |
| M4 | 2 | 2 |
| M5 | 3 | 2 |
| M6 | 26 | 41 |
| M7 | 3 | No drug released |
| M8 | 35 | 26 |
| M9 | No degradation | No drug released |
| M10 | No degradation | No drug released |
| M17 | 50 | 34 |
| M18 | 8 | 5 |
| M19 | 6 | 4 |
| M20 | 51 | NA |
| M21 | 126 | NA |
| M22 | 23 | NA |
| M23 | 47 | NA |
| M24 | 36 | NA |
| M25 | 80 | NA |
| M26 | No degradation | NA |
| M27 | No degradation | NA |

Example 9

9-1. Release of Brolucizumab from Hydrogel-Drug Conjugates

In these examples the hydrogel drug conjugate was dosed intravitreally in rabbits at 2 different doses, followed by a VEGF dose after 32 days. After 34 days, the rabbits' eyes were examined by imaging to assess the extent of blocking of retinal blood vessel leakage. Terminal exposure of brolucizumab in the liquid portion of the vitreous of the eye was also determined.

Hydrogel-drug conjugate C2b, prepared at 10.2 mg/mL loading of brolucizumab was diluted prior to dosing to attain samples with brolucizumab loadings of 6 mg/mL (C2b1) and 0.6 mg/mL (C2b2). The amount of 1×PBS to be added was calculated by the following equation: (PBS diluent (mL))=[(total drug (mg)/desired drug loading (mg/mL)]−(initial volume of conjugate (mL).

To prepare conjugate with brolucizumab loading of 6 mg/mL (C2b1): To 0.9 mL of C2b in a 3 mL syringe was added 0.63 mL of 1×PBS. The syringe was capped and shaken vigorously to homogenize. This resulted in a total sample volume of 1.53 mL with protein loading=9.18 mg brolucizumab/1.53 mL=6.0 mg/mL brolucizumab in C2b1.

Conjugate C2b1 was dispensed for dosing in 0.5 mL insulin syringes with attached 30G needles, by removing the plunger and backfilling with the desired volume of C2b1. Air bubbles were removed by gentle manipulation of the syringe.

To prepare conjugate with brolucizumab loading of 0.6 mg/mL (C2b2): To 0.1 mL of C2b1 in a 3 mL syringe was added 0.9 mL of 1×PBS. The syringe was capped and shaken vigorously to homogenize. This resulted in a total sample volume of 1.0 mL with protein loading=0.60 mg brolucizumab/1.0 mL=0.6 mg/mL brolucizumab in C2b2.

Conjugate C2b2 was dispensed for dosing in 0.5 mL insulin syringes with attached 30G needles, by removing the plunger and backfilling with the desired volume of C2b2. Air bubbles were removed by gentle manipulation of the syringe.

Intravitreal administration of 400 ng/eye of human VEGF (hVEGF) in the eyes of male Dutch belted rabbit (body weight approximately 1.6-2 kg) results in maximal leakage at 48 hrs post treatment This vessel leakage can be completely inhibited by prior IVT administration of an anti-VEGF molecule such as ranibizumab, bevacizumab or brolucizumab. The interval between administration of the anti-VEGF molecule and the hVEGF challenge determines the duration of action of the anti-VEGF molecule. In this study, thirty-two days before the hVEGF challenge (34 days prior to imaging), anti-VEGF antibodies (either in solution or as the hydrogel-conjugate) or blank hydrogel (negative-control) were injected into the vitreous. Each rabbit cohort consisted of 3-5 animals (6-10 eyes) injected with the same antibody/construct at the same time. Inhibition of vascular leakage induced by each anti-VEGF construct is calculated relative to the vascular leakage observed in the blank hydrogel-treated group.

Male Dutch belted rabbit (body weight approximately 1.6-2 kg) eyes were dilated with topical 1% cyclopentolate and 2.5 phenylephrine and the cornea anesthetized with topical 0.5% proparacaine. The rabbits were then anesthetized with an intramuscular injection of ketamine/xylazine mix (17.5-35 and 2.5-5 mg/kg). Under direct visualization with a surgical microscope, 50 μL of the treatment was injected into the vitreous. The 30-gauge needle was inserted superotemporally approximately 2 mm from the limbus into the middle of the vitreous. The rabbit eye was examined for complications from the injection (e.g., hemorrhage, retinal detachment or a lens injury) and then the procedure was repeated on the fellow eye. Antibiotic ointment was applied to both eyes for all studies. At 32-days after initial injection of the hydrogel-drug conjugate, 400 ng of recombinant hVEGF was injected into the vitreous of the rabbit eyes. The human VEGF (Peprotech; cat AF 100-20, Lot 0508AF10) was diluted in sterile 0.9% saline. Following 48 hours after intravitreal injection of the VEGF challenge, the rabbit retinal vasculature was imaged as described below.

Human VEGF-induced retinal vessel changes were quantified through acquisition of images of retinal vessels after intravenous fluorescent dye administration. Images acquired after fluorescein delivery were utilized to determine vessel permeability. Generation of quantitative fluorescein leakage values also required imaging of a fluorescent dye selected to label the vessels (fluorescein isothiocyanate (FITC)-conjugated dextran). Ocular images were acquired 48 hours post-VEGF. Images were an average of up to 40 registered scanning laser ophthalmoscope (SLO) images acquired with a 30-degree lens on the nasal medullary ray adjacent to the optic nerve. The fluorescein channel from a 6-mode Spectralis© (Heidelberg Engineering) was used for all image acquisition. Prior to imaging, rabbits received 1-2 drops of 1% cyclopentolate and 1-2 drops of 2.5% phenylephrine topically for dilation; 0.5% proparacaine was also applied as a topical anesthetic. Rabbits were subsequently anesthetized as previously described. Vessels were labeled approximately 5-minutes before image acquisition with an intravenous injection of 1 mL of a solution of FITC-conjugated 2000 kD dextran (SIGMA©) into the marginal ear vein. The concentration of FITC-dextran used (35-70 mg/mL) was chosen empirically for each lot based on the fluorescence signal necessary to generate high quality images. Images of the labeled retinal vasculature were subsequently acquired. Retinal vessel permeability was then assessed through injection of 0.3 mL of a 10% fluorescein solution into the marginal ear vein. Images were then acquired 3-minutes after IV injection for one eye followed by an image approximately 4-6 minutes after IV fluorescein injection for the fellow eye.

The effects of VEGF on vessel permeability were assessed from the 3-6-minute fluorescein images. Analysis was performed quantitatively with custom-designed software developed for this purpose using MATLAB© (Mathworks©). Exclusions were made prior to unmasking in cases of insufficient image quality, if there was noted inflammation, or in cases where there were issues with injections.

Fluorescein leakage was quantified with image processing techniques using the method described below.

First, post-VEGF FITC-dextran and fluorescein images were aligned to each other using vessel features common to both images, then:

1. Regions outside of the medullary ray were then cropped from the co-registered images along with any localized areas with insufficient image quality for analysis.
2. Several regions of interest in the retinal vessels were delineated in both images and the intensity of one image was boosted until the signal in the region of interest was equal in both images (normalization).
3. The aligned FITC-dextran image was subtracted from the fluorescein leakage image yielding an image comprised of extravasated fluorescein.
4. Fluorescein leakage was reported for each eye as the average intensity of the pixels contained in the cropped region of interest in the extravasated dye image.

Inhibition of fluorescein leakage in each group was calculated versus the negative control group. Statistical analysis was performed with a one-way analysis of variance with a Dunnett's multiple comparison test.

The measured fluorescence signal is proportional to vascular leakage. Efficacy is defined as a reduction in the measured fluorescence signal intensity relative to the signal observed in animals that received saline or other negative control (such as blank hydrogel) injections. A lower value of the average fluorescence signal corresponds to a greater inhibition of leakage and, therefore, greater efficacy.

Figure 7A:
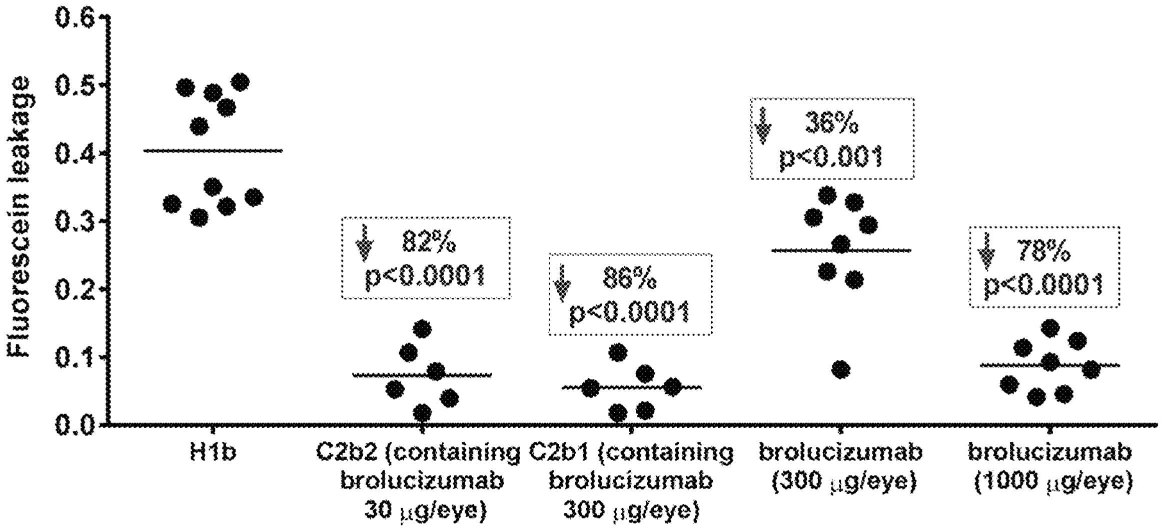
FIG. 7A-7B (illustrating Example 9.1) shows data from the in vivo testing of a brolucizumab-hydrogel at two different dose levels.

The data from this study shown in FIG. 7A show strong inhibition of fluorescein leakage with both doses (C2b1 and C2b2) of hydrogel-drug conjugate C2b, compared to the negative control (hydrogel $H_1b$). Similar strong inhibition is also observed for and the positive control (1000 μg/eye of brolucizumab). A lower dose of brolucizumab (300 μg/eye) demonstrated only partial blockage of fluorescein leakage, significantly less than either the dose-matched hydrogel-drug conjugate (C2b1) or the 10-fold lower dose hydrogel-drug conjugate (C2b2).

9-2. Drug Exposure in Rabbit Vitreous

Rabbits from the previous VEGF challenge study, which had been dosed with C2b1 and C2b2 were used to evaluate terminal drug levels in vitreous humor.

Serum and eyes were collected from rabbits at the terminal timepoints. The rabbit eyes were dissected to isolate the vitreous humor. Samples were stored at −80° C. before further processing or analysis. The vitreous humor was further separated into "liquid" and "gel" vitreous humor fractions as follows. The vitreous humor was thawed and the solid-like gel vitreous humor physically separated from the liquid vitreous humor from the sample using a plastic 1000 μL pipette tip. The remaining volume was considered the "liquid" fraction of the vitreous humor, analysis of which is shown in FIG. 7B.

Meso Scale Discovery (MSD) 384-well ELISA plates (catalog number L21XA-4) were coated with 15 μL (1 μg/mL) of a rabbit monoclonal antibody against the linker that joins the brolucizumab VH and VL in PBS and incubated overnight at 4° C. The plates were washed 3 times with 80 μL of TBST (Tris-buffered saline, pH 7.5, 0.05% Tween 20) and blocked with 40 μL of blocking buffer (5% BSA in PBS). BSA was purchased from either Millipore (catalog number 820452) or Roche (catalog number 03 116 964 001). The incubation times for blocking were 2-hours at room temperature or overnight at 4° C. The plates were then washed three times with 80 μL of TBST. Samples were mixed with diluent (2% BSA, 0.1% Tween-20, 0.1% Triton X-100 in Tris-buffered saline, pH 7.5), and then 15 μL aliquots of the samples were incubated on the MSD ELISA plate for 1 hour at room temperature with gentle shaking. The plates were then washed three times with TBST. A 15 μL (0.5 μg/mL) aliquot of the detection antibody, sulfo-tagged rabbit monoclonal antibody against the linker (SEQ ID NO:3) which joins the brolucizumab VH (SEQ ID NO:2) and VL (SEQ ID NO:1), was added to each well for 1 hour at room temperature with gentle shaking. A sulfo-tag was conjugated to the rabbit monoclonal antibody against the linker that joins the brolucizumab VH and VL as per the protocol in the MSD labelling kit (MSD Gold Sulfo-tag NHS-Easter Conjugation Pack 1 catalog R31AA-1). After one hour, plates were washed three times with 80 mL of TBST. MSD read buffer T (MSD catalog number R92TC-2) was diluted to a 1×concentration with water, and 37.5 μL of the 1×MSD read buffer T was added to each well. The plates were read on a Meso Scale Discovery M6000 detector. To quantitate the brolucizumab recovery levels from the hydrogel, purified brolucizumab was used as a standard.

A standard curve using purified brolucizumab was generated as follows. Twelve-point standard curves were generated by diluting brolucizumab 2-fold in ELISA diluent, with a starting concentration of 500 ng/mL. The Meso Scale Discovery analysis software (Discovery Workbench version 4.0) was utilized for the data analysis. The raw electrochemiluminescence (ECL) signal and brolucizumab concentrations were transformed to generate a standard curve by plotting the log of the concentration of brolucizumab on the x-axis and the log of the raw ECL units on the y-axis. Final brolucizumab concentrations were determined by multiplying the interpolated brolucizumab values from the standard curve by the appropriate dilution factor. Only the ECL signal values that were within the linear range of the standard curve were used.

Figure 7B:
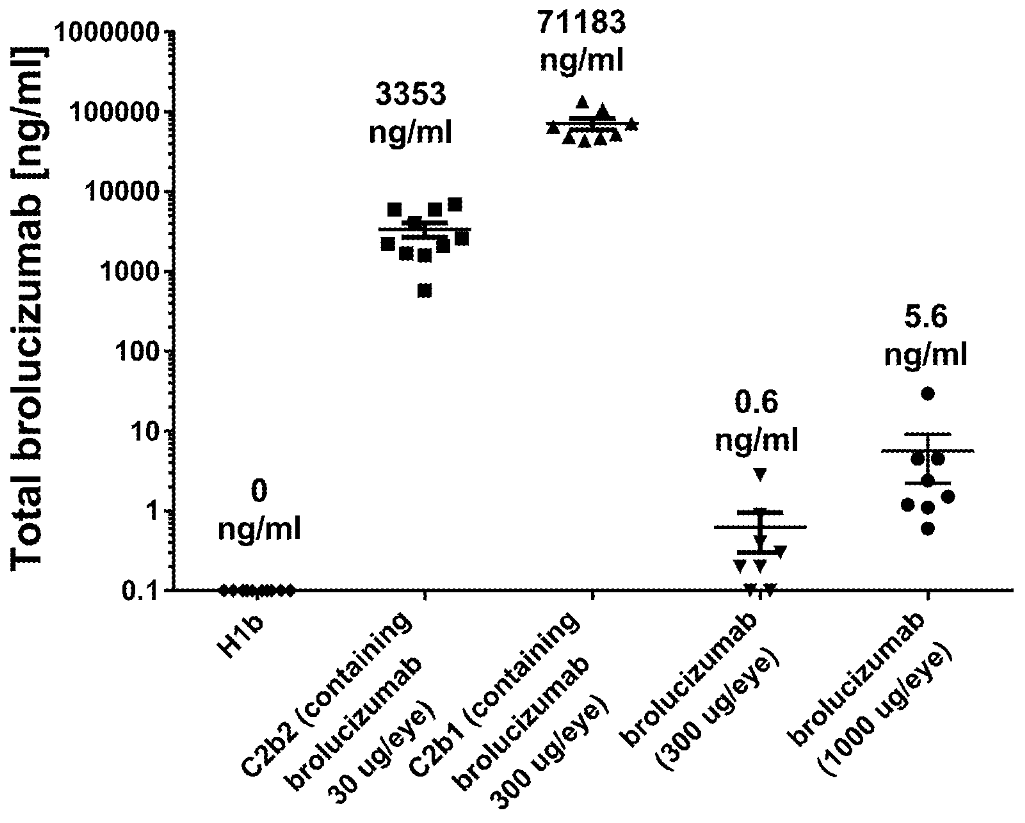

Results in FIG. 7B show significantly higher levels of brolucizumab in the liquid vitreous humor from rabbits dosed with both doses of hydrogel-drug conjugate C2b (C2b1 and C2b2), compared to the negative control (H1b) and to both doses of solution dosed brolucizumab. (Note that for graphing purposes, a value of 0.1 ng/mL is assigned for samples with zero drug detected).

9-3. In Vivo Release of D4 from Conjugate C13

Evaluation of In Vivo Peptide Release from Hydrogel Drug Conjugate C13 in a Rodent Model.

All studies were conducted according to NIBR approved Animal Care and Use Protocols. C57BL/6 mice (male, 1-11 weeks old) were obtained from Envigo. C13 in 1×PBS, pH 6.5 (D4 content=10 mg/mL) was transferred to insulin syringes with fixed 27 gauge needles. The formulations were injected subcutaneously at the dorsal midpoint of the mice at a dose volume of 5 mL/kg (50 mg/kg D4). Two groups of animals, n=3 each, were dosed. Blood samples of 50 μL were taken by tail transection at times after dosing with EDTA as anticoagulant. Blood samples were centrifuged at 4000×g for 20 minutes to obtain 20 μL plasma supernatant.

Figure 8:
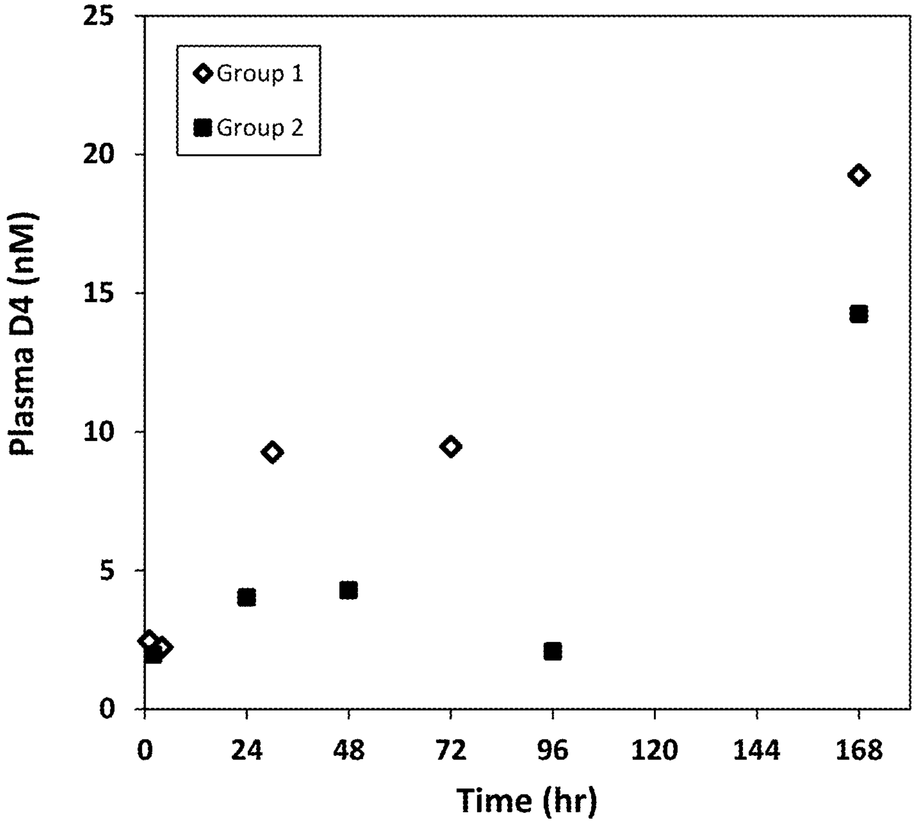
FIG. 8 (illustrating Example 9.3) shows the in vivo release of D4 from a hydrogel conjugate.

Concentration of D4 in plasma samples was determined by LC/MS methods. 150 μL extraction solvent (acetonitrile: methanol:water:formic acid; 1:1:1:0.003) was added to 20 μL plasma and vortexed for 30-seconds in a 96-well deep-well plate. This was centrifuged at 4000×g for 10 minutes. A 150 μL aliquot of supernatant was transferred to a fresh deepwell plate. A standard curve for D4 was prepared by serial dilution of D4 in EDTA plasma from 10,000 to 0.5 ng/mL D4 and co-extracted with the unknown samples. Unknown and standard curve samples were injected (10 μL, CTC PAL HTS autosampler) into an ACE C18 LC column (30×2.1, 3 μm) on an Agilent 1290 HPLC with a flow rate of 700 μL/min. The column was pre-equilibrated with 95% buffer A (0.1% formic acid in water), 5% buffer B (0.1% formic acid in acetonitrile). D4 was eluted by a gradient of 5 to 98% buffer B over 1.3 minutes. Eluate was injected into a Sciex 6500 MS running in ESI mode (450° C., CE=15, DP=50). A m/z transition of 378.0 (parent) to 167.0 (daughter) was monitored for quantitation. Concentrations of released D4 in plasma at time points up to 7 d after dosing were determined. As is apparent from FIG. 8, a prolonged exposure of D4 is achieved when dosed as a hydrogel-drug conjugate, exemplified using traceless linker L8 described herein.

Example 10

Comparative Tissue Tolerability of Hydrogels

This study examined the ability of C57BL/6 mice to elicit a granulomatous immune response when given single subcutaneous injections of various hydrogels and examined 7 days later. The test articles were H9 (hyaluronic acid-based hydrogel particles cross-linked by reaction between thiol-functionalized hyaluronic acid and acrylate-functionalized PEG), H1f (hyaluronic acid-based hydrogel particles cross-linked by reaction between azide-functionalized hyaluronic acid and alkyne-modified PEG), and Synvisc-One© hyaluronic acid-based injectable solution for treatment of osteoarthritis knee pain (Sanofi).

Preparation of H9

A thiol-functionalized hyaluronic acid GLYCOSIL™ (commercially available from EsiBio, Alameda, CA) was used to prepare H9.

Based on published references (Shu, X. Z. et al., *J Biomed Mater Res A,* 2006, 79(4):902-12; Shu, X. Z., et al., *Biomaterials,* 2004, 25:1339-1348), GLYCOSIL™ is understood to be a thiol-functionalized hyaluronic acid polymer with molecular weight of 158-187 kDa and 42-45% functionalization with the thiol containing moiety. For purposes of calculating the concentration of reactive groups in the gelation reaction, the degree of substitution was assumed to be 45%. The molecular weight of the unsubstituted carboxylate sodium salt repeat dimer unit is 401.3 Da. The molecular weight of the thiolated repeat dimer unit with structure depicted in the publications is 481.5 Da. The average MW of a dimer unit for the sodium salt form of GLYCOSIL™ with an assumed 45% degree of substitution is 437.5 Da= ((401.3×0.55)+(481.5×0.45)).

GLYCOSIL™ (10 mg, 22.9 μmol) was dissolved in 1 mL of 1×PBS, pH 7.4 at room temperature over 40 min in the original sample vial. Using the average molecular weight of a sodium salt dimer unit, the total moles of repeat dimer unit was calculated to be 22.9 μmol and the number of moles of thiolated repeat dimer unit to be 10.3 μmol. To this solution was added 1×PBS (0.775 mL) and a 100 mg/mL (in PBS) solution of polyethylene glycol diacrylate, 5 kDa (0.125 mL, 12.5 mg, 0.0025 mmol of reagent, 0.005 mmol of reactive functionality, Creative PEGworks. The resultant solution had a concentration of 5.3 mg/mL with respect to GLYCOSIL™ and where 22% of the GLYCOSIL™ repeat units were cross-linked by the polyethylene glycol diacrylate, 5 kDa ((0.005 mmol [polyethylene glycol diacrylate, 5 kDa reactive functionality]/0.0229 mmol [HA-units])× 100=22%).

The mixture was vortexed briefly to mix, and transferred into a 3 mL syringe, which was capped and held at room temperature overnight to provide H9. Visual inspection (inversion test) showed successful gelation.

Hyaluronic acid-based hydrogel particles of H9 were prepared as described for H1a, except that an equal volume of PBS was added to the particles following the first extrusion. This resulted in a hydrogel particle suspension that was 2.65 mg/mL with respect to GLYCOSIL™. Hydrogel particles of H9 were dispensed for dosing in 0.5 mL insulin syringes with attached 30G needles by removing the plunger and backfilling with the desired volume of H9. Air bubbles were removed by gentle manipulation of the syringe.

Preparation of H1f

Hyaluronic acid-based hydrogel particles of H1f were prepared as described for H1a, where a half volume of PBS was added to the particles following the first extrusion. This resulted in a hydrogel particle suspension that was 6.7 mg/mL with respect to [HA-N3]-23% b. Hydrogel particles of H1f were dispensed for dosing in 0.5 mL insulin syringes with attached 30G needles by removing the plunger and backfilling with the desired volume of H1f. Air bubbles were removed by gentle manipulation of the syringe.

Synvisc-One®

Synvisc-One© was purchased and used as received.

Subcutaneous Implantation

Male C57BL/6 mice (5 per test article) were administered 60 μL of test article via subcutaneous injection (interscapular region) (Table 26). An additional 5 naive mice served as controls. In-life observations were obtained twice on the dosing day (predose and approximately 4 hours post-dose), and at least once daily thereafter until necropsy. Body weights were taken twice weekly.

TABLE 26

| Study design, animal allocation and test article doses | | | |
|---|---|---|---|
| Group | Number | Treatment | Dose Volume (µl) |
| 1 | 5 | Non-injected control | — |
| 2 | 5 | H9 | 60 µl |
| 3 | 5 | Synvisc-One ® | 60 µl |
| 4 | 5 | H1f | 60 µl |

After 7 days, animals were euthanized with $CO_2$ as the first form of euthanasia and a thoracotomy was performed as the second form of euthanasia. Necropsy was performed while recording macroscopic abnormalities. Representative samples of the protocol tissues were collected from all animals. Fixation and storage of specimens was in 10% neutral-buffered formalin. Specified tissues were processed to paraffin blocks and subsequently hematoxylin and eosin-stained tissue sections for animals in the control and all surviving dosed animals.

Clinical Observations:

Injection sites were palpated daily and observations were recorded. All of the mice that received H9 hydrogel particles, Synvisc-One®, and H1f hydrogel particles developed bumps in the subcutaneous tissue of the injection sites at time of injection. Mice that received the Synvisc-One©, and the H1f hydrogel particles had bumps that receded by day 4, whereas all of the mice that received H9 hydrogel particles still retained hard bumps by day 8. Scabs were observed on the skin over the bumps in two animals that received H9 starting on day 4 and were observed until day 6. There were no other notable clinical observations. Body weights did not significantly differ between the groups.

Microscopic Observations

All mice administered H9 hydrogel particles had a marked focally extensive granuloma in the subcutaneous tissue of the injection site. The granuloma was characterized by approximately a 4 mm well circumscribed subcutaneous mass containing a core of hyaline material admixed with eosinophilic granular debris and degenerate neutrophils, surrounded by a dense rim of abundant neutrophils, in turn containing a layer of macrophages and fibroblasts.

Mice administered Synvisc-One© or H1f hydrogel particles had minimal to slight focal mixed cell and/or small thin walled cysts in the subcutaneous tissue of the injection sites (Table 27).

TABLE 27

| Incidence and severity of Test article-related histopathological changes | | | | |
|---|---|---|---|---|
| Tissue: Finding | 1 | 2 | 3 | 4 |
| Number examined: | 5 | 5 | 5 | 5 |
| Skin: cyst(s) | | | | |
| Minimal | 0 | 0 | 1 | 0 |
| Mild | 0 | 0 | 1 | 0 |
| Skin: Granuloma | | | | |
| Marked | 0 | 5 | 0 | 0 |
| Skin: Infiltration | | | | |
| Minimal | 0 | 0 | 4 | 3 |
| Mild | 0 | 0 | 0 | 0 |

CONCLUSIONS

The microscopic findings in mice given subcutaneous injections of hyaluronic acid-based hydrogels differ depending on the composition of the hydrogel dosed. Mice administered Synvisc-One© or H1f had either no microscopic findings or focal mixed cell infiltrates and/or small thin walled cysts in the subcutaneous tissue of the injection sites, while H9 elicited a marked granulomatous immune response.

What is claimed is:

1. A drug delivery system or pharmaceutically acceptable salt thereof characterized in that is represented by Formula (XXX), where Drug is a biologically active moiety comprising at least one primary or secondary amine or a ring nitrogen atom of an azaheteroaryl ring; w is the number of repeating PEG monomer units having a nominal average molecular weight of 2 kDa; q is independently at each occurrence 1, 2, or 3; m is 1 or 0; p is a weighted average length of between 2 and 50; and $R^4$ is methyl, ethyl, propyl, isopropyl, 1-methyl-cyclopropyl, or methoxymethyl:

(XXX)

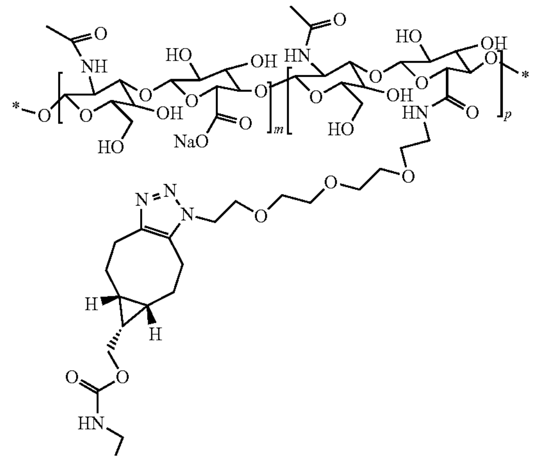

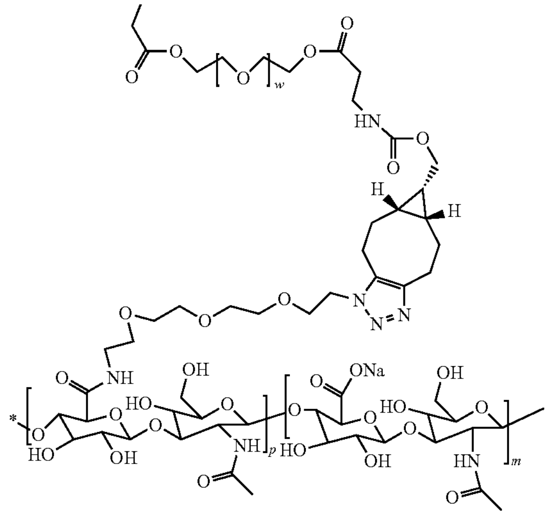

-continued

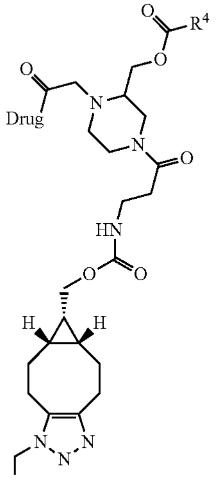

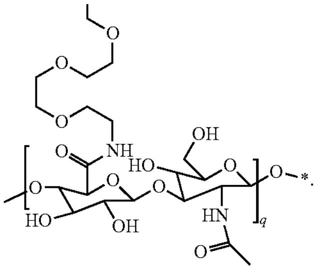

2. A drug delivery system or pharmaceutically acceptable salt thereof characterized in that is represented by Formula (XXXII), where Drug is a biologically active moiety comprising at least one primary or secondary amine or a ring nitrogen atom of an azaheteroaryl ring; w is the number of repeating PEG monomer units having a nominal average molecular weight of 2 kDa; q is independently at each occurrence 1, 2, or 3; m is 1 or 0; p is a weighted average length of between 2 and 50; and $R^4$ is methyl, ethyl, propyl, isopropyl, 1-methyl-cyclopropyl, or methoxymethyl:

(XXXII)

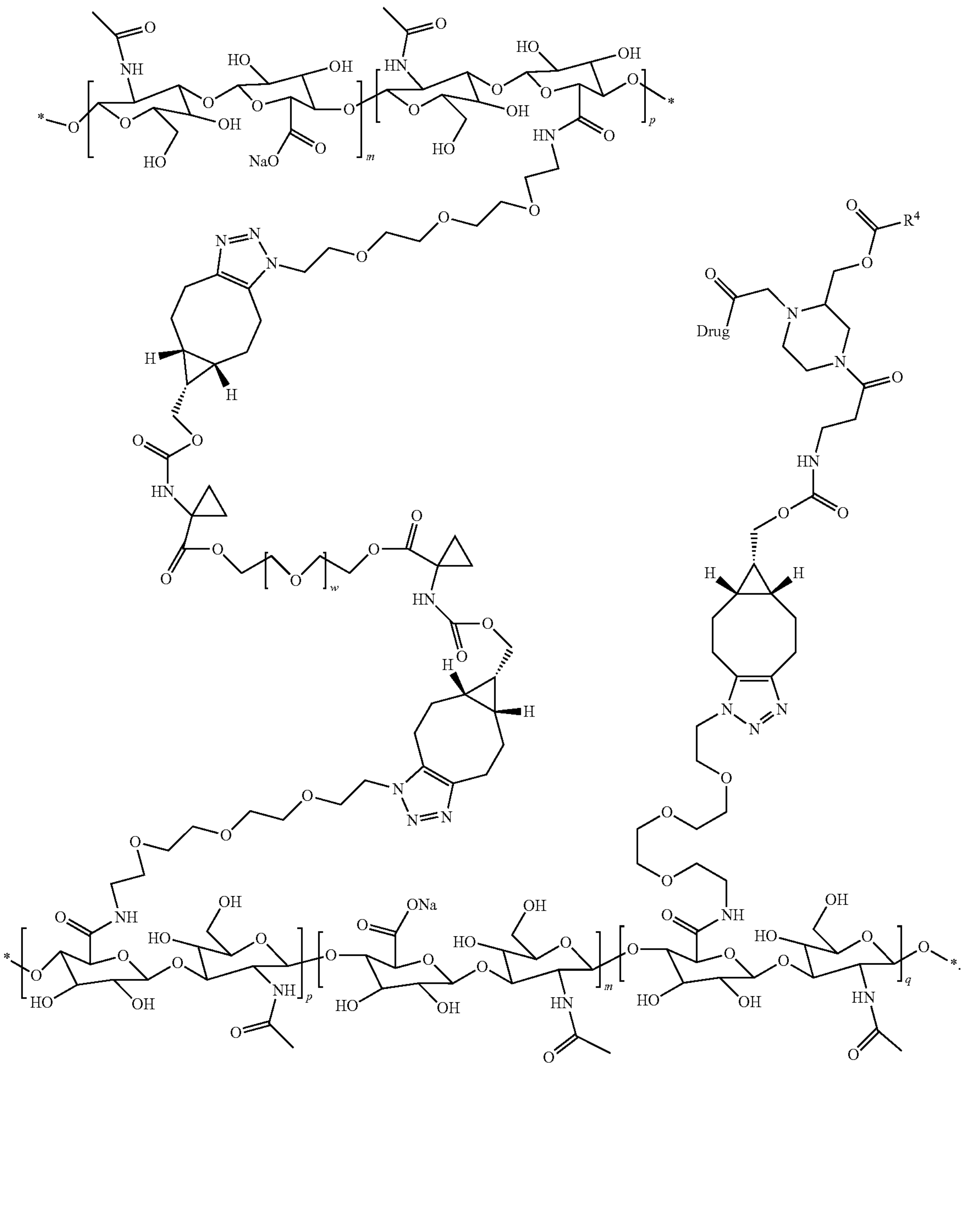

3. A drug delivery system or pharmaceutically acceptable salt thereof characterized in that is represented by Formula (XXXIV), where Drug is a biologically active moiety comprising at least one primary or secondary amine or a ring nitrogen atom of an azaheteroaryl ring; w is the number of repeating PEG monomer units having a nominal average molecular weight of 2 kDa; q is independently at each occurrence 1, 2, or 3; m is 1 or 0; p is a weighted average length of between 2 and 50; and $R^4$ is methyl, ethyl, propyl, isopropyl, 1-methyl-cyclopropyl, or methoxymethyl:

(XXXIV)

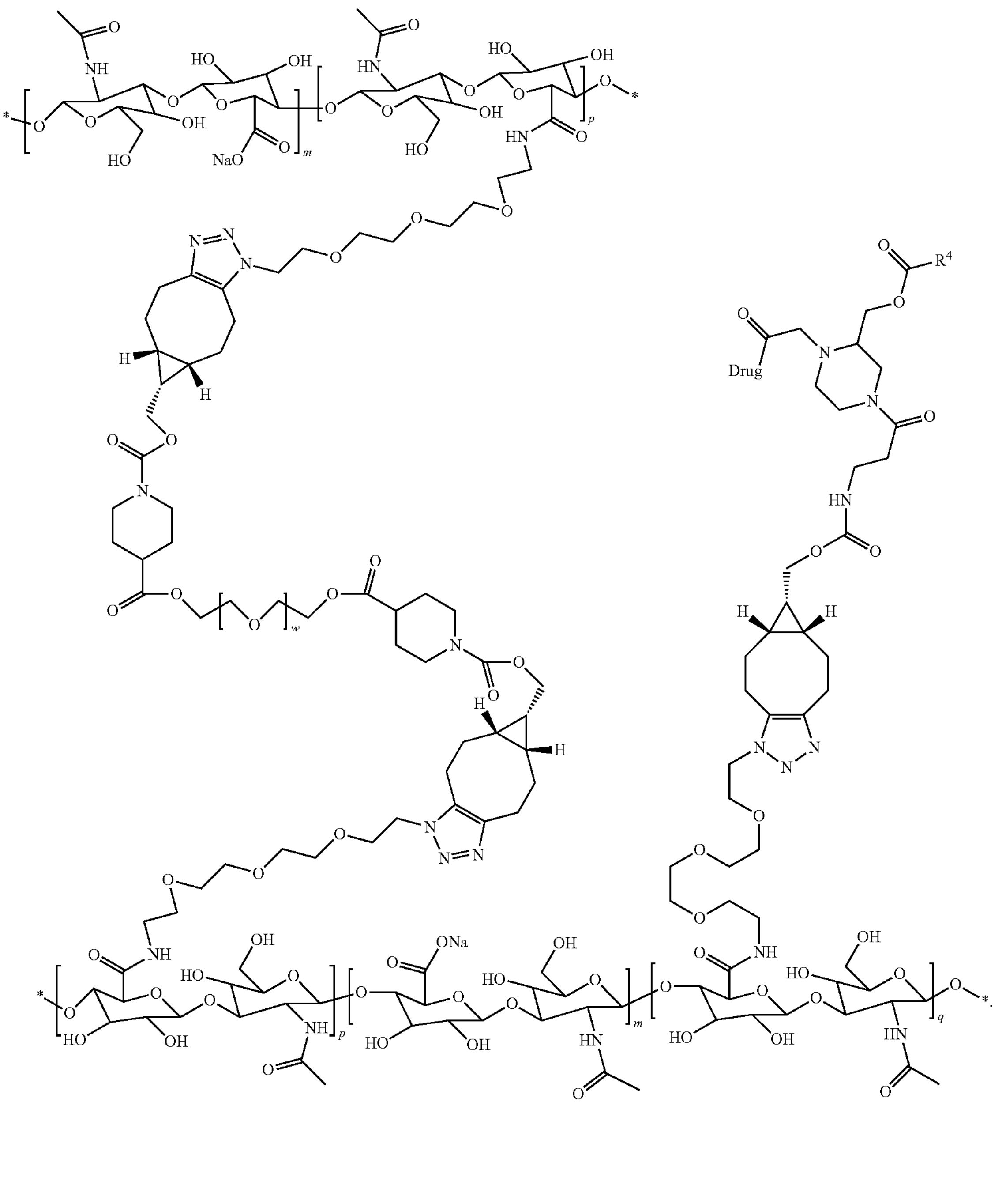

4. A drug delivery system or pharmaceutically acceptable salt thereof characterized in that is represented by Formula (XXXVI), where Drug is a biologically active moiety comprising at least one primary or secondary amine or a ring nitrogen atom of an azaheteroaryl ring; w is the number of repeating PEG monomer units having a nominal average molecular weight of 2 kDa; q is independently at each occurrence 1, 2, or 3; m is 1 or 0; p is a weighted average length of between 2 and 50; and $R^4$ is methyl, ethyl, propyl, isopropyl, 1-methyl-cyclopropyl, or methoxymethyl:

(XXXVI)

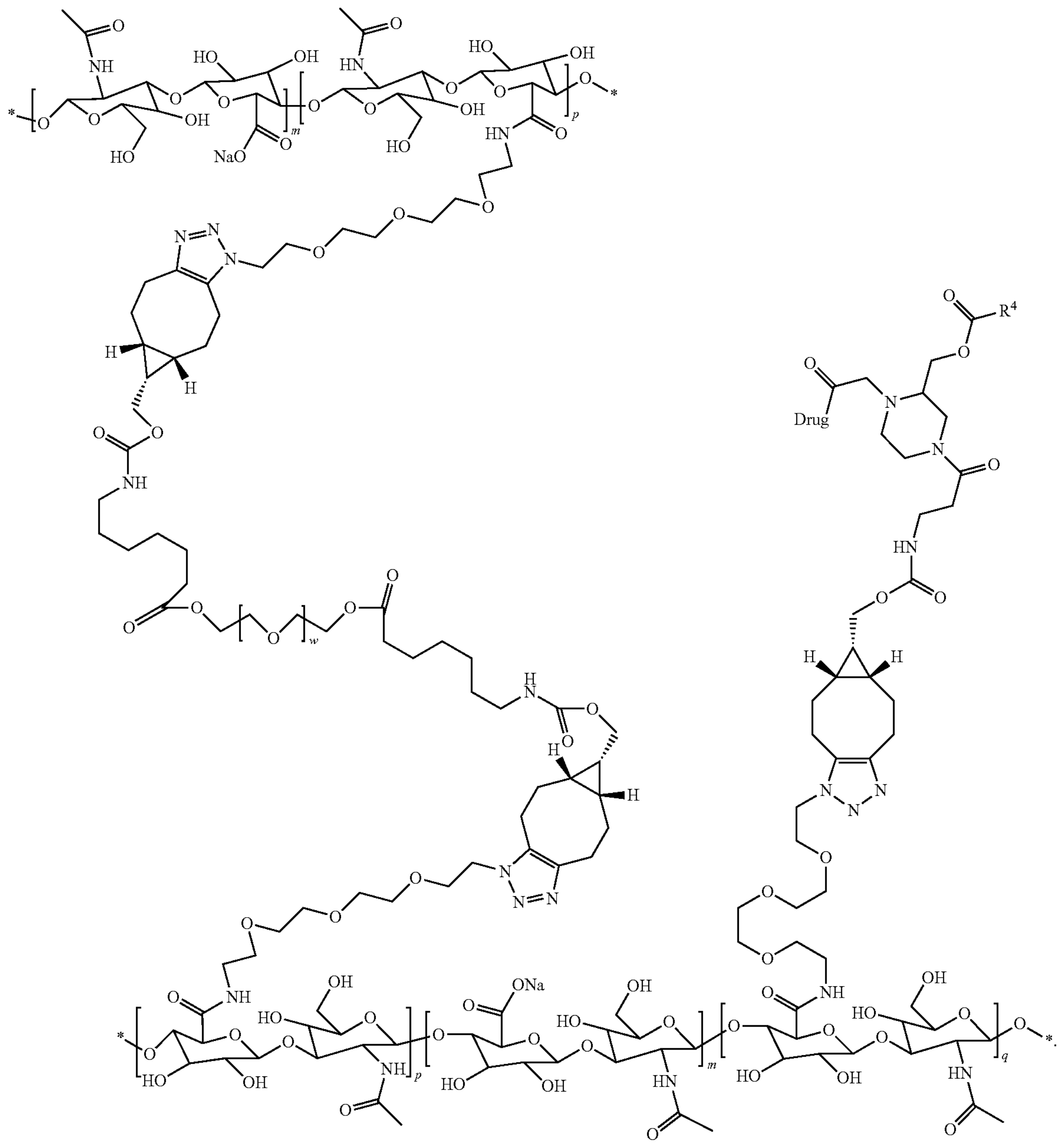

5. A drug delivery system or pharmaceutically acceptable salt thereof characterized in that is represented by Formula (XXXVIII), where Drug is a biologically active moiety comprising at least one primary or secondary amine or a ring nitrogen atom of an azaheteroaryl ring; w is the number of repeating PEG monomer units having a nominal average molecular weight of 2 kDa; q is independently at each occurrence 1, 2, or 3; m is 1 or 0; p is a weighted average length of between 2 and 50; and $R^4$ is methyl, ethyl, propyl, isopropyl, 1-methyl-cyclopropyl, or methoxymethyl:

(XXXVI)
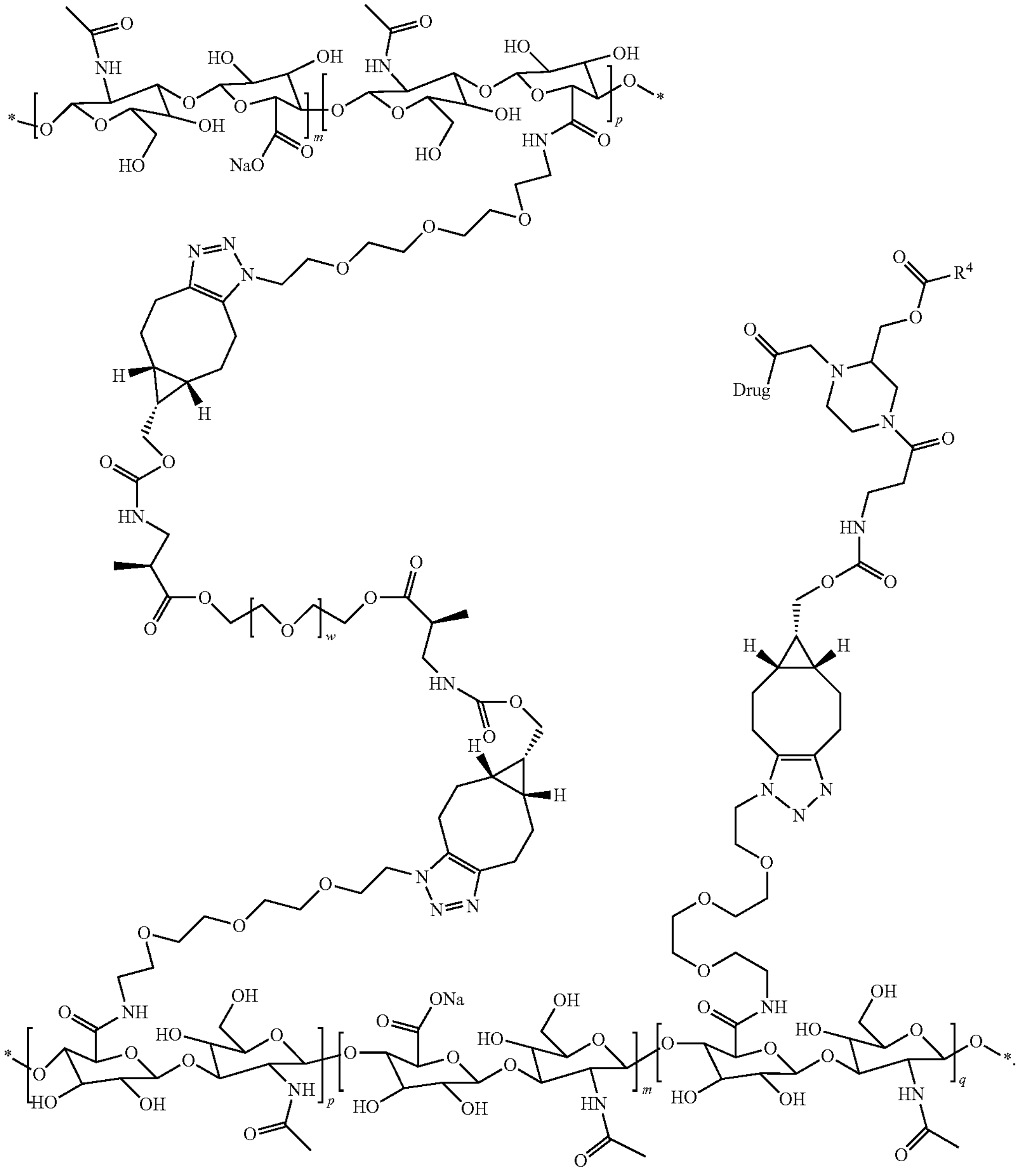

6. A carrier composition or pharmaceutically acceptable salt thereof, characterized in that is represented by formula:

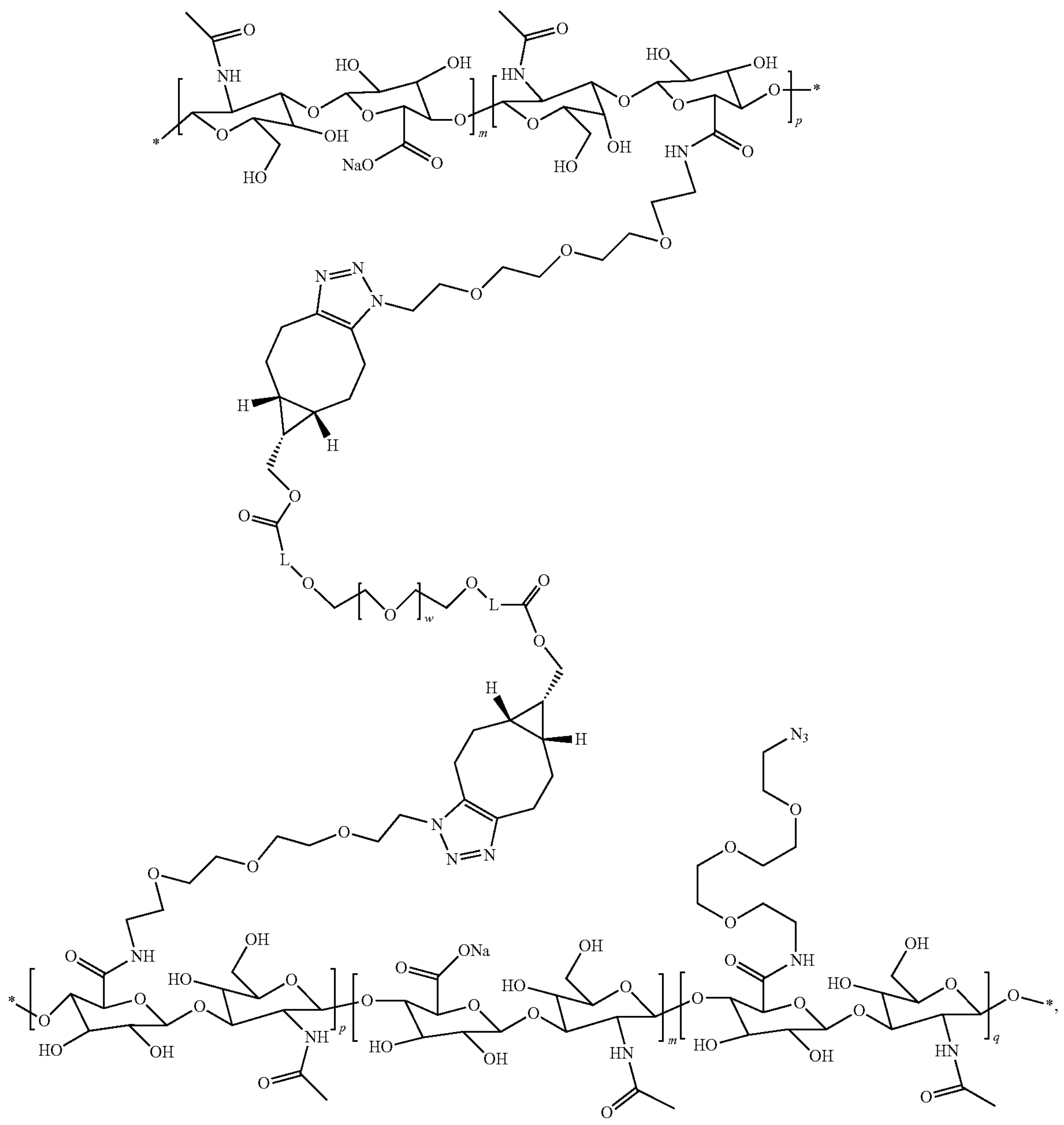

wherein

L is an optionally substituted bivalent linker Q-[Sp-Q]$_h$-Q;

Q is independently selected at each occurrence from a bond, O, C(O), N(H), N($C_1$-$C_4$alkyl), C(O)NH, C(O)N($C_1$-$C_4$alkyl), N(H)C(O), N($C_1$-$C_4$alkyl)C(O), N(H)C(O)O, N($C_1$-$C_4$alkyl)C(O)O, OC(O)N(H), OC(O)N(C1-C4alkyl), N(H)C(O)N(H), N($C_1$-$C_4$alkyl)C(O)N(H), N(H)C(O)N($C_1$-$C_4$alkyl), N($C_1$-$C_4$alkyl)C(O)N($C_1$-$C_4$alkyl), C(O)O, OC(O), OC(O)O, S, $S(O)_2$, N(H)$S(O)_2$, N($C_1$-$C_4$alkyl)$S(O)_2$, $S(O)_2$N(H), $S(O)_2$N($C_1$-$C_4$alkyl), $C_1$-$C_2$alkyl-C(O)N(H), N(H)C(O)$C_1$-$C_2$alkyl, $C_1$-$C_2$alkyl-C(O)O, OC(O)$C_1$-$C_2$alkyl, 1,2,3-triazole, $OP(O)_2$, $P(O)_2O$, $C_1$-$C_4$alkyl-$P(O)_2$—O, or O—$P(O)_2$—$C_{1-4}$alkyl;

Sp is independently selected at each occurrence from an optionally substituted $C_1$-$C_{20}$alkyl, $C_2$-$C_{20}$alkenyl, $C_2$-$C_{20}$alkynyl, [W—O]$_g$, $C_1$-$C_8$alkyl-[O—W]$_g$, [O—W]$_g$-O-$C_1$-$C_8$alkyl, $C_1$-$C_8$Calkyl-[O-W]$_g$-O-$C_1$-$C_8$alkyl, or oligopeptide;

h is an integer of between 1 and 20;

g is a weighted average number of between about 2 and about 50;

W is $C_2$-$C_4$alkyl-1,2-diyl in which a hydrogen, methyl, or ethyl side chain may be present on either backbone carbon atom;

q is independently at each occurrence 1, 2, or 3;

m is 1 or 0;

p is a weighted average length of between 2 and 50;

w is the number of repeating PEG monomer units having a nominal average molecular weight of 2 kDa; and $R^4$ is $C_1$-$C_8$alkyl or $C_3$-$C_7$cycloalkyl, wherein cycloalkyl is optionally substituted with 0, 1, or 2 independently selected $C_1$-$C_4$alkyl groups and wherein alkyl is optionally substituted by $C_1$-$C_4$alkoxy.

7. The carrier composition of claim 6, characterized by having one of the following formula:

(X)

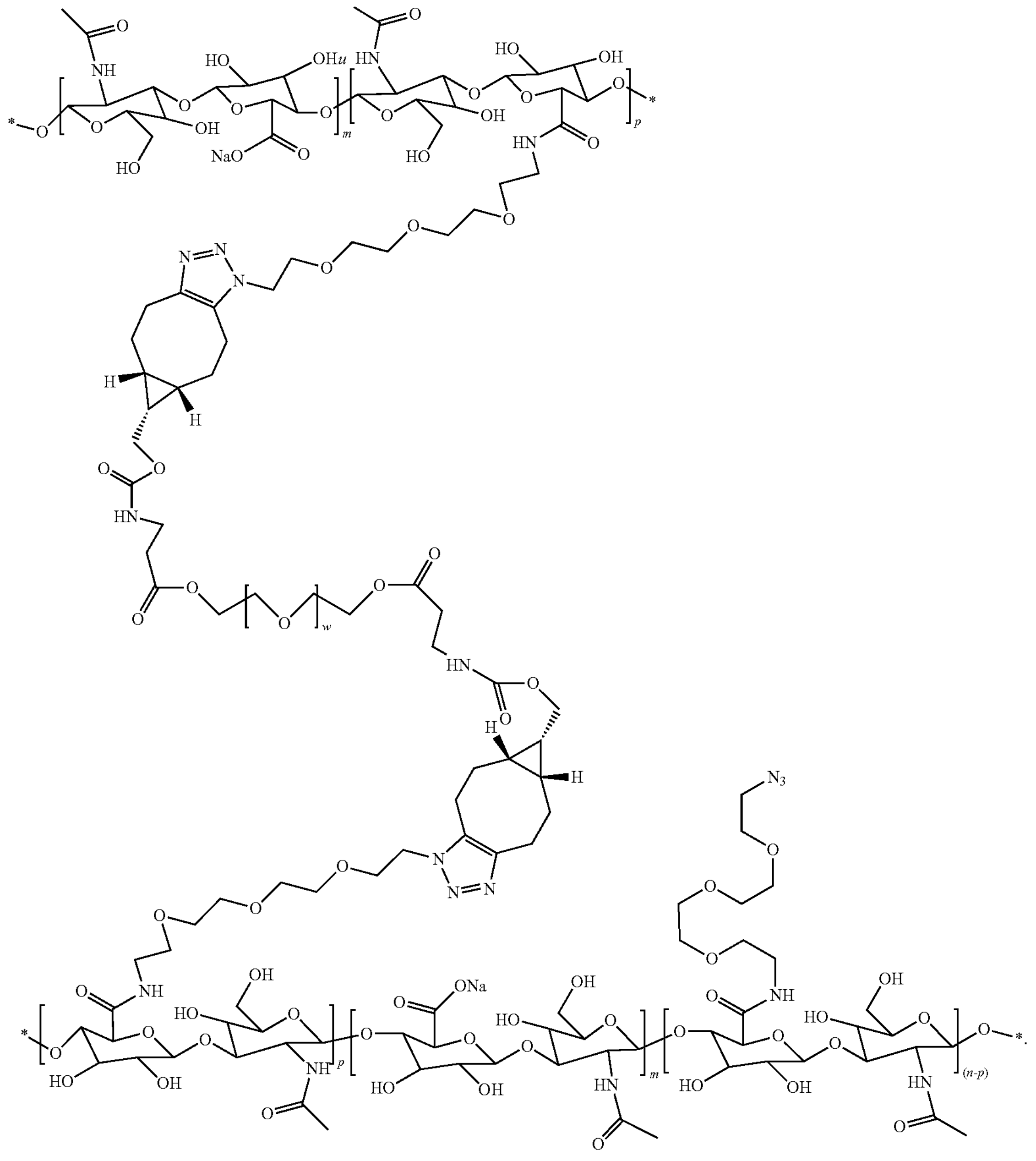

(XI)
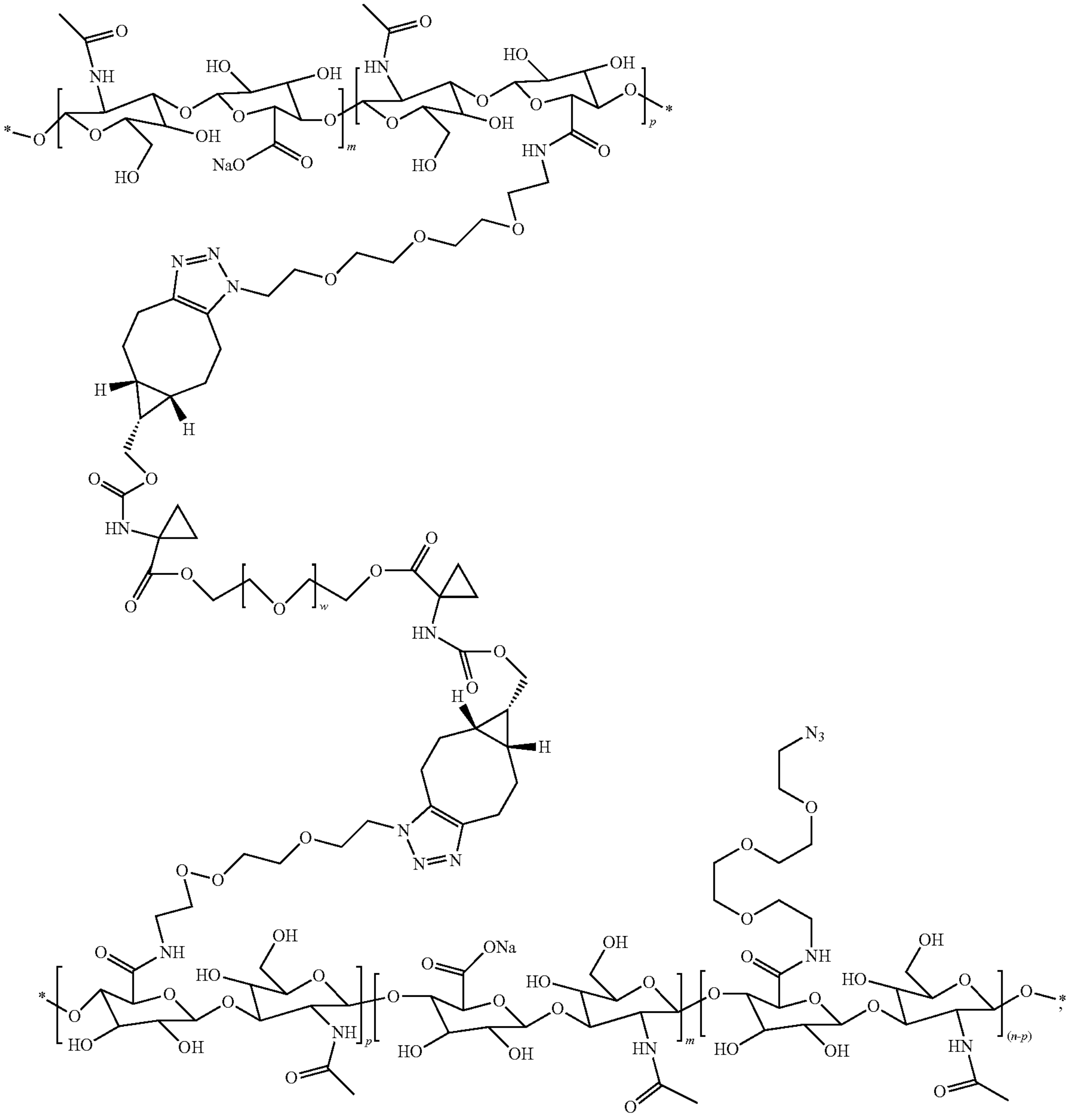

(XII)
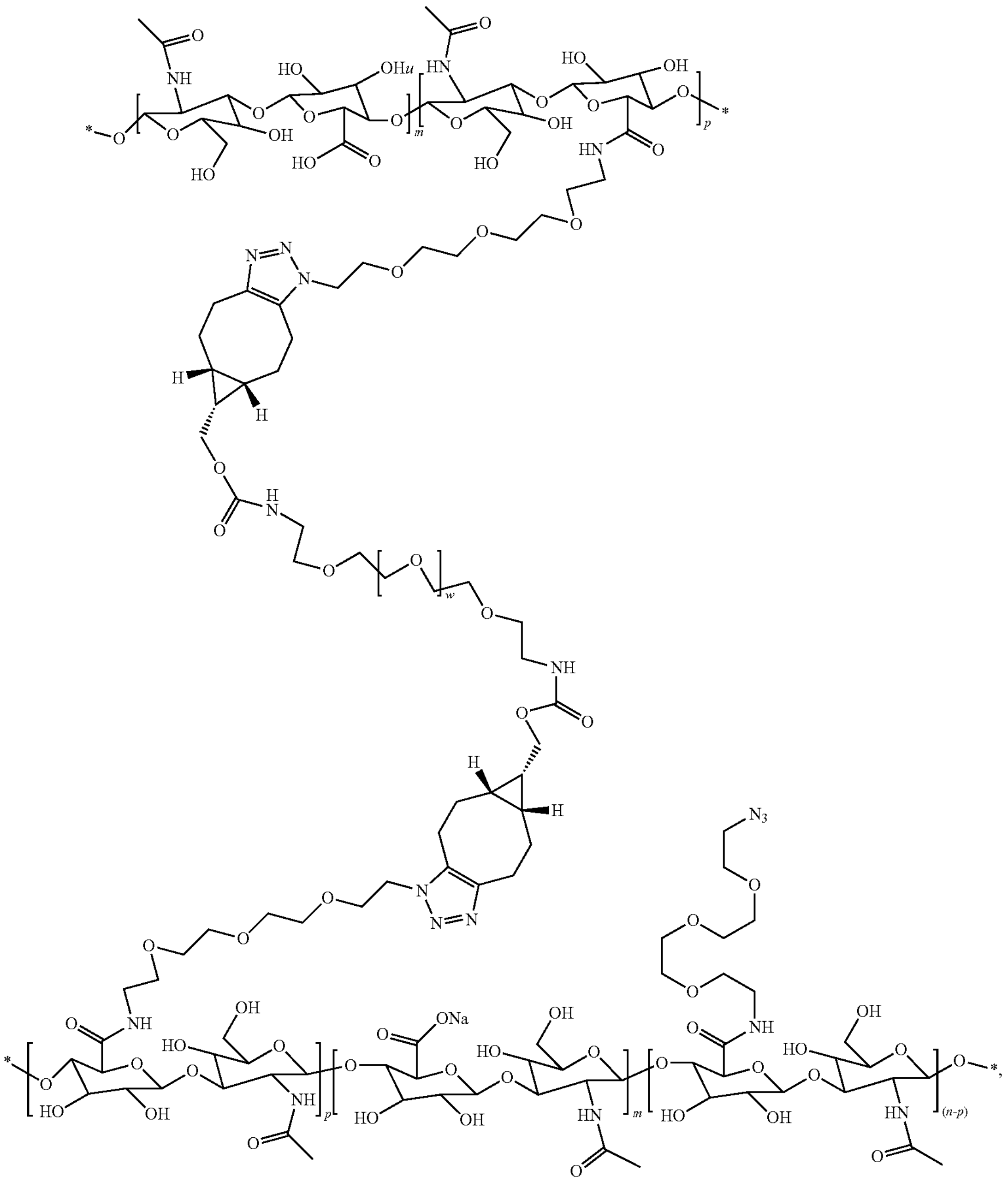

(XIIa)
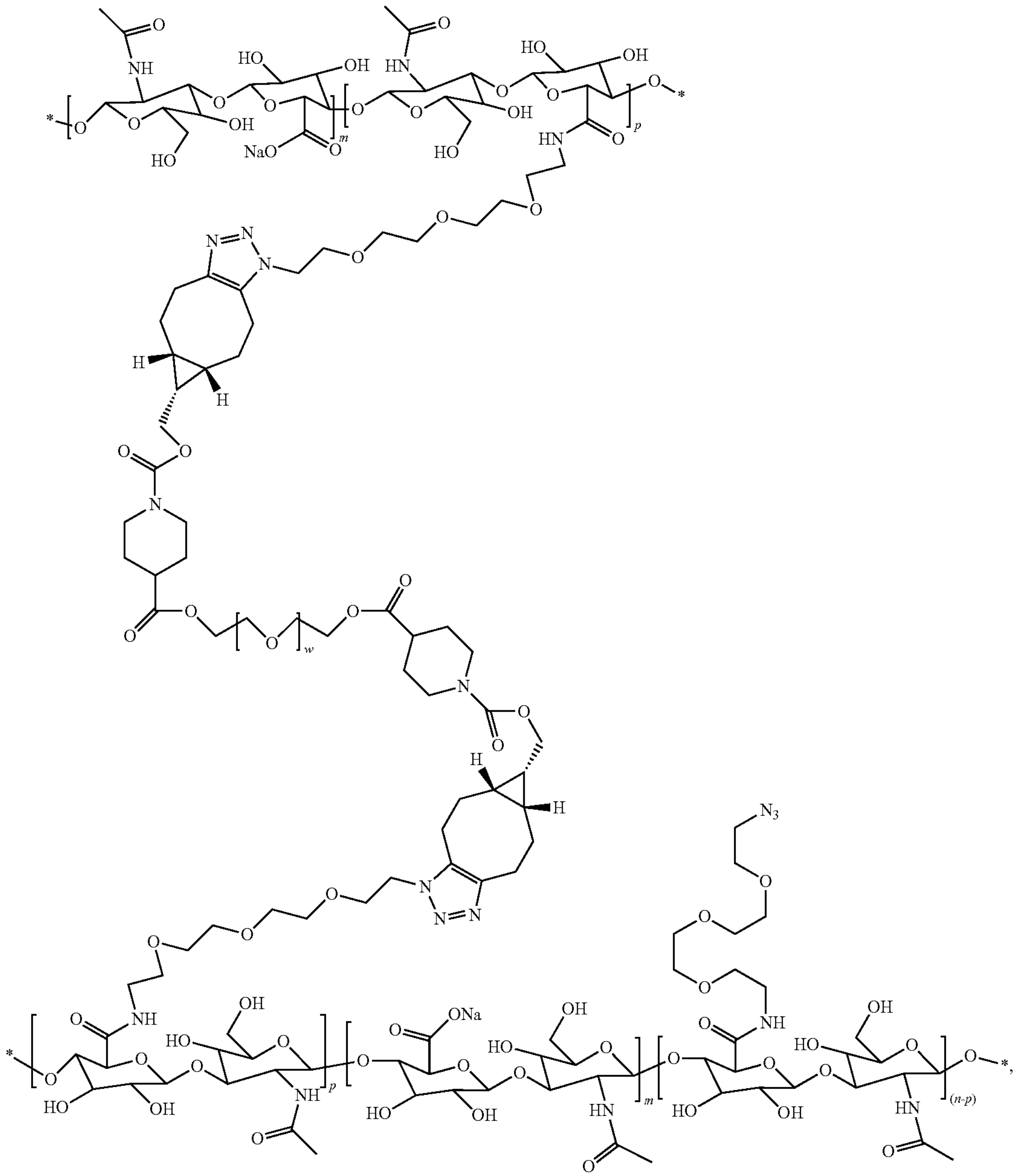

(XIIb)
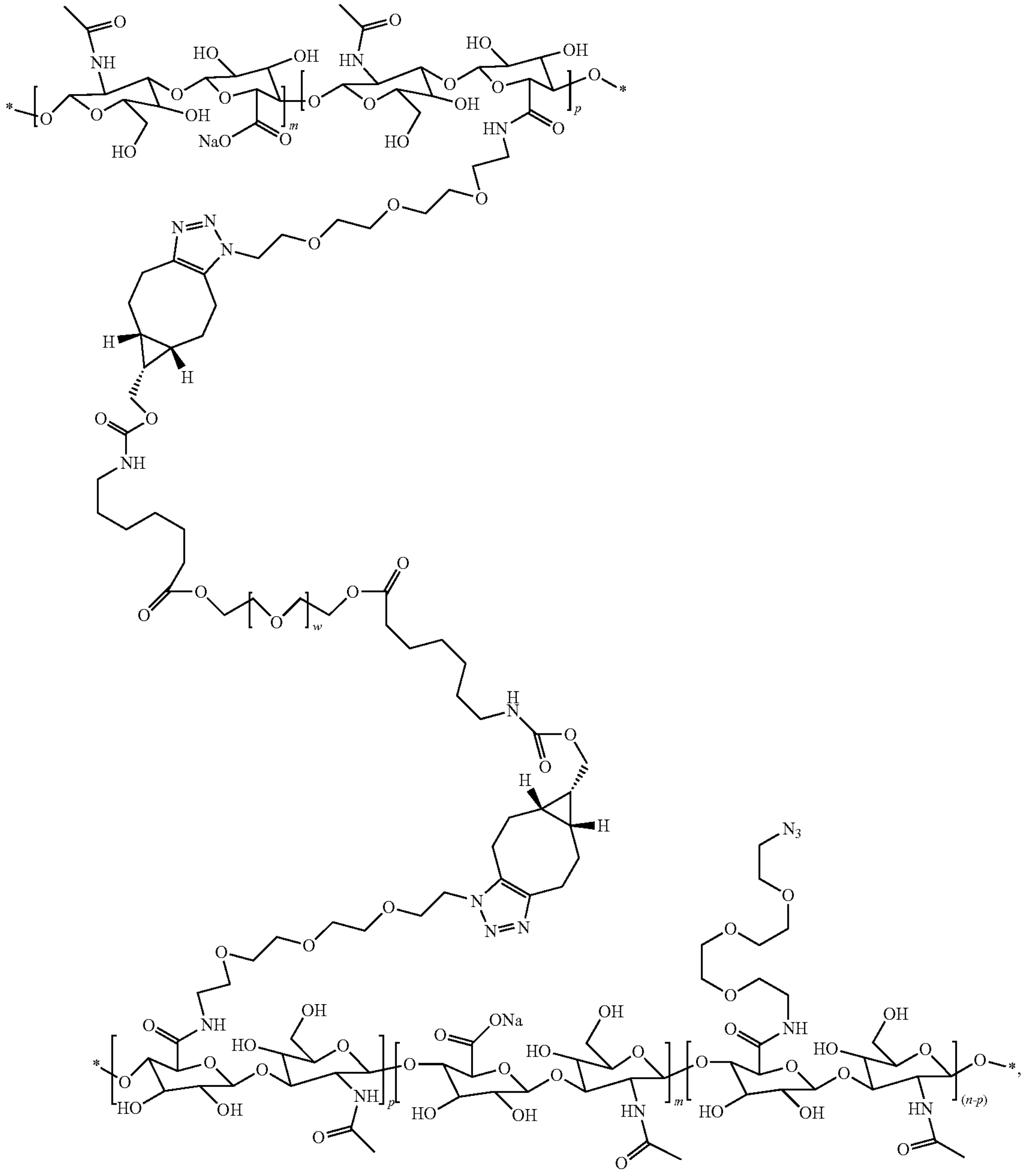

or
(XIIc)
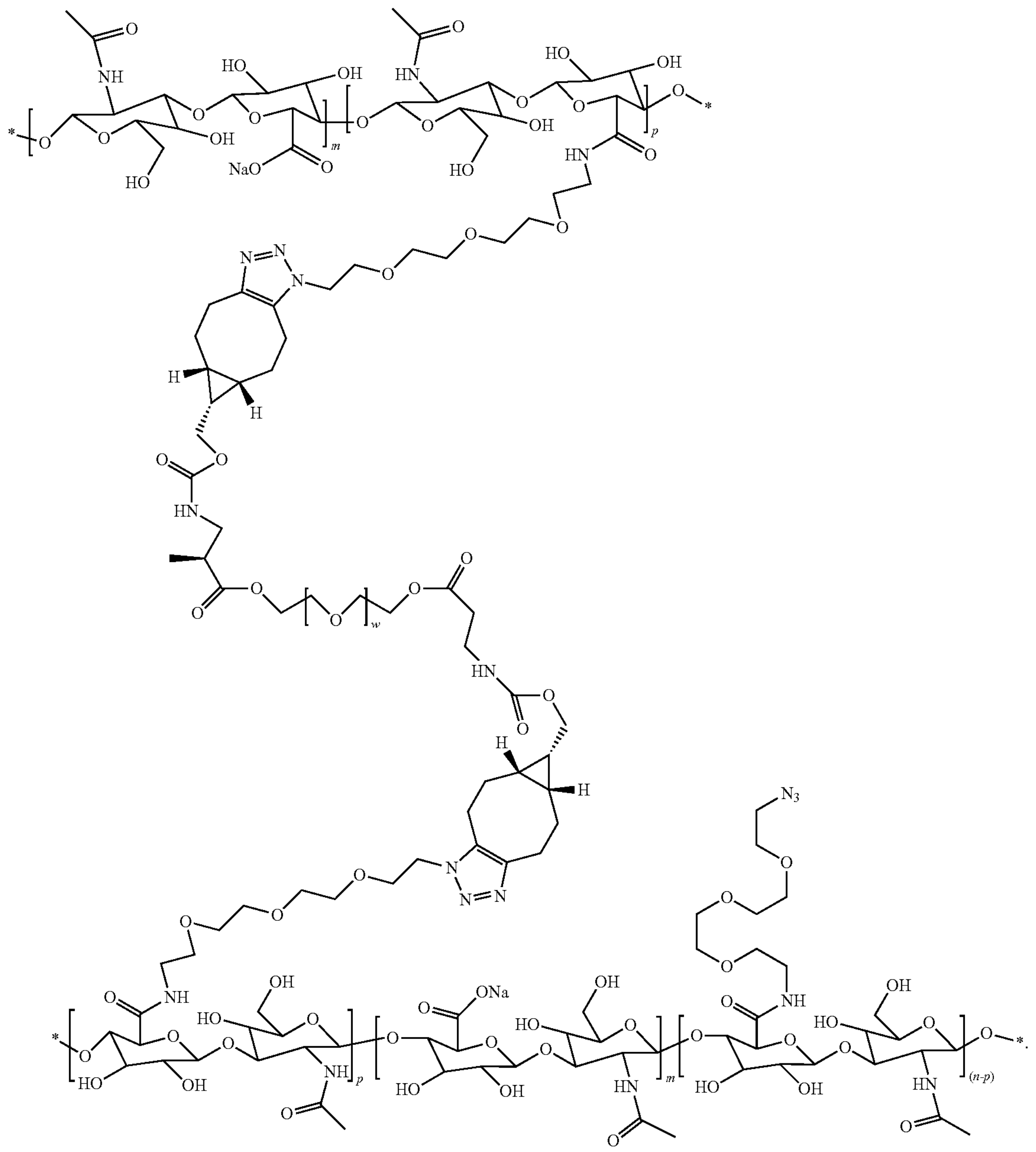
* * * * *